(12) United States Patent
Behrens et al.

(10) Patent No.: US 9,012,607 B2
(45) Date of Patent: Apr. 21, 2015

(54) MUTATED HUMANIZED 12G4 ANTIBODIES AND THE FRAGMENTS THEREOF AGAINST THE HUMAN ANTI-MULLERIAN HORMONE RECEPTOR TYPE II

(75) Inventors: Christian Behrens, Palaiseau (FR); Isabelle Navarro-Teulon, Saint Gely du Fesc (FR)

(73) Assignees: Laboratoire Francais du Fractionnement et des Biotechnologies, Les Ulis (FR); Universite Montpellier I, Montpellier (FR); Centre National de Lutte Contre le Cancer, Montpellier (FR); I.N.S.E.R.M. (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 13/697,575

(22) PCT Filed: Apr. 1, 2011

(86) PCT No.: PCT/FR2011/050745
§ 371 (c)(1),
(2), (4) Date: Feb. 4, 2013

(87) PCT Pub. No.: WO2011/141653
PCT Pub. Date: Nov. 17, 2011

(65) Prior Publication Data
US 2013/0136743 A1 May 30, 2013

(30) Foreign Application Priority Data
May 12, 2010 (FR) ..................... 10 53712

(51) Int. Cl.
C07K 16/28 (2006.01)
C07K 16/46 (2006.01)
A61K 31/282 (2006.01)
A61K 31/337 (2006.01)
A61K 31/7088 (2006.01)
A61K 33/24 (2006.01)
A61K 39/395 (2006.01)
A61K 39/00 (2006.01)

(52) U.S. Cl.
CPC ........... *C07K 16/46* (2013.01); *A61K 2039/505* (2013.01); *C07K 16/2869* (2013.01); *C07K 2317/24* (2013.01); *C07K 2317/565* (2013.01); *C07K 2317/567* (2013.01); *C07K 2317/622* (2013.01); *C07K 2317/73* (2013.01); *C07K 2317/732* (2013.01); *C07K 2317/92* (2013.01); *A61K 31/282* (2013.01); *A61K 31/337* (2013.01); *A61K 31/7088* (2013.01); *A61K 33/24* (2013.01); *A61K 39/39558* (2013.01); *C07K 2317/34* (2013.01)

(58) Field of Classification Search
CPC ................... A61K 2039/505; C07K 16/2869; C07K 16/46; C07K 2317/565; C07K 2317/567
See application file for complete search history.

(56) References Cited

U.S. PATENT DOCUMENTS

| | | | |
|---|---|---|---|
| 2004/0115209 A1* | 6/2004 | Saragovi et al. | 424/178.1 |
| 2005/0032114 A1* | 2/2005 | Hinton et al. | 435/7.1 |
| 2006/0188440 A1* | 8/2006 | Adams et al. | 424/1.49 |
| 2007/0190051 A1* | 8/2007 | Bedian et al. | 424/144.1 |
| 2007/0202552 A1* | 8/2007 | Sidhu et al. | 435/7.23 |

FOREIGN PATENT DOCUMENTS

WO 2008053330 A2 5/2008

OTHER PUBLICATIONS

Stancovski et al. (PNAS, 88:8691-8695, 1991).*
Jiang et al. (J. Biol. Chem., 280:4656-4662, 2005).*
Rudikoff, et al. (Proc. Natl. Acad. Sci. USA, 79(6):1979-1983, 1982).*
McCarthy and Hill (J. Immunol. Methods, 251(1-2):137-149, 2001).*
Salhi et al. (Biochem J., 379: 785-793, 2004).*
Yuan et al., "Isolation of anti-MISIIR scFv molecules from a phage display library by cell sorter biopanning", Cancer Immunology, Immunotherapy, 2008, vol. 57, pp. 367-378, XP-019586690.
Juarez-Gonzalez et al., "Directed Evolution, Phage Display and Combination of Evolved Mutants: A Strategy to Recover the Neutralization Properties of the scFv Version of BCF2 a Neutralizing Monoclonal Antibody Specific to Scorpion Toxin Cn2", Journal of Molecular Biology, 2005, vol. 346, No. 5, pp. 1287-1297.
Irving et al., "Phage-display library selection and mutation for the engineering of antibody affinity", Immunotechnology, 1996, vol. 2, No. 1, pp. 69, XP004052702.
Berg-Bakker et al., "Establishment and Characterization of 7 Ovarian Carcinoma Cell Lines and One Granulosa Tumor Cell Line: Growth Features and Cytogenetics", 1993, International Journal of Cancer, vol. 53, p. 613-620.
La Marca et al., "The Anti-Mullerian hormone and ovarian cancer", Human Reproduction Update, 2007, vol. 13, No. 3, pp. 265-273.
Ozols et al., "Focus on epithelial ovarian cancer", Cancer Cell, 2004, vol. 5, No. 1, pp. 19-24.
Reychler et al., "Aerosols: present et futur", Rev. Mal. Respir., 2007, vol. 24, pp. 1013-1023, English Summary is on p. 1014.
Zhang et al., "Characterization of an immortalized human granulosa cell line (COV434)", Molecular Human Reproduction, 2000, vol. 6, No. 2, pp. 146-153.
International Search Report, dated Jun. 24, 2011, from corresponding PCT application.

* cited by examiner

*Primary Examiner* — Brad Duffy
*Assistant Examiner* — Nelson B Moseley, II
(74) *Attorney, Agent, or Firm* — Young & Thompson

(57) ABSTRACT

Novel mutated humanized 12G4 antibodies, and fragments thereof, directed against the anti-Müllerian hormone type II receptor.

11 Claims, 34 Drawing Sheets

MUTATED HUMANIZED 12G4 ANTIBODIES AND THE FRAGMENTS THEREOF AGAINST THE HUMAN ANTI-MULLERIAN HORMONE RECEPTOR TYPE II

The invention relates to novel mutated humanized 12G4 antibodies, and fragments thereof, directed against the anti-Müllerian hormone type II receptor.

Ovarian cancer is the main cause of gynaecological cancers and is the fifth commonest cause of mortality from cancer in women, having the following three histological origins:
- the surface epithelium (epithelial tumour with various subtypes), which represents 85-90% of ovarian cancers,
- sexual cords/stroma (granulosa tumour (3% of total ovarian cancers)), representing about 10% of ovarian tumours,
- germ cells, representing 5% of ovarian cancers.

It is generally asymptomatic during the first stages, hence its nickname "silent killer" (La Marca A., Volpe A. The Anti-Mullerian hormone and ovarian cancer. Human Reproduction Update, Vol. 13, No. 3 pp. 265-273, 2007).

There are four stages and prognoses (FIGO classification: International Federation of Gynaecology and Obstetrics) for which the survival rate decreases considerably from stage 2:

Stage I: Tumour limited to the ovaries (5-year survival: 90-70%),

Stage II: Tumour in one or two ovaries and extends to pelvis (5-year survival: 70-40%), Stage III: Tumour in one or two ovaries, extending outside the pelvis (5-year survival: 20%), Stage IV: Distant metastases excluding peritoneal metastases (5-year survival: <10%), (Fauci, Braunwald et al. Principles of internal medicine. Harrison's 17th edition/National Cancer Institute cancer.gov/CNGOF (French National Colleges of Gynaecologists and Obstetricians).

The main strategies used for treating ovarian cancer are surgery and chemotherapy, in particular as first-line treatment, such as a mixture of carboplatin and paclitaxel.

Monoclonal antibodies have also recently been developed such as cetuximab, which is directed against the epidermal growth factor receptor (EGFR, Ozols R. F. et al., Focus on epithelial ovarian cancer, Cancer Cell. 2004, January; 5(1): 19-24).

Other monoclonal antibodies are currently in phase III, such as abagovomab directed against CA-125, Avastin directed against vascular endothelial growth factor (VEGF-A), or farletuzumab directed against folate receptor alpha (FRA).

The human anti-Müllerian hormone is a glycoprotein of 560 amino acids, a member of the TGF-β family. It is a hormone released by the Sertoli cells of the fetal testis, which causes degeneration of the Müller duct.

It is expressed in the adult in the Sertoli cells and Leydig cells (testis) and the granulosa cells (ovary).

It plays a role in the activity of the adult ovary in regulation of folliculogenesis.

The anti-Müllerian hormone type II receptor (AMHR-II) is a peptide of 573 amino acids and has serine-threonine kinase activity.

It is involved in regression of the Müller duct associated with development of the human reproductive system. It atrophies in men, where it only forms the prostatic vesicle and the sessile hydatid, but it persists in women, where it gives rise to the fallopian tubes, the uterus and most of the vagina.

This receptor is often expressed on the tumoral epithelial cells of human ovaries.

International application WO 2008/053330 describes a murine 12G4 monoclonal antibody directed against AMHR-II for treating ovarian cancers. However, it is well known to a person skilled in the art that the administration of murine monoclonal antibodies in humans causes an immune reaction.

This international application also mentions that the antibody can be chimeric or humanized, but does not describe them as such.

However, chimeric antibodies also trigger immune reactions, and humanized antibodies, slightly immunogenic, have the shortcoming that their antigen binding affinity can decrease and consequently they become less active.

It is possible according to this application to increase said affinity by mutation of the amino acids present in the humanized antibody, in particular by modifying the peptide sequence of the humanized antibody but maintaining the hydropathic index, i.e. their hydrophobicity and their charge, for example by substitution of the following amino acids: arginine-lysine or glutamate-aspartate or serine-threonine or glutamine-asparagine or valine-leucine-isoleucine substitution.

One of the aims of the invention is to provide mutated humanized 12G4 antibodies, or fragments thereof, having an affinity at least equal to that of the corresponding unmutated chimeric antibody and specificity with respect to the AMHR-II receptor, and not triggering an immune reaction.

Another aim of the invention is also to provide means for producing said specific antibodies of the AMHR-II receptor.

The invention further relates to the use of these antibodies as drugs for treating ovarian cancers.

The invention relates to a humanized 12G4 monoclonal antibody comprising or consisting of:
a) a light chain comprising or consisting of:
  a variable region the amino acid sequence of which is represented by SEQ ID NO: 2 (without leader) or SEQ ID NO: 4 (with leader), and
  a constant region the amino acid sequence of which is represented by SEQ ID NO: 6 or by a sequence having at least 80% homology with SEQ ID NO: 6,
b) a heavy chain comprising or consisting of:
  a variable region the amino acid sequence of which is represented by SEQ ID NO: 8 (without leader), or SEQ ID NO: 10 (with leader), and
  a constant region the amino acid sequence of which is represented by SEQ ID NO: 12 or by a sequence having at least 80% homology with SEQ ID NO: 12,
and said humanized 12G4 monoclonal antibody is mutated, comprises at least one mutation in the light and/or heavy chain, and has a $K_D$ for the human anti-Müllerian hormone type II receptor (AMHRII) at least equal to that of the chimeric 12G4 monoclonal antibody comprising or consisting of:
  a variable region the amino acid sequence of which is represented by SEQ ID NO: 14 (without leader), and
  a constant region the amino acid sequence of which is represented by SEQ ID NO: 6,
b) a heavy chain consisting of:
  a variable region the amino acid sequence of which is represented by SEQ ID NO: 18 (without leader) or SEQ ID NO: 10 (with leader), and
  a constant region the amino acid sequence of which is represented by SEQ ID NO: 12,
for said receptor, preferably below $10^{-7}$M, in particular below $10^{-8}$M, in particular from $10^{-9}$M to $10^{-11}$M.

The antibodies of the invention also display an affinity at least equal to a third or a half of that of the murine 12G4 antibody.

Throughout the description, the expression in parentheses "with leader" after the sequence number indicates that said sequence comprises the signal peptide or the sequence encoding for the signal peptide, i.e. the peptide that defines that the protein will be secreted.

Conversely, the expression in parentheses "without leader" indicates that said sequence does not comprise the signal peptide or the sequence encoding for the signal peptide.

The invention is based on the inventors' finding that mutated humanized 12G4 antibodies of the invention, although having at least one mutation in the CDR (three regions determining recognition of the antigen) the hydropathic index of which is not respected, i.e. in a region that is crucial for the affinity and binding to the antigen, and which as a general rule only allows substitutions of amino acids of the same hydropathic index (for example arginine-lysine, glutamate-aspartate, serine-threonine, glutamine-asparagine or valine-leucine-isoleucine), still has the following properties:
- it has for a $K_D$ for the AMHR-II receptor (determined according to Example 1) at least similar to or even less than that of the corresponding chimeric 12G4 antibody and therefore an affinity greater than or equal to that of the corresponding chimeric 12G4 antibody, or relative to the antibodies or antibody fragments of the prior art.
- it has a specificity for the AMHR-II receptor,
- it does not trigger an immune reaction or a smaller reaction than the murine antibody By way of example, Example 1 presents the $K_D$ obtained with antibodies of the invention produced in CHO or YB2/0 cells.

Throughout the description, the term "12G4" and the term "LFB112", which is also used, denote the same thing and represent the same antibody.

The affinity of said antibody can be determined by a BIAcore assay that is well known to a person skilled in the art.

In the invention, the term "antibody" refers to an immunoglobulin, a multimeric protein consisting of 4 chains participating in the acquired immune response.

The immunoglobulins are well known to a person skilled in the art and consist of an assembly of two dimers, each consisting of a heavy chain and a light chain. The multimeric complex assembled by the binding of a light chain and a heavy chain by a disulphide bridge between two cysteines, the two heavy chains themselves also being joined together by two disulphide bridges.

Each of the heavy chains and of the light chains consists of a constant region and a variable region. The assembly of chains making up an antibody can define a characteristic Y-shaped three-dimensional structure, where
- the base of the Y corresponds to the constant region Fc that is recognized by complement and the Fc receptors, and
- the ends of the arms of the Y correspond to the respective assembly of variable regions of the light chain and variable of the heavy chain.

More precisely, each light chain consists of a variable region ($V_L$) and a constant region ($C_L$). Each heavy chain consists of a variable region ($V_H$) and a constant region consisting of three constant domains $C_{H1}$, $C_{H2}$ and $C_{H3}$. The domains $C_{H2}$ and $C_{H3}$ make up the domain Fc.

The structure of an antibody is shown schematically in FIG. 1.

The variable region of the light chain consists of three regions determining recognition of the antigen (CDR) surrounded by four framework regions. The three-dimensional folding of the variable region is such that the 3 CDRs are exposed on the same side of the protein and allow the formation of a specific structure recognizing a particular antigen.

The string-of-pearls structure of a variable region of a light or heavy chain of an antibody is shown in FIG. 2.

The antibodies described in the invention have been isolated and purified, and are different from natural antibodies because they are humanized. These antibodies are mature, i.e. they have an ad hoc three-dimensional structure allowing them to recognize the antigen, and they have all the post-translational modifications essential for their antigen recognition, in particular glycosylation and the formation of intramolecular and intermolecular disulphide bridges.

They are monoclonal antibodies, i.e. they only recognize a single antigenic determinant in the AMHR-II receptor, in contrast to polyclonal antibodies, which correspond to a mixture of antibodies, and can therefore recognize several antigenic determinants in one and the same protein.

By "chimeric monoclonal antibody" is meant, in the invention, an isolated antibody, in which the sequence of each light chain and/or of each heavy chain of the antibody of which it is constituted comprises or consists of a hybrid sequence derived from at least two different animals (or human).

In particular the chimeric 12G4 antibody is a mouse/human hybrid, which indicates that a region of the sequence of the light chains and of the heavy chains is derived from the sequence of a mouse 12G4 immunoglobulin, and that the rest of the sequence of said heavy chains and of said light chains is derived from the sequence of one, or optionally several, human immunoglobulins.

FIG. 18 gives the map of the expression vector for producing the chimeric 12G4 antibody.

By "humanized 12G4 monoclonal antibody" is meant, in the invention, an isolated antibody, in which only the CDRs of each light and heavy chain of the 12G4 antibody, in particular murine, have been grafted in the light and heavy chains of a human antibody.

FIG. 19 gives the map of the expression vector for producing the humanized 12G4 antibody.

Hereinafter, the expressions "chimeric 12G4 antibody" and "unmutated chimeric 12G4 antibody" denote the same antibody.

By "mutated humanized 12G4 monoclonal antibody" is meant, in the invention, a humanized 12G4 monoclonal antibody in which at least one mutation was carried out in the variable region of the light chain and/or the constant region of the light chain and/or the variable region of the heavy chain or the constant region of the heavy chain.

Thus, the definition of the mutated humanized monoclonal antibody of the invention covers both:
- the precursor of the mutated humanized antibody, in particular the human/mouse antibody as defined above, and
- the mutated humanized antibody, in particular human/mouse, defined above.

In an advantageous embodiment, the present invention relates to a mutated humanized 12G4 monoclonal antibody as defined above, comprising at least one mutation in at least one CDR of the variable region of the light chain, and having an affinity for said receptor at least equal to that of said chimeric 12G4 monoclonal antibody.

In this embodiment, when a single mutation is present, it is located in CDR1 or CDR2 or CDR3.

When more than one mutation is present, the second as well as the others can be located in CDR1 and/or CDR2 and/or CDR3 and/or any other region of the antibody.

In an advantageous embodiment, the present invention relates to a mutated humanized 12G4 monoclonal antibody as defined above, further comprising at least one mutation in the FR regions of the light chain (VL).

In the present invention, the inventors discovered that when at least one mutation is carried out in CDR1 or CDR2 or CDR3 of the humanized 12G4 antibody, and at least one mutation in the variable region, in particular FR of the light chain, said at least one mutation not necessarily complying with the hydropathic index of the amino acids, nevertheless make it possible not only to preserve the activity of the humanized antibody but even obtain a mutated humanized antibody having an affinity at least equal to that of the unmutated chimeric antibody, and do not cause an immune or less important reaction.

In an advantageous embodiment, the present invention relates to a mutated humanized 12G4 monoclonal antibody as defined above, comprising at least one mutation in CDR1 and at least one mutation in the FR regions of the light chain (VL).

In the present invention, the inventors discovered that when at least one mutation is carried out in CDR1 of the humanized 12G4 antibody, and at least one mutation in the variable region, in particular FR of the light chain, said at least one mutation not necessarily complying with the hydropathic index of the amino acids, nevertheless make it possible not only to preserve the activity of the humanized antibody but even obtain a mutated humanized antibody having an affinity at least equal to that of the unmutated chimeric antibody, and do not cause an immune reaction.

In an advantageous embodiment, the present invention relates to a mutated humanized 12G4 monoclonal antibody as defined above, comprising at least one mutation in CDR2 and at least one mutation in the FR regions of the light chain (VL).

In the present invention, the inventors discovered that when at least one mutation is carried out in CDR2 of the humanized 12G4 antibody, and at least one mutation in the variable region, in particular FR of the light chain, said at least one mutation not necessarily complying with the hydropathic index of the amino acids, nevertheless make it possible not only to preserve the activity of the humanized antibody but even obtain a mutated humanized antibody having an affinity at least equal to that of the unmutated chimeric antibody, and do not cause an immune reaction.

In an advantageous embodiment, the present invention relates to a mutated humanized 12G4 monoclonal antibody as defined above, comprising at least one mutation in CDR3 and at least one mutation in the FR regions of the light chain (VL).

In the present invention, the inventors discovered that when at least one mutation is carried out in CDR3 of the humanized 12G4 antibody, and at least one mutation in the variable region, in particular FR of the light chain, said at least one mutation not necessarily complying with the hydropathic index of the amino acids, nevertheless make it possible not only to preserve the activity of the humanized antibody but even obtain a mutated humanized antibody having an affinity at least equal to that of the unmutated chimeric antibody, and do not cause an immune reaction.

In an advantageous embodiment, the present invention relates to a mutated humanized 12G4 monoclonal antibody as defined above, having an ADCC against cells, in particular Cov434, Asc 1 and META 2815, expressing the AMHR II receptor, in particular greater than the ADCC against the same cells of said unmutated humanized 12G4 monoclonal antibody.

ADCC (antibody-dependent cellular cytotoxicity) is a mechanism in which, when the antibody has recognized an antigen, the portion Fc of the antibody is recognized by a receptor Fcγ of a killer cell which, after binding, is capable of killing the cell bearing the antigen.

In the present invention, the inventors discovered that when at least one mutation is carried out in one or more of the CDRs of the humanized 12G4 antibody, the affinity of which is particularly reduced relative to the corresponding chimeric or murine antibody (Example 2), and although the CDR corresponds to a particularly large region of antigen recognition, said at least one mutation makes it possible not only to preserve the activity of the humanized antibody but even obtain a mutated humanized antibody having an affinity at least equal to that of the unmutated chimeric antibody, and they do not cause an immune reaction or a less pronounced reaction.

In the context of the present invention, the numbering used is based on the numbering of an ScFv fragment, the heavy chain being numbered from 1 to 115 and the light chain from 131 to 236, as shown in FIGS. 3A and 3B for the humanized 12G4 antibody in which the grey-shaded beads correspond to the amino acids that are absent from said sequence.

The two chains are joined together by a linker comprising the amino acids 116 to 130.

In an advantageous embodiment, the present invention relates to a mutated humanized 12G4 monoclonal antibody as defined above, in which at least one of said mutations in at least one CDR of the variable region of the light chain, is located in the CDR comprised in the region containing amino acid 179 to amino acid 184 of the variable region of the light chain, the amino acid sequence of which is represented by SEQ ID NO: 2.

The region containing amino acid 179 to amino acid 184 does not correspond to the complete CDR.

In this embodiment, if the antibody only has one mutation, it is located in the region of the CDR of the light chain containing amino acid 179 to amino acid 184.

It can of course have other mutations in other CDRs.

In the present invention, the inventors discovered that when at least one mutation is carried out in the region comprising amino acid 179 to 184 of the CDR of the humanized 12G4 antibody, said at least one mutation makes it possible not only to preserve the activity of the humanized antibody but even obtain a mutated humanized antibody having an affinity at least equal to that of the unmutated chimeric antibody and do not cause an immune reaction.

In an advantageous embodiment, the present invention relates to a mutated humanized 12G4 monoclonal antibody as defined above, in which at least one of said mutations located in the CDR comprised in the region containing amino acid 179 to amino acid 184 corresponds to the substitution of at least one of the following amino acids: S179P, E184K, E184G, E184D, S182F.

The notation used here corresponds to the single-letter codes that are familiar to a person skilled in the art.

The notation S179P means for example that the amino acid serine in position 179 is replaced with a proline.

In the present invention, the inventors discovered that when at least one mutation is carried out in the region comprising amino acid 179 to 184 of the CDR of the humanized 12G4 antibody, said at least one mutation not necessarily complying with the hydropathic index of the substituted amino acids, nevertheless makes it possible not only to preserve the activity of the humanized antibody but even obtain a mutated humanized antibody having an affinity at least equal to that of the unmutated chimeric antibody.

By way of example, FIG. 17 shows the affinity of binding to the AMHR-II receptor of mutated humanized antibodies according to the invention. The 6B_78 antibody only has one mutation located in the CDR of the variable region of the light chain (E184K) in which a glutamic acid is replaced with a lysine, i.e. replacement of an acidic amino acid with a basic amino acid, consequently having a totally different charge since opposite, and yet still displaying an activity but in particular an appreciably better affinity than the unmutated humanized 12G4 antibody, and equal to that of the unmutated chimeric 12G4 antibody, and do not cause an immune reaction.

In an advantageous embodiment, the present invention relates to a mutated humanized 12G4 monoclonal antibody as defined above, further comprising at least one mutation in the FR regions of the light chain (VL).

In the present invention, the inventors discovered that when at least one mutation is carried out in the region comprising amino acid 179 to 184 of the CDR of the humanized 12G4 antibody, and at least one mutation in the variable region, in particular FR of the light chain, said at least one mutation not necessarily complying with the hydropathic index of amino acids nevertheless make it possible not only to preserve the activity of the humanized antibody but even obtain a mutated humanized antibody having an affinity at least equal to that of the unmutated chimeric antibody, and do not cause an immune reaction.

In an advantageous embodiment, the present invention relates to a mutated humanized 12G4 monoclonal antibody as defined above, further comprising at least one mutation in the heavy chain.

In the present invention, the inventors discovered that when at least one mutation is carried out in the region comprising amino acid 179 to 184 of the CDR of the humanized 12G4 antibody, at least one mutation in the variable region, in particular FR of the light chain, and at least one mutation in the heavy chain, said at least one mutation not necessarily complying with the hydropathic index of the amino acids, nevertheless make it possible not only to preserve the activity of the humanized antibody but even obtain a mutated humanized antibody having an affinity at least equal to that of the unmutated chimeric antibody, and do not cause an immune reaction.

In an advantageous embodiment, the present invention relates to a mutated humanized 12G4 monoclonal antibody as defined above, in which at least one of said mutations in the FR regions of the light chain (VL) is located in the FR region adjacent to the region containing amino acid 179 to amino acid 184.

By way of example, FIG. 17 and Tables I and VII (fixation to the target AMHRII-Fc determined by ELISA) present the affinity of binding to the AMHR-II receptor of the mutated humanized antibody according to the invention.

Thus, the 3C_23 antibody has three mutations:
a mutation in the CDR of the variable region of the light chain (S179P) in which a serine is replaced with a proline, i.e. replacement of a hydrophilic amino acid with a hydrophobic amino acid,
a mutation in the variable region, in particular FR of the light chain (I177T), i.e. replacement of a hydrophobic amino acid with a hydrophilic amino acid, moreover having an entirely different value of hydropathic index, according to international application WO 2008/053330 (+4.5 for isoleucine and −0.7 for threonine), and
a mutation in the heavy chain (Q3R), i.e. replacement of a glutamine with an arginine for which the value of the hydropathic index, according to international application WO 2008/053330, varies from −3.5 for glutamine to −4.5 for arginine, and yet having an appreciably better affinity than that of the unmutated humanized 12G4 antibody, and greater than that of the unmutated chimeric 12G4 antibody.

Moreover, the 3C_23K antibody, which apart from the mutations of the 3C_23 antibody also has a second mutation in the CDR of the variable region of the light chain (E184K) in which a glutamic acid is replaced with a lysine, i.e. replacement of an acidic amino acid with a basic amino acid, consequently having a totally different charge since it is of opposite sign, nevertheless still displays an activity, but especially an affinity that is appreciably better than that of the unmutated humanized 12G4 antibody, and greater than that of the unmutated chimeric 12G4 antibody, and does not cause an immune reaction.

In an advantageous embodiment, the present invention relates to a mutated humanized 12G4 monoclonal antibody as defined above, in which at least one of said mutations in the FR regions of the light chain (VL) corresponds to the substitution of at least one of the following amino acids: I132T, A143T, T150A, S158P, L175Q, I177T, Y178H, V187A, S192T, G197D, F212S.

In an advantageous embodiment, the present invention relates to a mutated humanized 12G4 monoclonal antibody as defined above, in which at least one of said mutations in the heavy chain corresponds to the substitution of at least one of the following amino acids: Q1E, Q3E, Q3R, Q6E, A9T, V11A, K12R, K13R, K19E, V20A, A24G, A24V, A24T, Q39E, A40V, S31G, L45P, D56N, A76T, A79T, R87G, T58A, Q62R, V67M, I70N, T74A, S77P, A79T, S88P, E89D, F102S, A103T, L110P, S114T.

In an advantageous embodiment, the present invention relates to a mutated humanized 12G4 monoclonal antibody as defined above, having a light chain and a heavy chain selected from the following:
a) a light chain comprising or consisting of a variable region the amino acid sequence of which is represented by SEQ ID NO: 2 in which at least one following substitution of amino acids located in one of the CDRs has been carried out: S179P, E184K, E184G, E184D, S182F, or
a light chain comprising or consisting of a variable region the amino acid sequence of which is represented by SEQ ID NO: 2 in which at least one following substitution of amino acids located in one of the CDRs has been carried out: S179P, E184K, E184G, E184D, S182F, and at least one following substitution of amino acids located in regions FR has been carried out: I132T, A143T, T150A, S158P, L175Q, Y178H, V187A, S192T, G197D, F212S,
and of a constant region the amino acid sequence of which is represented by SEQ ID NO: 6,
b) a heavy chain the amino acid sequence of which is represented by SEQ ID NO: 58 in which a substitution of at least one of the following amino acids: Q1E, Q3E, Q3R, Q6E, A9T, V11A, K12R, K13R, K19E, V20A, A24G, A24V, A24T, Q39E, A40V, S31G, L45P, D56N, A76T, A79T, R87G, T58A, Q62R, V67M, I70N, T74A, S77P, A79T, S88P, E89D, F102S, A103T, L110P, S114T has been carried out.

Table VII of Example 3 presents the various clones obtained and their substitution. It also shows that the hydropathic index varies considerably as a function of the mutations, but without leading to a loss of activity and/or of affinity for the antigen and even makes it possible, for certain clones, to obtain an increase in affinity relative to the corresponding chimeric antibody (ratio Ab of the invention/chimeric antibody greater than or equal to 1).

In this embodiment, it is possible to constitute an antibody that is derived from the combination of two antibodies obtained previously and further increase the activity and the affinity for the AMHR-II receptor relative to the unmutated chimeric 12G4 antibody.

In an advantageous embodiment, the present invention relates to a mutated humanized 12G4 monoclonal antibody as defined above, having a light chain and a heavy chain selected from the following:
a) a light chain comprising or consisting of a variable region the amino acid sequence of which is represented by:
SEQ ID NO: 22 (without leader) or SEQ ID NO: 24 (with leader), or
SEQ ID NO: 30 (without leader) or SEQ ID NO: 32 (with leader), or
SEQ ID NO: 34 (without leader) or SEQ ID NO: 36 (with leader), or
SEQ ID NO: 46 (without leader) or SEQ ID NO: 48 (with leader),
and of a constant region the amino acid sequence of which is represented by SEQ ID NO: 6,
b) a heavy chain comprising or consisting of a variable region the amino acid sequence of which is represented by:
SEQ ID NO: 38 (without leader), or SEQ ID NO: 40 (with leader),
SEQ ID NO: 26 (without leader), or SEQ ID NO: 28 (with leader),
SEQ ID NO: 8 (without leader), or SEQ ID NO: 10 (with leader),
SEQ ID NO: 42 (without leader), or SEQ ID NO: 44 (with leader),
SEQ ID NO: 50 (without leader), or SEQ ID NO: 52 (with leader), and of a constant region the amino acid sequence of which is represented by SEQ ID NO: 12.

In an advantageous embodiment, the present invention relates to a mutated humanized 12G4 monoclonal antibody as defined above, having:
a) a light chain consisting of the amino acid sequence represented by:
SEQ ID NO: 70 (without leader) or SEQ ID NO: 72 (with leader), and
b) a heavy chain consisting of the amino acid sequence represented by:
SEQ ID NO: 74 (without leader), or SEQ ID NO: 76 (with leader), (3C_23 antibody)
or,
a) a light chain consisting of the amino acid sequence represented by:
SEQ ID NO: 78 (without leader) or SEQ ID NO: 80 (with leader), and
b) a heavy chain consisting of the amino acid sequence represented by:
SEQ ID NO: 58 (without leader), or SEQ ID NO: 60 (with leader), (6B—78 antibody) or, a) a light chain consisting of the amino acid sequence represented by: SEQ ID NO: 82 (without leader) or SEQ ID NO: 84 (with leader), and
b) a heavy chain consisting of the amino acid sequence represented by:
SEQ ID NO: 86 (without leader), or SEQ ID NO: 88 (with leader), (3C_23K antibody)
or,
a) a light chain consisting of the amino acid sequence represented by:
SEQ ID NO: 78 (without leader) or SEQ ID NO: 80 (with leader), and
b) a heavy chain consisting of the amino acid sequence represented by:
SEQ ID NO: 90 (without leader), or SEQ ID NO: 92 (with leader), (4C_35 antibody)
or,
a) a light chain consisting of the amino acid sequence represented by:
SEQ ID NO: 94 (without leader) or SEQ ID NO: 96 (with leader), and
b) a heavy chain consisting of the amino acid sequence represented by:
SEQ ID NO: 98 (without leader), or SEQ ID NO: 100 (with leader), (5B_42 antibody)

According to another aspect, the invention relates to a fragment of a mutated humanized 12G4 monoclonal antibody as defined above, selected from the group of fragments consisting of: Fv, Fab, F(ab')2, Fab', dsFv, scFv, Sc(Fv)$_2$, "diabodies".

According to another aspect, the invention relates to a nucleic acid comprising or consisting of a sequence encoding for the light chain of a monoclonal antibody defined above and/or comprising or consisting of a sequence encoding for the heavy chain of the monoclonal antibody defined above.

In an advantageous embodiment, the invention relates to a nucleic acid defined above, in which the sequence encoding for the light chain comprises or consists of the following sequences:
a) a sequence encoding for the variable region of the light chain represented by SEQ ID NO: 53 in which a substitution of at least one codon permitting the substitution, in one of the CDRs, of one or more of the following amino acids: S179P, E184K, E184G, E184D, S182F has been carried out,
or,
b) a sequence encoding for the variable region of the light chain represented by SEQ ID NO: 53 in which:
at least one substitution of a codon permitting the substitution, in one of the CDRs, of one or more of the following amino acids: S179P, E184K, E184G, E184D, S182F has been carried out, and
at least one substitution of at least one codon permitting the substitution, in one of the FRs, of one or more of the following amino acids: I132T, A143T, T150A, S158P, L175Q, Y178H, V187A, S192T, G197D, F212S, has been carried out,
and a sequence encoding for the constant region represented by SEQ ID NO: 5.

In an advantageous embodiment, the invention relates to a nucleic acid defined above, in which the sequence encoding for the heavy chain comprises or consists of the following sequences:
a) SEQ ID NO: 57 in which a substitution of at least one codon permitting the substitution of one or more of the following amino acids: Q1E, Q3E, Q3R, Q6E, A9T, V11A, K12R, K13R, K19E, V20A, A24G, A24V, A24T, Q39E, A40V, S31G, L45P, D56N, A76T, A79T, R87G, T58A, Q62R, V67M, I70N, T74A, S77P, A79T, S88P, E89D, F102S, A103T, L110P, S114T has been carried out.

In an advantageous embodiment, the invention relates to a nucleic acid defined above, comprising a light chain defined above and a heavy chain defined above.

In an advantageous embodiment, the invention relates to a nucleic acid defined above, in which the sequence encoding for the light chain comprises or consists of a sequence encoding for a variable region and a sequence encoding for a constant region selected from the following:
  a) variable region:
    SEQ ID NO: 21 (without leader) or SEQ ID NO: 23 (with leader), or
    SEQ ID NO: 29 (without leader) or SEQ ID NO: 31 (with leader), or
    SEQ ID NO: 33 (without leader) or SEQ ID NO: 35 (with leader), or
    SEQ ID NO: 45 (without leader) or SEQ ID NO: 47 (with leader), or
  b) constant region
    SEQ ID NO: 5.

In an advantageous embodiment, the invention relates to a nucleic acid defined above, in which the sequence encoding for the heavy chain comprises or consists of a sequence encoding for a variable region and a sequence encoding for a constant region selected from the following:
  a) variable region:
    SEQ ID NO: 25 (without leader) or SEQ ID NO: 27 (with leader), or
    SEQ ID NO: 7 (without leader) or SEQ ID NO: 9 (with leader), or
    SEQ ID NO: 37 (without leader) or SEQ ID NO: 39 (with leader), or
    SEQ ID NO: 41 (without leader) or SEQ ID NO: 43 (with leader), or
    SEQ ID NO: 49 (without leader) or SEQ ID NO: 51 (with leader),
  b) constant region
    SEQ ID NO: 11.

In an advantageous embodiment, the invention relates to a nucleic acid defined above, in which the sequence encoding for the light chain is selected from the following sequences:
  SEQ ID NO: 69 (without leader) or SEQ ID NO: 71 (with leader), or
  SEQ ID NO: 77 (without leader) or SEQ ID NO: 79 (with leader), or
  SEQ ID NO: 81 (without leader) or SEQ ID NO: 83 (with leader), or
  SEQ ID NO: 93 (without leader) or SEQ ID NO: 95 (with leader),
and the sequence encoding for the heavy chain is selected from the following sequences:
  SEQ ID NO: 73 (without leader) or SEQ ID NO: 75 (with leader), or
  SEQ ID NO: 57 (without leader) or SEQ ID NO: 59 (with leader), or
  SEQ ID NO: 85 (without leader) or SEQ ID NO: 87 (with leader), or
  SEQ ID NO: 89 (without leader) or SEQ ID NO: 91 (with leader), or
  SEQ ID NO: 97 (without leader) or SEQ ID NO: 99 (with leader).

In an advantageous embodiment, the invention relates to a nucleic acid defined above, in which the sequence encoding for the light chain and the sequence encoding for the heavy chain are as follows:
  a) sequence encoding for the light chain SEQ ID NO: 69 (without leader) or SEQ ID NO: 71 (with leader), and
  b) sequence encoding for the heavy chain SEQ ID NO: 73 (without leader) or SEQ ID NO: 75 (with leader),
  (3C__23 antibody)
  or,
  a) sequence encoding for the light chain SEQ ID NO: 77 (without leader) or SEQ ID NO: 79 (with leader), and
  b) sequence encoding for the heavy chain SEQ ID NO: 57 (without leader) or SEQ ID NO: 59 (with leader),
  (6B__78 antibody)
  or,
  a) sequence encoding for the light chain SEQ ID NO: 81 (without leader) or SEQ ID NO: 83 (with leader), and
  b) sequence encoding for the heavy chain SEQ ID NO: 85 (without leader) or SEQ ID NO: 87 (with leader),
  (3C__23K antibody)
  or,
  a) sequence encoding for the light chain SEQ ID NO: 77 (without leader) or SEQ ID NO: 79 (with leader), and
  b) sequence encoding for the heavy chain SEQ ID NO: 89 (without leader) or SEQ ID NO: 91 (with leader),
  (4C__35 antibody)
  or,
  a) sequence encoding for the light chain SEQ ID NO: 93 (without leader) or SEQ ID NO: 95 (with leader), and
  b) sequence encoding for the heavy chain SEQ ID NO: 97 (without leader) or SEQ ID NO: 99 (with leader),
  (5B__42 antibody).

According to another aspect, the invention relates to an expression vector comprising at least one nucleic acid defined above, said nucleic acid being under the control of the elements permitting its expression.

"Expression vector" defines, in the invention, a DNA molecule that has elements permitting its replication (duplication) in at least one living organism. These elements permitting replication are in particular origins of replication in yeast or bacteria, or elements controlling the replication of a virus.

The vectors according to the invention are in particular plasmids, phages, yeast artificial chromosomes (YAC), bacterial artificial chromosomes (BAC), modified genomes of replicative viruses or of integrative viruses etc.

These vectors are called "expression vectors" as they have nucleotide sequences that permit the expression, i.e. the transcription to RNA, of the nucleotide sequences that they control.

In the invention, said nucleic acid sequence contained in said vector is placed "under the control of the elements permitting its expression". This means that said expression vector has at least one transcription initiation sequence such as a promoter of a virus, for instance the early promoter of the simian virus SV40, or of the Cytomegalovirus (CMV) or the promoter sequences of the Rous sarcoma virus (RSV), and in particular a sequence or promoter comprising a TATAA box. Moreover, said vector also has at least one transcription termination sequence, and in particular a polyadenylation sequence, derived from a mammalian, in particular human, gene.

To these sequences, which are indispensable for expression of the nucleotide sequence contained in said vector, other sequences may be added for regulating or modulating the expression of said sequence. A non-limitative list comprises: introns of mammalian, and in particular human, genes, sequences for regulating transcription of the enhancer type or sequences of mammalian, and in particular human, genes that have been transcribed but not translated.

An advantageous embodiment of the invention relates to an expression vector as defined above, comprising at least one nucleic acid selected from the nucleic acids comprising the following sequences SEQ ID NO 59, 71, 75, 79, 83, 87, 91, 95 or 99.

In another advantageous embodiment, the invention relates to an expression vector as defined above, comprising
- a first nucleic acid selected from the nucleic acids with the following sequences: SEQ ID NO 71, 79, 83 or 95, said first nucleic acid being under the control of the elements permitting its expression, and
- a second nucleic acid selected from the nucleic acids with the following sequences:
SEQ ID NO 59, 75, 87, 91 or 99, said second nucleic acid being under the control of the elements permitting its expression.

This expression vector therefore comprises two aforementioned sequences of nucleic acids, and more particularly comprises a nucleic acid sequence encoding for the light chain of the monoclonal antibody defined above, and a nucleic acid sequence encoding for the heavy chain of the monoclonal antibody defined above.

Preferably said expression vector contains a first element permitting expression of the nucleic acid sequence encoding for the light chain of the monoclonal antibody defined above and a second element permitting expression of the nucleic acid sequence encoding for the heavy chain of the monoclonal antibody defined above, said first element and said second element, permitting expression of said sequences of nucleic acids, being identical or different, and preferably identical. These control elements are in particular the long terminal repeat (LTR) sequences of the virus RSV.

Another embodiment of the invention relates to an expression vector defined above, comprising at least one antibiotic resistance gene.

By "at least one resistance gene" is meant, in the invention, that said expression vector can contain 1 or 2, or 3 or 4 or 5 or 6 antibiotic resistance genes.

"Antibiotic resistance gene" defines, in the invention, a gene the expression product of which exerts a cytostatic effect (inhibition of growth) or cytolytic effect (cellular death) on cells. The antibiotics to which the invention relates in particular have an effect on prokaryotic cells, but can also have an effect on eukaryotic cells, whether of yeasts, plants, insects, amphibians or mammals.

More particularly, the aforementioned expression vector has an antibiotic resistance gene specific to prokaryotic cells and at least one, preferably 2, antibiotic resistance genes specific to eukaryotic cells.

As antibiotics specific to prokaryotic cells: ampicillin, tetracycline and derivatives thereof, hygromycin, kanamycin etc. may be mentioned. As antibiotics specific to eukaryotic cells: G418, Geneticin (salts of G418), puromycin, methotrexate, blasticidin etc. may be mentioned.

The transcription units (TUs) of interest coding for the heavy chain and the light chain are cloned in the form of cDNA and under the dependence of the RSV promoter. This promoter corresponds to the LTR (long terminal repeat) of the Rous sarcoma virus, which contains an enhancer element in its 5' region.

An artificial intron optimized for alternative splicing and composed of a donor sequence at 5' isolated from human beta-globin and at 3' of an acceptor sequence derived from the gene of the variable of the heavy chain of immunoglobulin is cloned immediately at 3' of the promoter. The TUs of interest are terminated with polyadenylation sequences derived from the growth hormone (GH) gene of human origin (hGH) for the heavy chain and bovine origin (bGH) for the light chain. This difference of origin in the choice of the polyAs has the aim of limiting recombinations between the genes of interest. This combination of LTRRSV promoter, chimeric intron, cDNA and polyA sequence was selected as it confers high transcriptional and translational activity in the YB2/0 cell line.

The expression vector contains in addition to the TUs of interest, several TUs for resistances to chemical molecules:

Bla gene: This gene (called Amp in the restriction maps of the vectors) expresses the enzyme beta-lactamase in the bacterium (prokaryotic promoter) and confers resistance to ampicillin.

Neo gene: This gene codes for the enzyme npt II (neomycin-phosphotransferase II) under the control of the promoter SV40 and confers resistance to various antibiotics such as neomycin, kanamycin or G418 on transfected mammalian cells expressing this gene.

Dhfr gene: This gene codes for the enzyme DHFR (DiHydroFolate Reductase) under the control of the promoter SV40 and confers resistance to methotrexate (MTX). This method can be used for gene amplification by increasing the concentration of MTX thus resulting from an increase in antibody production by the transfected cells.

FIGS. 18 to 22 give the maps of the expression vectors used for producing clones 3C_23, 6B_78, 3C_23K, 4C_35 and 5B_42.

In another aspect, the present invention relates to a host cell or cell line transformed by a nucleic acid defined above and/or an expression vector defined above.

In particular, said cell or cell line is characterized in that it
- displays apoptosis of less than 25%,
- is stable during cell divisions, and
- secretes at least 14 µg/ml of monoclonal antibody defined above.

The concept of cellular stability implies that the cells resulting from cloning of the cloned cells derived from the cells containing at least one vector permitting expression of a monoclonal antibody according to the invention are capable, during the various divisions, of conserving their properties of antibiotic resistances and of producing monoclonal antibodies.

In yet another aspect, the invention relates to a pharmaceutical composition, and in particular a vaccine composition, comprising at least
- a monoclonal antibody defined above, or
- a nucleic acid defined above, or
- a vector defined above, or
- a fragment of said monoclonal antibody defined above, together with a pharmaceutically acceptable vehicle.

Advantageously, the invention relates to a pharmaceutical composition, and in particular a vaccine composition, comprising at least one monoclonal antibody defined above, together with a pharmaceutically acceptable vehicle.

The dosage of the active ingredient depends in particular on the method of administration, and is easily determined by a person skilled in the art.

"A pharmaceutically acceptable vehicle" refers to a non-toxic material that is compatible with a biological system such as a cell, a cell culture, a tissue or an organism.

A therapeutically effective amount (unit dose) can vary from 0.01 mg/kg to 500 mg/kg, preferably from 0.1 mg/kg to 500 mg/kg, preferably from 0.1 mg/kg to 100 mg/kg, preferably from 0.1 mg/kg to 20 mg/kg, preferably from 0.1 mg/kg to 10 mg/kg, and more preferably from 1 mg/kg to 10 mg/kg, in one or more weekly administrations, for several weeks or months.

Moreover, a therapeutically effective amount (unit dose) can vary from 0.2 mg/m$^2$ to 10 g/m$^2$, preferably from 0.2 mg/m$^2$ to 1 g/m$^2$, preferably from 2 mg/m$^2$ to 1 g/m$^2$, preferably from 20 mg/m² to 1 g/m², and more preferably from 20 mg/m² to 0.5 g/m², in one or more weekly administrations, for several weeks or months.

The pharmaceutical composition of the invention can in particular be administered intravenously, in particular by injection or by gradual perfusion, subcutaneously, systemically, locally by infiltrations, per os, or by the respiratory or pulmonary route by means of an aerosol.

The preparations for parenteral administration can include sterile aqueous or non-aqueous solutions, suspensions or emulsions. Examples of non-aqueous solvents are propylene glycol, polyethylene glycol, vegetable oils, such as olive oil, or injectable organic esters such as ethyl oleate. Aqueous vehicles comprise water, alcohol/water solutions, emulsions or suspensions.

The advantageous pharmaceutical form of the pharmaceutical composition of the invention can be administered by the oral route and comprises
- a monoclonal antibody defined above, or
- a nucleic acid defined above, or
- a expression vector defined above, or
- a fragment of said monoclonal antibody defined above, together with an excipient, in the presence or absence of a propellant.

In one embodiment of the invention, the aerosol is in the form of a liquid containing the mutated humanized antibody and an excipient. The excipients are most often alcohols, but any other excipient known to a person skilled in the art can be used in the context of the invention. The aerosol in liquid form can be combined with a propellant gas such as chlorofluorocarbons (CFCs) or hydrofluorocarbons (HFAs).

The aerosol in liquid form can also consist of lipid microparticles and an excipient. In this case, the excipients can be selected from synthetic dipalmitoylphosphatidylcholine (DPPC), lactose or hydroxyethyl starch (HES). The microparticles are then administered by means of an insufflator.

In another embodiment of the invention, the aerosol is in the form of powder. The powder is composed of particles with a size between 1 and 10 μm and preferably less than 9 μm, or preferably less than 5 μm. As a non-limitative example, the following methods can be used for obtaining a dry powder: spraying accompanied by freeze-drying or crystallization by ultrasound, directed precipitation.

The aerosol will be administered, depending on whether it is in liquid or solid form, by means of a nebulizer which can be pneumatic, ultrasonic or of the sieve type or by means of a metering aerosol (of pressurized liquid, mechanical, electro-hydrodynamic, thermal) for the liquid formulations or by means of an inhaler for the solid formulations. (Reychler G., Dessanges J F and Vecellio L, Rev. Mal. Respir, 2007; 24: 1013-1023).

According to another aspect, the invention relates to a product comprising a first pharmaceutical preparation comprising a monoclonal antibody defined above, and a second pharmaceutical preparation comprising a conventional anti-cancer compound, in particular paclitaxel or a platinum salt, in particular oxaliplatin, cisplatin or carboplatin, as a combined preparation for simultaneous, separate or sequential use in the treatment of patients with diseases associated with the human anti-Müllerian hormone type II receptor, in particular
- ovarian cancer, in particular metastatic ovarian cancer, serous cancer, hypernephroma,
- endometrioid, colloidal epithelium,
- prostate cancer,
- germ cell cancer,
- endometrial cancer,
- mixed Müllerian malignant tumour of the uterus,
- leiomyosarcoma,
- endometrial stromal sarcoma.

According to another aspect, the invention relates to the use of at least:
- a monoclonal antibody defined above, or
- a fragment of said monoclonal antibody defined above, or
- a nucleic acid defined above, or
- a vector defined above, or
- a cell defined above,
- for preparing a drug intended for treating or preventing a disease associated with the human anti-Müllerian hormone type II receptor, in particular:
- ovarian cancer, in particular metastatic ovarian cancer, serous cancer, hypernephroma,
- endometrioid, colloidal epithelium,
- prostate cancer,
- germ cell cancer,
- endometrial cancer,
- mixed Müllerian malignant tumour of the uterus,
- leiomyosarcoma,
- endometrial stromal sarcoma.

By "treatment" is meant the manner of treating a pathology that has developed, the symptoms of which are visible. By "prevention" is meant the manner of preventing said pathology from developing.

In an advantageous embodiment, the invention relates to the use of an antibody defined above, or of a fragment of the latter defined above, for diagnosing and/or monitoring ovarian cancer.

In an advantageous embodiment, the invention relates to the use of an antibody defined above, or of a fragment of the latter defined above, additionally comprising a conventional anticancer drug, in particular paclitaxel or a platinum salt, in particular oxaliplatin, cisplatin or carboplatin.

According to another aspect, the invention relates to:
- a monoclonal antibody as defined above, or
- a fragment of said monoclonal antibody as defined above, or
- a nucleic acid as defined above, or
- a vector as defined above, or
- a cell as defined above,
- for use in the treatment or prevention of a pathology associated with the human anti-Müllerian hormone type II receptor, in particular:
- ovarian cancer, in particular metastatic ovarian cancer, serous cancer, hypernephroma,
- endometrioid, colloidal epithelium,
- prostate cancer,
- germ cell cancer,
- endometrial cancer,
- mixed Müllerian malignant tumour of the uterus,
- leiomyosarcoma,
- endometrial stromal sarcoma.

In an advantageous embodiment, the monoclonal antibody defined above or a fragment of the latter defined above is used for diagnosing and/or monitoring a cancer associated with the human anti-Müllerian hormone type II receptor, in particular:
- ovarian cancer, in particular metastatic ovarian cancer, serous cancer, hypernephroma,
- endometrioid, colloidal epithelium,
- prostate cancer,
- germ cell cancer,
- endometrial cancer,
- mixed Müllerian malignant tumour of the uterus,
- leiomyosarcoma,
- endometrial stromal sarcoma.

In an advantageous embodiment, the monoclonal antibody defined above or a fragment of the latter defined above, or the nucleic acid defined above or the vector defined above or the cell defined above, additionally comprises a conventional anticancer drug, in particular paclitaxel or a platinum salt, in particular oxaliplatin, cisplatin or carboplatin.

According to another aspect, the invention relates to a kit comprising at least:
- a monoclonal antibody as defined above, or
- a fragment of said monoclonal antibody as defined above, or
- a nucleic acid as defined above, or
- a vector as defined above, or
- a cell as defined above,
- for use in diagnosing a pathology associated with the human anti-Müllerian hormone type II receptor, in particular ovarian cancer.

According to another aspect, the invention relates to a method of diagnosing a pathology associated with the human anti-Müllerian hormone type II receptor, in particular ovarian cancer, on a human biological sample, comprising the following steps:
  a. labelling a biopsy previously obtained from a patient,
  b. determining the presence of a human anti-Müllerian hormone type II receptor.

According to another aspect, the invention relates to a method of diagnosing a pathology associated with the human anti-Müllerian hormone type II receptor, in particular ovarian cancer, on a human biological sample, comprising the following steps:
  a. obtaining a biopsy from a patient,
  b. labelling the biopsy,
  c. determining the presence of a human anti-Müllerian hormone type II receptor.

Labelling of the biopsy is carried out according to techniques that are well known to a person skilled in the art.

The presence of the receptor can be determined by techniques that are well known to a person skilled in the art, such as immunoassay, binding etc.

According to another aspect, the invention relates to a method of treating a pathology associated with the human anti-Müllerian hormone type II receptor, in particular ovarian cancer, on a human biological sample, comprising the following steps:
  a. obtaining a biopsy from a patient,
  b. labelling the biopsy,
  c. determining the presence of a human anti-Müllerian hormone type II receptor,
  d. if the presence of a human anti-Müllerian hormone type II receptor is determined, treating the patient with:
    i. a monoclonal antibody as defined above, or
    ii. a fragment of said monoclonal antibody as defined above, or
    iii. a nucleic acid as defined above, or
    iv. a vector as defined above, or
    v. a cell as defined above.

The X-axis shows the concentration of (Fab) in µg/ml and the Y-axis shows the OD at 450 nm.

The dotted curve with empty white circles represents the binding of the unmutated humanized 12G4 antibody.

The curve with filled black triangles represents the binding of the mutated humanized 12G4 antibody, having a mutation in the CDR (E184K) of the variable region of the light chain (6B_78 antibody).

The curve with empty white triangles represents the binding of the mutated humanized 12G4 antibody, having a mutation in the CDR (S179P) of the variable region of the light chain, a mutation in the FR region (I177T) of the variable region of the light chain and a mutation in the variable region of the heavy chain (Q3R) (3C_23 antibody).

The curve with empty white circles represents the binding of the mutated humanized 12G4 antibody, having a mutation in the CDR (E184K) of the variable region of the light chain, a mutation in the CDR (S179P) of the variable region of the light chain, a mutation in the FR region (I177T) of the variable region of the light chain and a mutation in the variable region of the heavy chain (Q3R) (3C_23K antibody).

The curve with filled black circles represents the binding of the unmutated chimeric 12G4 antibody.

Figure 18:
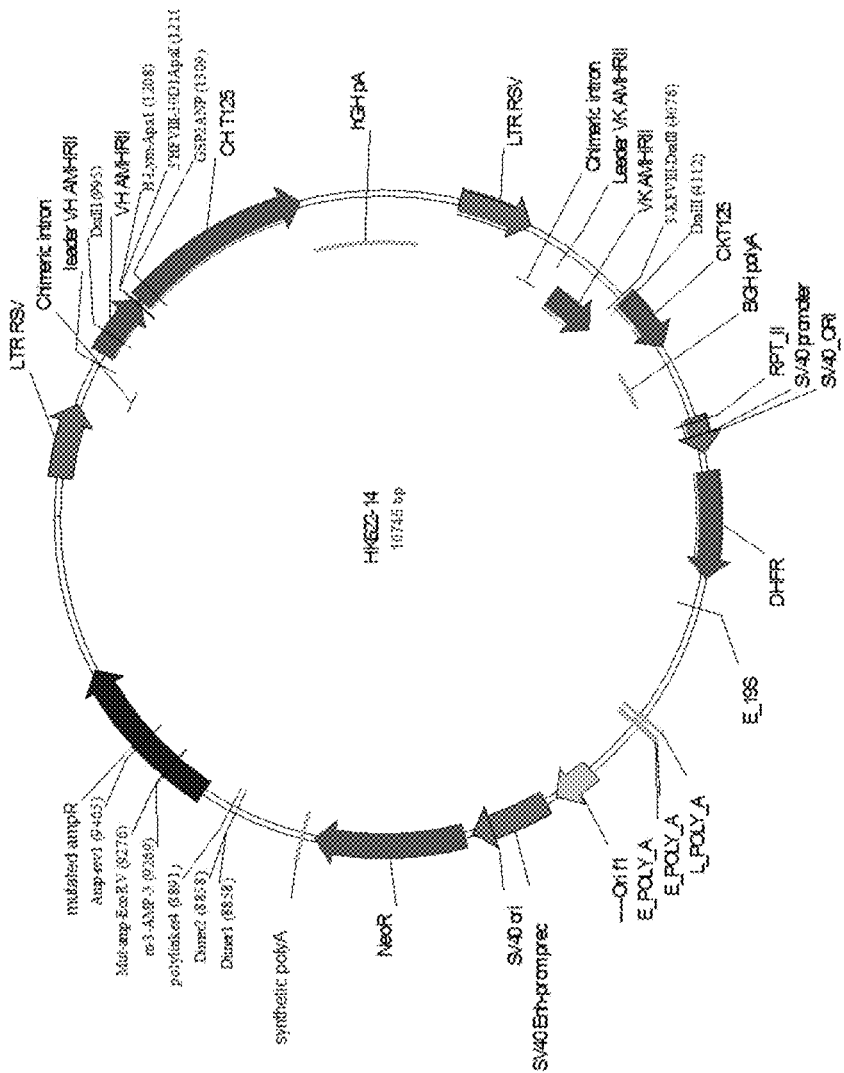

FIG. 18 corresponds to the diagrammatic representation of the H622-14 cloning vector for the chimeric 12G4 antibody containing the heavy chain where the leader VH AMHR-II is fused to the variable region of the heavy chain (VH AMHR-II), itself fused to the constant region of human immunoglobulin (CH T125), and the light chain where the leader VK AMHR-II is fused to the variable region of the light chain (VK AMHR-II), itself fused to the constant region of human immunoglobulin (CK T125).

The various regulatory elements (promoters, chimeric introns, polyadenylation sites, etc.) as well as the antibiotic resistance genes and the origins of replication are also shown.

Figure 19:
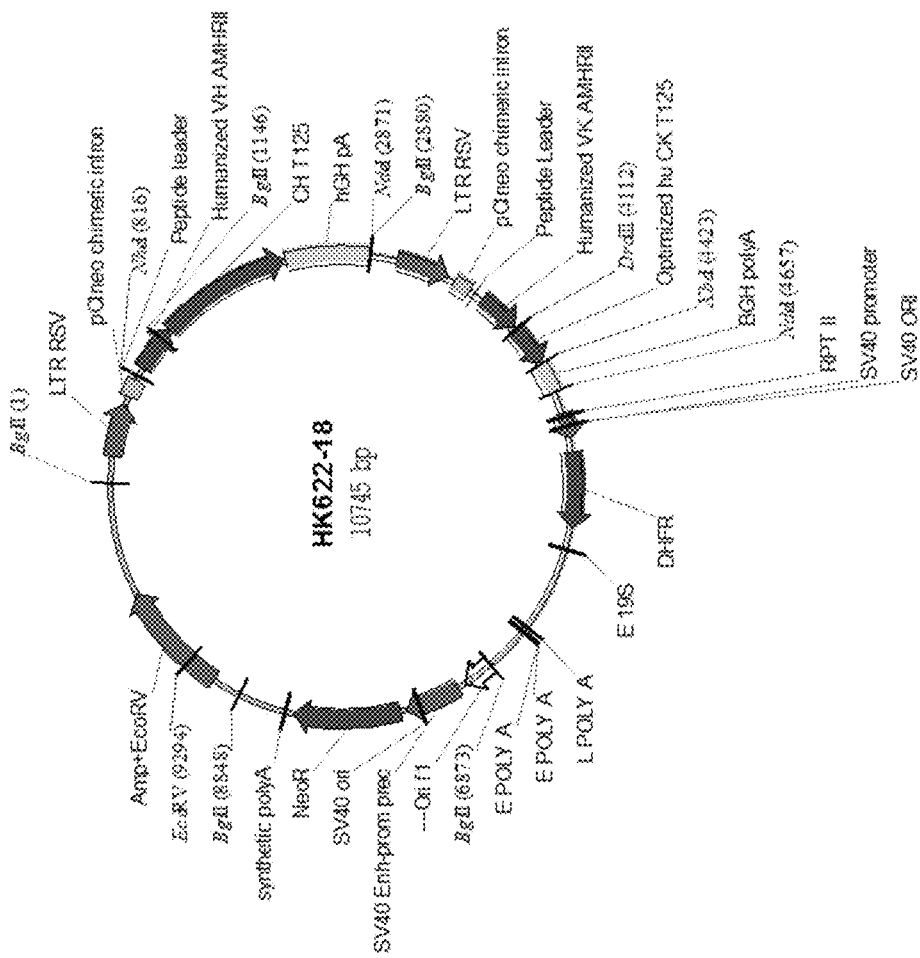

FIG. 19 corresponds to the diagrammatic representation of the H622-18 cloning vector for the unmutated humanized 12G4 antibody containing the heavy chain where the humanized leader VH AMHR-II is fused to the variable region of the heavy chain (humanized VH AMHR-II), itself fused to the constant region of human immunoglobulin (CH T125), and the light chain where the leader VK AMHR-II is fused to the variable region of the light chain (humanized VK AMHR-II), itself fused to the constant region of human immunoglobulin (CK T125).

The various regulatory elements (promoters, chimeric introns, polyadenylation sites, etc.) as well as the antibiotic resistance genes and the origins of replication are also shown.

Figure 20:
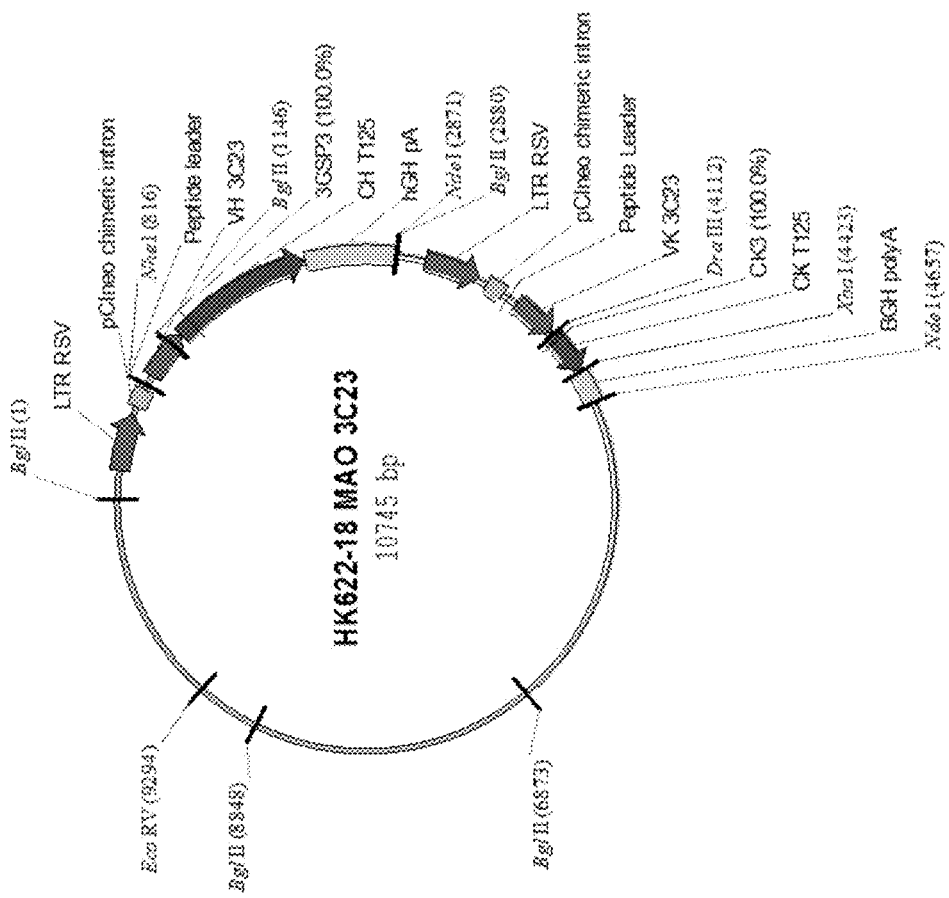

FIG. 20 corresponds to the diagrammatic representation of the H622-18 cloning vector MAO 3C23 for the mutated humanized 12G4 antibody 3C_23 containing the heavy chain where the leader VH 3C_23 is fused to the variable region of the heavy chain (VH 3C_23), itself fused to the constant region of human immunoglobulin (CH T125), and the light chain where the leader VK 3C_23 is fused to the variable region of the light chain (VK 3C_23), itself fused to the constant region of human immunoglobulin (CK T125).

The various regulatory elements (promoters, chimeric introns, polyadenylation sites, etc.) as well as the antibiotic resistance genes and the origins of replication are also shown.

Figure 21:
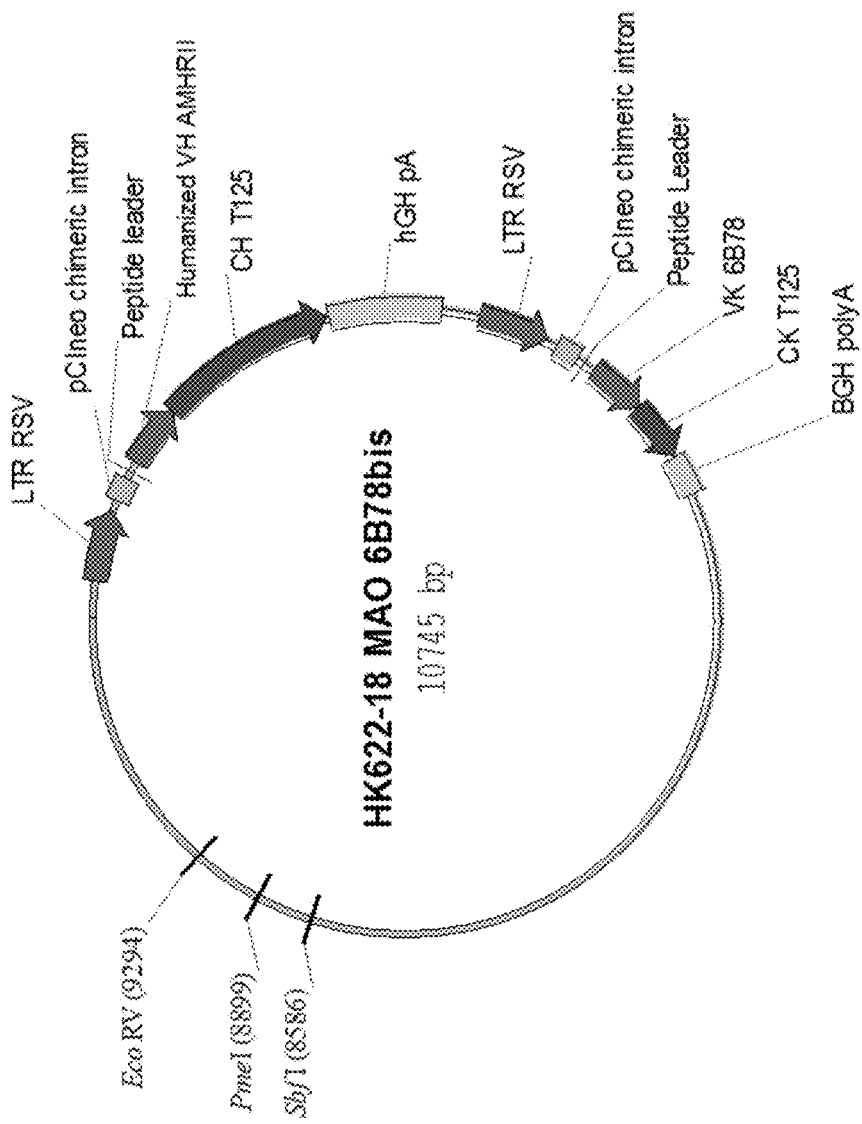

FIG. 21 corresponds to the diagrammatic representation of the H622-18 cloning vector MAO 6B_78 for the mutated humanized 12G4 antibody 6B_78 containing the heavy chain where the humanized leader VH AMHR-II is fused to the variable region of the heavy chain (humanized VH AMHR-II), itself fused to the constant region of human immunoglobulin (CH T125), and the light chain where the leader VK 6B_78 is fused to the variable region of the light chain (VK 6B_78), itself fused to the constant region of human immunoglobulin (CK T125).

The various regulatory elements (promoters, chimeric introns, polyadenylation sites, etc.) as well as the antibiotic resistance genes and the origins of replication are also shown.

Figure 22:
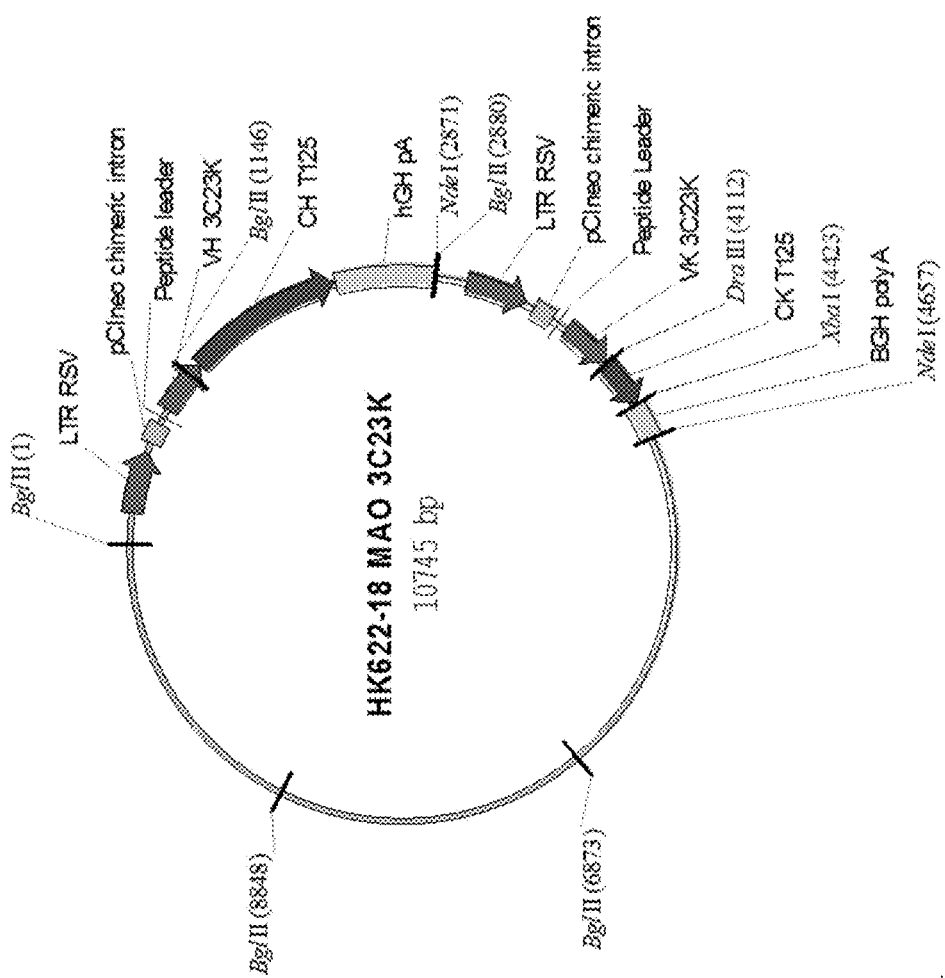

FIG. 22 corresponds to the diagrammatic representation of the H622-18 cloning vector MAO 3C_23K for the mutated humanized 12G4 antibody 3C_23K containing the heavy chain where the leader VH 3C_23K is fused to the variable region of the heavy chain (VH 3C_23K), itself fused to the constant region of human immunoglobulin (CH T125), and the light chain where the leader VK 3C_23K is fused to the variable region of the light chain (VK 3C_23K), itself fused to the constant region of human immunoglobulin (CK T125).

The various regulatory elements (promoters, chimeric introns, polyadenylation sites, etc.) as well as the antibiotic resistance genes and the origins of replication are also shown.

Figure 23:
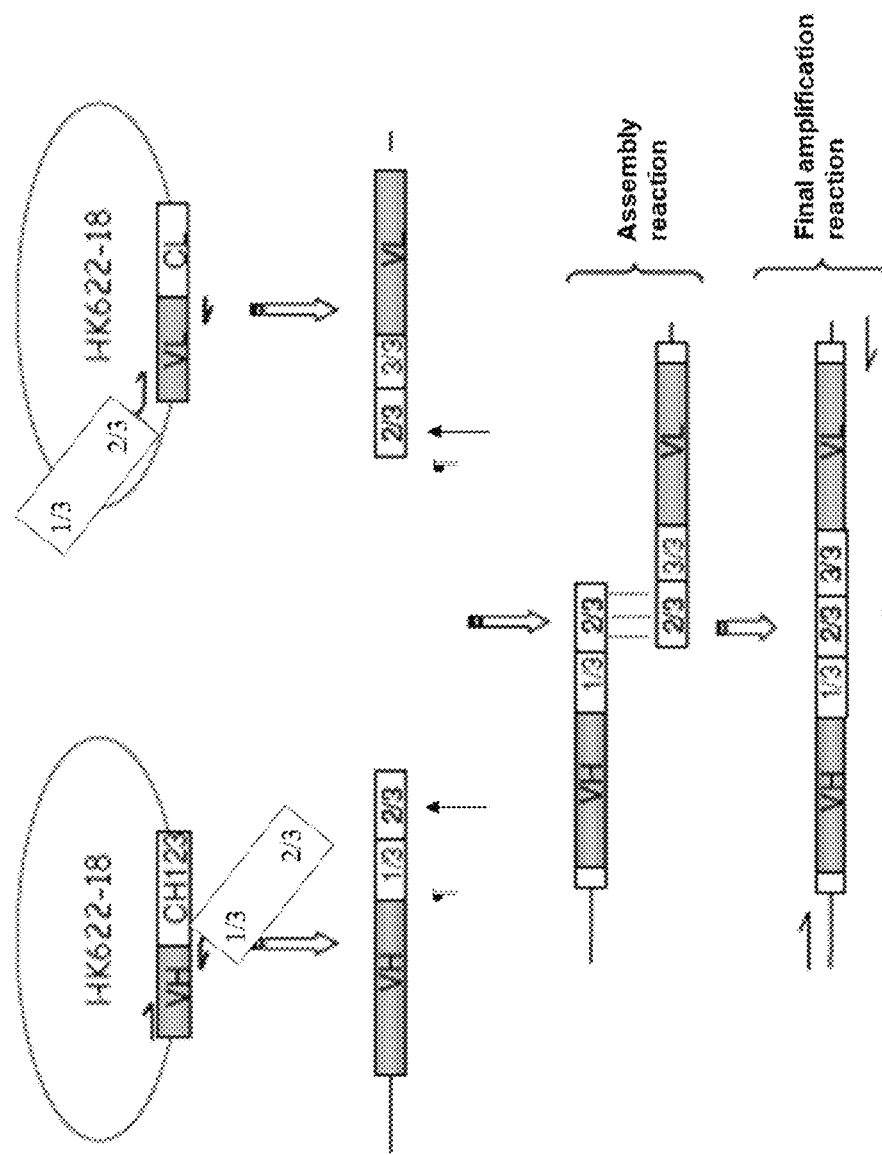

FIG. 23 presents the diagrammatic protocols for construction of the scFv fragments.

The black arrow under region 2/3 of VH indicates the sequence encoding for the N-terminal 2/3 of the peptide bond.

The black arrow under region 2/3 of VL indicates the sequence encoding for the C-terminal 2/3 of the peptide bond.

Figure 24:
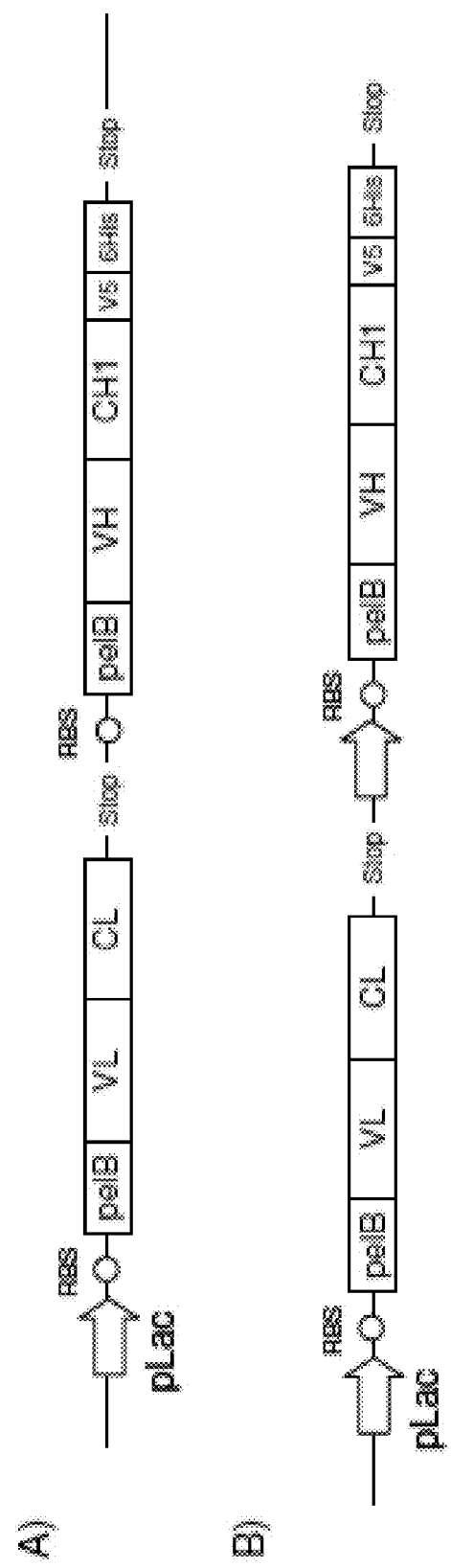

FIGS. 24A and 24B show the subcloning of the nucleotide sequences of the light chains VL-CL and heavy chains VH-CH1 of the mLFB112 and huLFB112 antibodies into the pMG62-Fab expression vectors.

FIG. 24A: mLFB112

FIG. 24B: huLFB112

Figure 25:
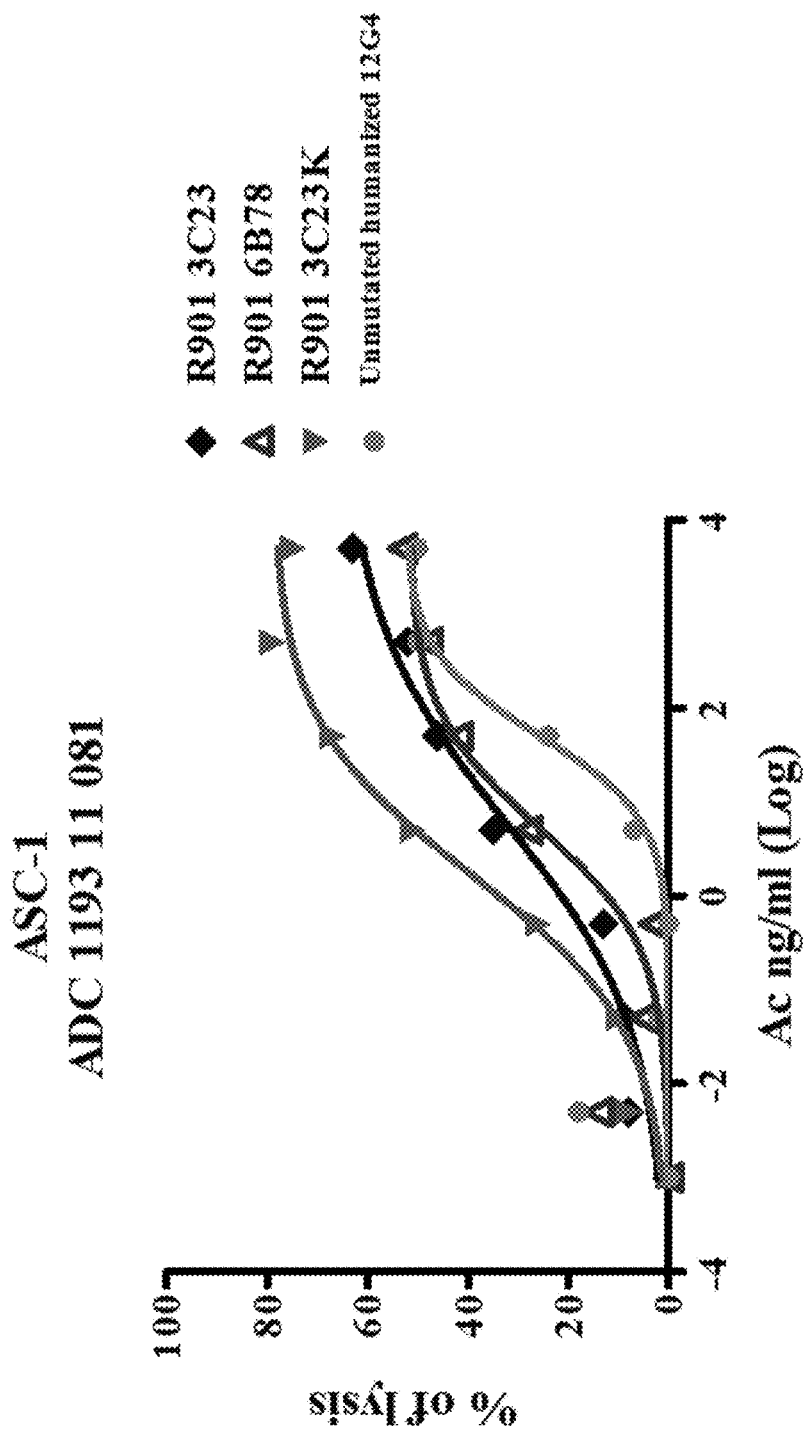

FIG. 25 presents the ADCC activity of the humanized anti-AMHRII antibodies of the invention compared to that of the unmutated humanized 12G4 antibody. The results are expressed as percentage lysis of the ASC1 cell (Y-axis) as a function of the amount of antibody added in ng/ml (X-axis). Mean±SEM.

The curve with diamonds represents the anti-AMHRII antibody 3C_23 (R901 3C_23), the curve with triangles with the point upwards represents the anti-AMHRII antibody 6B_78 (R901 6B_78), the curve with triangles with the point downwards represents the anti-AMHRII antibody 3C_23K (R901 3C_23K), the curve with circles represents the unmutated humanized anti-AMHRII antibody 12G4.

Figure 26:
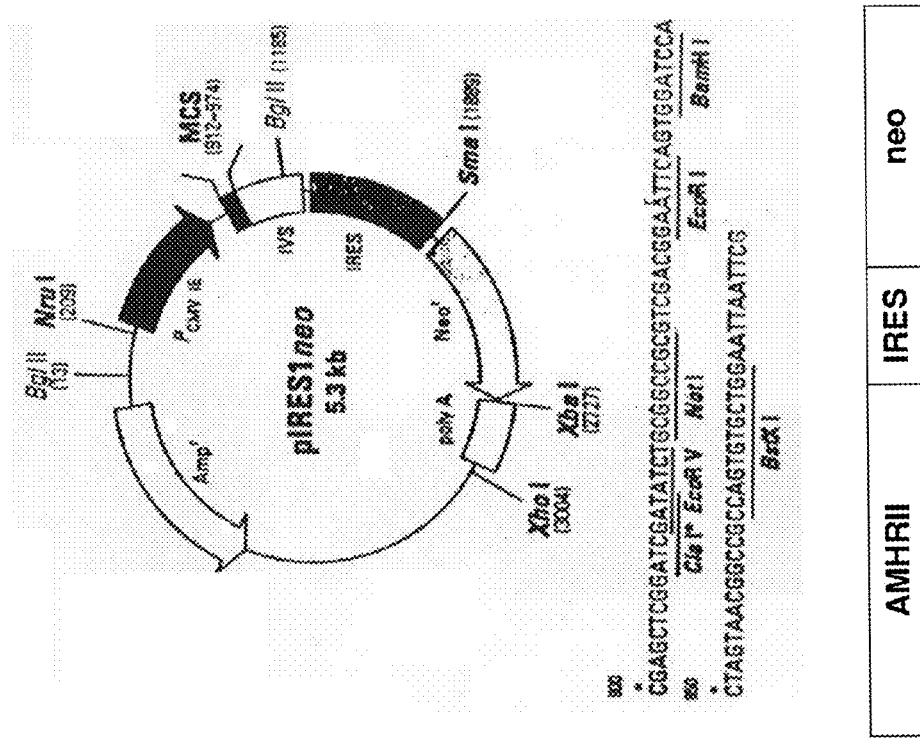

FIG. 26 shows the map of the pIRES-neo plasmid expression vector used for generating the cov434-AMHRII line.

FIGS. 27A and 27B present the ADCC activity of chimeric and humanized anti-AMHRII antibodies produced in the YB2/0 cells (FIG. 27A) and the CHO cells (FIG. 27B) on the COV434-AMHRII line.

The results are expressed as percentage lysis of the COV434-AMHRII cells (Y-axis) as a function of the amount of antibody added in ng/ml (X-axis). Mean of 3 assays±SEM.

FIG. 27A: the curve with diamonds represents the unmutated chimeric 12G4 anti-AMHRII antibody, the curve with filled squares represents the anti-AMHRII antibody YB2/0 3C_23 (R901 3C_23), the curve with triangles with the point downwards represents the anti-AMHRII antibody YB2/0 6B_78 (R901 6B_78), the curve with triangles with the point upwards represents the anti-AMHRII antibody YB2/0 3C_23K (R901 3C_23K) and the curve with empty rectangles represents the anti-CD20 antibody used as negative control.

FIG. 27B: the curve with diamonds represents the unmutated chimeric 12G4 anti-AMHRII antibody, the curve with triangles with the point upwards represents the anti-AMHRII antibody CHO 3C_23 (R901 3C_23), the curve with triangles with the point downwards represents the anti-AMHRII antibody CHO 3C_23K (R901 3C_23K), the curve with circles represents the anti-AMHRII antibody CHO 6B_78 (R901 6B_78) and the curve with empty rectangles represents the anti-CD20 antibody used as negative control.

Figure 28:
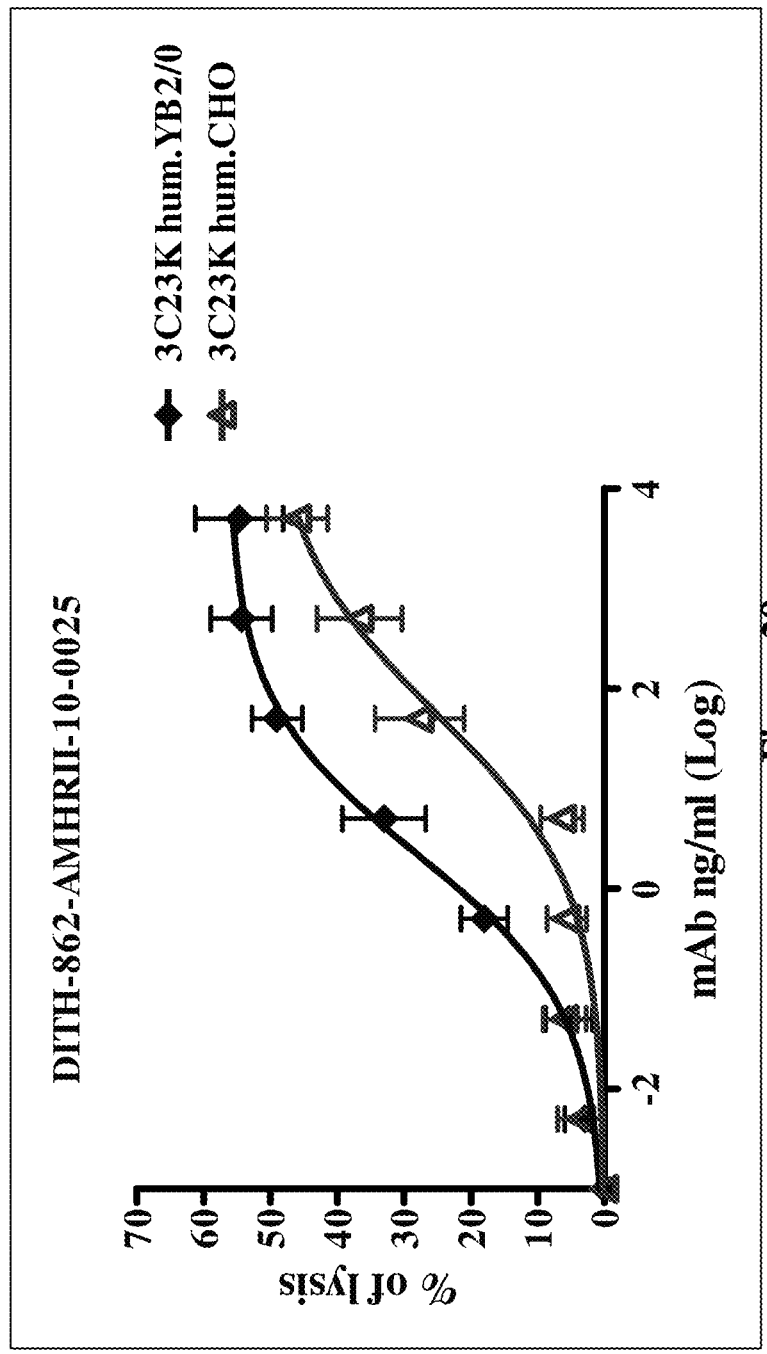

FIG. 28 shows the ADCC activity of the humanized anti-AMHRII antibodies produced in YB2/0 and CHO cells on the Asc 1 line. The results are expressed as percentage lysis of the Asc 1 cells (Y-axis) as a function of the amount of antibody added in ng/ml (X-axis). Mean of 3 tests±SEM.

The curve with diamonds represents the anti-AMHRII antibody YB2/0 3C_23K, the curve with triangles with the point upwards represents the anti-AMHRII antibody CHO 3C_23K.

Figure 29:
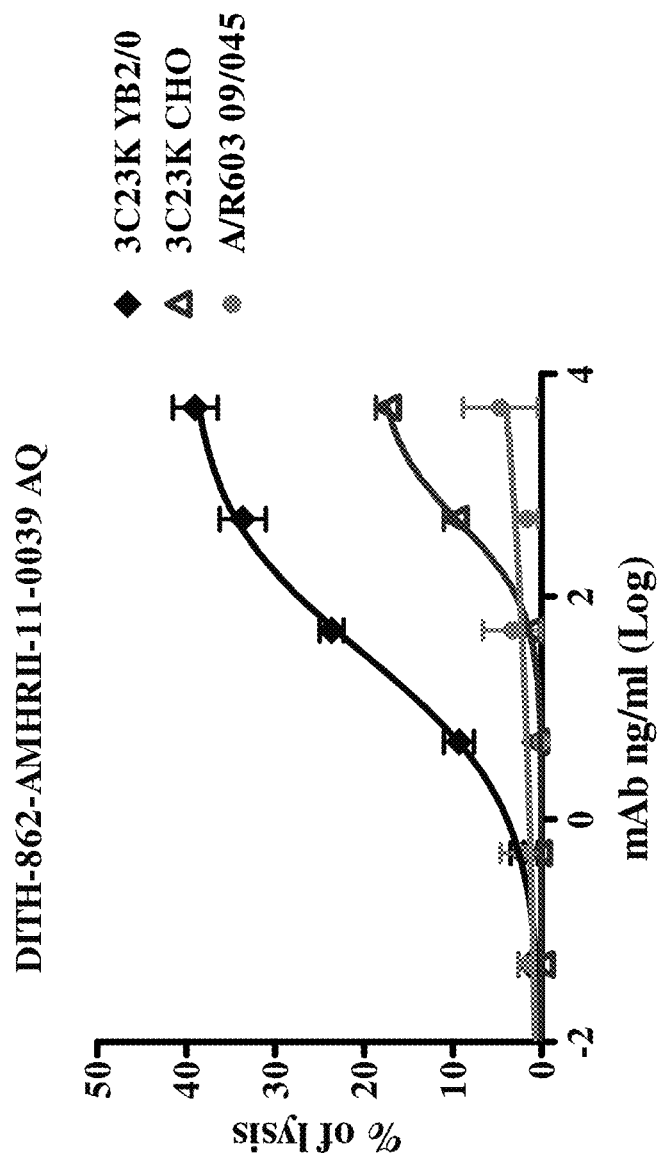

FIG. 29 shows the ADCC activity of the humanized anti-AMHRII antibodies produced in YB2/0 and CHO on the META 2815 line. The results are expressed as percentage lysis of the META 2815 cells (Y-axis) as a function of the amount of antibody added in ng/ml (X-axis). Mean of 3 tests±SEM.

The curve with diamonds represents the anti-AMHRII antibody YB2/0 3C_23K, the curve with triangles with the point upwards represents the anti-AMHRII antibody CHO 3C_23K, the curve with circles represents the anti-CD20 antibody used as negative control (anti-CD20 A/R603 09/045).

Figure 30:
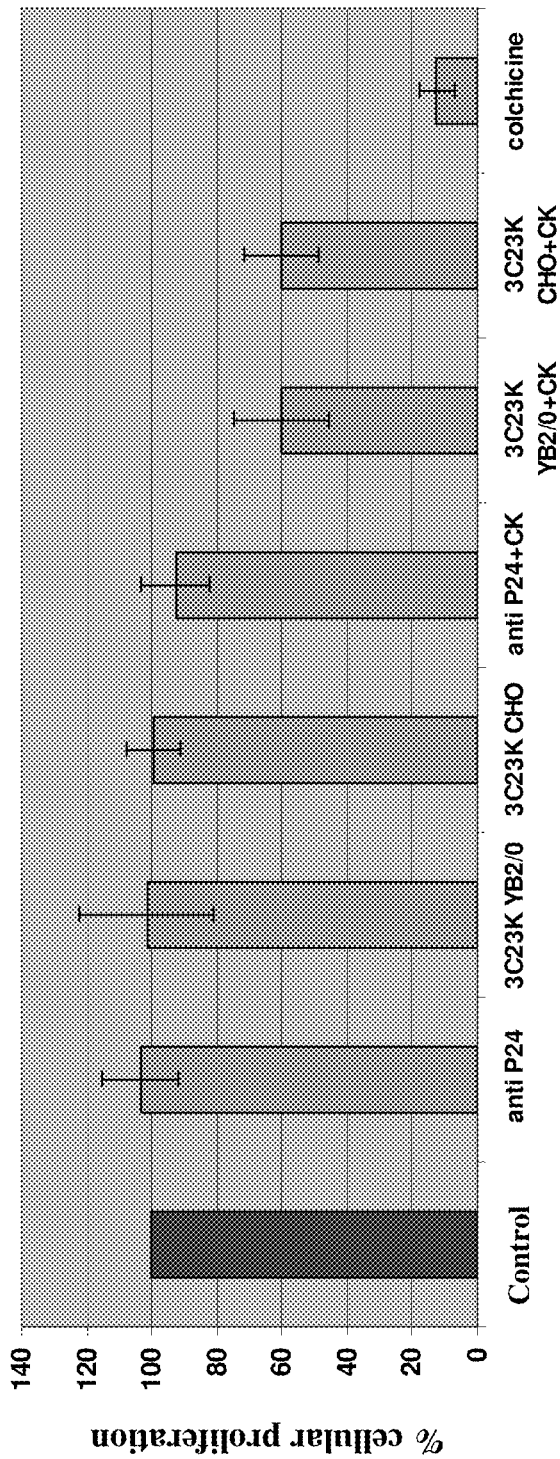

FIG. 30 shows the effect of the anti-AMHRII antibody 3C_23K on proliferation of the COV434-AMHRII cells. The value 100% corresponds to the proliferation of the COV434-AMHRII cells observed without antibody (mean of 3 tests±SD).

From left to right, the histograms show:

The control without antibody, an antiP24 antibody, the anti-AMHRII antibody YB2/0 3C_23K, the anti-AMHRII antibody CHO 3C_23K, an antiP24 antibody in the presence of a cross-linking agent (CK), the anti-AMHRII antibody YB2/0 3C_23K in the presence of CK, the anti-AMHRII antibody CHO 3C_23K in the presence of CK, colchicine at 1 µg/ml.

Figure 31:
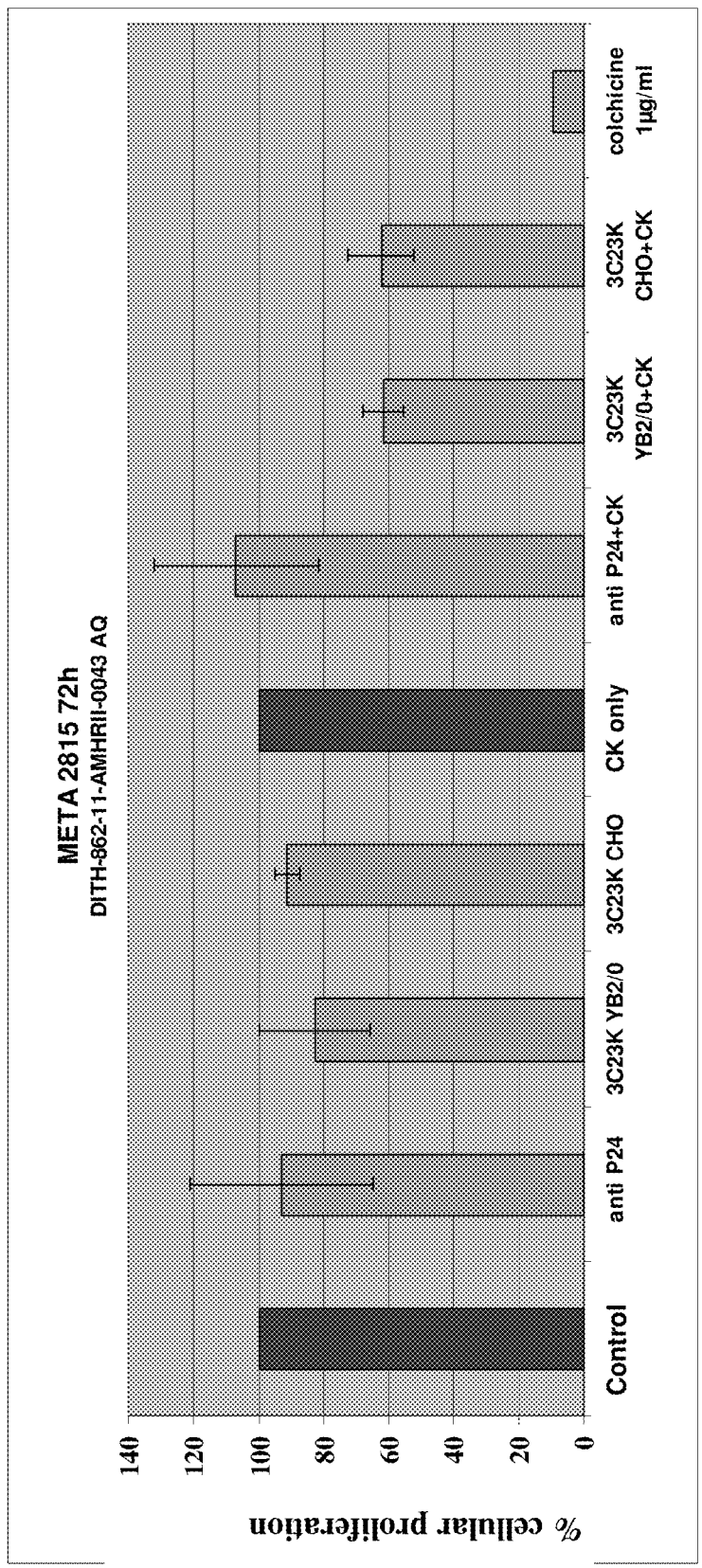

FIG. 31 shows the effect of the anti-AMHRII antibody 3C_23K on the proliferation of META 2815 cells. The value 100% corresponds to the proliferation of the META 2815 cells observed without antibody (mean of 3 tests±SD).

From left to right, the histograms show:

The control without antibody, an antiP24 antibody, the anti-AMHRII antibody YB2/0 3C_23K, the anti-AMHRII antibody CHO 3C_23K, a cross-linking agent alone, an antiP24 antibody in the presence of a cross-linking agent (CK), the anti-AMHRII antibody YB2/0 3C_23K in the presence of CK, the anti-AMHRII antibody CHO 3C_23K in the presence of CK, colchicine at 1 µg/ml.

Figure 32:
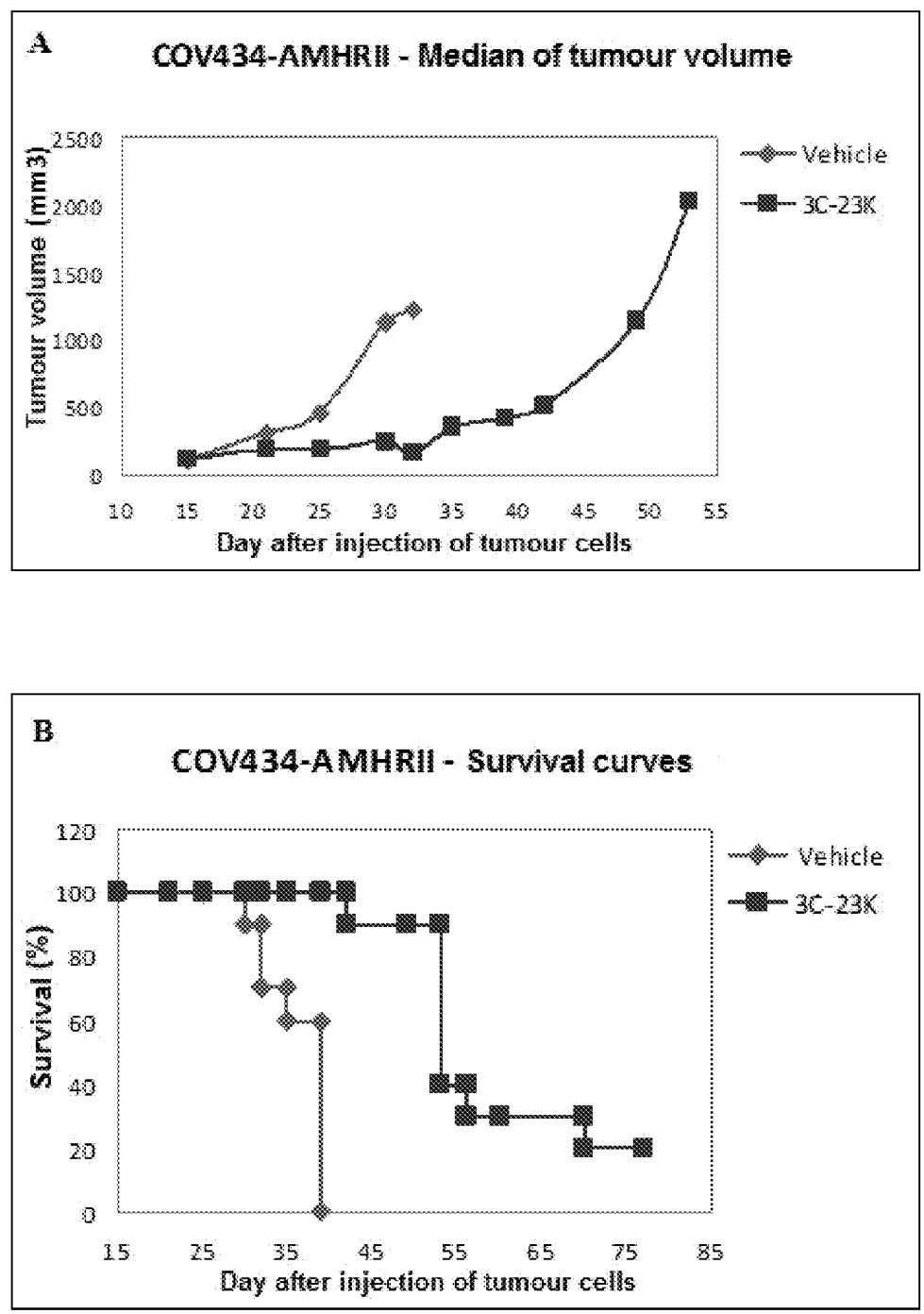

FIGS. 32A and 32B show the variation of tumour volumes (FIG. 32A) and the survival curves (FIG. 32B) under the effect of the treatment with 3C23K-YB2/0 with intraperitoneal injections of antibody performed at intervals of 2-3 days at a dose of 10 mg/kg/inj for a total of 18 injections (black arrows) in the cov434-AMHRII model.

FIG. 32A:
Y-axis: tumour volumes in mm$^3$,
X-axis: days after injection of the tumour cells.
Curve with diamonds: vehicle
Curve with rectangles: anti-AMHRII antibody YB2/0 3C_23K.

FIG. 32B:
Y-axis: percentage survival
X-axis: days after injection of the tumour cells.
Curve with diamonds: vehicle
Curve with rectangles: anti-AMHRII antibody YB2/0 3C_23K.

Figure 33:
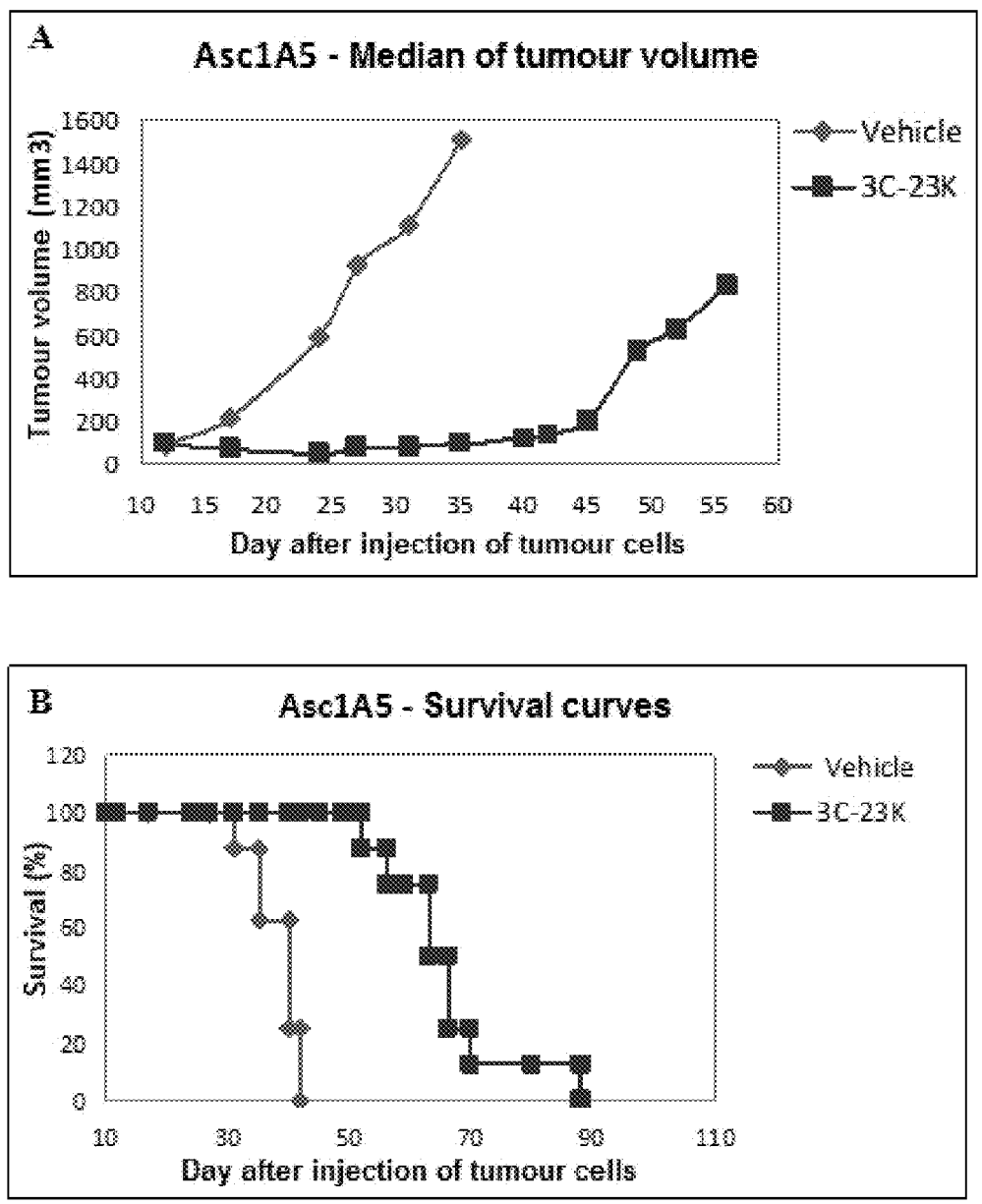

FIGS. 33A and 33B show the variation of the tumour volumes (FIG. 33A) and the survival curves (FIG. 33B) under the effect of the treatment with 3C_23K-YB2/0, intraperitoneal injections of antibody performed at intervals of 2-3 days at a dose of 10 mg/kg/inj for a total of 18 injections (black arrows) in an Asc1a5 model.

FIG. 33A:
Y-axis: tumour volumes in mm$^3$,
X-axis: days after injection of the tumour cells.
Curve with diamonds: vehicle
Curve with rectangles: anti-AMHRII antibody YB2/0 3C_23K.

FIG. 33B:
Y-axis: percentage survival
X-axis: days after injection of the tumour cells.
Curve with diamonds: vehicle
Curve with rectangles: anti-AMHRII antibody YB2/0 3C_23K.

Figure 34:
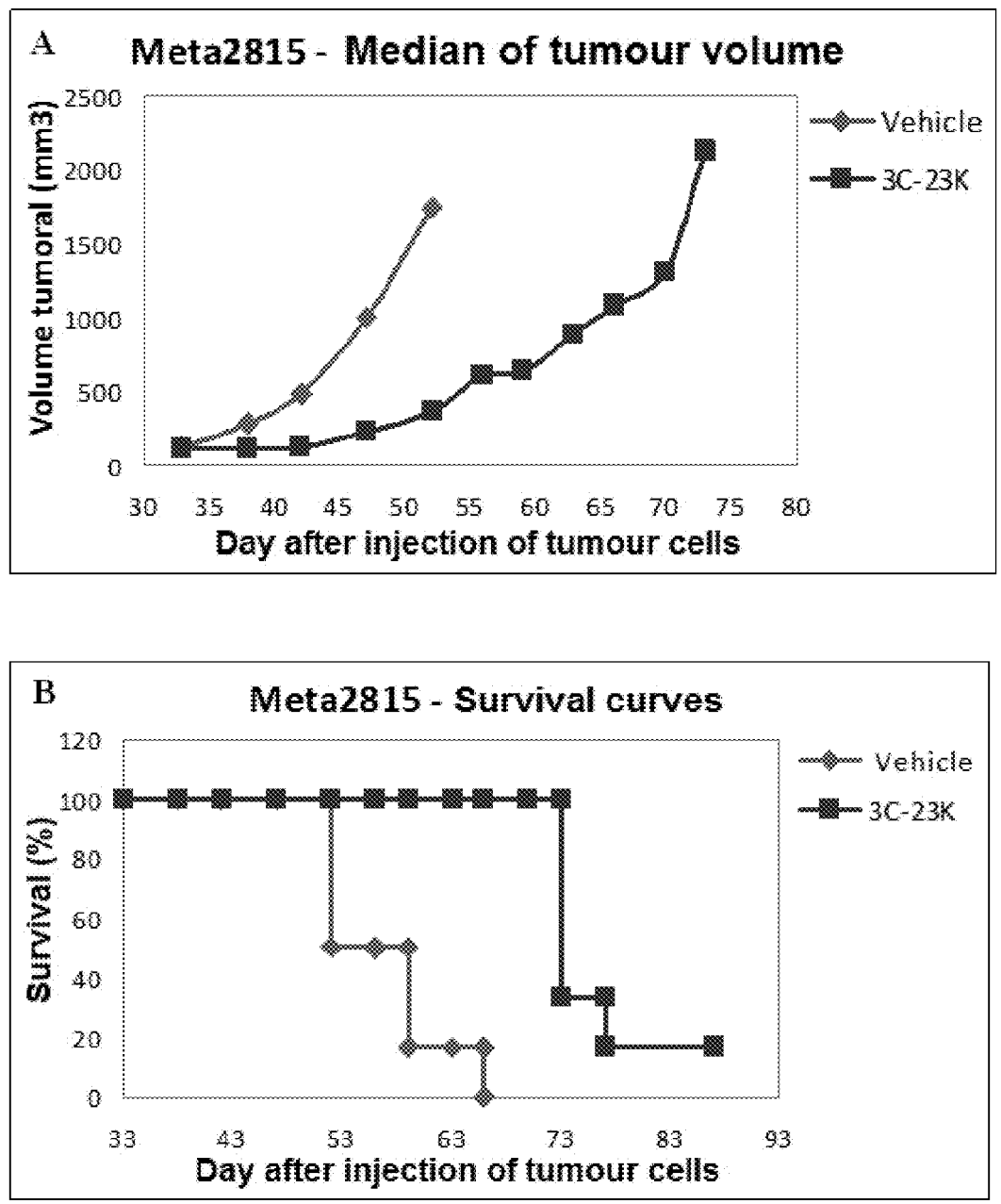

FIGS. 34A and 34B show the variation of the tumour volumes (FIG. 34A) and survival curves (FIG. 34B) under the effect of the treatment with 3C_23K-YB2/0, intraperitoneal injections of antibody performed at intervals of 2-3 days at a dose of 10 mg/kg/inj for a total of 18 injections (black arrows) in the META 2815 model.

FIG. 34A:
Y-axis: tumour volumes in mm$^3$,
X-axis: days after injection of the tumour cells.
Curve with diamonds: vehicle
Curve with rectangles: anti-AMHRII antibody YB2/0 3C_23K.

FIG. 34B:
Y-axis: percentage survival
X-axis: days after injection of the tumour cells.
Curve with diamonds: vehicle
Curve with rectangles: anti-AMHRII antibody YB2/0 3C_23K.

EXAMPLES

Example 1

Determination of the Affinity of the Anti-AMHR-II Antibodies

The affinity of the antibodies for their antigen, AMHR-II, is determined by the SPR (Surface Plasmon Resonance) technique on BIACore X100 (BIACore, GE Healthcare). The AMHR-II recombinant receptor, expressed in the form of fusion protein with a region Fc, is immobilized by covalent coupling between its amine functions and the carboxyl groups of dextran activated in succinimide esters, present on the surface of the type CM5 sensor chip. The COOH groups of the sensor chip are activated for 7 minutes with EDC/NHS mixture (0.1 M of N-hydroxysuccinimide and 0.1 M of 3-(N, N-dimethylamino)propyl-N-ethylcarbodiimide) at a flow of 10 µl/min then the AMHR-II/Fc fusion protein, diluted to 5 µg/ml in 10 mM sodium acetate buffer, pH 4.0, is injected at 5 µl/min on track 2 of the sensor chip so as to reach 300 RU. The ester groups that have not reacted with the amines of the fusion protein are deactivated by injection of a solution of ethanolamine-HCl 1M, pH 8.5 for 7 min at a flow of 10 µl:min. Track 1, serving as negative control, was activated and deactivated like track 2.

All the measurements are carried out at 25° C. The antibodies to be analysed are diluted in HBS-EP running buffer (BIACore, GE Healthcare) at concentrations from 6.25 to 3333 nM and injected on the sensor chip for 2 min at a flow of 30 µl/min. The dissociation step is monitored for 10 min and then the surface is regenerated by injection of 10 mM glycine buffer, pH 1.5 for 30 s at 10 µl/min.

The sensorgrams obtained are analysed using the 1:2 kinetic model of the BIAevaluation 3.1 software.

Results

The antibodies were produced in CHO or YB 2/0 cells (Table I)

TABLE I

| Antibody | Mutations | $k_a$ (M$^{-1}$s$^{-1}$) | $k_d$ (s$^{-1}$) | $K_D$ (nM) | $K_D^{chimeric}/K_D^{mutated}$ |
|---|---|---|---|---|---|
| 12G4-Chimeric | NA | $3.5 \times 10^3$ | $7.4 \times 10^{-4}$ | 212 | — |
| 6B_78 YB2/0 | VL-E184K | $1.6 \times 10^4$ | $1.3 \times 10^{-3}$ | 82 | 2.6 |
| 3C_23 YB2/0 | VH-Q3R VL-I177T/ S179P | $3.6 \times 10^4$ | $3.3 \times 10^{-3}$ | 92 | 2.3 |
| 3C_23K YB2/0 | VH-Q3R VL-I177T/ S179P/ E184K | $4 \times 10^4$ | $8.6 \times 10^{-4}$ | 21 | 10 |
| 6B_78 CHO | VL-E184K | $1.5 \times 10^4$ | $1.2 \times 10^{-3}$ | 81 | 2.6 |
| 3C_23 CHO | VH-Q3R VL-I177T/ S179P | $5 \times 10^4$ | $4.3 \times 10^{-3}$ | 86 | 2.5 |
| 3C_23K CHO | VH-Q3R VL-I177T/ S179P/ E184K | $4.1 \times 10^4$ | $1 \times 10^{-3}$ | 25 | 8.5 |

The mutations introduced in the 6B_78 and 3C_23 antibodies induce an increase in affinity for the AMHR-II antigen by a factor of 2.3 to 2.6 relative to the chimeric antibody (12G4—chimeric).

The mutations of the two antibodies 6B_78 and 3C_23 have a synergistic effect; introduction of the mutation of the 6B_78 antibody into the 3C_23 antibody causes an increase in affinity by a factor of 10.

Example 2

Determination of the Affinity of Chimeric or Humanized Murine 12G4 Antibody on cov434-AMHR-II Cells (Epitope Peptide of Sequence: GGGGNLTQDRAQVEMQGSR (SEQ ID NO: 101) and GGGGNLTQARGQVEMQGSR (SEQ ID NO: 102) for the Negative Control Peptide)

| | Association constant | Dissociation constant | Affinity constant at equilibrium |
|---|---|---|---|
| humanized 12G4 | $1.83 \times 10^3$ M$^{-1} \cdot$s$^{-1}$ | $9.62 \times 10^{-3}$ s$^{-1}$ | $5.26 \times 10^{-6}$ M |
| chimeric 12G4 | $6.49 \times 10^3$ M$^{-1} \cdot$s$^{-1}$ | $1.53 \times 10^{-3}$ s$^{-1}$ | $2.35 \times 10^{-7}$ M |
| murine 12G4 | | $1.47 \times 10^{-3}$ s$^{-1}$ | of the order of $10^{-7}$ M |

The affinity of the chimeric antibody determined on the AMHR-II human receptor is about $10^{-8}$ M.

Example 3

Preparation of Mutated Humanized 12G4 Antibodies

The murine antibody is substantially equivalent to the chimeric antibody and displays strong affinity.

The humanized 12G4 antibody (huLFB112) was obtained by grafting hypervariable CDR loops of the murine 12G4 antibody (mLFB112) on a protein framework of a human nature ("CDR grafting").

The humanized antibody has an appreciable loss of affinity compared with the murine antibody.

The final objective is therefore to increase the affinity of the humanized antibody so as to restore the initial binding characteristics of the murine antibody. This optimization will be performed by means of a cycle of molecular evolution by the MutaGen technology owned by the Millegen company.

3.1 Construction and Validation of the Molecular Tools 3.1.1. Construction of the scFv Fragments The nucleotide sequences coding for the variable regions of the light chains (VL) and of the heavy chains (VH) of the murine and humanized antibodies were amplified by PCR using suitable primers. The amplified sequences were then combined together so as to generate a recombinant antibody fragment of the scFv type. Several constructions were performed in this way: VH-VL or VL-VH orientation and use of two different peptide bonds (peptide bond of 15 or of 18 amino acids). A total of 8 constructions were performed, 4 for the murine antibody and 4 for the humanized antibody. The principle for construction of the scFv fragments is illustrated below (scheme I). The sequences coding for these scFv were then subcloned into the MilleGen phagemid expression vector (pMG58). This vector makes it possible to express antibody fragments of the scFv type and display them on the surface of a type M13 bacteriophage (phage-scFv).

The nucleotide sequences of the VH and VL domains of the murine and humanized antibodies were verified by DNA sequencing.

The protocol is summarized in FIG. 23.

3.1.2. Expression of the scFv on the Surface of the Phages and Characterization by ELISA The amount of target supplied (80 µg) did not allow us to test all 8 constructions made. The murine antibody mLFB112 expressed in the form of a scFv is called mVH-VL hereinafter whereas the humanized antibody huLFB112 is called huVH-VL.

3.1.2.1. Production of the Phages-scFv

The XL1-Blue bacteria transformed by the pMG58 vectors containing the DNA coding for the scFv mVH-VL on the one hand and the scFv huVH-VL on the other hand are cultured at 30° C. to an OD600 nm of 0.5-0.6. After adding IPTG and infecting the bacteria with auxiliary phages (M13KO7, New England Biolabs), the cultures are cultured at 26° C. overnight. The next day, the phage particles (phages-scFv) are recovered from the culture supernatant, precipitated by means of a PEG/NaCl solution, concentrated (100×) and quantified.

In this case, a concentration of the order of $8 \times 10^{11}$ phages/ml is obtained for the two scFv.

3.1.2.2. ELISA-Phages Assay

The functionality of the scFv mVH-VL and huVH-VL produced on the surface of the phages was verified by direct ELISA assays.

Protocol:
1) Immobilization of the target: 100 µl/well of the recombinant target diluted to 5 µg/ml in PBS1X i.e. 500 ng/well, overnight at 4°. Use of Nunc-Immuno Plate Maxisorp microtitre plates,
2) Saturation: 200 µl/well of PBS1X-Skimmed milk 4%, incubation 2 h at 37° C.,
3) Binding: 100 µl/well of the solutions of murine and humanized phages-scFv diluted in PBS1X-Milk 2%-Tween20 0.05% (twofold dilution series), incubation 2 h at 37° C.,
4) Detection: 100 µl/well of the anti-phages M13 antibody coupled to peroxidase (dilution 1/10000, GE Healthcare), incubation 2 h at 37° C.
5) Detection: 100 µl/well of TMB
6) Neutralization: 100 µl/well of $H_2SO_4$
7) Measurement of OD at 450 nm Results (Table II):

3.1.3: Construction of the Fab Fragments

The nucleotide sequences of the light chains VL-CL and heavy chains VH-CH1 of the antibodies mLFB112 and huLFB112 were subcloned into the pMG62-Fab expression vectors (FIGS. 24A and 24B).

pMG62-Fab Expression Vectors

A) The two chains VL-CL and VH-CH1 are expressed starting from the pLac promoter upstream of the light chain, the heavy chain VH-CH1 is fused to a tag for detection (peptide V5) and a tag for purification with IMAC (6×His).

B) Each of the light and heavy chains is dependent on a promoter. RBS: Ribosome Binding Site.

3.2 Construction and Validation of the Molecular Tools

Construction of the Library by MutaGen™

The objective defined for this step was to obtain a database of $5 \times 10^6$ variants with 1 to 2 amino acid mutations per scFv.

Mutations were introduced within the domains VL and VH of the humanized antibody huLFB112 by means of MutaGen™ technology. Finally, a large database composed of about $5 \times 10^7$ mutated clones with 1 to 5 mutations of amino acids per scFv, i.e. 10 times the diversity initially envisaged was obtained.

For this, several sub-databases were constructed according to different experimental conditions: conditions U, M, US and UE defined by different nucleotide primers, mutase enzymes used and number of replications. These sub-databases are 4 in number and are designated R20U, 45M, R20US and R20UE. For all of these sub-databases, a total of 295 sequences was carried out for accurately defining the different characteristics of mutagenesis. Table III below gives an idea of the principal data obtained from analysis of the sequencing operations.

TABLE III

Analysis of the mutations of the different sub-databases

| | Name of database | | | | |
|---|---|---|---|---|---|
| | R20U | 45M | R20US | R20UEta | TOTAL |
| Size of database | 2.0E+07 | 6.0E+06 | 9.9E+07 | 5.0E+05 | 1.3E+08 |
| Condition | U | M | US | UE | |
| Number of sequences | 87 | 67 | 85 | 56 | 295 |

TABLE II

| Number of phages per well | mVH-VL | | | huVH-VL | | | Ratio |
| | +covering | Without covering | Diff | +covering | Without covering | Diff | mVH-VL/huVH-VL |
|---|---|---|---|---|---|---|---|
| 3.00E+10 | 2.805 | 0.158 | 2.647 | 1.247 | 0.150 | 1.097 | 2.4 |
| 3.00E+10 | 2.193 | 0.085 | 2.107 | 0.689 | 0.096 | 0.593 | 3.6 |
| 3.00E+09 | 1.570 | 0.064 | 1.506 | 0.395 | 0.072 | 0.323 | 4.7 |
| 3.00E+09 | 0.946 | 0.059 | 0.887 | 0.226 | 0.056 | 0.170 | 5.2 |
| 3.00E+09 | 0.495 | 0.049 | 0.446 | 0.135 | 0.049 | 0.086 | 5.2 |

Diff: specific binding (difference between the wells with covering and without covering
The ratio mVH-VL/huVH-VL was calculated with the value of specific binding ("Diff")

TABLE III-continued

Analysis of the mutations of the different sub-databases

| | Name of database | | | | |
|---|---|---|---|---|---|
| | R20U | 45M | R20US | R20UEta | TOTAL |
| Analysis of the nucleotide sequences | | | | | |
| Frequency of mutations per kb | 2.76 | 3.66 | 3.31 | 4.9 | |
| % of deletions | 10% | 20% | 6% | 5% | |
| % of additions | 2% | — | 0.8% | — | |
| % of substitutions | 72% | 80% | 93% | 95% | |
| Frequency of mutations per kb (without deletions) | 2.0 | 2.45 | 3.10 | 3.68 | |
| Analysis of the amino acid sequences | | | | | |
| % of sequences (by weight) (+ silent mutation) | 63% | 46% | 44% | 41% | |
| % of sequences with reading frame shift (+ stop codon) | 13% | 28% | 13% | 27% | |
| % of sequences with mutated amino acids | 24% | 25% | 43% | 32% | |
| Number of scFv clones with mutated amino acids | 4.8E+06 | 1.5E+06 | 4.3E+07 | 1.6E+05 | 4.9E+07 |
| Number of mutations of amino acids per scFv | 1.3 | 1.2 | 1.8 | 2.11 | |
| scFv clones with 1 mutated amino acid | 65% | 49% | 50% | 33% | 2.5E+07 |
| scFv clones with 2 mutated amino acids | 25% | 34% | 33% | 39% | 1.6E+07 |
| scFv clones with 3 mutated amino acids | 10% | 13% | 8% | 6% | 4.2E+06 |
| scFv clones with 4 mutated amino acids | — | 4% | 6% | 22% | 2.5E+06 |
| scFv clones with 5 mutated amino acids | — | — | 3% | — | 1.2E+06 |

3.2. Elaboration of the Selection Conditions

In order to evaluate different selection strategies, an artificial mixture was prepared between the murine and humanized phages-scFv (1/200 mixture, mLFB112/huLFB112), the objective being to simulate screening of the database. This simulation of screening must make it possible to validate different selection conditions which have the aim of rapidly amplifying the most affine clone within this artificial mixture (i.e. the murine clone mLFB112 in this case).

The various strategies evaluated:

i) Use of a constant amount of immobilized target in the course of the selection cycles (Cond 1)

ii) Decrease of the amount of immobilized target in the course of the selection cycles (Cond 2)

ii) Test for a "$k_{off}$" condition: long incubation time of the phages-scFv with the target (Cond 3)

These various conditions were performed in 3 selection cycles. Sequencing was performed on the clones retained after each selection cycle. The results are shown in Table IV below.

TABLE IV

Evaluation of the three screening strategies

| | Bp1 | Bp2 | Bp3 |
|---|---|---|---|
| Conditions 1 | | | |
| Covering | 500 ng | 500 ng | 500 ng |
| Number of scFv phages used for the selection cycle | 1.6E+11 | 1.2E+11 | 2.0E+11 |
| Number of scFv phages recovered at the end of the selection cycle | 3.3E+5 | 2.4E+5 | 2.7E+6 |
| % of mLFB112/huLFB112 | 0/100 | 1/99 | 90/10 |
| Conditions 2 | | | |
| Covering | 500 ng | 100 ng | 100 ng |
| Number of scFv phages used for the selection cycle | 1.6E+11 | 1.2E+11 | 1.8E+11 |
| Number of scFv phages recovered at the end of the selection cycle | 3.3E+5 | 2.4E+5 | 2.7E+6 |
| % of mLFB112/huLFB112 | 0/100 | 1/99 | 30/70 |
| Conditions 3 | | | |
| Covering | 500 ng | 100 ng $k_{off}$ | 100 ng $k_{off}$ |
| Number of scFv phages used for the selection cycle | 1.6E+11 | 1.8E+11 | 1.6E+11 |
| Number of scFv phages recovered at the end of the selection cycle | 3.3E+5 | 6.7E+5 | 2.0E+6 |
| % of mLFB112/huLFB112 | 0/100 | 1/99 | 30/70 |

It appears from these results that condition 1 (fixed amount of target) gives best performance for amplifying the clone with better affinity, mLFB112 (9 clones out of 10). Using a smaller amount of target (100 ng/well) seems less suitable; only 3 clones out of 10 after 3 selection cycles correspond to the clone with better affinity. The same applies to condition 3 based on a long incubation time ("$k_{off}$ selection") which does not allow sufficient amplification of clone mLFB112. Moreover, the number of phages recovered for this last-mentioned condition after 3 cycles is not high ($2 \times 10^4$ phages). It therefore seemed to us to be inadvisable to use conditions 2 and 3 for a more diversified mixture of clones, as is the case for the database constructed in the context of this project.

3.3. Primary Screening (Selection Cycles)

After elaborating the screening conditions, it was therefore decided to use 2 screening conditions:

Cond A: 1 µg/well of target for 4 selection cycles then 2 cycles with 0.5 µg/well Cond B: 0.5 µg/well for 6 selection cycles.

The results obtained are presented in Table V below.

TABLE V

Results of the selection cycles

| | Selection cycle 1 | Selection cycle 2 | Selection cycle 3 | Selection cycle 4 | Selection cycle 5 | Selection cycle 6 |
|---|---|---|---|---|---|---|
| Conditions A | | | | | | |
| Covering | 1 µg | 1 µg | 1 µg | 1 µg | 0.5 µg | 0.5 µg |
| Number of scFv phages used for the selection cycle | 4.8E+11 | 8.0E+11 | 2.8E+11 | 8.0E+11 | 4.5E+11 | 6.0E+11 |
| Number of scFv phages recovered at the end of the selection cycle | 2.0E+5 | 1.3E+5 | 2.4E+5 | 7.5E+5 | 7.3E+5 | 1.4E+5 |
| Conditions B | | | | | | |
| Covering | 0.5 µg | 0.5 µg | 0.5 µg | 0.5 µg | 0.5 µg | 0.5 µg |
| Number of scFv phages used for the selection cycle | 4.8E+11 | 8.0E+11 | 3.2E+11 | 6.4E+11 | 7.5E+10 | 4.2E+11 |
| Number of scFv phages recovered at the end of the selection cycle | 2.0E+5 | 8.6E+5 | 5.4E+5 | 1.3E+5 | 2.6E+5 | 6.5E+5 |

After these selections, the clones obtained were sequenced starting from the 3rd selection cycle. The results obtained were compared with those obtained for the starting database (Table VI).

TABLE VI

Results of the sequencing operations

| | Database | Selection cycle 3 | Selection cycle 4 | Selection cycle 5 | Selection cycle 6 |
|---|---|---|---|---|---|
| Number of sequences | 295 | 87 | 168 | 114 | 98 |
| % of sequences with mutated amino acids | 39% | 26% | 26% | 35% | 20% |
| % of sequences with reading frame shift | 14% | 13% | 27% | 32% | 49% |
| % of sequences (by weight) (+ silent mutation) | 47% | 61% | 48% | 34% | 32% |

Database: initial database resulting from mixing the 4 databases R20U, 45M, R20US, R20Ueta.
Analysis of these sequencing operations revealed the presence of redundant clones. In total, from all of the clones sequenced, 113 unique mutated clones were obtained.

3.4. Secondary Screening (ELISA-Phages)

The secondary screening consists of analysing the clones selected at the end of the primary screening individually. For this, the 113 unique mutated clones were transferred to a culture plate (96 well-1.2 ml).

After production of the phage particles, the culture supernatants containing the phages-scFv were used for carrying out an ELISA binding assay. The binding of the mutated clones was evaluated at two dilutions (½ and ¼ of the supernatants containing the scFv-phages). The murine clones (mLFB112) and humanized clones (huLFB112) constructed under the scFv-phages format were used as references on each of the assay plates. Each of the mutated clones was tested at least twice.

The results are expressed as a ratio, i.e. the differences in binding (OD405 nm) between the mutated clones and the references huLFB112 and mLFB112.

Ratio relative to the humanized scFv, huLFB112 (Ratio/huLFB112)

Ratio relative to the murine scFv, mLFB112 (Ratio/mLFB112)

Out of the 113 clones tested, only the best clones are presented below.

Table VII below presents the various clones obtained and the mutations present (position and substitution of amino acids) in the light and/or heavy chain, as well as the binding affinity of clones determined by ELISA.

The values shown after the substitutions correspond to the changes in the values of the hydropathic index as a function of the various substitutions.

The values of binding affinity correspond to the ratio of the binding affinity of the antibody of the invention for the AMHRR-II receptor to the binding affinity of the unmutated humanized 12G4 antibody or the binding affinity of the unmutated chimeric 12G4 antibody.

The values of binding affinity given are the mean values of at least four values and the figures in parentheses correspond to the standard deviation.

Table VII shows that with the substitutions that were carried out, although the latter lead to a large change in the hydropathic index, the binding affinity of the antibody for the receptor is much greater than that of the unmutated humanized 12G4 antibody and at least equal to that of the unmutated chimeric 12G4 antibody: ratio AB invention/chimeric 12G4 greater than or equal to 1.

The mutated humanized antibody displays an affinity that is restored or even greater than that of the chimeric or murine antibody.

TABLE VII

| clone | Numbering VH 1-115 | Numbering VL 131-236 | FIXATION TO THE TARGET AMHRII-Fc DETERMINED BY ELISA | |
|---|---|---|---|---|
| | | | Ratio AB invention/humanized 12G4 | Ratio AB invention/chimeric 12G4 |
| 4C_35 | L45P +3.8__−1.6 | E184K −3.5__−3.9 | 4.3 (0.5) | 1.9 0.4) |
| 5B_81 | L45P +3.8__−1.6 | — | 3.5 (0.9) | 1.6 (0.3) |
| 6B_78 | — | E184K −3.5__−3.9 | NT | NT |
| 3C_23 | Q3R −3.5__−4.5 | I177T +4.5__−0.7<br>S179P −0.8__−1.6 | 2.6 (1.1) | 1.2 (0.3) |
| 3C_23K | Q3R −3.5__−4.5 | I177T +4.5__−0.7<br>S179P −0.8__−1.6<br>E184K −3.5__−3.9 | NT | NT |
| 5B_42 | T74A −0.7_1.8 | S179P −0.8__−1.6 | NT | NT |
| 4F_196 | Q3E −3.5__−3.5<br>Q62R −3.5__−4.5<br>E89D −3.5__−3.5 | — | 3.0 (1.0) | 1.5 (0.3) |
| 6B_87 | Q1E −3.5__−3.5<br>A24V +1.8__+4.2 | — | 2.1 (0.2) | 1.0 (0.1) |
| 4F_169 | Q6E −3.5__−3.5<br>T58A −0.7__+1.8 | — | 2.0 (0.7) | 1.0 (0.2) |
| 3D_74 | — | S158P −0.8__−1.6 | 2 (0.7) | 0.8 (0.2) |
| 4C_44 | R87G −3.9__−0.4 | — | NT | NT |
| 5A_66 | V67M +4.2__+1.9 | F212S +2.8__−0.8 | 2.2 (0.4) | 1.1 (0.1) |
| 6B_14 | S31G −0.8__−0.4<br>Q39E −3.5__−3.5 | — | 2.6 0.3) | 1.1 (0.2) |
| 4C_47 | Q3E −3.5__−3.5<br>S88P −0.8__−1.6 | — | NT | NT |
| 4E_153 | D56N −3.5__−3.5<br>I70N +4.5__−3.5<br>F102S +2.8__−0.8 | — | 2.0 (0.4) | 1.0 (0.1) |
| 3C_24 | — | E184G −3.5__−0.4 | NT | NT |
| 5B_18 | Q3E −3.5__−3.5<br>A9T +1.8__−0.7<br>A103T +1.8__−0.7 | — | 1.8 (0.2) | 0.9 (0.2) |
| 5B_84 | Q1E −3.5__−3.5<br>A24G +1.8__−0.4 | — | NT | NT |
| 6B_86 | Q3E −3.5__−3.5 | G179D −0.4__−3.5 | NT | NT |
| 4D_91 | Q1E −3.5__−3.5<br>V11A +4.2__+1.8 | — | 1.7 (0.1) | 0.8 (0.2) |
| 6B_76 | A40V +1.8__+4.2 | S179P −0.8__−1.6 | 1.7 (0.1) | 0.8 (0.2) |
| 5A_28 | — | Y178H −1.3__−3.2<br>S179P −0.8__−1.6 | 1.6 (0.6) | 0.8 (0.2) |
| 3D_57 | A76T +1.8__−0.7<br>A79T +1.8__−0.7 | — | NT | NT |
| 6A_80 | A24V +1.8__+4.2<br>Q62E −3.5__−3.5 | — | 1.5 (0.2) | 1.3 (0.1) |
| 5B_67 | K12R −3.9__−4.5 | — | NT | NT |
| 5B_86 | S31G −0.8__−0.4<br>Q39E −3.5__−3.5 | I132T +4.5__−0.7<br>A143T +1.8__−0.7 | NT | NT |
| 5A_73 | A24V +1.8__+4.2 | — | NT | NT |
| 5B_33 | A76T +1.8__−0.7 | — | NT | NT |
| 3B_71 | S114T −0.8__−0.7 | S179P −0.8__−1.6 | NT | NT |
| 3B_87 | — | L175Q +3.8__−3.5 | NT | NT |
| 3D_68 | — | T150A −0.7_1.8 | NT | NT |
| 4E_112 | L110P +3.8__−1.6 | V187A +4.2__+1.8<br>S192T −0.8__−0.7 | NT | NT |
| 5B_54 | A24T +1.8__−0.7 | — | NT | NT |
| 6A_18 | K13R −3.9__−4.5 | — | NT | NT |
| 3C_40 | — | P224A −1.6__+1.8 | NT | NT |
| 5A_83 | Q62E −3.5__−3.5<br>S179P −0.8__−1.6<br>A79T +1.8__−0.7 | — | NT | NT |
| 5A_19 | Q3E −3.5__−3.5 | S182F −0.8__+2.8 | NT | NT |
| 3A_29 | V20A +4.2__+1.8 | — | NT | NT |

(Q1E, Q3E, Q6E, K19E, Q39E and Q62E: TAG codon suppressed, translated to E in the *E. coli* bacteria XL1-blue used)
NT: not tested

Example 4

Comparison of Clones Having an Improvement of Affinity

Figure 1:
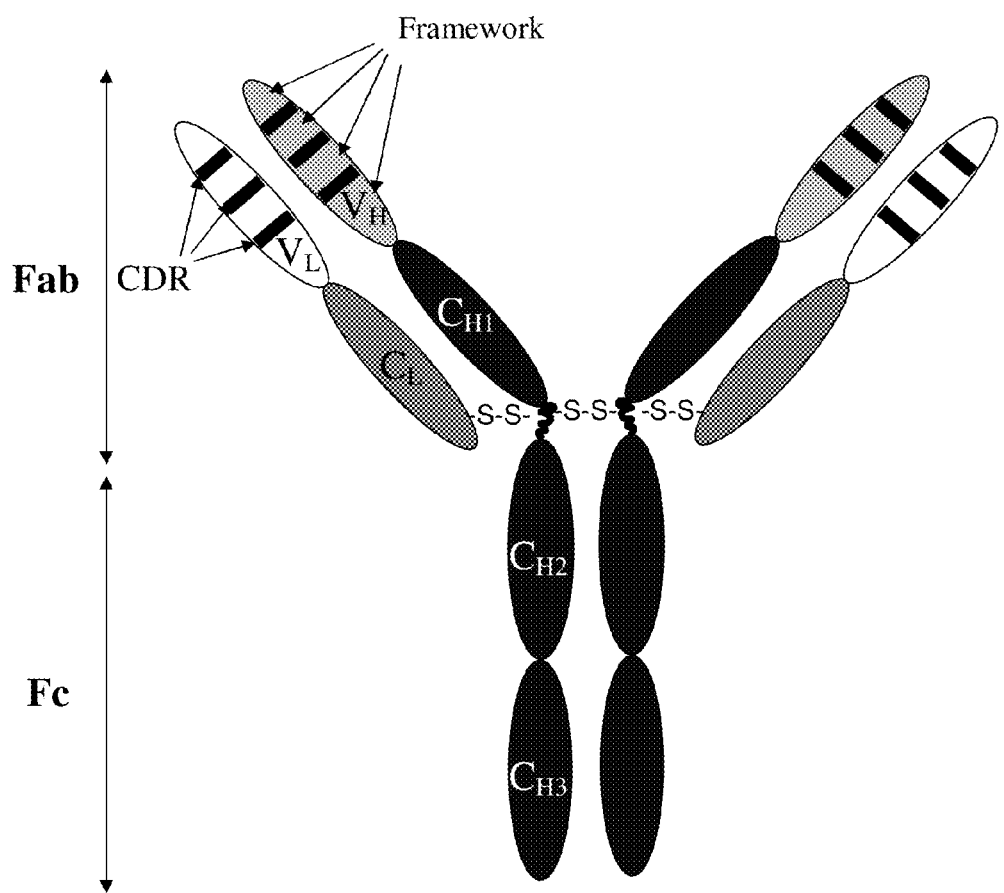
FIG. 1 corresponds to a diagrammatic representation of an antibody. The black parts correspond to the constant parts of the heavy chains, the parts in dark grey correspond to the constant part of the light chain, the parts in light grey correspond to the variable part of the heavy chain, and the white parts correspond to the variable part of the light chain. —S—S— represents the disulphide bridges established between two cysteines. The CDR and framework regions are indicated by arrows. The Fab and Fc fragments are also shown.
Figure 2:
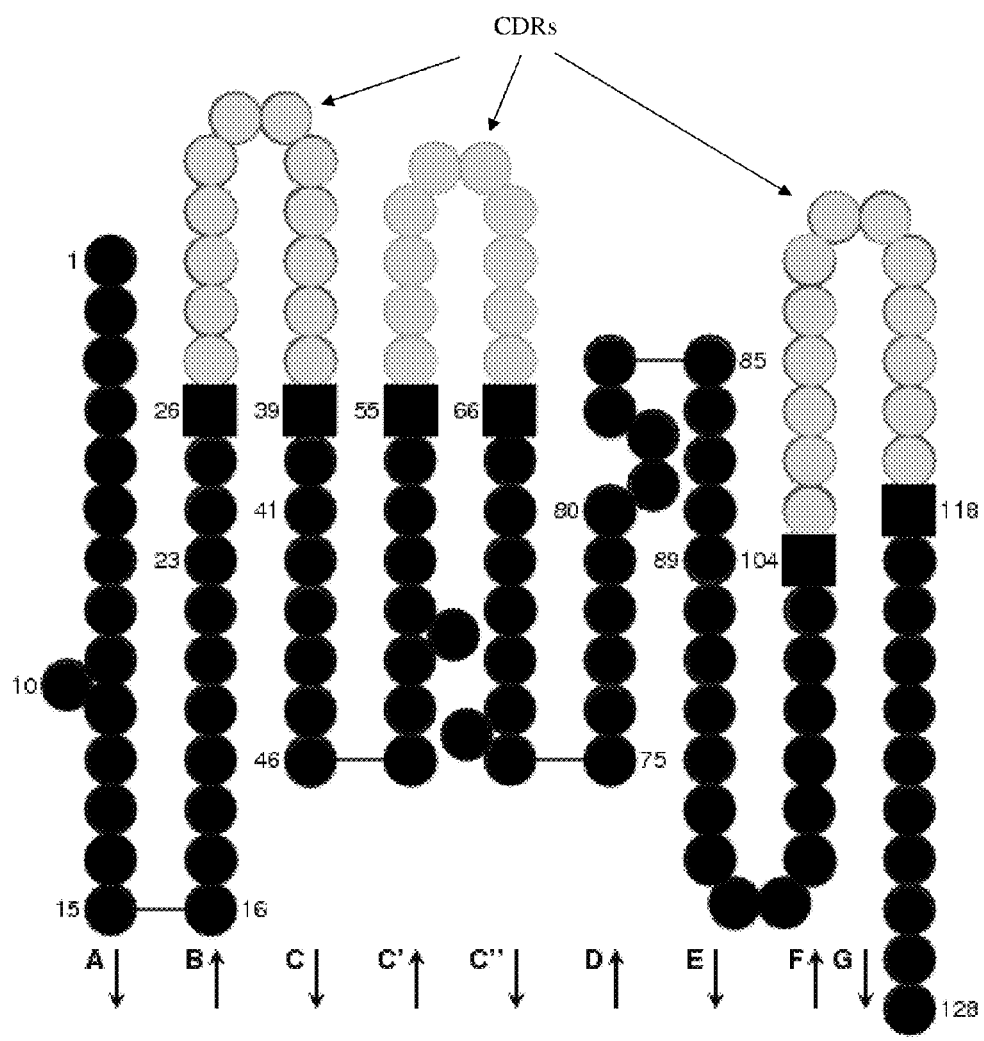
FIG. 2 corresponds to a diagrammatic string-of-pearls representation of the amino acid sequence of a variable part of a light chain or of a heavy chain of immunoglobulin. The black beads correspond to the amino acids forming the framework regions, and the grey beads correspond to the amino acids representing the CDRs.
Figure 3:
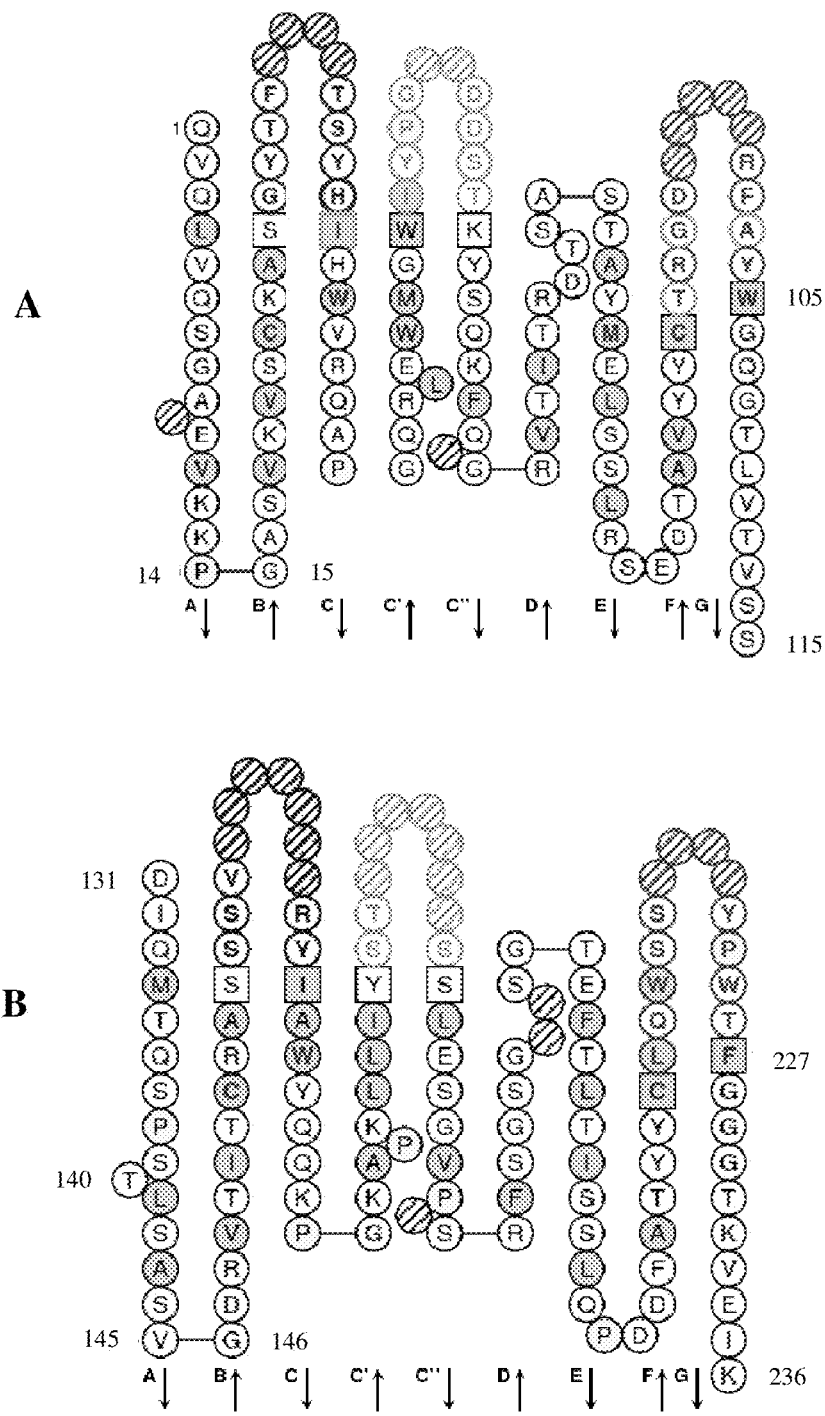
FIG. 3 corresponds to a diagrammatic string-of-pearls representation of the amino acid sequence of the variable part of the heavy chain (FIG. 3A: amino acids 1-115, SEQ ID NO: 8) and of the light chain (FIG. 3B: amino acids 131-236, SEQ ID NO: 2) of the humanized 12G4 antibody with the numbering adopted for defining the position of the mutations. The grey-shaded beads correspond to amino acids that are not present in the sequence and which therefore are not counted in the numbering.
Figure 4:
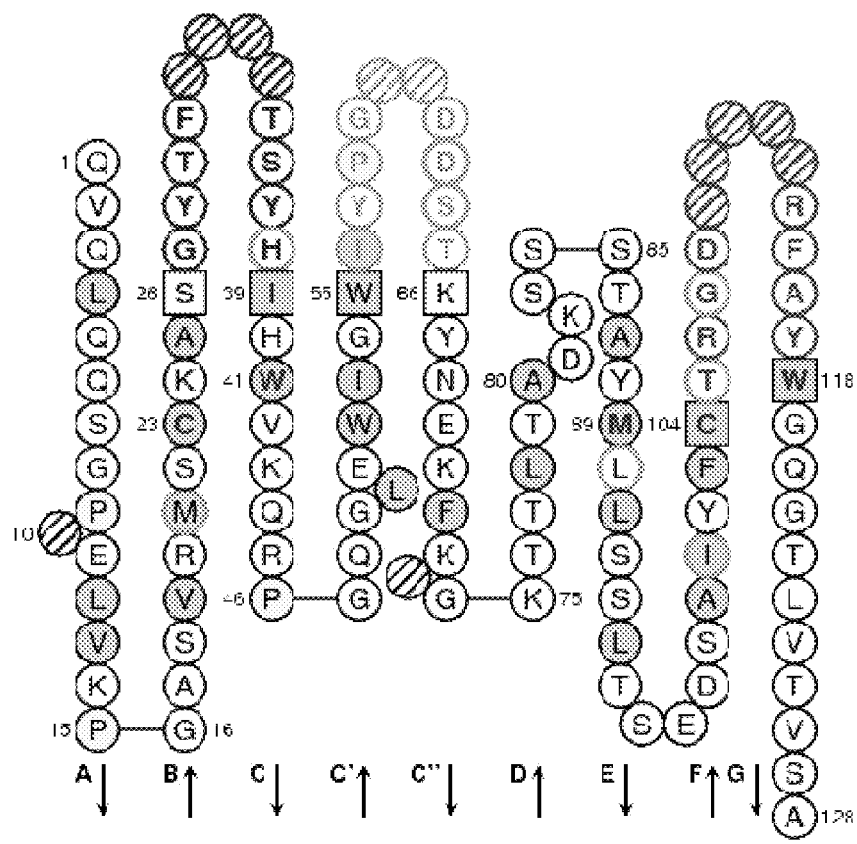
FIG. 4 corresponds to a diagrammatic string-of-pearls representation of the amino acid sequence of the variable part of the heavy chain of the chimeric 12G4 antibody (SEQ ID NO: 66).
Figure 5:
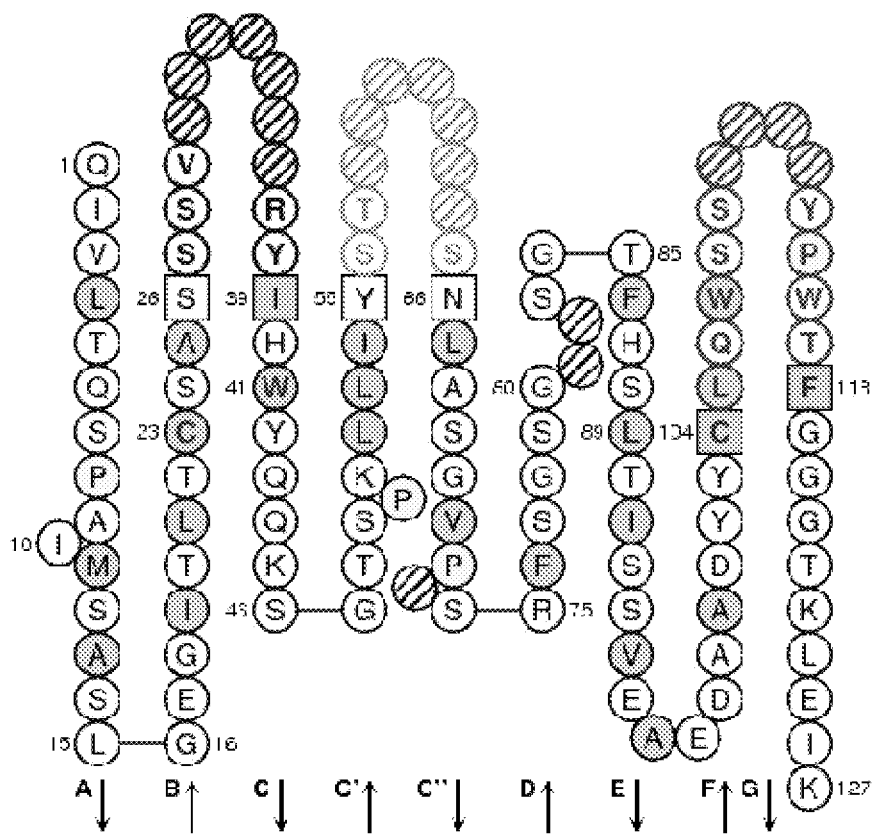
FIG. 5 corresponds to a diagrammatic string-of-pearls representation of the amino acid sequence of the variable part of the light chain of the chimeric 12G4 antibody (SEQ ID NO: 62).
Figure 6:
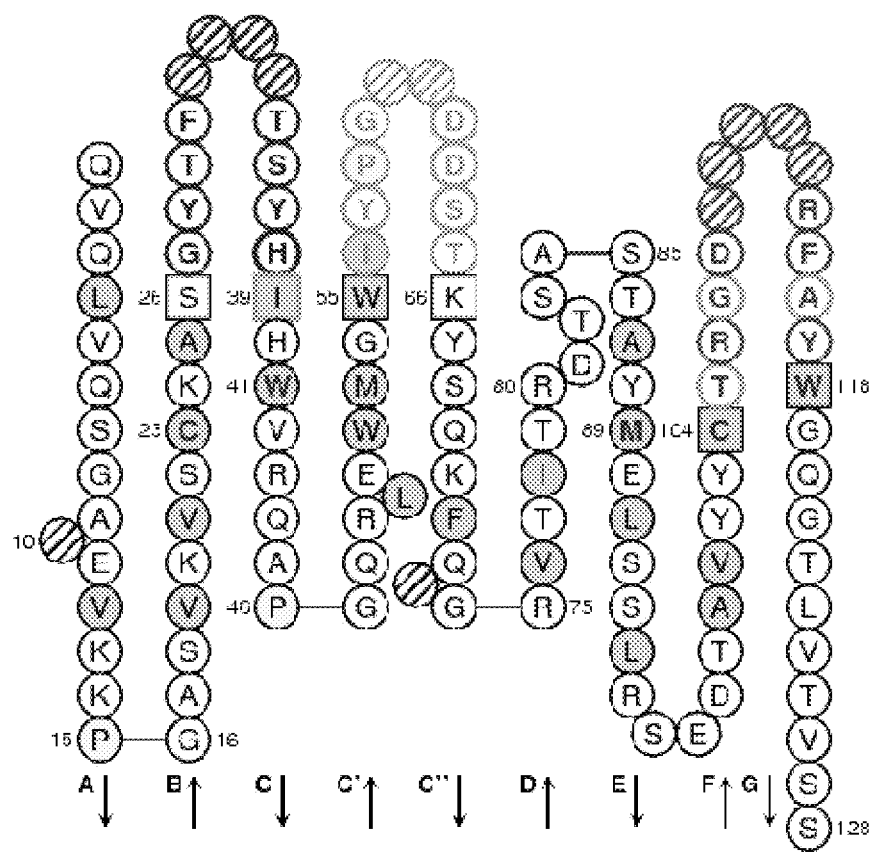
FIG. 6 corresponds to a diagrammatic string-of-pearls representation of the amino acid sequence of the variable part of the heavy chain of the unmutated humanized 12G4 antibody (SEQ ID NO: 58) and of the mutated humanized 12G4 antibody (6B__78; SEQ ID NO: 58).
Figure 7:
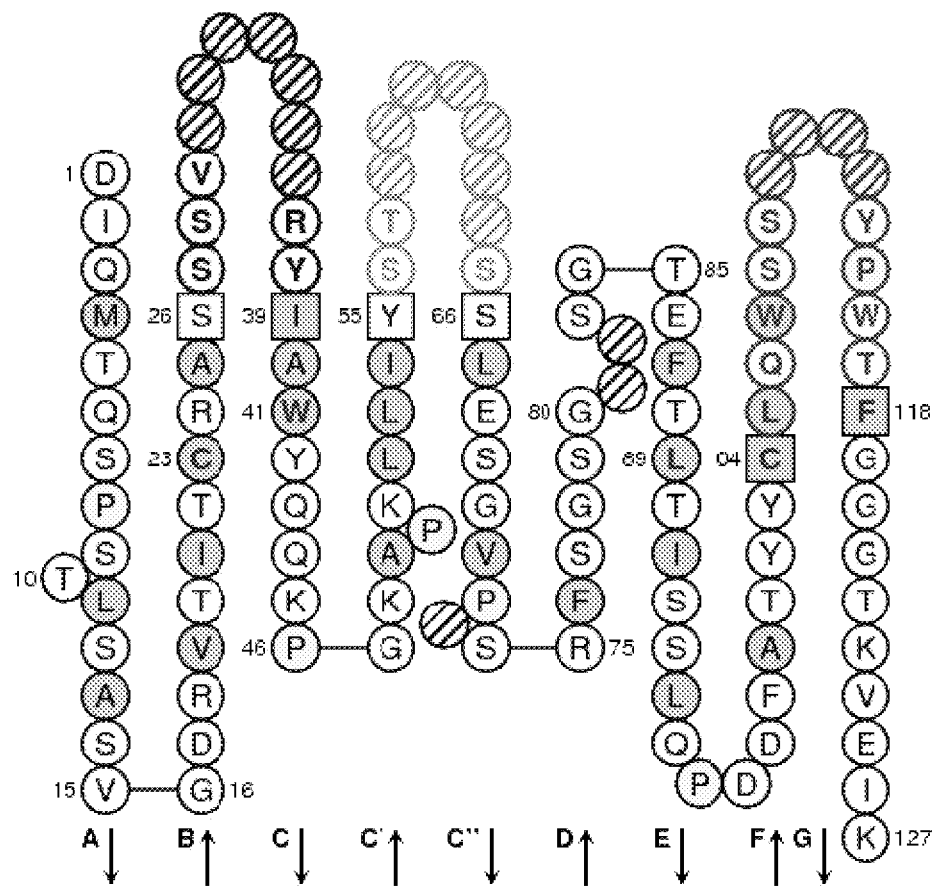
FIG. 7 corresponds to a diagrammatic string-of-pearls representation of the amino acid sequence of the variable part of the light chain of the unmutated humanized 12G4 antibody (SEQ ID NO: 54).
Figure 8:
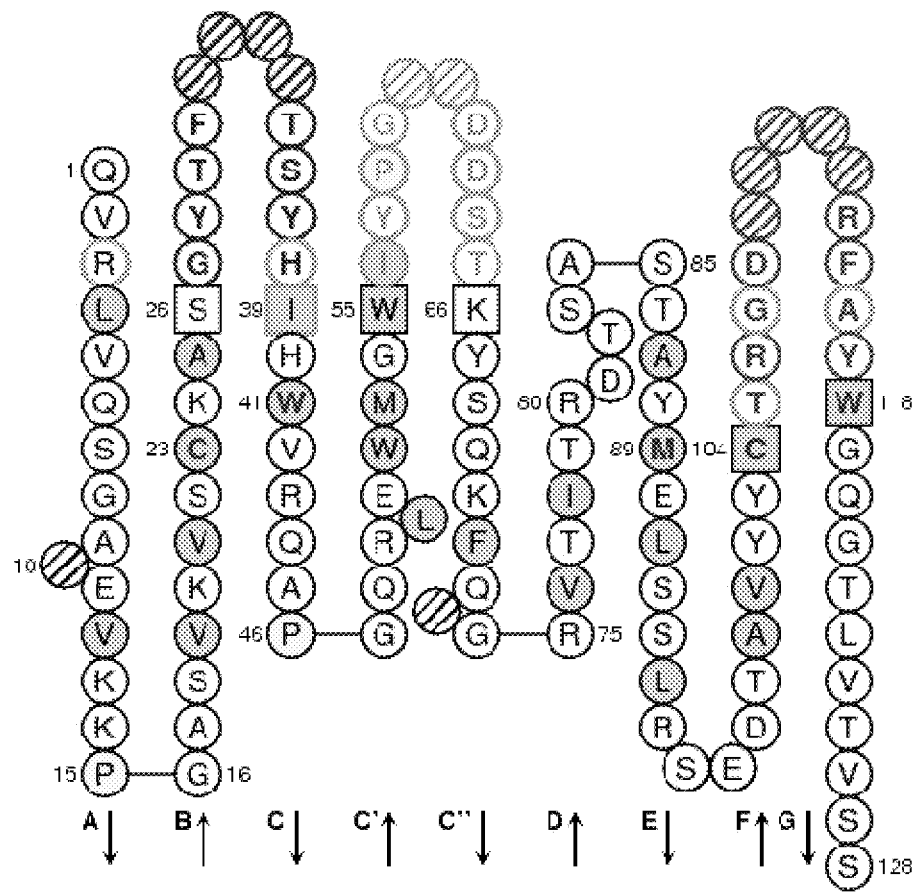
FIG. 8 corresponds to a diagrammatic string-of-pearls representation of the amino acid sequence of the variable part of the heavy chain of the mutated humanized 12G4 antibody (3C__23; SEQ ID NO: 74).
Figure 9:
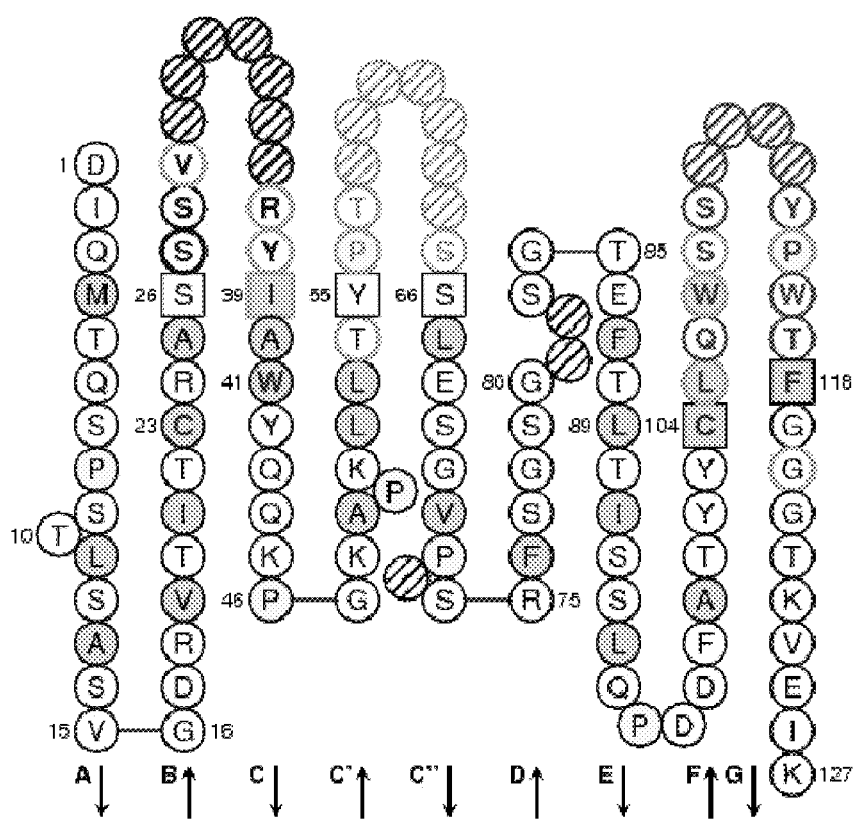
FIG. 9 corresponds to a diagrammatic string-of-pearls representation of the amino acid sequence of the variable part of the light chain of the mutated humanized 12G4 antibody (3C__23; SEQ ID NO: 70).
Figure 10:
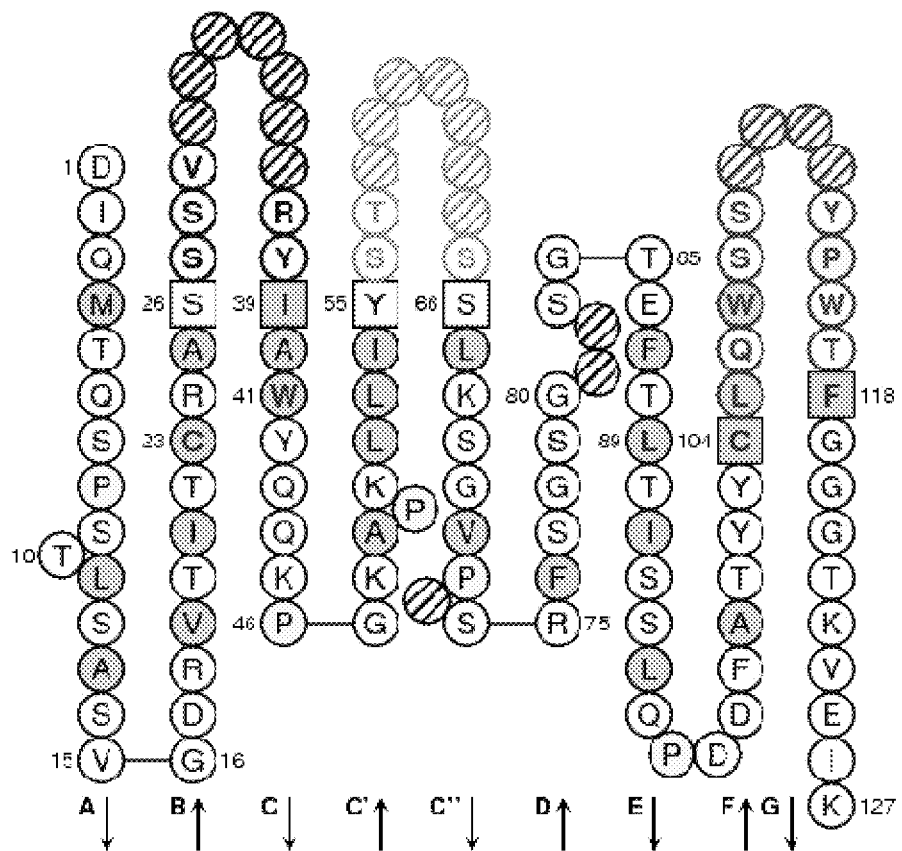
FIG. 10 corresponds to a diagrammatic string-of-pearls representation of the amino acid sequence of the variable part of the light chain of the mutated humanized 12G4 antibody (6B__78; SEQ ID NO: 78).
Figure 11:
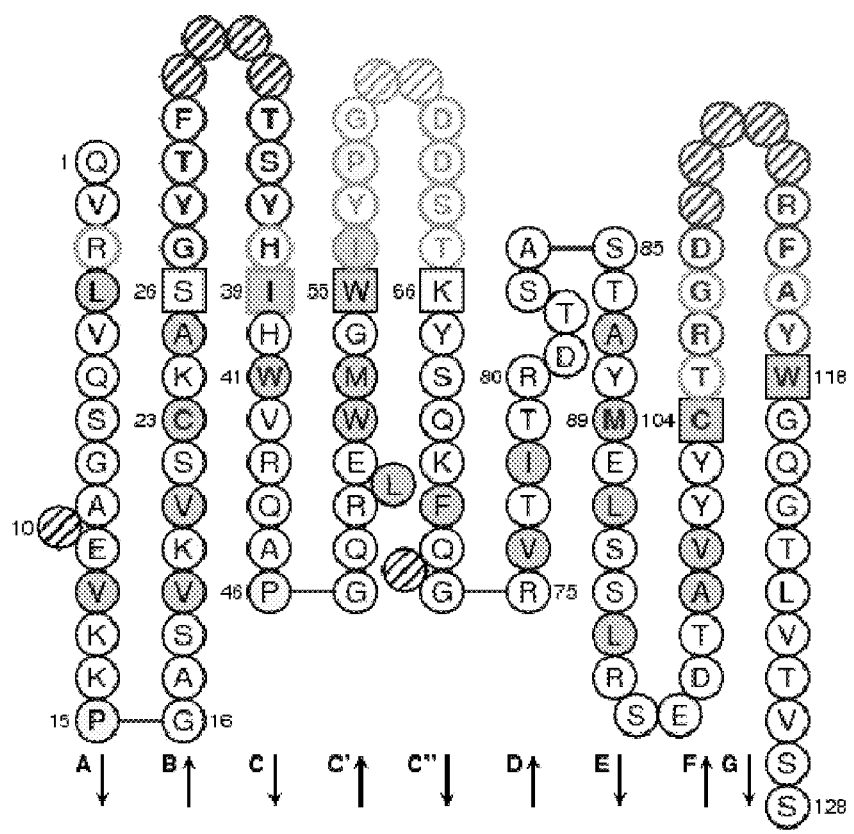
FIG. 11 corresponds to a diagrammatic string-of-pearls representation of the amino acid sequence of the variable part of the heavy chain of the mutated humanized 12G4 antibody (3C__23K; SEQ ID NO: 86).
Figure 12:
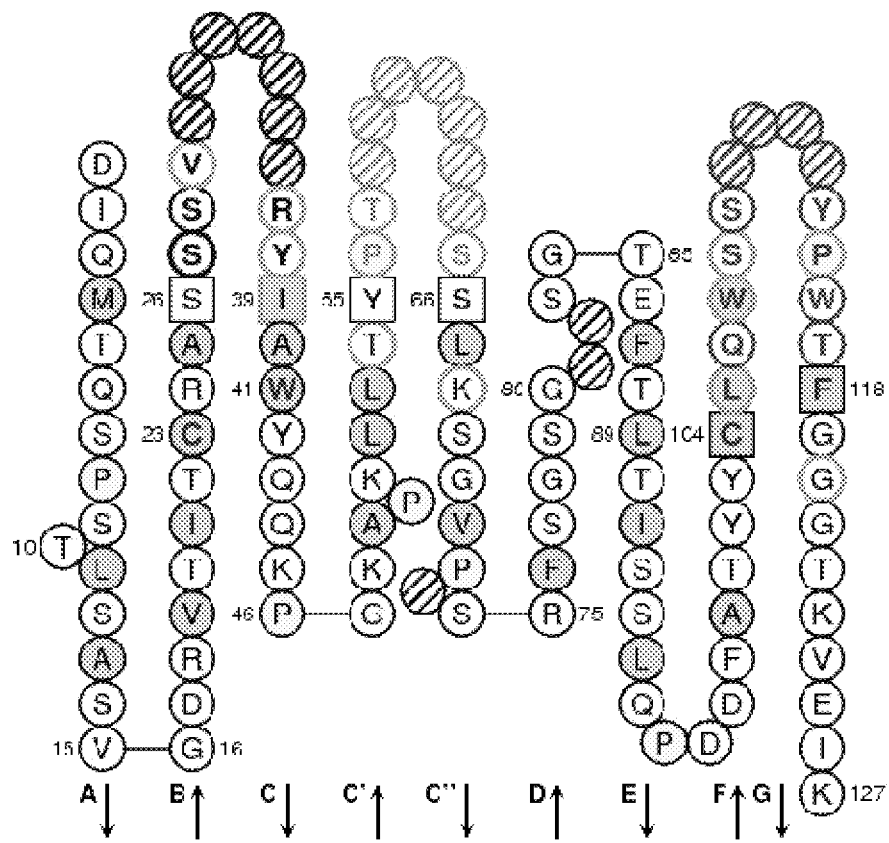
FIG. 12 corresponds to a diagrammatic string-of-pearls representation of the amino acid sequence of the variable part of the light chain of the mutated humanized 12G4 antibody (3C__23K; SEQ ID NO: 82).
Figure 13:
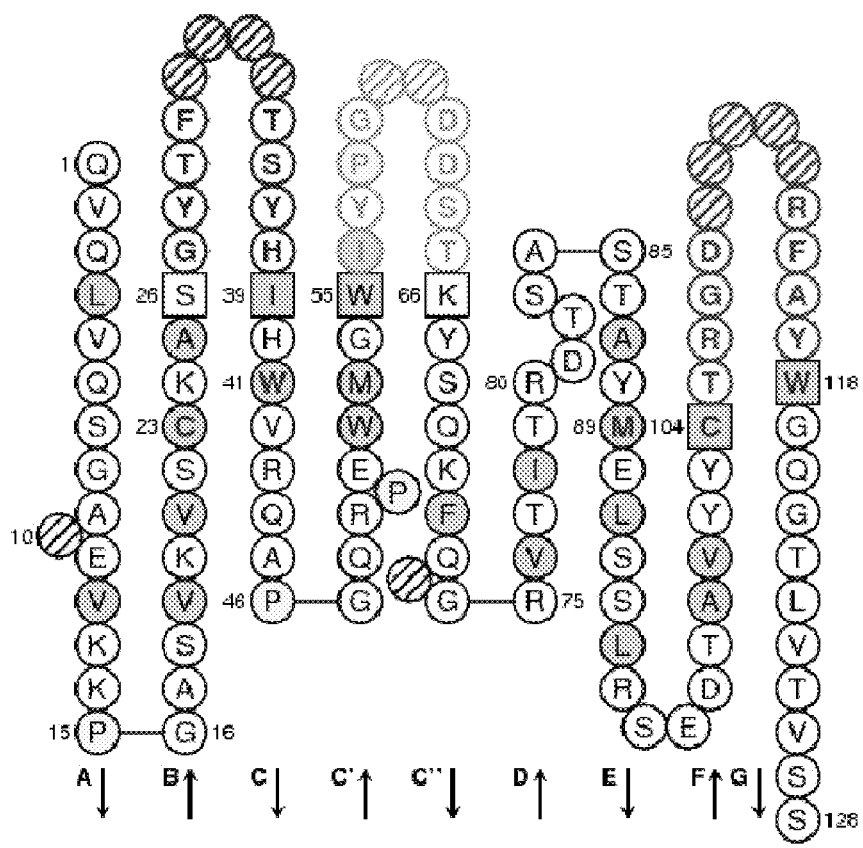
FIG. 13 corresponds to a diagrammatic string-of-pearls representation of the amino acid sequence of the variable part of the heavy chain of the mutated humanized 12G4 antibody (4C__35; SEQ ID NO: 90).
Figure 14:
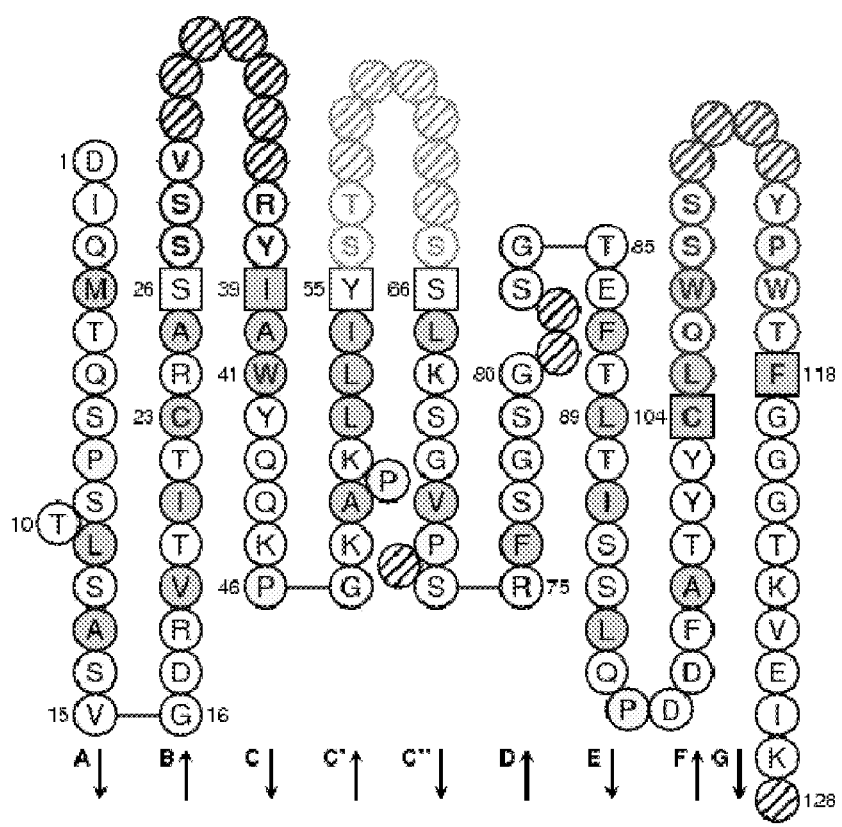
FIG. 14 corresponds to a diagrammatic string-of-pearls representation of the amino acid sequence of the variable part of the light chain of the mutated humanized 12G4 antibody (4C__35; SEQ ID NO: 78).
Figure 15:
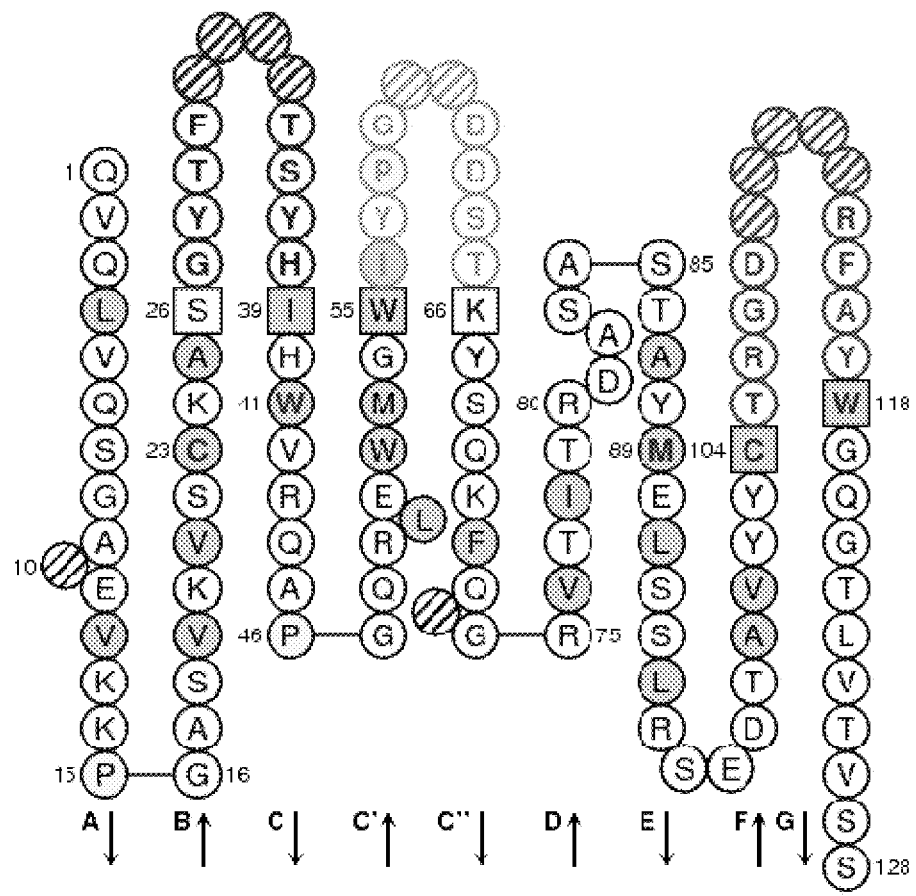
FIG. 15 corresponds to a diagrammatic string-of-pearls representation of the amino acid sequence of the variable part of the heavy chain of the mutated humanized 12G4 antibody (5B__42; SEQ ID NO: 98).
Figure 16:
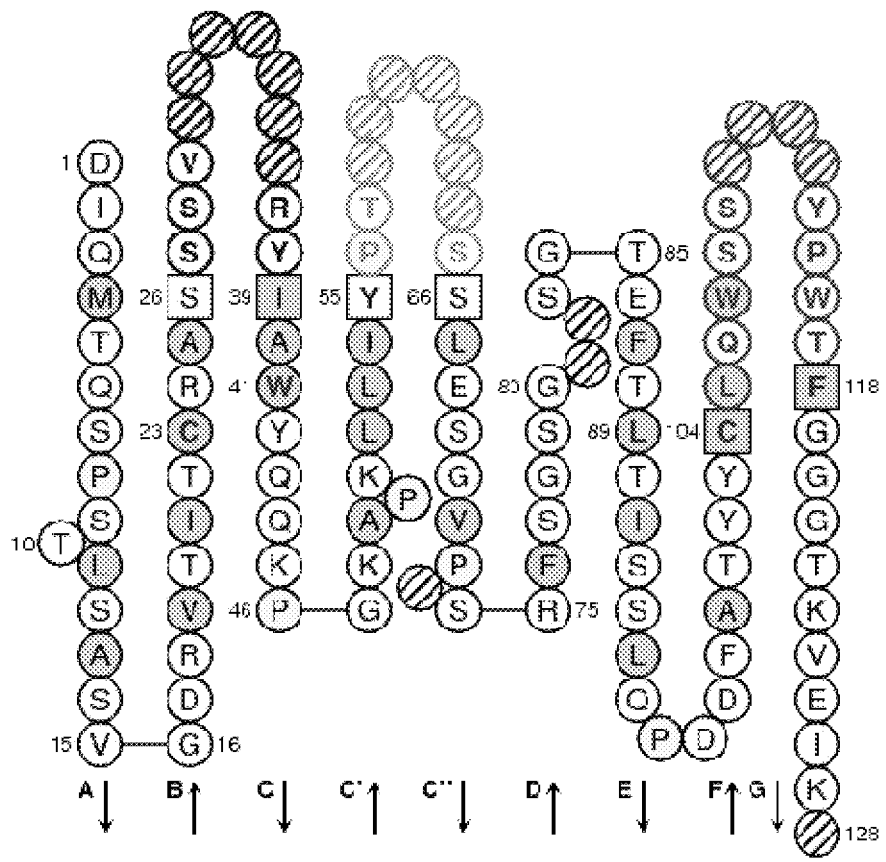
FIG. 16 corresponds to a diagrammatic string-of-pearls representation of the amino acid sequence of the variable part of the light chain of the mutated humanized 12G4 antibody (5B_42; SEQ ID NO: 94).
Figure 17:
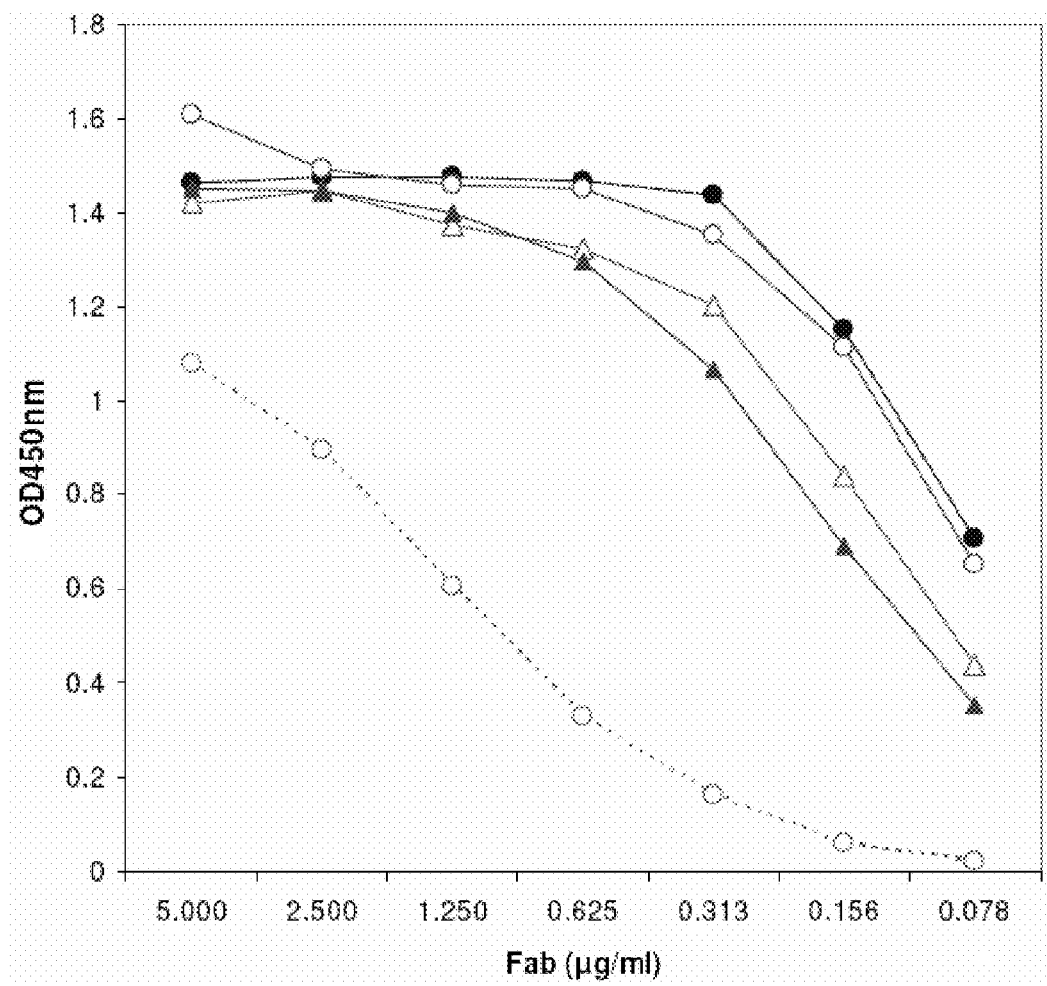
FIG. 17 presents determination of the binding affinity of the antibody to the AMHR-II receptor in a conventional ELISA assay obtained with mutated antibodies (Fab) according to the invention.

The positive clones 3C_23K, 3C_23 and 6B_78 were compared with one another by determining the binding affinity of the antibody to the AMHR-II receptor in a conventional ELISA assay obtained with soluble mutated antibodies (Fab) according to the invention.
The results obtained are presented in FIG. 17.

Example 5

Establishment of the Transfected Line AMHRII cov434-AMHRII

The cov434-AMHRII line was generated by transfection of a plasmid expressing the cDNA coding for AMHRII in the granulosa tumour line cov434 (van den Berg-Bakker, C., et al., 1993. Establishment and characterization of 7 ovarian carcinoma cell lines and one granulosa tumour cell line: Growth features and cytogenetics. *International Journal of Cancer* 53: 613; Zhang, H. et al., 2000. Characterization of an immortalized human granulosa cell line (COV434). *Molecular Human Reproduction* 6: 146) not expressing AMHRII.

Briefly, the cDNA of AMHRII was cloned into the commercial plasmid pIRES-neo (Clontech—Takara Bio Europe, France; references 6060-1). Owing to the IRES sequence, AMHRII and neo are expressed under the control of one and the same promoter CMV (FIG. 26).

This construction was stably transfected in the granulosa cancer line cov434 (transfection agent Fugene, Roche). The transfectants obtained were then screened by cytometry and by Western blotting for expression of the AMHRII receptor. After subcloning, the cellular clone cov434-AMHRII-1F3, containing a vector of the pIRES-neo type, was retained for the in vitro and in vivo studies. This line is designated cov434-AMHRII hereinafter.

Example 6

Establishment of Primary Lines from Ascitic Fluid or Biopsy from Patients with Ovarian Epithelial Carcinoma The main steps in establishing the lines derived from samples of ascitic fluid (Asc 1 line) are as follows:
D0: Receiving the ascitic fluid and starting culture of the sample immediately. The sample is centrifuged for 5 min at 1000 rev/min and the pellet is taken up in 2 mL of medium for seeding a T25 flask (RPMI 10% FCS medium).
D2-D46: Culture with regular microscopic observation. Fresh medium is added regularly during this period. Washing with PBS is also carried out every other day in order to remove the contaminating erythrocytes and fibroblasts.
Around D13, all the contaminating cells have disappeared and a still heterogeneous confluent lawn of cells is observed (two different types).
D46: Transfer: on D46 a homogeneous lawn of tumour cells is observed and the cells are then washed and transferred by scraping to be re-seeded in two T75 flasks.
D61: Evaluation of AMHRII expression by FACS: after washing with PBS, the cells are detached from the scraper and analysed by flow cytometry (labelling AcM 12G4 10 µg/mL, AcII anti-mouse FITC). The databases are constructed at this stage. The positive AMHRII line is cultured for 10 more days in order to confirm expression of the AMHRII receptor.
D71: Confirmation of AMHRII expression by FACS.

The lines thus established are kept in RPMI 10% FCS medium, with one passage per week (1/15 dilution).

In the case of biopsies (META 2815 line), the primary tumour is first maintained on nude mice (grafts of the sample in the interscapular space, 3 successive passages on mice) then the tumour is removed and dilacerated before being taken up in culture medium. A protocol identical to that of the samples of ascitic fluid is then applied.

Example 7

Evaluation of the Affinity of the Various Candidate Humanized Antibodies

This study was conducted on the original murine 12G4 antibody as well as on the candidate humanized antibodies 3C23, 6B78 and 3C23K (of sequence 3C_23, 6B_78 and 3C_23K respectively) produced in YB2/0. The affinity of these antibodies was evaluated on the cov434-AMHRII cells.

Briefly, $K_D$ was determined by the saturation method, by adding increasing doses of radiolabelled antibody to a constant number of cov434-AMHRII cells. The cells ($1 \times 10^6$ in 50 µl PBS/BSA 0.5%) were incubated (final volume 150 µl) for 1 h at 4° C. in the presence of increasing doses of antibody labelled beforehand with iodine 125 ($^{125}I$). For each antibody, fourfold dilutions were carried out in PBS/BSA 0.5% from the solutions of labelled and unlabelled antibody (84.4 µg/ml). The nonspecific fixation was evaluated by incubating the cells in the presence of a 100 times molar excess of unlabelled antibody.

After incubation, the samples were frozen in liquid nitrogen and then analysed in a gamma counter. The specific fixation was determined by subtracting the fixation obtained in the presence of an excess of unlabelled antibody.

Scatchard analysis, performed on PRISM software, made it possible to determine the affinity constants presented in Table VIII.

TABLE VIII

| Dissociation constant ($K_D$) of the anti-AMHRII antibodies | | | |
|---|---|---|---|
| murine 12G4 | 3C23 | 6B78 | 3C23K |
| $K_D$ (nM) 15.41 +/− 0.97 | 7.33 +/− 0.44 | 6.68 +/− 0.21 | 5.30 +/− 0.38 |

According to this study, it appears that the humanized anti-AMHRII antibody 3C23K has the best affinity ($K_D=5.3$ nM) compared with the two other candidate antibodies 6B78 and 3C23. The 3C23K antibody also has an affinity about three times greater than that of the original murine 12G4 antibody ($K_D=15.4$ nM).

Example 8

Comparison of the ADCC Activity of the Antibodies of the Invention Versus the ADCC Activity of the Unmutated Humanized 12G4 Antibody 1 Material and Methods 1.1 Principle of the Methods

ADCC

The ASC1 target cells obtained from patients are adherent and are prepared on the day before the assay. They are detached with trypsin and incubated in EMS+5% FCS in a flat-bottomed plate at a rate of 50 µl per well at a concentration of $6 \times 10^5$ cells/ml. The plates are incubated overnight at 37° C., 7% $CO_2$.

The next day, the cells have adhered to the bottom of the well. The supernatant is aspirated and the necessary volume of buffer per well is added for carrying out the assay in the presence of NK and antibody.

The killer cells (NK cells) are purified beforehand by the negative depletion technique developed by the company Miltenyi (Miltenyi Biotec—NK cell isolation kit human ref 130-092-657), from peripheral blood of healthy donors. The ADCC technique consists of incubating the NK cells with ASC1 target cells in the presence of different concentrations of the humanized anti-AMHRII antibody (0.005 to 5000 ng/ml) with E/T ratio of 10/1. After 4 hours of incubation, the cytotoxic activity induced by the anti-AMHRII antibodies is measured by colorimetry by determining, in the supernatants, an intracellular enzyme called lactate dehydrogenase (LDH) released by the lysed target cells (Roche Diagnostics—Cytotoxicity Detection Kit LDH ref 11644793001).

1.2 Elements Studied

Anti-AMHRII antibodies:

829 10 054, humanized YB2/0, R901 3C23K 829 10 050, humanized YB2/0, R901 3C23

829 10 051, humanized YB2/0, R901 6B78

632 07 107, unmutated humanized anti-AMHRII 12G4

ASC1 cells culture dossier 871 10 063

The results are presented in FIG. 25.

Table IX presents the raw data corresponding to FIG. 25.

TABLE IX

| | | % of lysis (ADC 1193 11 081) | | | |
|---|---|---|---|---|---|
| Ac ng/ml | Ac ng/ml (Log) | 829 10 050 3C23 YB20 | 829 10 051 6B78 YB20 | 829 10 054 3C23K YB20 | 632 07 107 Anti AMHRII hum 1st |
| 0.001 | −3.000 | 0 | 0 | 0 | 0 |
| 0.005 | −2.301 | 8 | 14 | 8 | 18 |
| 0.05 | −1.301 | 9 | 5 | 10 | 2 |
| 0.5 | −0.301 | 13 | 3 | 26 | 0 |
| 5 | 0.699 | 35 | 28 | 51 | 7 |
| 50 | 1.699 | 46 | 42 | 67 | 24 |
| 500 | 2.699 | 52 | 48 | 79 | 50 |
| 5000 | 3.699 | 63 | 53 | 75 | 50 |

Table X presents the Emax and EC50 obtained with the various antibodies.

TABLE X

| | 829 10 050 3C23 YB20 | 829 10 051 6B78 YB20 | 829 10 054 3C23K YB20 | 632 07 107 Anti AMHRII hum 1st |
|---|---|---|---|---|
| Emax (% of lysis) | 65.55 | 51.89 | 79.02 | 52.40 |
| EC50 (ng/ml) | 6.298 | 5.383 | 1.704 | 52.35 |

Example 9

Comparison of the ADCC Activity of the Antibodies of the Invention Versus the Chimeric 12G4 Antibody The ADCC activity of the humanized candidate antibody 3C_23K (hal2G4 of sequence 3C_23K: mutations VHQ3R (SEQ ID NO: 82 (without leader) or SEQ ID NO: 84 (with leader)), and VLI177T/S179P/E184K (SEQ ID NO: 86 (without leader), or SEQ ID NO: 88 (with leader)) was evaluated.

Briefly, the effector cells (NK killer cells; NK: Natural Killer) are purified beforehand by the negative depletion technique developed by the company Miltenyi (Miltenyi Biotec—NK cell isolation kit human ref 130-092-657), from peripheral blood of healthy donors, after a first step of purification of the mononucleated cells on Ficoll.

The in vitro assay of ADCC activity consists of incubating the NK cells with target cells (cov434-AMHRII, Asc 1 and META 2815 lines), in the presence of different concentrations of anti-AMHRII antibodies (chimeric antibody ch12G4, humanized 3C_23K-YB2/0 antibody, produced in YB2/0, and 3C_23K-CHO, produced in CHO). The effector/target ratio applied is 15/1. The antibodies are diluted in culture medium at concentrations ranging from 0.005 to 5000 ng/ml.

After 4 hours of incubation, the cytotoxic activity induced by the anti-AMHRII antibodies is measured by colorimetry by determining, in the supernatants, an intracellular enzyme called lactate dehydrogenase (LDH) released by the lysed target cells (Roche Diagnostics—Cytotoxicity Detection Kit LDH ref 11644793001).

The percentage lysis is calculated from the following formula:

$$\% \text{ of lysis} = [(ER-SR)/(100-SR)] - [(NC-SR)/(100-SR)]$$

with: ER=release of LDH in the presence of antibodies and of NK cells

SR=spontaneous release of LDH from the target cell alone

NC=release of LDH in the presence of NK cells and absence of antibodies.

The results are expressed in percentage lysis as a function of the amount of antibody. The Emax and EC50 values are calculated with the PRISM software.

Figure 27:
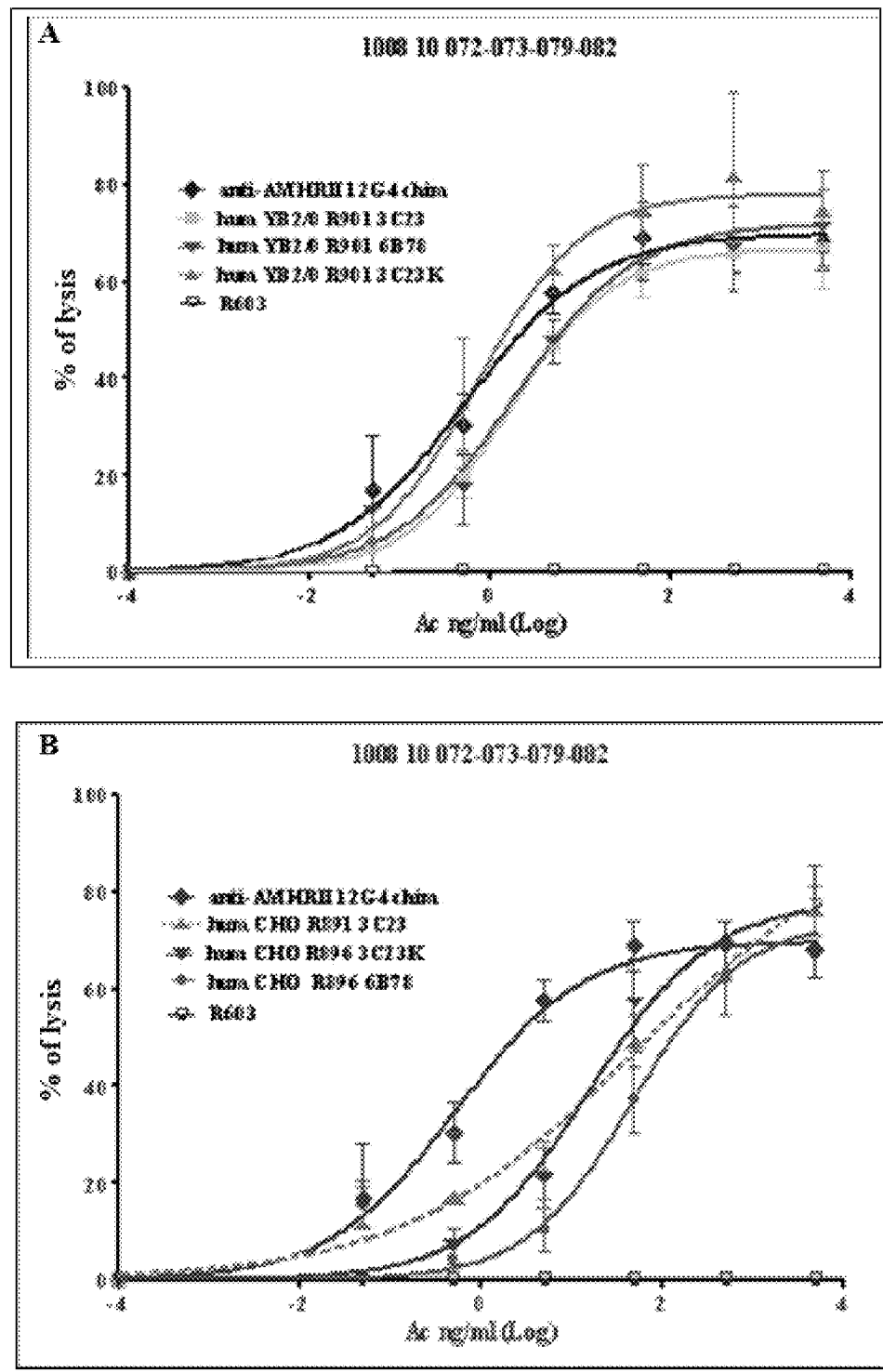

The results obtained on the cov434-AMHRII line are presented in FIG. 27. The low activity of the 3C_23K-CHO antibody does not allow a plateau to be obtained under the assay conditions. In order to compare the efficacy of the antibodies, calculation of 50% relative is carried out in this case, which represents the amount of 3C_23K-CHO antibody required to reach 50% of the plateau of the chimeric antibody (50% relative=1). According to this evaluation, the humanized antibody having the best ADCC activity on the COV434-AMRHII line is the 3C_23K antibody (50% relative: 0.84) produced in YB2/0. The humanized antibodies of sequence 3C_23 and 6B_78 have a value of 50% relative, equal to 6.41 and 36.92, respectively.

The results obtained on the Asc 1 line are presented in FIG. 28. The 3C_23K-YB2/0 antibody has a dose-dependent cytotoxic activity on the Asc 1 cells with an EC50 estimated at 2.24 ng/ml. The low activity of the 3C_23K-CHO antibody does not allow a plateau to be obtained under the assay conditions. In order to compare the efficacy of the two antibodies, calculation of 50% relative is carried out in this case, which represents the amount of 3C_23K-CHO antibody required to reach 50% of the plateau of the 3C_23K-YB2/0 antibody (50% relative=1). According to this evaluation, the cytotoxic activity of the 3C_23K-YB2/0 antibody is about 40 times greater than that of the antibody produced in CHO (50% relative=39.4).

Similarly, the results presented in FIG. 29 show that the antibodies 3C_23K-YB2/0 and 3C_23K-CHO induce dose-dependent lysis on the META 2815 cells. The cytotoxic activity of the 3C_23K-YB2/0 antibody (EC50=30.5 ng/ml) is about 146 times greater than that of the 3C_23K-CHO antibody (EC50=466.9 ng/ml).

Taken together, these results indicate that the 3C_23K anti-AMHRII antibodies produced in YB2/0 have the capacity to induce lysis of the cells expressing the AMHRII antigen. The difference in EC50 between the anti-AMHRII-YB2/0 and anti-AMHRII-CHO antibodies suggests a particular advantage for the anti-AMHRII-YB2/0 antibody under conditions of low antigenic expression, or of low penetrance of the antibody to the tumour.

Example 10

Studies of Cellular Proliferation

Inhibition of cellular proliferation was demonstrated by measuring cell growth over time in the presence or absence of the anti-AMHRII antibodies tested.

Briefly, the target cells (cov434-AMHRII, Asc 1, META2815) are cultured in P6 plates ($1 \times 10^5$ cells/well) for 72 h at 37° C., in the presence of the anti-AMHRII antibodies (10 µg/ml) expressed in CHO or YB2/0, with or without cross-linking agent (AffiniPure F(ab')2 Fragment Goat Anti-Human IgG, Fcγ Fragment Specific ref: 109-006-008, Jackson Immunoresearch, France). The cells are treated with trypsin for 5 minutes and then counted in the CEDEX, an automatic cell counter based on cellular viability (trypan blue). A positive control of inhibition of proliferation is established in the presence of 1 µg/ml of colchicine (Ref: C3915, Sigma-Aldrich, France). A negative control is established in the presence of a non-relevant antibody (anti-P24). All the dilutions are prepared in culture medium (RPMI, 10% FCS). The results are expressed as percentage proliferation, the value 100% corresponding to the proliferation of the cells observed in the absence of antibody.

The results obtained with the cov434-AMHRII line are presented in FIG. 30.

According to these observations the antibodies 3C_23K-YB2/0 and 3C_23K-CHO induce about 40% inhibition of cellular proliferation of the cov434-AMHRII cells, in the presence of a cross-linking agent (CK). This cytostatic effect is not observed in the presence of a non-relevant antibody (antibody p24) whereas the colchicine positive control (10 µg/ml) induces 88% inhibition.

Similarly, the results presented in FIG. 31 show that the antibodies 3C_23K-YB2/0 and 3C_23K-CHO induce about 40% inhibition of cellular proliferation on the META 2815 line in the presence of a cross-linking agent (CK).

This inhibition of cellular proliferation might be the consequence of cellular signalling induced by the anti-AMHRII antibodies on the cov434-AMHRII and META 2815 lines.

Example 11

Effect In Vivo of the 3C_23K-YB2/0 Antibody on COV434-AMHRII Tumours

The antitumour efficacy of the 3C_23K-YB2/0 antibody was evaluated in late treatment on female Swiss nude mice after subcutaneous injection (s.c.) of COV434-AMHRII tumour cells. The intraperitoneal (i.p.) injections (inj) of antibody were performed at intervals of 2-3 days at a dose of 10 mg/kg/inj for a total of 18 injections. The group treated with the 3C_23K-YB2/0 antibody was compared with the group treated with the vehicle (PBS).

Material and Methods

Female Swiss nude mice were used (Harlan). On day 0 of the experiment, the mice were given a subcutaneous injection of $7.10^6$ COV434-AMHRII tumour cells mixed with Matrigel (ratio 1:1). The animals were then treated by i.p. injection of PBS or 3C_23K-YB2/0 with 10 mg/kg/inj starting from day 16 (tumour volume between 84 and 270 mm$^3$, 3 injections per week for 6 weeks (total 18 injections).

Tumour volume was measured 2 to 3 times per week. Tumour volume (TV) was calculated using the following formula: TV (mm$^3$)=(length×width×height)/2, in which the length corresponds to the largest diameter of the tumour and the width corresponds to the smallest diameter of the tumour.

The curves of tumour growth were plotted using the mean of the tumour volumes (MTV). The animals were euthanased when the individual tumour volume had reached 2000 mm$^3$. In each of the groups, the curves were stopped when 30% of the animals in the group had been euthanased.

The inhibition of tumour growth (T/C), defined as the ratio of the median tumour volume of the treated groups relative to the control group treated with the vehicle, was calculated as follows: T/C=(median TV of the treated group/median TV of the vehicle group)×100

T/C above 42%, the product is considered to be ineffective.
T/C between 42% and 10%, the product has an anti-tumour effect.
T/C below 10%, the product is truly effective.

The statistical differences between the different groups were obtained with the Kruskal-Wallis test, using the ANOVA comparison (Statgraphics centurion XV software). The differences were regarded as significant if P<0.05. A logrank test, for comparing the survival parameters of the study, was also performed via ANOVA (Statgraphics centurion XV software). The differences were regarded as significant if P<0.05.

Results

The 3C_23K-YB2/0 antibody shows anti-tumour activity, since a delay is observed in COV434-AMHRII (FIGS. 32A and 32B).

Statistical comparison of the tumour volumes at each measurement point, once the treatment has been started, shows that the 3C_23K-YB2/0 antibody delays tumour growth (Kruskal-Wallis, via ANOVA). The T/C ratio calculated between the groups treated with 3C_23K-YB2/0 and vehicle shows a significant difference at all the measurement points, also once the treatment has been started. The logrank test also shows that in terms of survival, the group treated with 3C_23K-YB2/0 is statistically different from the group treated with the vehicle.

Table XI below shows the evolution of the tumour volumes (treated/control ratio, T/C in %) under the effect of the treatment with 3C_23K-YB2/0 in the cov434-AMHRII model.

TABLE XI

| | Measurement day | | | | |
|---|---|---|---|---|---|
| | 15 | 21 | 25 | 30 | 32 |
| T/C % | 108 | 60 | 42 | 22 | 13 |

Table XII below presents the statistical analyses obtained in the cov434-AMHRII model.

TABLE XII

| | ANOVA | | | Kruskall-Wallis | | |
|---|---|---|---|---|---|---|
| Measurement day | F-ratio | P-value | Sig. | Test | P-value | Sig. |
| 15 | 0.03 | 0.8628 | | 0.00577 | 0.93945 | |
| 21 | 8.34 | 0.0098 | * | 5.67427 | 0.01721 | * |
| 5 | 12.95 | 0.0021 | * | 10.56570 | 0.00115 | * |
| 30 | 34.94 | 0.0000 | * | 13.73030 | 0.00021 | * |
| 32 | 39.04 | 0.0000 | * | 12.90670 | 0.00033 | * |

Example 12

Effect In Vivo of the 3C_23K-YB2/0 Antibody on Asc1A5 Tumours

The antitumour efficacy of the 3C_23K-YB2/0 antibody was evaluated in late treatment on female Swiss nude mice after subcutaneous injection (s.c.) of Asc1A5 tumour cells (clone of the original Asc 1 line). The intraperitoneal (i.p.) injections (inj) of the antibody were performed at intervals of 2-3 days at a dose of 10 mg/kg/inj for a total of 18 injections. The group treated with the 3C_23K-YB2/0 antibody was compared with the group treated with the vehicle (PBS).

Material and Methods

Female Swiss nude mice were used (Harlan). On day 0 of the experiment, the mice were given a subcutaneous injection of $7.10^6$ Asc 1A5 tumour cells mixed with Matrigel (1:1 ratio). The animals were then treated by i.p. injection of PBS or 3C_23K-YB2/0 with 10 mg/kg/inj starting from day 12 (tumour volume between 40 and 160 mm$^3$, 3 injections per week for 6 weeks (total 18 injections)).

Tumour volume was measured 2 to 3 times per week. Tumour volume (TV) was calculated using the following formula: TV (mm$^3$)=(length×width×height)/2, in which length corresponds to the largest diameter of the tumour and width corresponds to the smallest diameter of the tumour.

The curves of tumour growth were plotted using the mean of the tumour volumes (MTV). The animals were euthanased when the individual tumour volume had reached 2000 mm$^3$. In each of the groups, the curves were stopped when 30% of the animals in the group had been euthanased.

The inhibition of tumour growth (T/C), defined as the ratio of the median tumour volume of the treated groups to the control group treated with the vehicle, was calculated as follows: T/C=(median TV of treated group/median TV of vehicle group)×100

T/C above 42%, the product is considered to be ineffective.
T/C between 42% and 10%, the product has an anti-tumour effect.
T/C below 10%, the product is truly effective.

The statistical differences between the different groups were obtained with the Kruskal-Wallis test, using the ANOVA comparison (Statgraphics centurion XV software). The differences were regarded as significant if P<0.05. A logrank test, for comparing the survival parameters of the study, was also performed via ANOVA (Statgraphics centurion XV software). The differences were regarded as significant if P<0.05.

Results

The 3C_23K-YB2/0 antibody shows anti-tumour activity, since a delay is observed in tumour growth compared to the group treated with the vehicle in the Asc1A5 model (FIGS. 33A and 33B).

Statistical comparison of the tumour volumes at each measurement point, once the treatment has been started, shows that the 3C_23K-YB2/0 antibody delays tumour growth (Kruskal-Wallis, via ANOVA). The T/C ratio calculated between the groups treated with 3C_23K-YB2/0 and vehicle shows a significant difference at all the measurement points, also once the treatment has been started. The logrank test also shows that in terms of survival, the group treated with 3C_23K-YB2/0 is statistically different from the group treated with the vehicle.

Table XIII below presents the evolution of the tumour volumes (treated/control ratio, T/C in %) under the effect of the treatment with 3C_23K-YB2/0 obtained in the Asc1a5 model.

TABLE XIII

| | Measurement day | | | | | |
|---|---|---|---|---|---|---|
| | 12 | 17 | 24 | 27 | 31 | 35 |
| T/C % | 101 | 33 | 8 | 8 | 7 | 6 |

Table XIV below presents the statistical analyses obtained in the Asc1a5 model.

TABLE XIV

| | ANOVA | | | Kruskall-Wallis | | |
|---|---|---|---|---|---|---|
| Measurement day | F-ratio | P-value | Sig. | Test | P-value | Sig. |
| 12 | 0.02 | 0.8817 | | 0.0995 | 0.7523 | |
| 17 | 29.19 | 0.0001 | * | 11.3108 | 0.0007 | * |
| 24 | 103.56 | 0 | * | 11.2941 | 0.0007 | * |
| 27 | 32.08 | 0.0001 | * | 11.3108 | 0.0007 | * |
| 31 | 33.37 | 0 | * | 11.3274 | 0.0007 | * |
| 35 | 57.97 | 0 | * | 10.5788 | 0.0011 | * |

Example 13

Effect In Vivo of the 3C_23K-YB2/0 Antibody on Meta2815 Tumours

The antitumour efficacy of the 3C_23K-YB2/0 antibody was evaluated in late treatment on female Swiss nude mice after subcutaneous injection (s.c.) of Meta 2815 tumour cells. The intraperitoneal (i.p.) injections (inj) of antibody were performed at intervals of 2-3 days at a dose of 10 mg/kg/inj for a total of 18 injections. The group treated with the 3C_23K-YB2/0 antibody was compared with the group treated with the vehicle (PBS).

Material and Methods

Female Swiss nude mice were used (Harlan). On day 0 of the experiment, the mice were given a subcutaneous injection of 8.10⁶ Meta2815 tumour cells. The animals were then treated by i.p. injection of PBS or 3C_23K-YB2/0 with 10 mg/kg/inj starting from day 33 (tumour volume between 45 and 240 mm³, 3 injections per week for 6 weeks (total 18 injections).

Tumour volume was measured 2 to 3 times per week. Tumour volume (TV) was calculated using the following formula: TV (mm³)=(length×width×height)/2, in which length corresponds to the largest diameter of the tumour and width corresponds to the smallest diameter of the tumour. The curves of tumour growth were plotted using the mean of the tumour volumes (MTV). The animals were euthanased when the individual tumour volume had reached 2000 mm³. In each of the groups, the curves were stopped when 30% of the animals in the group had been euthanased.

The inhibition of tumour growth (T/C), defined as the ratio of the median tumour volume of the treated groups to the control group treated with the vehicle, was calculated as follows: T/C=(median TV of treated group/median TV of vehicle group)×100

T/C above 42%, the product is considered to be ineffective.
T/C between 42% and 10%, the product has an anti-tumour effect.
T/C below 10%, the product is truly effective.

The statistical differences between the different groups were obtained with the Kruskal-Wallis test, using the ANOVA comparison (Statgraphics centurion XV software). The differences were regarded as significant if P<0.05. A logrank test, for comparing the survival parameters of the study, was also performed via ANOVA (Statgraphics centurion XV software). The differences were regarded as significant if P<0.05.

Results

The 3C_23K-YB2/0 antibody shows anti-tumour activity, since a delay is observed in tumour growth compared to the group treated with the vehicle in the Meta2815 model (FIGS. 34A and 34B).

Statistical comparison of the tumour volumes at each measurement point, once the treatment has been started, shows that the 3C_23K-YB2/0 antibody delays tumour growth (Kruskal-Wallis, via ANOVA). The T/C ratio calculated between the groups treated with 3C_23K-YB2/0 and vehicle shows a significant difference at all the measurement points, also once the treatment has been started. The logrank test also shows that in terms of survival, the group treated with 3C_23K-YB2/0 is statistically different from the group treated with the vehicle.

Table XV below presents the evolution of the tumour volumes (treated/control ratio, T/C in %) under the effect of the treatment with 3C_23K-YB2/0 in the META 2815 model.

TABLE XV

| | Measurement day | | | | |
|---|---|---|---|---|---|
| | 33 | 38 | 42 | 47 | 52 |
| T/C % | 92 | 38 | 26 | 22 | 21 |

Table XVI presents the statistical analyses obtained in the META 2815 model.

TABLE XVI

| | ANOVA | | | Kruskall-Wallis | | |
|---|---|---|---|---|---|---|
| Measurement day | F-ratio | P-value | Sig. | Test | P-value | Sig. |
| 33 | 0 | 0.9899 | | 0 | 1 | |
| 38 | 11.21 | 0.0007 | * | 8.30769 | 0.0039 | * |
| 42 | 9.51 | 0.0116 | * | 7.41026 | 0.0064 | * |
| 47 | 12.7 | 0.0052 | * | 8.33684 | 0.0038 | * |
| 52 | 16.14 | 0.0024 | * | 8.30769 | 0.0039 | * |

The invention claimed is:

1. A mutated humanized 12G4 monoclonal antibody, comprising or consisting of:
   a) a light chain comprising or consisting of:
      a variable region (VL) according to amino acid sequence SEQ ID NO: 2 or SEQ ID NO: 4, said VL consisting of three regions determining antigen recognition (CDR) surrounded by four framework regions (FR), and a constant region according to amino acid sequence SEQ ID NO: 6 or a sequence having at least 80% homology with SEQ ID NO: 6, and
   b) a heavy chain comprising or consisting of:
      a variable region (VH) according to amino acid sequence SEQ ID NO: 8, or SEQ ID NO: 10, and
      a constant region according to amino acid sequence of SEQ ID NO: 12 or a sequence having at least 80% homology with SEQ ID NO: 12,
   wherein said mutated humanized 12G4 monoclonal antibody comprises at least one mutation selected from the group consisting of:
   a mutation located in one of the CDR regions of the VL that is a substitution of at least one amino acid selected from the group consisting of S179P, one of E184K, E184G, or E184D, and S182F,
   a mutation located in one of the FR regions of VL that is a substitution of at least one amino acid selected from the group consisting of: I177T, I132T, A1431, 1150A, S158P, L175Q, Y178H, V187A, 51921, G197D, and F212S, and
   a mutation located in the heavy chain that is a substitution of at least one amino acid selected from the group consisting of: Q1E, Q3E or Q3R, Q6E, A9T, V11A, K12R, K13R, K19E, V20A, one of A24G, A24V or A24T, Q39E, A40V, S31G, L45P, D56N, A76T, A79T, R87G, T58A, Q62R, V67M, I70N, T74A, S77P, A79T, S88P, E89D, F102S, A1031, L110P, and 51141, and
   said mutated humanized 12 G4 monoclonal antibody has a $K_D$ for the human anti-Müllerian hormone type II receptor (AMHRII) at least equal to that of the chimeric 12G4 monoclonal antibody, comprising or consisting of:
   a) a light chain consisting of:
      a variable region according to amino acid sequence SEQ ID NO: 14, and
      a constant region according to amino acid sequence SEQ ID NO: 6,
   b) a heavy chain consisting of:
      a variable region according to amino acid sequence SEQ ID NO: 18, or SEQ ID NO: 10, and
      a constant region according to amino acid sequence SEQ ID NO: 12,
   for said receptor below $10^{-7}$M.

2. The mutated humanized 12G4 monoclonal antibody according to claim 1, wherein said at least one mutation is said substitution in said CDR region.

3. The mutated humanized 12G4 monoclonal antibody according to claim 1, wherein said at least one mutation is said substitution in said FR regions of VL.

4. The mutated humanized 12G4 monoclonal antibody according to claim 1, wherein said at least one mutation is said substitution in the heavy chain.

5. The mutated humanized 12G4 monoclonal antibody according to claim 1, wherein:
   a) the light chain comprises or consists of a variable region according to amino acid sequence of SEQ ID NO: 2 in which said at least one substitution in said CDR region is selected from the group consisting of: S179P, one of E184K, E184G, or E184D, or the light chain comprises or consists of a variable region according to amino acid sequence SEQ ID NO: 2 in which said at least one substitution in said CDR region is selected from the group consisting of: S179P, one of E184K, E184G, or E184D, and S182F, and said at least one substitution in the FR regions of VL is a substitution of at least one amino acid selected from the group consisting of: of I177T, I132T, A143T, T150A, S158P, L175Q, Y178H, V187A, S192T, G197D, or F212S, and a constant region according to amino acid sequence SEQ ID NO: 6, and
   b) the heavy chain comprises or consists of a variable region according to amino acid sequence SEQ ID NO: 8 in which said at least one substitution is selected from the group consisting of: Q1E, Q3E or Q3R, Q6E, A9T, V11A, K12R, K13R, K19E, V20A, one of A24G, A24V or A24T, Q39E, A40V, S31G, L45P, D56N, A76T, A79T, R87G, T58A, Q62R, V67M, I70N, T74A, S77P, A79T, S88P, E89D, F102S, A103T, L110P, and 5114T.

6. The mutated humanized 12G4 monoclonal antibody according to claim 1, wherein
   a) the light chain comprises or consists of a variable region according to an amino acid sequence selected from the group consisting of: SEQ ID NO: 22 or SEQ ID NO: 24, SEQ ID NO: 30 or SEQ ID NO: 32, SEQ ID NO: 34 or SEQ ID NO: 36, and SEQ ID NO: 46 or SEQ ID NO: 48, and of a constant region according to amino acid sequence SEQ ID NO: 6, and
   b) the heavy chain comprises or consists of a variable region according to an amino acid sequence selected from the group consisting of: SEQ ID NO: 38 or SEQ ID NO: 40, SEQ ID NO: 26 or SEQ ID NO: 28, SEQ ID NO: 8 or SEQ ID NO: 10, SEQ ID NO: 42 or SEQ ID NO: 44, and SEQ ID NO: 50 or SEQ ID NO: 52, and of a constant region according to amino acid sequence SEQ ID NO: 12.

7. The mutated humanized 12G4 monoclonal antibody according to claim 5, wherein the combination of the light chain and the heavy chain is selected from the group consisting of:
   a) the light chain consists of SEQ ID NO: 70 or SEQ ID NO: 72, and
   b) the heavy chain consists of SEQ ID NO: 74 or SEQ ID NO: 76;
   a) the light chain consists of SEQ ID NO: 78 or SEQ ID NO: 80, and
   b) the heavy chain consists of SEQ ID NO: 58 or SEQ ID NO: 60;
   a) the light chain consists of SEQ ID NO: 82 or SEQ ID NO: 84, and
   b) the heavy chain consists of SEQ ID NO: 86 or SEQ ID NO: 88;
   a) the light chain consists of SEQ ID NO: 78 or SEQ ID NO: 80, and
   b) the heavy chain consists of SEQ ID NO: 90 or SEQ ID NO: 92; and
   a) the light chain consists of SEQ ID NO: 94 or SEQ ID NO: 96, and
   b) the heavy chain consists of SEQ ID NO: 98 or SEQ ID NO: 100.

8. A fragment of the mutated humanized 12G4 monoclonal antibody according to claim 1, selected from the group consisting of: Fv, Fab, F(ab')2, Fab', dsFv, scFv, Sc(Fv)$_2$, and diabodies.

9. Pharmaceutical composition, comprising at least a monoclonal antibody according to claim 1, or a fragment of said monoclonal antibody selected from the group consisting of: Fv, Fab, F(ab')2, Fab', dsFv, scFv, Sc(Fv)$_2$, and diabodies, together with a pharmaceutically acceptable vehicle.

10. Product comprising a first pharmaceutical preparation comprising a monoclonal antibody according to claim 1, and a second pharmaceutical preparation comprising a conventional anticancer compound as a combined preparation for simultaneous, separate or sequential use in the treatment of patients with ovarian cancers.

11. A kit comprising at least:

the mutated monoclonal antibody according to claim 1, or a fragment of said mutated monoclonal antibody selected from the group of fragments consisting of: Fv, Fab, F(ab')2, Fab', dsFv, scFv, Sc(Fv)$_2$, and diabodies, for use in diagnosing a pathology associated with the human anti-Müllerian hormone type II receptor.

\* \* \* \* \*

SEQUENCE LISTING

```
<160> NUMBER OF SEQ ID NOS: 102

<210> SEQ ID NO 1
<211> LENGTH: 318
<212> TYPE: DNA
<213> ORGANISM: Artificial Sequence
<220> FEATURE:
<223> OTHER INFORMATION: Humanized 12G4 VL without leader
<220> FEATURE:
<221> NAME/KEY: CDS
<222> LOCATION: (1)..(318)

<400> SEQUENCE: 1 gac atc cag atg aca cag tcc cca tct acc ctg tct gct tcc gtg gga        48
Asp Ile Gln Met Thr Gln Ser Pro Ser Thr Leu Ser Ala Ser Val Gly
1               5                   10                  15 gat cgg gtg act atc acc tgc aga gca agc tcc gtg agg tac atc        96
Asp Arg Val Thr Ile Thr Cys Arg Ala Ser Ser Ser Val Arg Tyr Ile
                20                  25                  30 gct tgg tac cag cag aag cca gga aag gcc cca aag ctg ctg atc tac       144
Ala Trp Tyr Gln Gln Lys Pro Gly Lys Ala Pro Lys Leu Leu Ile Tyr
            35                  40                  45 tca acc tcc tcc ctg gaa tcc ggg gtg ccc agc aga ttc tca ggc agt       192
Ser Thr Ser Ser Leu Glu Ser Gly Val Pro Ser Arg Phe Ser Gly Ser
        50                  55                  60 ggc tcc ggc acc gaa ttc acc ctg acc atc agc tca ctg cag cct gac       240
Gly Ser Gly Thr Glu Phe Thr Leu Thr Ile Ser Ser Leu Gln Pro Asp
65                  70                  75                  80
```

```
gac ttc gca acc tac tac tgt ctg cag tgg agt agc tac cct tgg aca      288
Asp Phe Ala Thr Tyr Tyr Cys Leu Gln Trp Ser Ser Tyr Pro Trp Thr
                85                  90                  95 ttc ggc ggc ggc acc aag gtg gag atc aag                              318
Phe Gly Gly Gly Thr Lys Val Glu Ile Lys
            100                 105

<210> SEQ ID NO 2
<211> LENGTH: 106
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Ile Tyr
        35                  40                  45

Ser Thr Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys
            100                 105

<210> SEQ ID NO 3
<211> LENGTH: 384
<212> TYPE: DNA
<213> ORGANISM: Artificial Sequence
<220> FEATURE:
<223> OTHER INFORMATION: Humanized 12G4 VL with leader
<220> FEATURE:
<221> NAME/KEY: CDS
<222> LOCATION: (1)..(384)

<400> SEQUENCE: 3 atg gat atg aga gtg ccc gca cag ctg ctg ggt ctg ctg ctg ctg tgg      48
Met Asp Met Arg Val Pro Ala Gln Leu Leu Gly Leu Leu Leu Leu Trp
1               5                   10                  15 ctg ccc gga gcc aaa tgt gac atc cag atg aca cag tcc cca tct acc      96
Leu Pro Gly Ala Lys Cys Asp Ile Gln Met Thr Gln Ser Pro Ser Thr
            20                  25                  30 ctg tct gct tcc gtg gga gat cgg gtg act atc acc tgc aga gca agc      144
Leu Ser Ala Ser Val Gly Asp Arg Val Thr Ile Thr Cys Arg Ala Ser
        35                  40                  45 tcc tcc gtg agg tac atc gct tgg tac cag cag aag cca gga aag gcc      192
Ser Ser Val Arg Tyr Ile Ala Trp Tyr Gln Gln Lys Pro Gly Lys Ala
    50                  55                  60 cca aag ctg ctg atc tac tca acc tcc tcc ctg gaa tcc ggg gtg ccc      240
Pro Lys Leu Leu Ile Tyr Ser Thr Ser Ser Leu Glu Ser Gly Val Pro
65                  70                  75                  80 agc aga ttc tca ggc agt ggc tcc ggc acc gaa ttc acc ctg acc atc      288
Ser Arg Phe Ser Gly Ser Gly Ser Gly Thr Glu Phe Thr Leu Thr Ile
                85                  90                  95 agc tca ctg cag cct gac gac ttc gca acc tac tac tgt ctg cag tgg      336
Ser Ser Leu Gln Pro Asp Asp Phe Ala Thr Tyr Tyr Cys Leu Gln Trp
```

```
                100                 105                 110
agt agc tac cct tgg aca ttc ggc ggc ggc acc aag gtg gag atc aag          384
Ser Ser Tyr Pro Trp Thr Phe Gly Gly Gly Thr Lys Val Glu Ile Lys
        115                 120                 125
```

<210> SEQ ID NO 4
<211> LENGTH: 128
<212> TYPE: PRT
<213> ORGANISM: Artificial Sequence
<220> FEATURE:
<223> OTHER INFORMATION: Synthetic Construct

<400> SEQUENCE: 4

```
Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Ile Tyr Ser Thr Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125
```

<210> SEQ ID NO 5
<211> LENGTH: 321
<212> TYPE: DNA
<213> ORGANISM: Artificial Sequence
<220> FEATURE:
<223> OTHER INFORMATION: Humanized 12G4 CL
<220> FEATURE:
<221> NAME/KEY: CDS
<222> LOCATION: (1)..(321)

<400> SEQUENCE: 5

```
cgg acc gtc gcc gca cca agt gtc ttc atc ttc ccg cca tct gat gag          48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc          96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa         144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc         192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag         240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg         288
Lys His Lys Val Tyr Ala Cys Glu Val Thr His Gln Gly Leu Ser Ser
                85                  90                  95 ccc gtc aca aag agc ttc aac agg gga gag tgt                             321
Pro Val Thr Lys Ser Phe Asn Arg Gly Glu Cys
            100                 105
```

-continued

<210> SEQ ID NO 6
<211> LENGTH: 107
<212> TYPE: PRT
<213> ORGANISM: Artificial Sequence
<220> FEATURE:
<223> OTHER INFORMATION: Synthetic Construct

<400> SEQUENCE: 6

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 7
<211> LENGTH: 345
<212> TYPE: DNA
<213> ORGANISM: Artificial Sequence
<220> FEATURE:
<223> OTHER INFORMATION: Humanized 12G4 VH without leader
<220> FEATURE:
<221> NAME/KEY: CDS
<222> LOCATION: (1)..(345)

<400> SEQUENCE: 7

```
cag gtg cag ctg gtg cag agc ggg gcc gag gtg aag aag cct gga gcc    48
Gln Val Gln Leu Val Gln Ser Gly Ala Glu Val Lys Lys Pro Gly Ala
1               5                   10                  15 tca gtg aag gtg agt tgc aag gcc tcc ggt tac acc ttc acc agc tac    96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg   144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc   192
Gly Trp Ile Tyr Pro Gly Asp Asp Ser Thr Lys Tyr Ser Gln Lys Phe
    50                  55                  60 cag ggt cgc gtg acc att acc agg gac acc agc gcc tcc act gcc tac   240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt   288
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc   336
Thr Arg Gly Asp Arg Phe Ala Tyr Trp Gly Gln Gly Thr Leu Val Thr
            100                 105                 110 gtc agc agc                                                       345
Val Ser Ser
        115
```

```
<210> SEQ ID NO 8
<211> LENGTH: 115
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 9
<211> LENGTH: 402
<212> TYPE: DNA
<213> ORGANISM: Artificial Sequence
<220> FEATURE:
<223> OTHER INFORMATION: Humanized 12G4 VH with leader
<220> FEATURE:
<221> NAME/KEY: CDS
<222> LOCATION: (1)..(402)

<400> SEQUENCE: 9 atg gat tgg aca tgg cga atc ctg ttc ctg gtg gct gcc gca acc ggc       48
Met Asp Trp Thr Trp Arg Ile Leu Phe Leu Val Ala Ala Ala Thr Gly
1               5                   10                  15 gcc cac agc cag gtg cag ctg gtg cag agc ggg gcc gag gtg aag aag       96
Ala His Ser Gln Val Gln Leu Val Gln Ser Gly Ala Glu Val Lys Lys
            20                  25                  30 cct gga gcc tca gtg aag gtg agt tgc aag gcc tcc ggt tac acc ttc      144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga ctg      192
Thr Ser Tyr His Ile His Trp Val Arg Gln Ala Pro Gly Gln Arg Leu
    50                  55                  60 gag tgg atg ggc tgg atc tac cct gga gat gac tcc acc aag tac tcc      240
Glu Trp Met Gly Trp Ile Tyr Pro Gly Asp Asp Ser Thr Lys Tyr Ser
65                  70                  75                  80 cag aag ttc cag ggt cgc gtg acc att acc agg gac acc agc gcc tcc      288
Gln Lys Phe Gln Gly Arg Val Thr Ile Thr Arg Asp Thr Ser Ala Ser
                85                  90                  95 act gcc tac atg gag ctg tct tcc ctg aga tct gag gat acc gca gtc      336
Thr Ala Tyr Met Glu Leu Ser Ser Leu Arg Ser Glu Asp Thr Ala Val
            100                 105                 110 tac tac tgt aca cgg ggg gac cgc ttt gct tac tgg ggg cag ggc act      384
Tyr Tyr Cys Thr Arg Gly Asp Arg Phe Ala Tyr Trp Gly Gln Gly Thr
        115                 120                 125 ctg gtg acc gtc agc agc                                              402
Leu Val Thr Val Ser Ser
```

Leu Val Thr Val Ser Ser
    130

<210> SEQ ID NO 10
<211> LENGTH: 134
<212> TYPE: PRT
<213> ORGANISM: Artificial Sequence
<220> FEATURE:
<223> OTHER INFORMATION: Synthetic Construct

<400> SEQUENCE: 10

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr His Ile His Trp Val Arg Gln Ala Pro Gly Gln Arg Leu
    50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser
    130

<210> SEQ ID NO 11
<211> LENGTH: 990
<212> TYPE: DNA
<213> ORGANISM: Artificial Sequence
<220> FEATURE:
<223> OTHER INFORMATION: Humanized 12G4 CH
<220> FEATURE:
<221> NAME/KEY: CDS
<222> LOCATION: (1)..(990)

<400> SEQUENCE: 11 gcc agc acc aag ggc cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc       240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag       288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc       336
Lys Val Glu Pro Lys Ser Cys Asp Lys Thr His Thr Cys Pro Pro Cys

```
                100                 105                 110
cca gca cct gaa ctc ctg ggg gga ccg tca gtc ttc ctc ttc ccc cca    384
Pro Ala Pro Glu Leu Leu Gly Gly Pro Ser Val Phe Leu Phe Pro Pro
            115                 120                 125 aaa ccc aag gac acc ctc atg atc tcc cgg acc cct gag gtc aca tgc    432
Lys Pro Lys Asp Thr Leu Met Ile Ser Arg Thr Pro Glu Val Thr Cys
130                 135                 140 gtg gtg gtg gac gtg agc cac gaa gac cct gag gtc aag ttc aac tgg    480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag    528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg    576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac    624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg    672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag    720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat    768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac    816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc    864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac    912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg    960
Val Phe Ser Cys Ser Val Met His Glu Ala Leu His Asn His Tyr Thr
305                 310                 315                 320 cag aag agc ctc tcc ctg tct ccg ggt aaa                            990
Gln Lys Ser Leu Ser Leu Ser Pro Gly Lys
                325                 330

<210> SEQ ID NO 12
<211> LENGTH: 330
<212> TYPE: PRT
<213> ORGANISM: Artificial Sequence
<220> FEATURE:
<223> OTHER INFORMATION: Synthetic Construct

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 318
<212> TYPE: DNA
<213> ORGANISM: Artificial Sequence
<220> FEATURE:
<223> OTHER INFORMATION: Chimeric 12G4 VL without leader
<220> FEATURE:
<221> NAME/KEY: CDS
<222> LOCATION: (1)..(318)

<400> SEQUENCE: 13 caa att gtt ctc acc cag tct cca gca atc atg tct gca tct cta ggg    48
Gln Ile Val Leu Thr Gln Ser Pro Ala Ile Met Ser Ala Ser Leu Gly
 1               5                  10                  15 gag ggg atc acc cta acc tgc agt gcc agc tcg agt gta cgt tac ata    96
Glu Gly Ile Thr Leu Thr Cys Ser Ala Ser Ser Ser Val Arg Tyr Ile
                20                  25                  30 cac tgg tac cag cag aag tca ggc act tct ccc aaa ctc ttg att tat   144
His Trp Tyr Gln Gln Lys Ser Gly Thr Ser Pro Lys Leu Leu Ile Tyr
            35                  40                  45 agc aca tcc aac ctg gct tct gga gtc cct tct cgc ttc agt ggc agt   192
Ser Thr Ser Asn Leu Ala Ser Gly Val Pro Ser Arg Phe Ser Gly Ser
```

```
                    50                  55                  60
ggg tct ggg acc ttt cat tct ctc aca atc agc agt gtg gag gct gaa    240
Gly Ser Gly Thr Phe His Ser Leu Thr Ile Ser Ser Val Glu Ala Glu
 65                  70                  75                  80 gat gct gcc gat tat tac tgc ctt cag tgg agt agt tat ccg tgg acg    288
Asp Ala Ala Asp Tyr Tyr Cys Leu Gln Trp Ser Ser Tyr Pro Trp Thr
                     85                  90                  95 ttc ggt gga ggc acc aag ctg gaa atc aaa                            318
Phe Gly Gly Gly Thr Lys Leu Glu Ile Lys
                100                 105

<210> SEQ ID NO 14
<211> LENGTH: 106
<212> TYPE: PRT
<213> ORGANISM: Artificial Sequence
<220> FEATURE:
<223> OTHER INFORMATION: Synthetic Construct

<400> SEQUENCE: 14

Gln Ile Val Leu Thr Gln Ser Pro Ala Ile Met Ser Ala Ser Leu Gly
  1               5                  10                  15

Glu Gly Ile Thr Leu Thr Cys Ser Ala Ser Ser Ser Val Arg Tyr Ile
                 20                  25                  30

His Trp Tyr Gln Gln Lys Ser Gly Thr Ser Pro Lys Leu Leu Ile Tyr
             35                  40                  45

Ser Thr Ser Asn Leu Ala Ser Gly Val Pro Ser Arg Phe Ser Gly Ser
         50                  55                  60

Gly Ser Gly Thr Phe His Ser Leu Thr Ile Ser Ser Val Glu Ala Glu
 65                  70                  75                  80

Asp Ala Ala Asp Tyr Tyr Cys Leu Gln Trp Ser Ser Tyr Pro Trp Thr
                     85                  90                  95

Phe Gly Gly Gly Thr Lys Leu Glu Ile Lys
                100                 105

<210> SEQ ID NO 15
<211> LENGTH: 384
<212> TYPE: DNA
<213> ORGANISM: Artificial Sequence
<220> FEATURE:
<223> OTHER INFORMATION: Chimeric 12G4 VL with leader
<220> FEATURE:
<221> NAME/KEY: CDS
<222> LOCATION: (1)..(384)

<400> SEQUENCE: 15 atg gat ttt cag gtg cag att ttc agc ttc ctg cta atc agt gcc tca    48
Met Asp Phe Gln Val Gln Ile Phe Ser Phe Leu Leu Ile Ser Ala Ser
  1               5                  10                  15 gtc ata atg tcc aga gga caa att gtt ctc acc cag tct cca gca atc    96
Val Ile Met Ser Arg Gly Gln Ile Val Leu Thr Gln Ser Pro Ala Ile
                 20                  25                  30 atg tct gca tct cta ggg gag ggg atc acc cta acc tgc agt gcc agc    144
Met Ser Ala Ser Leu Gly Glu Gly Ile Thr Leu Thr Cys Ser Ala Ser
             35                  40                  45 tcg agt gta cgt tac ata cac tgg tac cag cag aag tca ggc act tct    192
Ser Ser Val Arg Tyr Ile His Trp Tyr Gln Gln Lys Ser Gly Thr Ser
         50                  55                  60 ccc aaa ctc ttg att tat agc aca tcc aac ctg gct tct gga gtc cct    240
Pro Lys Leu Leu Ile Tyr Ser Thr Ser Asn Leu Ala Ser Gly Val Pro
 65                  70                  75                  80 tct cgc ttc agt ggc agt ggg tct ggg acc ttt cat tct ctc aca atc    288
Ser Arg Phe Ser Gly Ser Gly Ser Gly Thr Phe His Ser Leu Thr Ile
```

```
Ser Arg Phe Ser Gly Ser Gly Ser Gly Thr Phe His Ser Leu Thr Ile
            85                  90                  95 agc agt gtg gag gct gaa gat gct gcc gat tat tac tgc ctt cag tgg      336
Ser Ser Val Glu Ala Glu Asp Ala Ala Asp Tyr Tyr Cys Leu Gln Trp
            100                 105                 110 agt agt tat ccg tgg acg ttc ggt gga ggc acc aag ctg gaa atc aaa      384
Ser Ser Tyr Pro Trp Thr Phe Gly Gly Gly Thr Lys Leu Glu Ile Lys
            115                 120                 125

<210> SEQ ID NO 16
<211> LENGTH: 128
<212> TYPE: PRT
<213> ORGANISM: Artificial Sequence
<220> FEATURE:
<223> OTHER INFORMATION: Synthetic Construct

<400> SEQUENCE: 16

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Gly Ile Thr Leu Thr Cys Ser Ala Ser
            35                  40                  45

Ser Ser Val Arg Tyr Ile His Trp Tyr Gln Gln Lys Ser Gly Thr Ser
    50                  55                  60

Pro Lys Leu Leu Ile Tyr Ser Thr Ser Asn Leu Ala Ser Gly Val Pro
65                  70                  75                  80

Ser Arg Phe Ser Gly Ser Gly Ser Gly Thr Phe His Ser Leu Thr Ile
            85                  90                  95

Ser Ser Val Glu Ala Glu Asp Ala Ala Asp Tyr Tyr Cys Leu Gln Trp
            100                 105                 110

Ser Ser Tyr Pro Trp Thr Phe Gly Gly Gly Thr Lys Leu Glu Ile Lys
            115                 120                 125

<210> SEQ ID NO 17
<211> LENGTH: 345
<212> TYPE: DNA
<213> ORGANISM: Artificial Sequence
<220> FEATURE:
<223> OTHER INFORMATION: Chimeric 12G4 VH without leader
<220> FEATURE:
<221> NAME/KEY: CDS
<222> LOCATION: (1)..(345)

<400> SEQUENCE: 17 cag gtc cag ctg cag cag tct gga cct gaa ctg gtg aag cct ggg gct      48
Gln Val Gln Leu Gln Gln Ser Gly Pro Glu Leu Val Lys Pro Gly Ala
1               5                   10                  15 tca gtg agg atg tcc tgc aag gct tct ggc tac acc ttc aca agt tac      96
Ser Val Arg Met Ser Cys Lys Ala Ser Gly Tyr Thr Phe Thr Ser Tyr
            20                  25                  30 cat ata cac tgg gtg aag cag agg cct gga cag gga ctt gag tgg att      144
His Ile His Trp Val Lys Gln Arg Pro Gly Gln Gly Leu Glu Trp Ile
            35                  40                  45 gga tgg att tat cct ggc gat gat tct act aaa tac aat gag aag ttc      192
Gly Trp Ile Tyr Pro Gly Asp Asp Ser Thr Lys Tyr Asn Glu Lys Phe
    50                  55                  60 aag ggc aag acc aca ctg act gca gac aaa tcc tcc agc aca gcc tac      240
Lys Gly Lys Thr Thr Leu Thr Ala Asp Lys Ser Ser Ser Thr Ala Tyr
65                  70                  75                  80 atg ttg ctc agc agc ctg acc tct gag gac tct gcg atc tat ttc tgt      288
```

```
Met Leu Leu Ser Ser Leu Thr Ser Glu Asp Ser Ala Ile Tyr Phe Cys
             85                  90                  95 aca agg ggg gac cgg ttt gct tac tgg ggc caa ggg act ctg gtc act    336
Thr Arg Gly Asp Arg Phe Ala Tyr Trp Gly Gln Gly Thr Leu Val Thr
            100                 105                 110 gtc tct gca                                                        345
Val Ser Ala
        115

<210> SEQ ID NO 18
<211> LENGTH: 115
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Ser Tyr
            20                  25                  30

His Ile His Trp Val Lys Gln Arg Pro Gly Gln Gly Leu Glu Trp Ile
        35                  40                  45

Gly Trp Ile Tyr Pro Gly Asp Asp Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Ser Leu Thr Ser Glu Asp Ser Ala Ile Tyr Phe Cys
             85                  90                  95

Thr Arg Gly Asp Arg Phe Ala Tyr Trp Gly Gln Gly Thr Leu Val Thr
            100                 105                 110

Val Ser Ala
        115

<210> SEQ ID NO 19
<211> LENGTH: 402
<212> TYPE: DNA
<213> ORGANISM: Artificial Sequence
<220> FEATURE:
<223> OTHER INFORMATION: Chimeric 12G4 VH with leader
<220> FEATURE:
<221> NAME/KEY: CDS
<222> LOCATION: (1)..(402)

<400> SEQUENCE: 19 atg cga tgg agc tgg atc ttt ctc ttc ctc ctg tca ata act gca agt    48
Met Arg Trp Ser Trp Ile Phe Leu Phe Leu Leu Ser Ile Thr Ala Ser
1               5                   10                  15 gtc cat tgc cag gtc cag ctg cag cag tct gga cct gaa ctg gtg aag    96
Val His Cys Gln Val Gln Leu Gln Gln Ser Gly Pro Glu Leu Val Lys
            20                  25                  30 cct ggg gct tca gtg agg atg tcc tgc aag gct tct ggc tac acc ttc    144
Pro Gly Ala Ser Val Arg Met Ser Cys Lys Ala Ser Gly Tyr Thr Phe
        35                  40                  45 aca agt tac cat ata cac tgg gtg aag cag agg cct gga cag gga ctt    192
Thr Ser Tyr His Ile His Trp Val Lys Gln Arg Pro Gly Gln Gly Leu
    50                  55                  60 gag tgg att gga tgg att tat cct ggc gat gat tct act aaa tac aat    240
Glu Trp Ile Gly Trp Ile Tyr Pro Gly Asp Asp Ser Thr Lys Tyr Asn
65                  70                  75                  80 gag aag ttc aag ggc aag acc aca ctg act gca gac aaa tcc tcc agc    288
```

```
                                                                                       -continued Glu Lys Phe Lys Gly Lys Thr Thr Leu Thr Ala Asp Lys Ser Ser Ser
                85                  90                  95 aca gcc tac atg ttg ctc agc agc ctg acc tct gag gac tct gcg atc        336
Thr Ala Tyr Met Leu Leu Ser Ser Leu Thr Ser Glu Asp Ser Ala Ile
            100                 105                 110 tat ttc tgt aca agg ggg gac cgg ttt gct tac tgg ggc caa ggg act        384
Tyr Phe Cys Thr Arg Gly Asp Arg Phe Ala Tyr Trp Gly Gln Gly Thr
        115                 120                 125 ctg gtc act gtc tct gca                                                402
Leu Val Thr Val Ser Ala
    130

<210> SEQ ID NO 20
<211> LENGTH: 134
<212> TYPE: PRT
<213> ORGANISM: Artificial Sequence
<220> FEATURE:
<223> OTHER INFORMATION: Synthetic Construct

<400> SEQUENCE: 20

Met Arg Trp Ser Trp Ile Phe Leu Phe Leu Leu Ser Ile Thr Ala Ser
1               5                   10                  15

Val His Cys Gln Val Gln Leu Gln Gln Ser Gly Pro Glu Leu Val Lys
            20                  25                  30

Pro Gly Ala Ser Val Arg Met Ser Cys Lys Ala Ser Gly Tyr Thr Phe
        35                  40                  45

Thr Ser Tyr His Ile His Trp Val Lys Gln Arg Pro Gly Gln Gly Leu
    50                  55                  60

Glu Trp Ile Gly Trp Ile Tyr Pro Gly Asp Asp Ser Thr Lys Tyr Asn
65                  70                  75                  80

Glu Lys Phe Lys Gly Lys Thr Thr Leu Thr Ala Asp Lys Ser Ser Ser
                85                  90                  95

Thr Ala Tyr Met Leu Leu Ser Ser Leu Thr Ser Glu Asp Ser Ala Ile
            100                 105                 110

Tyr Phe Cys Thr Arg Gly Asp Arg Phe Ala Tyr Trp Gly Gln Gly Thr
        115                 120                 125

Leu Val Thr Val Ser Ala
    130

<210> SEQ ID NO 21
<211> LENGTH: 318
<212> TYPE: DNA
<213> ORGANISM: Artificial Sequence
<220> FEATURE:
<223> OTHER INFORMATION: 3C_23 VL without leader
<220> FEATURE:
<221> NAME/KEY: CDS
<222> LOCATION: (1)..(318)

<400> SEQUENCE: 21 gac atc cag atg aca cag tcc cca tct acc ctg tct gct tcc gtg gga        48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc        96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac        144
Ala Trp Tyr Gln Gln Lys Pro Gly Lys Ala Pro Lys Leu Leu Thr Tyr
        35                  40                  45 cca acc tcc tcc ctg gaa tcc ggg gtg ccc agc aga ttc tca ggc agt        192
Pro Thr Ser Ser Leu Glu Ser Gly Val Pro Ser Arg Phe Ser Gly Ser
```

```
ggc tcc ggc acc gaa ttc acc ctg acc atc agc tca ctg cag cct gac    240
Gly Ser Gly Thr Glu Phe Thr Leu Thr Ile Ser Ser Leu Gln Pro Asp
 65                  70                  75                  80 gac ttc gca acc tac tac tgt ctg cag tgg agt agc tac cct tgg aca    288
Asp Phe Ala Thr Tyr Tyr Cys Leu Gln Trp Ser Ser Tyr Pro Trp Thr
                 85                  90                  95 ttc ggc ggc ggc acc aag gtg gag atc aag                            318
Phe Gly Gly Gly Thr Lys Val Glu Ile Lys
            100                 105
```

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Ser Ser Val Arg Tyr Ile
                 20                  25                  30

Ala Trp Tyr Gln Gln Lys Pro Gly Lys Ala Pro Lys Leu Leu Thr Tyr
             35                  40                  45

Pro Thr Ser Ser Leu Glu Ser Gly Val Pro Ser Arg Phe Ser Gly Ser
         50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
            100                 105
```

<210> SEQ ID NO 23
<211> LENGTH: 384
<212> TYPE: DNA
<213> ORGANISM: Artificial Sequence
<220> FEATURE:
<223> OTHER INFORMATION: 3C_23 VL with leader
<220> FEATURE:
<221> NAME/KEY: CDS
<222> LOCATION: (1)..(384)

<400> SEQUENCE: 23

```
atg gat atg aga gtg ccc gca cag ctg ctg ggt ctg ctg ctg ctg tgg     48
Met Asp Met Arg Val Pro Ala Gln Leu Leu Gly Leu Leu Leu Leu Trp
  1               5                  10                  15 ctg ccc gga gcc aaa tgt gac atc cag atg aca cag tcc cca tct acc     96
Leu Pro Gly Ala Lys Cys Asp Ile Gln Met Thr Gln Ser Pro Ser Thr
                 20                  25                  30 ctg tct gct tcc gtg gga gat cgg gtg act atc acc tgc aga gca agc    144
Leu Ser Ala Ser Val Gly Asp Arg Val Thr Ile Thr Cys Arg Ala Ser
             35                  40                  45 tcc tcc gtg agg tac atc gct tgg tac cag cag aag cca gga aag gcc    192
Ser Ser Val Arg Tyr Ile Ala Trp Tyr Gln Gln Lys Pro Gly Lys Ala
         50                  55                  60 cca aag ctg ctg acc tac cca acc tcc tcc ctg gaa tcc ggg gtg ccc    240
Pro Lys Leu Leu Thr Tyr Pro Thr Ser Ser Leu Glu Ser Gly Val Pro
 65                  70                  75                  80 agc aga ttc tca ggc agt ggc tcc ggc acc gaa ttc acc ctg acc atc    288
Ser Arg Phe Ser Gly Ser Gly Ser Gly Thr Glu Phe Thr Leu Thr Ile
```

```
Ser Arg Phe Ser Gly Ser Gly Ser Gly Thr Glu Phe Thr Leu Thr Ile
                85                  90                  95 agc tca ctg cag cct gac gac ttc gca acc tac tac tgt ctg cag tgg      336
Ser Ser Leu Gln Pro Asp Asp Phe Ala Thr Tyr Tyr Cys Leu Gln Trp
            100                 105                 110 agt agc tac cct tgg aca ttc ggc ggc ggc acc aag gtg gag atc aag      384
Ser Ser Tyr Pro Trp Thr Phe Gly Gly Gly Thr Lys Val Glu Ile Lys
        115                 120                 125

<210> SEQ ID NO 24
<211> LENGTH: 128
<212> TYPE: PRT
<213> ORGANISM: Artificial Sequence
<220> FEATURE:
<223> OTHER INFORMATION: Synthetic Construct

<400> SEQUENCE: 24

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Thr Tyr Pro Thr Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

<210> SEQ ID NO 25
<211> LENGTH: 345
<212> TYPE: DNA
<213> ORGANISM: Artificial Sequence
<220> FEATURE:
<223> OTHER INFORMATION: 3C_23 VH without leader
<220> FEATURE:
<221> NAME/KEY: CDS
<222> LOCATION: (1)..(345)

<400> SEQUENCE: 25 cag gtg cgg ctg gtg cag agc ggg gcc gag gtg aag aag cct gga gcc      48
Gln Val Arg Leu Val Gln Ser Gly Ala Glu Val Lys Lys Pro Gly Ala
1               5                   10                  15 tca gtg aag gtg agt tgc aag gcc tcc ggt tac acc ttc acc agc tac      96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg      144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc      192
Gly Trp Ile Tyr Pro Gly Asp Asp Ser Thr Lys Tyr Ser Gln Lys Phe
    50                  55                  60 cag ggt cgc gtg acc att acc agg gac acc agc gcc tcc act gcc tac      240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt      288
```

```
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc      336
Thr Arg Gly Asp Arg Phe Ala Tyr Trp Gly Gln Gly Thr Leu Val Thr
            100                 105                 110 gtc tcg agc                                                          345
Val Ser Ser
        115

<210> SEQ ID NO 26
<211> LENGTH: 115
<212> TYPE: PRT
<213> ORGANISM: Artificial Sequence
<220> FEATURE:
<223> OTHER INFORMATION: Synthetic Construct

<400> SEQUENCE: 26

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 27
<211> LENGTH: 402
<212> TYPE: DNA
<213> ORGANISM: Artificial Sequence
<220> FEATURE:
<223> OTHER INFORMATION: 3C_23 VH with leader
<220> FEATURE:
<221> NAME/KEY: CDS
<222> LOCATION: (1)..(402)

<400> SEQUENCE: 27 atg gat tgg aca tgg cga atc ctg ttc ctg gtg gct gcc gca acc ggc      48
Met Asp Trp Thr Trp Arg Ile Leu Phe Leu Val Ala Ala Ala Thr Gly
1               5                   10                  15 gcc cac agc cag gtg cgg ctg gtg cag agc ggg gcc gag gtg aag aag      96
Ala His Ser Gln Val Arg Leu Val Gln Ser Gly Ala Glu Val Lys Lys
            20                  25                  30 cct gga gcc tca gtg aag gtg agt tgc aag gcc tcc ggt tac acc ttc      144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga ctg      192
Thr Ser Tyr His Ile His Trp Val Arg Gln Ala Pro Gly Gln Arg Leu
    50                  55                  60 gag tgg atg ggc tgg atc tac cct gga gat gac tcc acc aag tac tcc      240
Glu Trp Met Gly Trp Ile Tyr Pro Gly Asp Asp Ser Thr Lys Tyr Ser
65                  70                  75                  80 cag aag ttc cag ggt cgc gtg acc att acc agg gac acc agc gcc tcc      288
```

```
Gln Lys Phe Gln Gly Arg Val Thr Ile Thr Arg Asp Thr Ser Ala Ser
                85                  90                  95 act gcc tac atg gag ctg tct tcc ctg aga tct gag gat acc gca gtc    336
Thr Ala Tyr Met Glu Leu Ser Ser Leu Arg Ser Glu Asp Thr Ala Val
            100                 105                 110 tac tac tgt aca cgg ggg gac cgc ttt gct tac tgg ggg cag ggc act    384
Tyr Tyr Cys Thr Arg Gly Asp Arg Phe Ala Tyr Trp Gly Gln Gly Thr
        115                 120                 125 ctg gtg acc gtc tcg agc                                            402
Leu Val Thr Val Ser Ser
    130

<210> SEQ ID NO 28
<211> LENGTH: 134
<212> TYPE: PRT
<213> ORGANISM: Artificial Sequence
<220> FEATURE:
<223> OTHER INFORMATION: Synthetic Construct

<400> SEQUENCE: 28

Met Asp Trp Thr Trp Arg Ile Leu Phe Leu Val Ala Ala Ala Thr Gly
 1               5                  10                  15

Ala His Ser Gln Val Arg Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr His Ile His Trp Val Arg Gln Ala Pro Gly Gln Arg Leu
    50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser
    130

<210> SEQ ID NO 29
<211> LENGTH: 318
<212> TYPE: DNA
<213> ORGANISM: Artificial Sequence
<220> FEATURE:
<223> OTHER INFORMATION: 6B_78 VL without leader
<220> FEATURE:
<221> NAME/KEY: CDS
<222> LOCATION: (1)..(318)

<400> SEQUENCE: 29 gac atc cag atg aca cag tcc cca tct acc ctg tct gct tcc gtg gga    48
Asp Ile Gln Met Thr Gln Ser Pro Ser Thr Leu Ser Ala Ser Val Gly
 1               5                  10                  15 gat cgg gtg act atc acc tgc aga gca agc tcc tcc gtg agg tac atc    96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg atc tac    144
Ala Trp Tyr Gln Gln Lys Pro Gly Lys Ala Pro Lys Leu Leu Ile Tyr
        35                  40                  45 tca acc tcc tcc ctg aaa tcc ggg gtg ccc agc aga ttc tca ggc agt    192
Ser Thr Ser Ser Leu Lys Ser Gly Val Pro Ser Arg Phe Ser Gly Ser
```

```
ggc tcc ggc acc gaa ttc acc ctg acc atc agc tca ctg cag cct gac      240
Gly Ser Gly Thr Glu Phe Thr Leu Thr Ile Ser Ser Leu Gln Pro Asp
 65                  70                  75                  80 gac ttc gca acc tac tac tgt ctg cag tgg agt agc tac cct tgg aca      288
Asp Phe Ala Thr Tyr Tyr Cys Leu Gln Trp Ser Ser Tyr Pro Trp Thr
                 85                  90                  95 ttc ggc ggc ggc acc aag gtg gag atc aag                              318
Phe Gly Gly Gly Thr Lys Val Glu Ile Lys
            100                 105

<210> SEQ ID NO 30
<211> LENGTH: 106
<212> TYPE: PRT
<213> ORGANISM: Artificial Sequence
<220> FEATURE:
<223> OTHER INFORMATION: Synthetic Construct

<400> SEQUENCE: 30

Asp Ile Gln Met Thr Gln Ser Pro Ser Thr Leu Ser Ala Ser Val Gly
 1               5                  10                  15

Asp Arg Val Thr Ile Thr Cys Arg Ala Ser Ser Ser Val Arg Tyr Ile
                20                  25                  30

Ala Trp Tyr Gln Gln Lys Pro Gly Lys Ala Pro Lys Leu Leu Ile Tyr
             35                  40                  45

Ser Thr Ser Ser Leu Lys Ser Gly Val Pro Ser Arg Phe Ser Gly Ser
         50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
            100                 105

<210> SEQ ID NO 31
<211> LENGTH: 384
<212> TYPE: DNA
<213> ORGANISM: Artificial Sequence
<220> FEATURE:
<223> OTHER INFORMATION: 6B_78 VL with leader
<220> FEATURE:
<221> NAME/KEY: CDS
<222> LOCATION: (1)..(384)

<400> SEQUENCE: 31 atg gat atg aga gtg ccc gca cag ctg ctg ggt ctg ctg ctg ctg tgg       48
Met Asp Met Arg Val Pro Ala Gln Leu Leu Gly Leu Leu Leu Leu Trp
 1               5                  10                  15 ctg ccc gga gcc aaa tgt gac atc cag atg aca cag tcc cca tct acc       96
Leu Pro Gly Ala Lys Cys Asp Ile Gln Met Thr Gln Ser Pro Ser Thr
                20                  25                  30 ctg tct gct tcc gtg gga gat cgg gtg act atc acc tgc aga gca agc      144
Leu Ser Ala Ser Val Gly Asp Arg Val Thr Ile Thr Cys Arg Ala Ser
             35                  40                  45 tcc tcc gtg agg tac atc gct tgg tac cag cag aag cca gga aag gcc      192
Ser Ser Val Arg Tyr Ile Ala Trp Tyr Gln Gln Lys Pro Gly Lys Ala
         50                  55                  60 cca aag ctg ctg atc tac tca acc tcc tcc ctg aaa tcc ggg gtg ccc      240
Pro Lys Leu Leu Ile Tyr Ser Thr Ser Ser Leu Lys Ser Gly Val Pro
 65                  70                  75                  80 agc aga ttc tca ggc agt ggc tcc ggc acc gaa ttc acc ctg acc atc      288
Ser Arg Phe Ser Gly Ser Gly Ser Gly Thr Glu Phe Thr Leu Thr Ile
```

```
Ser Arg Phe Ser Gly Ser Gly Ser Gly Thr Glu Phe Thr Leu Thr Ile
            85                  90                  95 agc tca ctg cag cct gac gac ttc gca acc tac tac tgt ctg cag tgg       336
Ser Ser Leu Gln Pro Asp Asp Phe Ala Thr Tyr Tyr Cys Leu Gln Trp
            100                 105                 110 agt agc tac cct tgg aca ttc ggc ggc ggc acc aag gtg gag atc aag       384
Ser Ser Tyr Pro Trp Thr Phe Gly Gly Gly Thr Lys Val Glu Ile Lys
            115                 120                 125

<210> SEQ ID NO 32
<211> LENGTH: 128
<212> TYPE: PRT
<213> ORGANISM: Artificial Sequence
<220> FEATURE:
<223> OTHER INFORMATION: Synthetic Construct

<400> SEQUENCE: 32

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
            35                  40                  45

Ser Ser Val Arg Tyr Ile Ala Trp Tyr Gln Gln Lys Pro Gly Lys Ala
        50                  55                  60

Pro Lys Leu Leu Ile Tyr Ser Thr Ser Ser Leu Lys Ser Gly Val Pro
65                  70                  75                  80

Ser Arg Phe Ser Gly Ser Gly Ser Gly Thr Glu Phe Thr Leu Thr Ile
            85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
            115                 120                 125

<210> SEQ ID NO 33
<211> LENGTH: 318
<212> TYPE: DNA
<213> ORGANISM: Artificial Sequence
<220> FEATURE:
<223> OTHER INFORMATION: 3C_23K VL without leader
<220> FEATURE:
<221> NAME/KEY: CDS
<222> LOCATION: (1)..(318)

<400> SEQUENCE: 33 gac atc cag atg aca cag tcc cca tct acc ctg tct gct tcc gtg gga        48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc        96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac       144
Ala Trp Tyr Gln Gln Lys Pro Gly Lys Ala Pro Lys Leu Leu Thr Tyr
            35                  40                  45 cca acc tcc tcc ctg aaa tcc ggg gtg ccc agc aga ttc tca ggc agt       192
Pro Thr Ser Ser Leu Lys Ser Gly Val Pro Ser Arg Phe Ser Gly Ser
        50                  55                  60 ggc tcc ggc acc gaa ttc acc ctg acc atc agc tca ctg cag cct gac       240
Gly Ser Gly Thr Glu Phe Thr Leu Thr Ile Ser Ser Leu Gln Pro Asp
65                  70                  75                  80 gac ttc gca acc tac tac tgt ctg cag tgg agt agc tac cct tgg aca       288
```

```
Asp Phe Ala Thr Tyr Tyr Cys Leu Gln Trp Ser Ser Tyr Pro Trp Thr
            85                  90                  95 ttc ggc ggc ggc acc aag gtg gag atc aag                              318
Phe Gly Gly Gly Thr Lys Val Glu Ile Lys
            100                 105

<210> SEQ ID NO 34
<211> LENGTH: 106
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
            85                  90                  95

Phe Gly Gly Gly Thr Lys Val Glu Ile Lys
            100                 105

<210> SEQ ID NO 35
<211> LENGTH: 384
<212> TYPE: DNA
<213> ORGANISM: Artificial Sequence
<220> FEATURE:
<223> OTHER INFORMATION: 3C_23K VL with leader
<220> FEATURE:
<221> NAME/KEY: CDS
<222> LOCATION: (1)..(384)

<400> SEQUENCE: 35 atg gat atg aga gtg ccc gca cag ctg ctg ggt ctg ctg ctg ctg tgg    48
Met Asp Met Arg Val Pro Ala Gln Leu Leu Gly Leu Leu Leu Leu Trp
1               5                   10                  15 ctg ccc gga gcc aaa tgt gac atc cag atg aca cag tcc cca tct acc    96
Leu Pro Gly Ala Lys Cys Asp Ile Gln Met Thr Gln Ser Pro Ser Thr
            20                  25                  30 ctg tct gct tcc gtg gga gat cgg gtg act atc acc tgc aga gca agc    144
Leu Ser Ala Ser Val Gly Asp Arg Val Thr Ile Thr Cys Arg Ala Ser
        35                  40                  45 tcc tcc gtg agg tac atc gct tgg tac cag cag aag cca gga aag gcc    192
Ser Ser Val Arg Tyr Ile Ala Trp Tyr Gln Gln Lys Pro Gly Lys Ala
    50                  55                  60 cca aag ctg ctg acc tac cca acc tcc tcc ctg aaa tcc ggg gtg ccc    240
Pro Lys Leu Leu Thr Tyr Pro Thr Ser Ser Leu Lys Ser Gly Val Pro
65                  70                  75                  80 agc aga ttc tca ggc agt ggc tcc ggc acc gaa ttc acc ctg acc atc    288
Ser Arg Phe Ser Gly Ser Gly Ser Gly Thr Glu Phe Thr Leu Thr Ile
            85                  90                  95 agc tca ctg cag cct gac gac ttc gca acc tac tac tgt ctg cag tgg    336
Ser Ser Leu Gln Pro Asp Asp Phe Ala Thr Tyr Tyr Cys Leu Gln Trp
            100                 105                 110
```

```
agt agc tac cct tgg aca ttc ggc ggc ggc acc aag gtg gag atc aag      384
Ser Ser Tyr Pro Trp Thr Phe Gly Gly Gly Thr Lys Val Glu Ile Lys
        115                 120                 125

<210> SEQ ID NO 36
<211> LENGTH: 128
<212> TYPE: PRT
<213> ORGANISM: Artificial Sequence
<220> FEATURE:
<223> OTHER INFORMATION: Synthetic Construct

<400> SEQUENCE: 36

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Thr Tyr Pro Thr Ser Ser Leu Lys Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

<210> SEQ ID NO 37
<211> LENGTH: 345
<212> TYPE: DNA
<213> ORGANISM: Artificial Sequence
<220> FEATURE:
<223> OTHER INFORMATION: 3C_23K VH without leader
<220> FEATURE:
<221> NAME/KEY: CDS
<222> LOCATION: (1)..(345)

<400> SEQUENCE: 37 cag gtg cgg ctg gtg cag agc ggg gcc gag gtg aag aag cct gga gcc      48
Gln Val Arg Leu Val Gln Ser Gly Ala Glu Val Lys Lys Pro Gly Ala
1               5                   10                  15 tca gtg aag gtg agt tgc aag gcc tcc ggt tac acc ttc acc agc tac      96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg      144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc      192
Gly Trp Ile Tyr Pro Gly Asp Asp Ser Thr Lys Tyr Ser Gln Lys Phe
    50                  55                  60 cag ggt cgc gtg acc att acc agg gac acc agc gcc tcc act gcc tac      240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt      288
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc      336
Thr Arg Gly Asp Arg Phe Ala Tyr Trp Gly Gln Gly Thr Leu Val Thr
            100                 105                 110
```

```
gtc tcg agc                                                   345
Val Ser Ser
        115

<210> SEQ ID NO 38
<211> LENGTH: 115
<212> TYPE: PRT
<213> ORGANISM: Artificial Sequence
<220> FEATURE:
<223> OTHER INFORMATION: Synthetic Construct

<400> SEQUENCE: 38

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 39
<211> LENGTH: 402
<212> TYPE: DNA
<213> ORGANISM: Artificial Sequence
<220> FEATURE:
<223> OTHER INFORMATION: 3C_23K VH with leader
<220> FEATURE:
<221> NAME/KEY: CDS
<222> LOCATION: (1)..(402)

<400> SEQUENCE: 39 atg gat tgg aca tgg cga atc ctg ttc ctg gtg gct gcc gca acc ggc    48
Met Asp Trp Thr Trp Arg Ile Leu Phe Leu Val Ala Ala Ala Thr Gly
1               5                   10                  15 gcc cac agc cag gtg cgg ctg gtg cag agc ggg gcc gag gtg aag aag    96
Ala His Ser Gln Val Arg Leu Val Gln Ser Gly Ala Glu Val Lys Lys
            20                  25                  30 cct gga gcc tca gtg aag gtg agt tgc aag gcc tcc ggt tac acc ttc   144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga ctg   192
Thr Ser Tyr His Ile His Trp Val Arg Gln Ala Pro Gly Gln Arg Leu
    50                  55                  60 gag tgg atg ggc tgg atc tac cct gga gat gac tcc acc aag tac tcc   240
Glu Trp Met Gly Trp Ile Tyr Pro Gly Asp Asp Ser Thr Lys Tyr Ser
65                  70                  75                  80 cag aag ttc cag ggt cgc gtg acc att acc agg gac acc agc gcc tcc   288
Gln Lys Phe Gln Gly Arg Val Thr Ile Thr Arg Asp Thr Ser Ala Ser
                85                  90                  95 act gcc tac atg gag ctg tct tcc ctg aga tct gag gat acc gca gtc   336
Thr Ala Tyr Met Glu Leu Ser Ser Leu Arg Ser Glu Asp Thr Ala Val
            100                 105                 110
```

| | | |
|---|---|---|
| tac tac tgt aca cgg ggg gac cgc ttt gct tac tgg ggg cag ggc act<br>Tyr Tyr Cys Thr Arg Gly Asp Arg Phe Ala Tyr Trp Gly Gln Gly Thr<br>              115                       120                    125 | | 384 |
| ctg gtg acc gtc tcg agc<br>Leu Val Thr Val Ser Ser<br>    130 | | 402 |

```
<210> SEQ ID NO 40
<211> LENGTH: 134
<212> TYPE: PRT
<213> ORGANISM: Artificial Sequence
<220> FEATURE:
<223> OTHER INFORMATION: Synthetic Construct

<400> SEQUENCE: 40
```

Met Asp Trp Thr Trp Arg Ile Leu Phe Leu Val Ala Ala Ala Thr Gly
1               5                   10                  15

Ala His Ser Gln Val Arg Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr His Ile His Trp Val Arg Gln Ala Pro Gly Gln Arg Leu
        50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser
    130

```
<210> SEQ ID NO 41
<211> LENGTH: 345
<212> TYPE: DNA
<213> ORGANISM: Artificial Sequence
<220> FEATURE:
<223> OTHER INFORMATION: 4C_35 VH with leader
<220> FEATURE:
<221> NAME/KEY: CDS
<222> LOCATION: (1)..(345)

<400> SEQUENCE: 41
```

| | | |
|---|---|---|
| cag gtg cag ctg gtg cag agc ggg gcc gag gtg aag aag cct gga gcc<br>Gln Val Gln Leu Val Gln Ser Gly Ala Glu Val Lys Lys Pro Gly Ala<br>1                   5                     10                    15 | | 48 |
| tca gtg aag gtg agt tgc aag gcc tcc ggt tac acc ttc acc agc tac<br>Ser Val Lys Val Ser Cys Lys Ala Ser Gly Tyr Thr Phe Thr Ser Tyr<br>             20                   25                   30 | | 96 |
| cac atc cac tgg gtc aga cag gct ccc ggc cag aga cca gag tgg atg<br>His Ile His Trp Val Arg Gln Ala Pro Gly Gln Arg Pro Glu Trp Met<br>        35                   40                   45 | | 144 |
| ggc tgg atc tac cct gga gat gac tcc acc aag tac tcc cag aag ttc<br>Gly Trp Ile Tyr Pro Gly Asp Asp Ser Thr Lys Tyr Ser Gln Lys Phe<br> 50                   55                   60 | | 192 |
| cag ggt cgc gtg acc att acc agg gac acc agc gcc tcc act gcc tac<br>Gln Gly Arg Val Thr Ile Thr Arg Asp Thr Ser Ala Ser Thr Ala Tyr<br>65                   70                    75                    80 | | 240 |
| atg gag ctg tct tcc ctg aga tct gag gat acc gca gtc tac tac tgt | | 288 |

```
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc    336
Thr Arg Gly Asp Arg Phe Ala Tyr Trp Gly Gln Gly Thr Leu Val Thr
        100                 105                 110 gtc agc agc                                                        345
Val Ser Ser
        115

<210> SEQ ID NO 42
<211> LENGTH: 115
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Pro Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115

<210> SEQ ID NO 43
<211> LENGTH: 402
<212> TYPE: DNA
<213> ORGANISM: Artificial Sequence
<220> FEATURE:
<223> OTHER INFORMATION: 4C_35 VH with leader
<220> FEATURE:
<221> NAME/KEY: CDS
<222> LOCATION: (1)..(402)

<400> SEQUENCE: 43 atg gat tgg aca tgg cga atc ctg ttc ctg gtg gct gcc gca acc ggc    48
Met Asp Trp Thr Trp Arg Ile Leu Phe Leu Val Ala Ala Ala Thr Gly
1               5                   10                  15 gcc cac agc cag gtg cag ctg gtg cag agc ggg gcc gag gtg aag aag    96
Ala His Ser Gln Val Gln Leu Val Gln Ser Gly Ala Glu Val Lys Lys
            20                  25                  30 cct gga gcc tca gtg aag gtg agt tgc aag gcc tcc ggt tac acc ttc    144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga cca    192
Thr Ser Tyr His Ile His Trp Val Arg Gln Ala Pro Gly Gln Arg Pro
    50                  55                  60 gag tgg atg ggc tgg atc tac cct gga gat gac tcc acc aag tac tcc    240
Glu Trp Met Gly Trp Ile Tyr Pro Gly Asp Asp Ser Thr Lys Tyr Ser
65                  70                  75                  80 cag aag ttc cag ggt cgc gtg acc att acc agg gac acc agc gcc tcc    288
```

```
Gln Lys Phe Gln Gly Arg Val Thr Ile Thr Arg Asp Thr Ser Ala Ser
                85                  90                  95 act gcc tac atg gag ctg tct tcc ctg aga tct gag gat acc gca gtc      336
Thr Ala Tyr Met Glu Leu Ser Ser Leu Arg Ser Glu Asp Thr Ala Val
            100                 105                 110 tac tac tgt aca cgg ggg gac cgc ttt gct tac tgg ggg cag ggc act      384
Tyr Tyr Cys Thr Arg Gly Asp Arg Phe Ala Tyr Trp Gly Gln Gly Thr
        115                 120                 125 ctg gtg acc gtc agc agc                                              402
Leu Val Thr Val Ser Ser
    130

<210> SEQ ID NO 44
<211> LENGTH: 134
<212> TYPE: PRT
<213> ORGANISM: Artificial Sequence
<220> FEATURE:
<223> OTHER INFORMATION: Synthetic Construct

<400> SEQUENCE: 44

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr His Ile His Trp Val Arg Gln Ala Pro Gly Gln Arg Pro
    50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser
    130

<210> SEQ ID NO 45
<211> LENGTH: 318
<212> TYPE: DNA
<213> ORGANISM: Artificial Sequence
<220> FEATURE:
<223> OTHER INFORMATION: 5B_42 VL without leader
<220> FEATURE:
<221> NAME/KEY: CDS
<222> LOCATION: (1)..(318)

<400> SEQUENCE: 45 gac atc cag atg aca cag tcc cca tct acc ctg tct gct tcc gtg gga      48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc      96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg atc tac      144
Ala Trp Tyr Gln Gln Lys Pro Gly Lys Ala Pro Lys Leu Leu Ile Tyr
        35                  40                  45 cca acc tcc tcc ctg gaa tcc ggg gtg ccc agc aga ttc tca ggc agt      192
Pro Thr Ser Ser Leu Glu Ser Gly Val Pro Ser Arg Phe Ser Gly Ser
```

```
ggc tcc ggc acc gaa ttc acc ctg acc atc agc tca ctg cag cct gac    240
Gly Ser Gly Thr Glu Phe Thr Leu Thr Ile Ser Ser Leu Gln Pro Asp
 65                  70                  75                  80 gac ttc gca acc tac tac tgt ctg cag tgg agt agc tac cct tgg aca    288
Asp Phe Ala Thr Tyr Tyr Cys Leu Gln Trp Ser Ser Tyr Pro Trp Thr
                 85                  90                  95 ttc ggc ggc ggc acc aag gtg gag atc aag                            318
Phe Gly Gly Gly Thr Lys Val Glu Ile Lys
            100                 105

<210> SEQ ID NO 46
<211> LENGTH: 106
<212> TYPE: PRT
<213> ORGANISM: Artificial Sequence
<220> FEATURE:
<223> OTHER INFORMATION: Synthetic Construct

<400> SEQUENCE: 46

Asp Ile Gln Met Thr Gln Ser Pro Ser Thr Leu Ser Ala Ser Val Gly
 1               5                  10                  15

Asp Arg Val Thr Ile Thr Cys Arg Ala Ser Ser Ser Val Arg Tyr Ile
                20                  25                  30

Ala Trp Tyr Gln Gln Lys Pro Gly Lys Ala Pro Lys Leu Leu Ile Tyr
            35                  40                  45

Pro Thr Ser Ser Leu Glu Ser Gly Val Pro Ser Arg Phe Ser Gly Ser
        50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys
            100                 105

<210> SEQ ID NO 47
<211> LENGTH: 384
<212> TYPE: DNA
<213> ORGANISM: Artificial Sequence
<220> FEATURE:
<223> OTHER INFORMATION: 5B_42 VL with leader
<220> FEATURE:
<221> NAME/KEY: CDS
<222> LOCATION: (1)..(384)

<400> SEQUENCE: 47 atg gat atg aga gtg ccc gca cag ctg ctg ggt ctg ctg ctg ctg tgg     48
Met Asp Met Arg Val Pro Ala Gln Leu Leu Gly Leu Leu Leu Leu Trp
 1               5                  10                  15 ctg ccc gga gcc aaa tgt gac atc cag atg aca cag tcc cca tct acc     96
Leu Pro Gly Ala Lys Cys Asp Ile Gln Met Thr Gln Ser Pro Ser Thr
                20                  25                  30 ctg tct gct tcc gtg gga gat cgg gtg act atc acc tgc aga gca agc    144
Leu Ser Ala Ser Val Gly Asp Arg Val Thr Ile Thr Cys Arg Ala Ser
            35                  40                  45 tcc tcc gtg agg tac atc gct tgg tac cag cag aag cca gga aag gcc    192
Ser Ser Val Arg Tyr Ile Ala Trp Tyr Gln Gln Lys Pro Gly Lys Ala
        50                  55                  60 cca aag ctg ctg atc tac cca acc tcc tcc ctg gaa tcc ggg gtg ccc    240
Pro Lys Leu Leu Ile Tyr Pro Thr Ser Ser Leu Glu Ser Gly Val Pro
 65                  70                  75                  80 agc aga ttc tca ggc agt ggc tcc ggc acc gaa ttc acc ctg acc atc    288
```

```
Ser Arg Phe Ser Gly Ser Gly Ser Gly Thr Glu Phe Thr Leu Thr Ile
                85                  90                  95 agc tca ctg cag cct gac gac ttc gca acc tac tac tgt ctg cag tgg      336
Ser Ser Leu Gln Pro Asp Asp Phe Ala Thr Tyr Tyr Cys Leu Gln Trp
            100                 105                 110 agt agc tac cct tgg aca ttc ggc ggc ggc acc aag gtg gag atc aag      384
Ser Ser Tyr Pro Trp Thr Phe Gly Gly Gly Thr Lys Val Glu Ile Lys
        115                 120                 125

<210> SEQ ID NO 48
<211> LENGTH: 128
<212> TYPE: PRT
<213> ORGANISM: Artificial Sequence
<220> FEATURE:
<223> OTHER INFORMATION: Synthetic Construct

<400> SEQUENCE: 48

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Ile Tyr Pro Thr Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

<210> SEQ ID NO 49
<211> LENGTH: 345
<212> TYPE: DNA
<213> ORGANISM: Artificial Sequence
<220> FEATURE:
<223> OTHER INFORMATION: 5B_42 VH without leader
<220> FEATURE:
<221> NAME/KEY: CDS
<222> LOCATION: (1)..(345)

<400> SEQUENCE: 49 cag gtg cag ctg gtg cag agc ggg gcc gag gtg aag aag cct gga gcc       48
Gln Val Gln Leu Val Gln Ser Gly Ala Glu Val Lys Lys Pro Gly Ala
1               5                   10                  15 tca gtg aag gtg agt tgc aag gcc tcc ggt tac acc ttc acc agc tac       96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg      144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc      192
Gly Trp Ile Tyr Pro Gly Asp Asp Ser Thr Lys Tyr Ser Gln Lys Phe
    50                  55                  60 cag ggt cgc gtg acc att acc agg gac gcc agc gcc tcc act gcc tac      240
Gln Gly Arg Val Thr Ile Thr Arg Asp Ala Ser Ala Ser Thr Ala Tyr
65                  70                  75                  80 atg gag ctg tct tcc ctg aga tct gag gat acc gca gtc tac tac tgt      288
```

```
Met Glu Leu Ser Ser Leu Arg Ser Glu Asp Thr Ala Val Tyr Tyr Cys
             85                  90                  95 aca cgg ggg gac cgc ttt gct tac tgg ggg cag ggc act ctg gtg acc    336
Thr Arg Gly Asp Arg Phe Ala Tyr Trp Gly Gln Gly Thr Leu Val Thr
            100                 105                 110 gtc agc agc                                                        345
Val Ser Ser
        115
```

<210> SEQ ID NO 50
<211> LENGTH: 115
<212> TYPE: PRT
<213> ORGANISM: Artificial Sequence
<220> FEATURE:
<223> OTHER INFORMATION: Synthetic Construct

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Ala Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser
        115
```

<210> SEQ ID NO 51
<211> LENGTH: 402
<212> TYPE: DNA
<213> ORGANISM: Artificial Sequence
<220> FEATURE:
<223> OTHER INFORMATION: 5B_42 VH with leader
<220> FEATURE:
<221> NAME/KEY: CDS
<222> LOCATION: (1)..(402)

<400> SEQUENCE: 51

```
atg gat tgg aca tgg cga atc ctg ttc ctg gtg gct gcc gca acc ggc     48
Met Asp Trp Thr Trp Arg Ile Leu Phe Leu Val Ala Ala Ala Thr Gly
1               5                   10                  15 gcc cac agc cag gtg cag ctg gtg cag agc ggg gcc gag gtg aag aag     96
Ala His Ser Gln Val Gln Leu Val Gln Ser Gly Ala Glu Val Lys Lys
            20                  25                  30 cct gga gcc tca gtg aag gtg agt tgc aag gcc tcc ggt tac acc ttc    144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga ctg    192
Thr Ser Tyr His Ile His Trp Val Arg Gln Ala Pro Gly Gln Arg Leu
    50                  55                  60 gag tgg atg ggc tgg atc tac cct gga gat gac tcc acc aag tac tcc    240
Glu Trp Met Gly Trp Ile Tyr Pro Gly Asp Asp Ser Thr Lys Tyr Ser
65                  70                  75                  80 cag aag ttc cag ggt cgc gtg acc att acc agg gac gcc agc gcc tcc    288
```

```
Gln Lys Phe Gln Gly Arg Val Thr Ile Thr Arg Asp Ala Ser Ala Ser
                85                  90                  95 act gcc tac atg gag ctg tct tcc ctg aga tct gag gat acc gca gtc      336
Thr Ala Tyr Met Glu Leu Ser Ser Leu Arg Ser Glu Asp Thr Ala Val
            100                 105                 110 tac tac tgt aca cgg ggg gac cgc ttt gct tac tgg ggg cag ggc act      384
Tyr Tyr Cys Thr Arg Gly Asp Arg Phe Ala Tyr Trp Gly Gln Gly Thr
        115                 120                 125 ctg gtg acc gtc agc agc                                              402
Leu Val Thr Val Ser Ser
    130

<210> SEQ ID NO 52
<211> LENGTH: 134
<212> TYPE: PRT
<213> ORGANISM: Artificial Sequence
<220> FEATURE:
<223> OTHER INFORMATION: Synthetic Construct

<400> SEQUENCE: 52

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr His Ile His Trp Val Arg Gln Ala Pro Gly Gln Arg Leu
    50                  55                  60

Glu Trp Met Gly Trp Ile Tyr Pro Gly Asp Ser Thr Lys Tyr Ser
65                  70                  75                  80

Gln Lys Phe Gln Gly Arg Val Thr Ile Thr Arg Asp Ala Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser
    130

<210> SEQ ID NO 53
<211> LENGTH: 639
<212> TYPE: DNA
<213> ORGANISM: Artificial Sequence
<220> FEATURE:
<223> OTHER INFORMATION: Humanized 12G4 light chain without leader
<220> FEATURE:
<221> NAME/KEY: CDS
<222> LOCATION: (1)..(639)

<400> SEQUENCE: 53 gac atc cag atg aca cag tcc cca tct acc ctg tct gct tcc gtg gga      48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc      96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg atc tac      144
Ala Trp Tyr Gln Gln Lys Pro Gly Lys Ala Pro Lys Leu Leu Ile Tyr
        35                  40                  45 tca acc tcc tcc ctg gaa tcc ggg gtg ccc agc aga ttc tca ggc agt      192
Ser Thr Ser Ser Leu Glu Ser Gly Val Pro Ser Arg Phe Ser Gly Ser
```

```
                   50                     55                     60
ggc tcc ggc acc gaa ttc acc ctg acc atc agc tca ctg cag cct gac       240
Gly Ser Gly Thr Glu Phe Thr Leu Thr Ile Ser Ser Leu Gln Pro Asp
 65                  70                     75                     80 gac ttc gca acc tac tac tgt ctg cag tgg agt agc tac cct tgg aca       288
Asp Phe Ala Thr Tyr Tyr Cys Leu Gln Trp Ser Ser Tyr Pro Trp Thr
                     85                     90                     95 ttc ggc ggc ggc acc aag gtg gag atc aag cgg acc gtc gcc gca cca       336
Phe Gly Gly Gly Thr Lys Val Glu Ile Lys Arg Thr Val Ala Ala Pro
                100                    105                    110 agt gtc ttc atc ttc ccg cca tct gat gag cag ttg aaa tct gga act       384
Ser Val Phe Ile Phe Pro Pro Ser Asp Glu Gln Leu Lys Ser Gly Thr
            115                    120                    125 gcc tct gtt gtg tgc ctg ctg aat aac ttc tat ccc aga gag gcc aaa       432
Ala Ser Val Val Cys Leu Leu Asn Asn Phe Tyr Pro Arg Glu Ala Lys
        130                    135                    140 gta cag tgg aag gtg gat aac gcc ctc caa tcg ggt aac tcc cag gag       480
Val Gln Trp Lys Val Asp Asn Ala Leu Gln Ser Gly Asn Ser Gln Glu
145                    150                    155                    160 agt gtc aca gag cag gac agc aag gac agc acc tac agc ctc agc agc       528
Ser Val Thr Glu Gln Asp Ser Lys Asp Ser Thr Tyr Ser Leu Ser Ser
                    165                    170                    175 acc ctg acg ctg agc aaa gca gac tac gag aaa cac aaa gtc tac gcc       576
Thr Leu Thr Leu Ser Lys Ala Asp Tyr Glu Lys His Lys Val Tyr Ala
                180                    185                    190 tgc gaa gtc acc cat cag ggc ctg agc tcg ccc gtc aca aag agc ttc       624
Cys Glu Val Thr His Gln Gly Leu Ser Ser Pro Val Thr Lys Ser Phe
            195                    200                    205 aac agg gga gag tgt                                                    639
Asn Arg Gly Glu Cys
    210

<210> SEQ ID NO 54
<211> LENGTH: 213
<212> TYPE: PRT
<213> ORGANISM: Artificial Sequence
<220> FEATURE:
<223> OTHER INFORMATION: Synthetic Construct

<400> SEQUENCE: 54

Asp Ile Gln Met Thr Gln Ser Pro Ser Thr Leu Ser Ala Ser Val Gly
 1               5                  10                  15

Asp Arg Val Thr Ile Thr Cys Arg Ala Ser Ser Ser Val Arg Tyr Ile
                20                  25                  30

Ala Trp Tyr Gln Gln Lys Pro Gly Lys Ala Pro Lys Leu Leu Ile Tyr
            35                  40                  45

Ser Thr Ser Ser Leu Glu Ser Gly Val Pro Ser Arg Phe Ser Gly Ser
        50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Leu Gln Trp Ser Ser Tyr Pro Trp Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 55
<211> LENGTH: 705
<212> TYPE: DNA
<213> ORGANISM: Artificial Sequence
<220> FEATURE:
<223> OTHER INFORMATION: Humanized 12G4 light chain with leader
<220> FEATURE:
<221> NAME/KEY: CDS
<222> LOCATION: (1)..(705)

<400> SEQUENCE: 55 atg gat atg aga gtg ccc gca cag ctg ctg ggt ctg ctg ctg tgg        48
Met Asp Met Arg Val Pro Ala Gln Leu Leu Gly Leu Leu Leu Trp
1               5                   10                  15 ctg ccc gga gcc aaa tgt gac atc cag atg aca cag tcc cca tct acc    96
Leu Pro Gly Ala Lys Cys Asp Ile Gln Met Thr Gln Ser Pro Ser Thr
            20                  25                  30 ctg tct gct tcc gtg gga gat cgg gtg act atc acc tgc aga gca agc    144
Leu Ser Ala Ser Val Gly Asp Arg Val Thr Ile Thr Cys Arg Ala Ser
        35                  40                  45 tcc tcc gtg agg tac atc gct tgg tac cag cag aag cca gga aag gcc    192
Ser Ser Val Arg Tyr Ile Ala Trp Tyr Gln Gln Lys Pro Gly Lys Ala
    50                  55                  60 cca aag ctg ctg atc tac tca acc tcc tcc ctg gaa tcc ggg gtg ccc    240
Pro Lys Leu Leu Ile Tyr Ser Thr Ser Ser Leu Glu Ser Gly Val Pro
65                  70                  75                  80 agc aga ttc tca ggc agt ggc tcc ggc acc gaa ttc acc ctg acc atc    288
Ser Arg Phe Ser Gly Ser Gly Ser Gly Thr Glu Phe Thr Leu Thr Ile
                85                  90                  95 agc tca ctg cag cct gac gac ttc gca acc tac tac tgt ctg cag tgg    336
Ser Ser Leu Gln Pro Asp Asp Phe Ala Thr Tyr Tyr Cys Leu Gln Trp
            100                 105                 110 agt agc tac cct tgg aca ttc ggc ggc ggc acc aag gtg gag atc aag    384
Ser Ser Tyr Pro Trp Thr Phe Gly Gly Gly Thr Lys Val Glu Ile Lys
        115                 120                 125 cgg acc gtc gcc gca cca agt gtc ttc atc ttc ccg cca tct gat gag    432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc    480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa    528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc    576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag    624
Thr Tyr Ser Leu Ser Ser Thr Leu Thr Leu Ser Lys Ala Asp Tyr Glu
        195                 200                 205
```

```
aaa cac aaa gtc tac gcc tgc gaa gtc acc cat cag ggc ctg agc tcg      672
Lys His Lys Val Tyr Ala Cys Glu Val Thr His Gln Gly Leu Ser Ser
    210                 215                 220 ccc gtc aca aag agc ttc aac agg gga gag tgt                          705
Pro Val Thr Lys Ser Phe Asn Arg Gly Glu Cys
225                 230                 235
```

<210> SEQ ID NO 56
<211> LENGTH: 235
<212> TYPE: PRT
<213> ORGANISM: Artificial Sequence
<220> FEATURE:
<223> OTHER INFORMATION: Synthetic Construct

<400> SEQUENCE: 56

```
Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Ile Tyr Ser Thr Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 57
<211> LENGTH: 1335
<212> TYPE: DNA
<213> ORGANISM: Artificial Sequence
<220> FEATURE:
<223> OTHER INFORMATION: Humanized 12G4 heavy chain without leader
<220> FEATURE:
<221> NAME/KEY: CDS
<222> LOCATION: (1)..(1335)

<400> SEQUENCE: 57

```
cag gtg cag ctg gtg cag agc ggg gcc gag gtg aag aag cct gga gcc       48
Gln Val Gln Leu Val Gln Ser Gly Ala Glu Val Lys Lys Pro Gly Ala
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |
| tca | gtg | aag | gtg | agt | tgc | aag | gcc | tcc | ggt | tac | acc | ttc | acc | agc | tac | 96 |
| Ser | Val | Lys | Val | Ser | Cys | Lys | Ala | Ser | Gly | Tyr | Thr | Phe | Thr | Ser | Tyr | |
| | | | 20 | | | | | 25 | | | | | 30 | | | |
| cac | atc | cac | tgg | gtc | aga | cag | gct | ccc | ggc | cag | aga | ctg | gag | tgg | atg | 144 |
| His | Ile | His | Trp | Val | Arg | Gln | Ala | Pro | Gly | Gln | Arg | Leu | Glu | Trp | Met | |
| | | 35 | | | | | 40 | | | | | 45 | | | | |
| ggc | tgg | atc | tac | cct | gga | gat | gac | tcc | acc | aag | tac | tcc | cag | aag | ttc | 192 |
| Gly | Trp | Ile | Tyr | Pro | Gly | Asp | Asp | Ser | Thr | Lys | Tyr | Ser | Gln | Lys | Phe | |
| | 50 | | | | | 55 | | | | | 60 | | | | | |
| cag | ggt | cgc | gtg | acc | att | acc | agg | gac | acc | agc | gcc | tcc | act | gcc | tac | 240 |
| Gln | Gly | Arg | Val | Thr | Ile | Thr | Arg | Asp | Thr | Ser | Ala | Ser | Thr | Ala | Tyr | |
| 65 | | | | | 70 | | | | | 75 | | | | | 80 | |
| atg | gag | ctg | tct | tcc | ctg | aga | tct | gag | gat | acc | gca | gtc | tac | tac | tgt | 288 |
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |
| aca | cgg | ggg | gac | cgc | ttt | gct | tac | tgg | ggc | cag | ggc | act | ctg | gtg | acc | 336 |
| Thr | Arg | Gly | Asp | Arg | Phe | Ala | Tyr | Trp | Gly | Gln | Gly | Thr | Leu | Val | Thr | |
| | | | 100 | | | | | 105 | | | | | 110 | | | |
| gtc | agc | agc | gcc | agc | acc | aag | ggc | cca | tcg | gtc | ttc | ccc | ctg | gca | ccc | 384 |
| Val | Ser | Ser | Ala | Ser | Thr | Lys | Gly | Pro | Ser | Val | Phe | Pro | Leu | Ala | Pro | |
| | | 115 | | | | | 120 | | | | | 125 | | | | |
| tcc | tcc | aag | agc | acc | tct | ggg | ggc | aca | gcg | gcc | ctg | ggc | tgc | ctg | gtc | 432 |
| Ser | Ser | Lys | Ser | Thr | Ser | Gly | Gly | Thr | Ala | Ala | Leu | Gly | Cys | Leu | Val | |
| | 130 | | | | | 135 | | | | | 140 | | | | | |
| aag | gac | tac | ttc | ccc | gaa | ccg | gtg | acg | gtg | tcg | tgg | aac | tca | ggc | gcc | 480 |
| Lys | Asp | Tyr | Phe | Pro | Glu | Pro | Val | Thr | Val | Ser | Trp | Asn | Ser | Gly | Ala | |
| 145 | | | | | 150 | | | | | 155 | | | | | 160 | |
| ctg | acc | agc | ggc | gtg | cac | acc | ttc | ccg | gct | gtc | cta | cag | tcc | tca | gga | 528 |
| Leu | Thr | Ser | Gly | Val | His | Thr | Phe | Pro | Ala | Val | Leu | Gln | Ser | Ser | Gly | |
| | | | | 165 | | | | | 170 | | | | | 175 | | |
| ctc | tac | tcc | ctc | agc | agc | gtg | gtg | acc | gtg | ccc | tcc | agc | agc | ttg | ggc | 576 |
| Leu | Tyr | Ser | Leu | Ser | Ser | Val | Val | Thr | Val | Pro | Ser | Ser | Ser | Leu | Gly | |
| | | | 180 | | | | | 185 | | | | | 190 | | | |
| acc | cag | acc | tac | atc | tgc | aac | gtg | aat | cac | aag | ccc | agc | aac | acc | aag | 624 |
| Thr | Gln | Thr | Tyr | Ile | Cys | Asn | Val | Asn | His | Lys | Pro | Ser | Asn | Thr | Lys | |
| | | 195 | | | | | 200 | | | | | 205 | | | | |
| gtg | gac | aag | aaa | gtt | gag | ccc | aaa | tct | tgt | gac | aaa | act | cac | aca | tgc | 672 |
| Val | Asp | Lys | Lys | Val | Glu | Pro | Lys | Ser | Cys | Asp | Lys | Thr | His | Thr | Cys | |
| | 210 | | | | | 215 | | | | | 220 | | | | | |
| cca | ccg | tgc | cca | gca | cct | gaa | ctc | ctg | ggg | gga | ccg | tca | gtc | ttc | ctc | 720 |
| Pro | Pro | Cys | Pro | Ala | Pro | Glu | Leu | Leu | Gly | Gly | Pro | Ser | Val | Phe | Leu | |
| 225 | | | | | 230 | | | | | 235 | | | | | 240 | |
| ttc | ccc | cca | aaa | ccc | aag | gac | acc | ctc | atg | atc | tcc | cgg | acc | cct | gag | 768 |
| Phe | Pro | Pro | Lys | Pro | Lys | Asp | Thr | Leu | Met | Ile | Ser | Arg | Thr | Pro | Glu | |
| | | | | 245 | | | | | 250 | | | | | 255 | | |
| gtc | aca | tgc | gtg | gtg | gtg | gac | gtg | agc | cac | gaa | gac | cct | gag | gtc | aag | 816 |
| Val | Thr | Cys | Val | Val | Val | Asp | Val | Ser | His | Glu | Asp | Pro | Glu | Val | Lys | |
| | | | 260 | | | | | 265 | | | | | 270 | | | |
| ttc | aac | tgg | tac | gtg | gac | ggc | gtg | gag | gtg | cat | aat | gcc | aag | aca | aag | 864 |
| Phe | Asn | Trp | Tyr | Val | Asp | Gly | Val | Glu | Val | His | Asn | Ala | Lys | Thr | Lys | |
| | | 275 | | | | | 280 | | | | | 285 | | | | |
| ccg | cgg | gag | gag | cag | tac | aac | agc | acg | tac | cgt | gtg | gtc | agc | gtc | ctc | 912 |
| Pro | Arg | Glu | Glu | Gln | Tyr | Asn | Ser | Thr | Tyr | Arg | Val | Val | Ser | Val | Leu | |
| | 290 | | | | | 295 | | | | | 300 | | | | | |
| acc | gtc | ctg | cac | cag | gac | tgg | ctg | aat | ggc | aag | gag | tac | aag | tgc | aag | 960 |
| Thr | Val | Leu | His | Gln | Asp | Trp | Leu | Asn | Gly | Lys | Glu | Tyr | Lys | Cys | Lys | |
| 305 | | | | | 310 | | | | | 315 | | | | | 320 | |
| gtc | tcc | aac | aaa | gcc | ctc | cca | gcc | ccc | atc | gag | aaa | acc | atc | tcc | aaa | 1008 |

```
Val Ser Asn Lys Ala Leu Pro Ala Pro Ile Glu Lys Thr Ile Ser Lys
                325                 330                 335 gcc aaa ggg cag ccc cga gaa cca cag gtg tac acc ctg ccc cca tcc    1056
Ala Lys Gly Gln Pro Arg Glu Pro Gln Val Tyr Thr Leu Pro Pro Ser
            340                 345                 350 cgg gat gag ctg acc aag aac cag gtc agc ctg acc tgc ctg gtc aaa    1104
Arg Asp Glu Leu Thr Lys Asn Gln Val Ser Leu Thr Cys Leu Val Lys
        355                 360                 365 ggc ttc tat ccc agc gac atc gcc gtg gag tgg gag agc aat ggg cag    1152
Gly Phe Tyr Pro Ser Asp Ile Ala Val Glu Trp Glu Ser Asn Gly Gln
    370                 375                 380 ccg gag aac aac tac aag acc acg cct ccc gtg ctg gac tcc gac ggc    1200
Pro Glu Asn Asn Tyr Lys Thr Thr Pro Pro Val Leu Asp Ser Asp Gly
385                 390                 395                 400 tcc ttc ttc ctc tac agc aag ctc acc gtg gac aag agc agg tgg cag    1248
Ser Phe Phe Leu Tyr Ser Lys Leu Thr Val Asp Lys Ser Arg Trp Gln
                405                 410                 415 cag ggg aac gtc ttc tca tgc tcc gtg atg cat gag gct ctg cac aac    1296
Gln Gly Asn Val Phe Ser Cys Ser Val Met His Glu Ala Leu His Asn
            420                 425                 430 cac tac acg cag aag agc ctc tcc ctg tct ccg ggt aaa                1335
His Tyr Thr Gln Lys Ser Leu Ser Leu Ser Pro Gly Lys
        435                 440                 445

<210> SEQ ID NO 58
<211> LENGTH: 445
<212> TYPE: PRT
<213> ORGANISM: Artificial Sequence
<220> FEATURE:
<223> OTHER INFORMATION: Synthetic Construct

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205
```

```
Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 59
<211> LENGTH: 1392
<212> TYPE: DNA
<213> ORGANISM: Artificial Sequence
<220> FEATURE:
<223> OTHER INFORMATION: Humanized 12G4 heavy chain with leader
<220> FEATURE:
<221> NAME/KEY: CDS
<222> LOCATION: (1)..(1392)

<400> SEQUENCE: 59 atg gat tgg aca tgg cga atc ctg ttc ctg gtg gct gcc gca acc ggc      48
Met Asp Trp Thr Trp Arg Ile Leu Phe Leu Val Ala Ala Ala Thr Gly
1               5                   10                  15 gcc cac agc cag gtg cag ctg gtg cag agc ggg gcc gag gtg aag aag      96
Ala His Ser Gln Val Gln Leu Val Gln Ser Gly Ala Glu Val Lys Lys
            20                  25                  30 cct gga gcc tca gtg aag gtg agt tgc aag gcc tcc ggt tac acc ttc      144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga ctg      192
Thr Ser Tyr His Ile His Trp Val Arg Gln Ala Pro Gly Gln Arg Leu
    50                  55                  60 gag tgg atg ggc tgg atc tac cct gga gat gac tcc acc aag tac tcc      240
Glu Trp Met Gly Trp Ile Tyr Pro Gly Asp Asp Ser Thr Lys Tyr Ser
65                  70                  75                  80
```

-continued

| | |
|---|---|
| cag aag ttc cag ggt cgc gtg acc att acc agg gac acc agc gcc tcc<br>Gln Lys Phe Gln Gly Arg Val Thr Ile Thr Arg Asp Thr Ser Ala Ser<br>                       85                    90                   95 | 288 |
| act gcc tac atg gag ctg tct tcc ctg aga tct gag gat acc gca gtc<br>Thr Ala Tyr Met Glu Leu Ser Ser Leu Arg Ser Glu Asp Thr Ala Val<br>                     100                    105                  110 | 336 |
| tac tac tgt aca cgg ggg gac cgc ttt gct tac tgg ggg cag ggc act<br>Tyr Tyr Cys Thr Arg Gly Asp Arg Phe Ala Tyr Trp Gly Gln Gly Thr<br>         115                    120                    125 | 384 |
| ctg gtg acc gtc agc agc gcc agc acc aag ggc cca tcg gtc ttc ccc<br>Leu Val Thr Val Ser Ser Ala Ser Thr Lys Gly Pro Ser Val Phe Pro<br>130                    135                    140                        160 | 432 |
| ctg gca ccc tcc tcc aag agc acc tct ggg ggc aca gcg gcc ctg ggc<br>Leu Ala Pro Ser Ser Lys Ser Thr Ser Gly Gly Thr Ala Ala Leu Gly<br>145                    150                    155                       160 | 480 |
| tgc ctg gtc aag gac tac ttc ccc gaa ccg gtg acg gtg tcg tgg aac<br>Cys Leu Val Lys Asp Tyr Phe Pro Glu Pro Val Thr Val Ser Trp Asn<br>                     165                    170                    175 | 528 |
| tca ggc gcc ctg acc agc ggc gtg cac acc ttc ccg gct gtc cta cag<br>Ser Gly Ala Leu Thr Ser Gly Val His Thr Phe Pro Ala Val Leu Gln<br>                  180                         185                   190 | 576 |
| tcc tca gga ctc tac tcc ctc agc agc gtg gtg acc gtg ccc tcc agc<br>Ser Ser Gly Leu Tyr Ser Leu Ser Ser Val Val Thr Val Pro Ser Ser<br>         195                    200                    205 | 624 |
| agc ttg ggc acc cag acc tac atc tgc aac gtg aat cac aag ccc agc<br>Ser Leu Gly Thr Gln Thr Tyr Ile Cys Asn Val Asn His Lys Pro Ser<br>210                    215                    220 | 672 |
| aac acc aag gtg gac aag aaa gtt gag ccc aaa tct tgt gac aaa act<br>Asn Thr Lys Val Asp Lys Lys Val Glu Pro Lys Ser Cys Asp Lys Thr<br>225                    230                    235                    240 | 720 |
| cac aca tgc cca ccg tgc cca gca cct gaa ctc ctg ggg gga ccg tca<br>His Thr Cys Pro Pro Cys Pro Ala Pro Glu Leu Leu Gly Gly Pro Ser<br>                     245                    250                    255 | 768 |
| gtc ttc ctc ttc ccc cca aaa ccc aag gac acc ctc atg atc tcc cgg<br>Val Phe Leu Phe Pro Pro Lys Pro Lys Asp Thr Leu Met Ile Ser Arg<br>         260                    265                    270 | 816 |
| acc cct gag gtc aca tgc gtg gtg gtg gac gtg agc cac gaa gac cct<br>Thr Pro Glu Val Thr Cys Val Val Val Asp Val Ser His Glu Asp Pro<br>275                    280                    285 | 864 |
| gag gtc aag ttc aac tgg tac gtg gac ggc gtg gag gtg cat aat gcc<br>Glu Val Lys Phe Asn Trp Tyr Val Asp Gly Val Glu Val His Asn Ala<br>         290                    295                    300 | 912 |
| aag aca aag ccg cgg gag gag cag tac aac agc acg tac cgt gtg gtc<br>Lys Thr Lys Pro Arg Glu Glu Gln Tyr Asn Ser Thr Tyr Arg Val Val<br>305                    310                    315                    320 | 960 |
| agc gtc ctc acc gtc ctg cac cag gac tgg ctg aat ggc aag gag tac<br>Ser Val Leu Thr Val Leu His Gln Asp Trp Leu Asn Gly Lys Glu Tyr<br>                     325                    330                    335 | 1008 |
| aag tgc aag gtc tcc aac aaa gcc ctc cca gcc ccc atc gag aaa acc<br>Lys Cys Lys Val Ser Asn Lys Ala Leu Pro Ala Pro Ile Glu Lys Thr<br>                  340                         345                   350 | 1056 |
| atc tcc aaa gcc aaa ggg cag ccc cga gaa cca cag gtg tac acc ctg<br>Ile Ser Lys Ala Lys Gly Gln Pro Arg Glu Pro Gln Val Tyr Thr Leu<br>         355                    360                    365 | 1104 |
| ccc cca tcc cgg gat gag ctg acc aag aac cag gtc agc ctg acc tgc<br>Pro Pro Ser Arg Asp Glu Leu Thr Lys Asn Gln Val Ser Leu Thr Cys<br>370                    375                    380 | 1152 |
| ctg gtc aaa ggc ttc tat ccc agc gac atc gcc gtg gag tgg gag agc<br>Leu Val Lys Gly Phe Tyr Pro Ser Asp Ile Ala Val Glu Trp Glu Ser<br>385                    390                    395                    400 | 1200 |

```
aat ggg cag ccg gag aac aac tac aag acc acg cct ccc gtg ctg gac    1248
Asn Gly Gln Pro Glu Asn Asn Tyr Lys Thr Thr Pro Pro Val Leu Asp
                405                 410                 415 tcc gac ggc tcc ttc ttc ctc tac agc aag ctc acc gtg gac aag agc    1296
Ser Asp Gly Ser Phe Phe Leu Tyr Ser Lys Leu Thr Val Asp Lys Ser
            420                 425                 430 agg tgg cag cag ggg aac gtc ttc tca tgc tcc gtg atg cat gag gct    1344
Arg Trp Gln Gln Gly Asn Val Phe Ser Cys Ser Val Met His Glu Ala
        435                 440                 445 ctg cac aac cac tac acg cag aag agc ctc tcc ctg tct ccg ggt aaa    1392
Leu His Asn His Tyr Thr Gln Lys Ser Leu Ser Leu Ser Pro Gly Lys
    450                 455                 460
```

<210> SEQ ID NO 60
<211> LENGTH: 464
<212> TYPE: PRT
<213> ORGANISM: Artificial Sequence
<220> FEATURE:
<223> OTHER INFORMATION: Synthetic Construct

<400> SEQUENCE: 60

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr His Ile His Trp Val Arg Gln Ala Pro Gly Gln Arg Leu
    50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
```

```
                  275                 280                 285
Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 61
<211> LENGTH: 645
<212> TYPE: DNA
<213> ORGANISM: Artificial Sequence
<220> FEATURE:
<223> OTHER INFORMATION: Chimeric 12G4 light chain without leader
<220> FEATURE:
<221> NAME/KEY: CDS
<222> LOCATION: (1)..(645)

<400> SEQUENCE: 61 caa att gtt ctc acc cag tct cca gca atc atg tct gca tct cta ggg       48
Gln Ile Val Leu Thr Gln Ser Pro Ala Ile Met Ser Ala Ser Leu Gly
1               5                   10                  15 gag ggg atc acc cta acc tgc agt gcc agc tcg agt gta cgt tac ata       96
Glu Gly Ile Thr Leu Thr Cys Ser Ala Ser Ser Ser Val Arg Tyr Ile
                20                  25                  30 cac tgg tac cag cag aag tca ggc act tct ccc aaa ctc ttg att tat      144
His Trp Tyr Gln Gln Lys Ser Gly Thr Ser Pro Lys Leu Leu Ile Tyr
            35                  40                  45 agc aca tcc aac ctg gct tct gga gtc cct tct cgc ttc agt ggc agt      192
Ser Thr Ser Asn Leu Ala Ser Gly Val Pro Ser Arg Phe Ser Gly Ser
        50                  55                  60 ggg tct ggg acc ttt cat tct ctc aca atc agc agt gtg gag gct gaa      240
Gly Ser Gly Thr Phe His Ser Leu Thr Ile Ser Ser Val Glu Ala Glu
65                  70                  75                  80 gat gct gcc gat tat tac tgc ctt cag tgg agt agt tat ccg tgg acg      288
Asp Ala Ala Asp Tyr Tyr Cys Leu Gln Trp Ser Ser Tyr Pro Trp Thr
                85                  90                  95 ttc ggt gga ggc acc aag ctg gaa atc aaa cga act gtg gct gca cca      336
Phe Gly Gly Gly Thr Lys Leu Glu Ile Lys Arg Thr Val Ala Ala Pro
            100                 105                 110 agt gtc ttc atc ttc ccg cca tct gat gag cag ttg aaa tct gga act      384
Ser Val Phe Ile Phe Pro Pro Ser Asp Glu Gln Leu Lys Ser Gly Thr
        115                 120                 125
```

```
gcc tct gtt gtg tgc ctg ctg aat aac ttc tat ccc aga gag gcc aaa        432
Ala Ser Val Val Cys Leu Leu Asn Asn Phe Tyr Pro Arg Glu Ala Lys
    130                 135                 140 gta cag tgg aag gtg gat aac gcc ctc caa tcg ggt aac tcc cag gag        480
Val Gln Trp Lys Val Asp Asn Ala Leu Gln Ser Gly Asn Ser Gln Glu
145                 150                 155                 160 agt gtc aca gag cag gac agc aag gac agc acc tac agc ctc agc agc        528
Ser Val Thr Glu Gln Asp Ser Lys Asp Ser Thr Tyr Ser Leu Ser Ser
                165                 170                 175 acc ctg acg ctg agc aaa gca gac tac gag aaa cac aaa gtc tac gcc        576
Thr Leu Thr Leu Ser Lys Ala Asp Tyr Glu Lys His Lys Val Tyr Ala
            180                 185                 190 tgc gaa gtc acc cat cag ggc ctg agc tcg ccc gtc aca aag agc ttc        624
Cys Glu Val Thr His Gln Gly Leu Ser Ser Pro Val Thr Lys Ser Phe
        195                 200                 205 aac agg gga gag tgt tag tga                                            645
Asn Arg Gly Glu Cys
    210
```

<210> SEQ ID NO 62
<211> LENGTH: 213
<212> TYPE: PRT
<213> ORGANISM: Artificial Sequence
<220> FEATURE:
<223> OTHER INFORMATION: Synthetic Construct

<400> SEQUENCE: 62

```
Gln Ile Val Leu Thr Gln Ser Pro Ala Ile Met Ser Ala Ser Leu Gly
1               5                   10                  15

Glu Gly Ile Thr Leu Thr Cys Ser Ala Ser Ser Val Arg Tyr Ile
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe His Ser Leu Thr Ile Ser Ser Val Glu Ala Glu
65                  70                  75                  80

Asp Ala Ala Asp Tyr Tyr Cys Leu Gln Trp Ser Ser Tyr Pro Trp Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 63

<211> LENGTH: 711
<212> TYPE: DNA
<213> ORGANISM: Artificial Sequence
<220> FEATURE:
<223> OTHER INFORMATION: Chimeric 12G4 light chain with leader
<220> FEATURE:
<221> NAME/KEY: CDS
<222> LOCATION: (1)..(711)

<400> SEQUENCE: 63

```
atg gat ttt cag gtg cag att ttc agc ttc ctg cta atc agt gcc tca        48
Met Asp Phe Gln Val Gln Ile Phe Ser Phe Leu Leu Ile Ser Ala Ser
1               5                   10                  15 gtc ata atg tcc aga gga caa att gtt ctc acc cag tct cca gca atc        96
Val Ile Met Ser Arg Gly Gln Ile Val Leu Thr Gln Ser Pro Ala Ile
            20                  25                  30 atg tct gca tct cta ggg gag ggg atc acc cta acc tgc agt gcc agc       144
Met Ser Ala Ser Leu Gly Glu Gly Ile Thr Leu Thr Cys Ser Ala Ser
        35                  40                  45 tcg agt gta cgt tac ata cac tgg tac cag cag aag tca ggc act tct       192
Ser Ser Val Arg Tyr Ile His Trp Tyr Gln Gln Lys Ser Gly Thr Ser
    50                  55                  60 ccc aaa ctc ttg att tat agc aca tcc aac ctg gct tct gga gtc cct       240
Pro Lys Leu Leu Ile Tyr Ser Thr Ser Asn Leu Ala Ser Gly Val Pro
65                  70                  75                  80 tct cgc ttc agt ggc agt ggg tct ggg acc ttt cat tct ctc aca atc       288
Ser Arg Phe Ser Gly Ser Gly Ser Gly Thr Phe His Ser Leu Thr Ile
                85                  90                  95 agc agt gtg gag gct gaa gat gct gcc gat tat tac tgc ctt cag tgg       336
Ser Ser Val Glu Ala Glu Asp Ala Ala Asp Tyr Tyr Cys Leu Gln Trp
            100                 105                 110 agt agt tat ccg tgg acg ttc ggt gga ggc acc aag ctg gaa atc aaa       384
Ser Ser Tyr Pro Trp Thr Phe Gly Gly Gly Thr Lys Leu Glu Ile Lys
        115                 120                 125 cga act gtg gct gca cca agt gtc ttc atc ttc ccg cca tct gat gag       432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc       480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa       528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc       576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag       624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg       672
Lys His Lys Val Tyr Ala Cys Glu Val Thr His Gln Gly Leu Ser Ser
    210                 215                 220 ccc gtc aca aag agc ttc aac agg gga gag tgt tag tga                   711
Pro Val Thr Lys Ser Phe Asn Arg Gly Glu Cys
225                 230                 235
```

<210> SEQ ID NO 64
<211> LENGTH: 235
<212> TYPE: PRT
<213> ORGANISM: Artificial Sequence
<220> FEATURE:
<223> OTHER INFORMATION: Synthetic Construct

```
<400> SEQUENCE: 64

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Gly Ile Thr Leu Thr Cys Ser Ala Ser
        35                  40                  45

Ser Ser Val Arg Tyr Ile His Trp Tyr Gln Gln Lys Ser Gly Thr Ser
    50                  55                  60

Pro Lys Leu Leu Ile Tyr Ser Thr Ser Asn Leu Ala Ser Gly Val Pro
65                  70                  75                  80

Ser Arg Phe Ser Gly Ser Gly Ser Gly Thr Phe His Ser Leu Thr Ile
                85                  90                  95

Ser Ser Val Glu Ala Glu Asp Ala Ala Asp Tyr Tyr Cys Leu Gln Trp
            100                 105                 110

Ser Ser Tyr Pro Trp Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 65
<211> LENGTH: 1335
<212> TYPE: DNA
<213> ORGANISM: Artificial Sequence
<220> FEATURE:
<223> OTHER INFORMATION: Chimeric 12G4 heavy chain without leader
<220> FEATURE:
<221> NAME/KEY: CDS
<222> LOCATION: (1)..(1335)

<400> SEQUENCE: 65 cag gtc cag ctg cag cag tct gga cct gaa ctg gtg aag cct ggg gct      48
Gln Val Gln Leu Gln Gln Ser Gly Pro Glu Leu Val Lys Pro Gly Ala
1               5                   10                  15 tca gtg agg atg tcc tgc aag gct tct ggc tac acc ttc aca agt tac      96
Ser Val Arg Met Ser Cys Lys Ala Ser Gly Tyr Thr Phe Thr Ser Tyr
            20                  25                  30 cat ata cac tgg gtg aag cag agg cct gga cag gga ctt gag tgg att     144
His Ile His Trp Val Lys Gln Arg Pro Gly Gln Gly Leu Glu Trp Ile
        35                  40                  45 gga tgg att tat cct ggc gat gat tct act aaa tac aat gag aag ttc     192
Gly Trp Ile Tyr Pro Gly Asp Asp Ser Thr Lys Tyr Asn Glu Lys Phe
    50                  55                  60 aag ggc aag acc aca ctg act gca gac aaa tcc tcc agc aca gcc tac     240
Lys Gly Lys Thr Thr Leu Thr Ala Asp Lys Ser Ser Ser Thr Ala Tyr
65                  70                  75                  80
```

```
atg ttg ctc agc agc ctg acc tct gag gac tct gcg atc tat ttc tgt     288
Met Leu Leu Ser Ser Leu Thr Ser Glu Asp Ser Ala Ile Tyr Phe Cys
                    85                  90                  95 aca agg ggg gac cgg ttt gct tac tgg ggc caa ggg act ctg gtc act     336
Thr Arg Gly Asp Arg Phe Ala Tyr Trp Gly Gln Gly Thr Leu Val Thr
                100                 105                 110 gtc tct gca gcc tcc acc aag ggc cca tcg gtc ttc ccc ctg gca ccc     384
Val Ser Ala Ala Ser Thr Lys Gly Pro Ser Val Phe Pro Leu Ala Pro
            115                 120                 125 tcc tcc aag agc acc tct ggg ggc aca gcg gcc ctg ggc tgc ctg gtc     432
Ser Ser Lys Ser Thr Ser Gly Gly Thr Ala Ala Leu Gly Cys Leu Val
130                 135                 140 aag gac tac ttc ccc gaa ccg gtg acg gtg tcg tgg aac tca ggc gcc     480
Lys Asp Tyr Phe Pro Glu Pro Val Thr Val Ser Trp Asn Ser Gly Ala
145                 150                 155                 160 ctg acc agc ggc gtg cac acc ttc ccg gct gtc cta cag tcc tca gga     528
Leu Thr Ser Gly Val His Thr Phe Pro Ala Val Leu Gln Ser Ser Gly
                165                 170                 175 ctc tac tcc ctc agc agc gtg gtg acc gtg ccc tcc agc agc ttg ggc     576
Leu Tyr Ser Leu Ser Ser Val Val Thr Val Pro Ser Ser Ser Leu Gly
            180                 185                 190 acc cag acc tac atc tgc aac gtg aat cac aag ccc agc aac acc aag     624
Thr Gln Thr Tyr Ile Cys Asn Val Asn His Lys Pro Ser Asn Thr Lys
        195                 200                 205 gtg gac aag aaa gtt gag ccc aaa tct tgt gac aaa act cac aca tgc     672
Val Asp Lys Lys Val Glu Pro Lys Ser Cys Asp Lys Thr His Thr Cys
210                 215                 220 cca ccg tgc cca gca cct gaa ctc ctg ggg gga ccg tca gtc ttc ctc     720
Pro Pro Cys Pro Ala Pro Glu Leu Leu Gly Gly Pro Ser Val Phe Leu
225                 230                 235                 240 ttc ccc cca aaa ccc aag gac acc ctc atg atc tcc cgg acc cct gag     768
Phe Pro Pro Lys Pro Lys Asp Thr Leu Met Ile Ser Arg Thr Pro Glu
                245                 250                 255 gtc aca tgc gtg gtg gtg gac gtg agc cac gaa gac cct gag gtc aag     816
Val Thr Cys Val Val Val Asp Val Ser His Glu Asp Pro Glu Val Lys
            260                 265                 270 ttc aac tgg tac gtg gac ggc gtg gag gtg cat aat gcc aag aca aag     864
Phe Asn Trp Tyr Val Asp Gly Val Glu Val His Asn Ala Lys Thr Lys
        275                 280                 285 ccg cgg gag gag cag tac aac agc acg tac cgt gtg gtc agc gtc ctc     912
Pro Arg Glu Glu Gln Tyr Asn Ser Thr Tyr Arg Val Val Ser Val Leu
290                 295                 300 acc gtc ctg cac cag gac tgg ctg aat ggc aag gag tac aag tgc aag     960
Thr Val Leu His Gln Asp Trp Leu Asn Gly Lys Glu Tyr Lys Cys Lys
305                 310                 315                 320 gtc tcc aac aaa gcc ctc cca gcc ccc atc gag aaa acc atc tcc aaa    1008
Val Ser Asn Lys Ala Leu Pro Ala Pro Ile Glu Lys Thr Ile Ser Lys
                325                 330                 335 gcc aaa ggg cag ccc cga gaa cca cag gtg tac acc ctg ccc cca tcc    1056
Ala Lys Gly Gln Pro Arg Glu Pro Gln Val Tyr Thr Leu Pro Pro Ser
            340                 345                 350 cgg gat gag ctg acc aag aac cag gtc agc ctg acc tgc ctg gtc aaa    1104
Arg Asp Glu Leu Thr Lys Asn Gln Val Ser Leu Thr Cys Leu Val Lys
        355                 360                 365 ggc ttc tat ccc agc gac atc gcc gtg gag tgg gag agc aat ggg cag    1152
Gly Phe Tyr Pro Ser Asp Ile Ala Val Glu Trp Glu Ser Asn Gly Gln
370                 375                 380 ccg gag aac aac tac aag acc acg cct ccc gtg ctg gac tcc gac ggc    1200
Pro Glu Asn Asn Tyr Lys Thr Thr Pro Pro Val Leu Asp Ser Asp Gly
```

```
                       385                 390                 395                 400
tcc ttc ttc ctc tac agc aag ctc acc gtg gac aag agc agg tgg cag        1248
Ser Phe Phe Leu Tyr Ser Lys Leu Thr Val Asp Lys Ser Arg Trp Gln
                405                 410                 415 cag ggg aac gtc ttc tca tgc tcc gtg atg cat gag gct ctg cac aac        1296
Gln Gly Asn Val Phe Ser Cys Ser Val Met His Glu Ala Leu His Asn
                420                 425                 430 cac tac acg cag aag agc ctc tcc ctg tct ccg ggt aaa                    1335
His Tyr Thr Gln Lys Ser Leu Ser Leu Ser Pro Gly Lys
                435                 440                 445

<210> SEQ ID NO 66
<211> LENGTH: 445
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Ser Tyr
            20                  25                  30

His Ile His Trp Val Lys Gln Arg Pro Gly Gln Gly Leu Glu Trp Ile
        35                  40                  45

Gly Trp Ile Tyr Pro Gly Asp Ser Thr Lys Tyr Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Ser Leu Thr Ser Glu Asp Ser Ala Ile Tyr Phe Cys
                85                  90                  95

Thr Arg Gly Asp Arg Phe Ala Tyr Trp Gly Gln Gly Thr Leu Val Thr
            100                 105                 110

Val Ser Ala Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
```

```
            290                 295                 300
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 67
<211> LENGTH: 1392
<212> TYPE: DNA
<213> ORGANISM: Artificial Sequence
<220> FEATURE:
<223> OTHER INFORMATION: Chimeric 12G4 heavy chain with leader
<220> FEATURE:
<221> NAME/KEY: CDS
<222> LOCATION: (1)..(1392)

<400> SEQUENCE: 67 atg cga tgg agc tgg atc ttt ctc ttc ctc ctg tca ata act gca agt    48
Met Arg Trp Ser Trp Ile Phe Leu Phe Leu Leu Ser Ile Thr Ala Ser
1               5                   10                  15 gtc cat tgc cag gtc cag ctg cag cag tct gga cct gaa ctg gtg aag    96
Val His Cys Gln Val Gln Leu Gln Gln Ser Gly Pro Glu Leu Val Lys
                20                  25                  30 cct ggg gct tca gtg agg atg tcc tgc aag gct tct ggc tac acc ttc    144
Pro Gly Ala Ser Val Arg Met Ser Cys Lys Ala Ser Gly Tyr Thr Phe
            35                  40                  45 aca agt tac cat ata cac tgg gtg aag cag agg cct gga cag gga ctt    192
Thr Ser Tyr His Ile His Trp Val Lys Gln Arg Pro Gly Gln Gly Leu
    50                  55                  60 gag tgg att gga tgg att tat cct ggc gat gat tct act aaa tac aat    240
Glu Trp Ile Gly Trp Ile Tyr Pro Gly Asp Asp Ser Thr Lys Tyr Asn
65                  70                  75                  80 gag aag ttc aag ggc aag acc aca ctg act gca gac aaa tcc tcc agc    288
Glu Lys Phe Lys Gly Lys Thr Thr Leu Thr Ala Asp Lys Ser Ser Ser
                85                  90                  95 aca gcc tac atg ttg ctc agc agc ctg acc tct gag gac tct gcg atc    336
Thr Ala Tyr Met Leu Leu Ser Ser Leu Thr Ser Glu Asp Ser Ala Ile
            100                 105                 110 tat ttc tgt aca agg ggg gac cgg ttt gct tac tgg ggc caa ggg act    384
Tyr Phe Cys Thr Arg Gly Asp Arg Phe Ala Tyr Trp Gly Gln Gly Thr
    115                 120                 125 ctg gtc act gtc tct gca gcc tcc acc aag ggc cca tcg gtc ttc ccc    432
Leu Val Thr Val Ser Ala Ala Ser Thr Lys Gly Pro Ser Val Phe Pro
130                 135                 140 ctg gca ccc tcc tcc aag agc acc tct ggg ggc aca gcg gcc ctg ggc    480
```

|  |  |
|---|---:|
| Leu Ala Pro Ser Ser Lys Ser Thr Ser Gly Gly Thr Ala Ala Leu Gly<br>145                    150                  155                160 | |
| tgc ctg gtc aag gac tac ttc ccc gaa ccg gtg acg gtg tcg tgg aac<br>Cys Leu Val Lys Asp Tyr Phe Pro Glu Pro Val Thr Val Ser Trp Asn<br>               165                    170                    175 | 528 |
| tca ggc gcc ctg acc agc ggc gtg cac acc ttc ccg gct gtc cta cag<br>Ser Gly Ala Leu Thr Ser Gly Val His Thr Phe Pro Ala Val Leu Gln<br>          180                    185                  190 | 576 |
| tcc tca gga ctc tac tcc ctc agc agc gtg gtg acc gtg ccc tcc agc<br>Ser Ser Gly Leu Tyr Ser Leu Ser Ser Val Val Thr Val Pro Ser Ser<br>195                    200                  205 | 624 |
| agc ttg ggc acc cag acc tac atc tgc aac gtg aat cac aag ccc agc<br>Ser Leu Gly Thr Gln Thr Tyr Ile Cys Asn Val Asn His Lys Pro Ser<br>          210                    215                  220 | 672 |
| aac acc aag gtg gac aag aaa gtt gag ccc aaa tct tgt gac aaa act<br>Asn Thr Lys Val Asp Lys Lys Val Glu Pro Lys Ser Cys Asp Lys Thr<br>225                    230                  235                  240 | 720 |
| cac aca tgc cca ccg tgc cca gca cct gaa ctc ctg ggg gga ccg tca<br>His Thr Cys Pro Pro Cys Pro Ala Pro Glu Leu Leu Gly Gly Pro Ser<br>                    245                    250                  255 | 768 |
| gtc ttc ctc ttc ccc cca aaa ccc aag gac acc ctc atg atc tcc cgg<br>Val Phe Leu Phe Pro Pro Lys Pro Lys Asp Thr Leu Met Ile Ser Arg<br>          260                    265                  270 | 816 |
| acc cct gag gtc aca tgc gtg gtg gtg gac gtg agc cac gaa gac cct<br>Thr Pro Glu Val Thr Cys Val Val Val Asp Val Ser His Glu Asp Pro<br>               275                    280                  285 | 864 |
| gag gtc aag ttc aac tgg tac gtg gac ggc gtg gag gtg cat aat gcc<br>Glu Val Lys Phe Asn Trp Tyr Val Asp Gly Val Glu Val His Asn Ala<br>          290                    295                  300 | 912 |
| aag aca aag ccg cgg gag gag cag tac aac agc acg tac cgt gtg gtc<br>Lys Thr Lys Pro Arg Glu Glu Gln Tyr Asn Ser Thr Tyr Arg Val Val<br>305                    310                  315                  320 | 960 |
| agc gtc ctc acc gtc ctg cac cag gac tgg ctg aat ggc aag gag tac<br>Ser Val Leu Thr Val Leu His Gln Asp Trp Leu Asn Gly Lys Glu Tyr<br>               325                    330                  335 | 1008 |
| aag tgc aag gtc tcc aac aaa gcc ctc cca gcc ccc atc gag aaa acc<br>Lys Cys Lys Val Ser Asn Lys Ala Leu Pro Ala Pro Ile Glu Lys Thr<br>          340                    345                  350 | 1056 |
| atc tcc aaa gcc aaa ggg cag ccc cga gaa cca cag gtg tac acc ctg<br>Ile Ser Lys Ala Lys Gly Gln Pro Arg Glu Pro Gln Val Tyr Thr Leu<br>               355                    360                  365 | 1104 |
| ccc cca tcc cgg gat gag ctg acc aag aac cag gtc agc ctg acc tgc<br>Pro Pro Ser Arg Asp Glu Leu Thr Lys Asn Gln Val Ser Leu Thr Cys<br>370                    375                  380 | 1152 |
| ctg gtc aaa ggc ttc tat ccc agc gac atc gcc gtg gag tgg gag agc<br>Leu Val Lys Gly Phe Tyr Pro Ser Asp Ile Ala Val Glu Trp Glu Ser<br>385                    390                  395                  400 | 1200 |
| aat ggg cag ccg gag aac aac tac aag acc acg cct ccc gtg ctg gac<br>Asn Gly Gln Pro Glu Asn Asn Tyr Lys Thr Thr Pro Pro Val Leu Asp<br>                    405                    410                  415 | 1248 |
| tcc gac ggc tcc ttc ttc ctc tac agc aag ctc acc gtg gac aag agc<br>Ser Asp Gly Ser Phe Phe Leu Tyr Ser Lys Leu Thr Val Asp Lys Ser<br>          420                    425                  430 | 1296 |
| agg tgg cag cag ggg aac gtc ttc tca tgc tcc gtg atg cat gag gct<br>Arg Trp Gln Gln Gly Asn Val Phe Ser Cys Ser Val Met His Glu Ala<br>               435                    440                  445 | 1344 |
| ctg cac aac cac tac acg cag aag agc ctc tcc ctg tct ccg ggt aaa<br>Leu His Asn His Tyr Thr Gln Lys Ser Leu Ser Leu Ser Pro Gly Lys<br>          450                    455                  460 | 1392 |

<210> SEQ ID NO 68
<211> LENGTH: 464
<212> TYPE: PRT
<213> ORGANISM: Artificial Sequence
<220> FEATURE:
<223> OTHER INFORMATION: Synthetic Construct

<400> SEQUENCE: 68

```
Met Arg Trp Ser Trp Ile Phe Leu Phe Leu Leu Ser Ile Thr Ala Ser
1               5                   10                  15

Val His Cys Gln Val Gln Leu Gln Gln Ser Gly Pro Glu Leu Val Lys
            20                  25                  30

Pro Gly Ala Ser Val Arg Met Ser Cys Lys Ala Ser Gly Tyr Thr Phe
        35                  40                  45

Thr Ser Tyr His Ile His Trp Val Lys Gln Arg Pro Gly Gln Gly Leu
    50                  55                  60

Glu Trp Ile Gly Trp Ile Tyr Pro Gly Asp Asp Ser Thr Lys Tyr Asn
65                  70                  75                  80

Glu Lys Phe Lys Gly Lys Thr Thr Leu Thr Ala Asp Lys Ser Ser Ser
                85                  90                  95

Thr Ala Tyr Met Leu Leu Ser Ser Leu Thr Ser Glu Asp Ser Ala Ile
            100                 105                 110

Tyr Phe Cys Thr Arg Gly Asp Arg Phe Ala Tyr Trp Gly Gln Gly Thr
        115                 120                 125

Leu Val Thr Val Ser Ala Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365
```

```
Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 69
<211> LENGTH: 639
<212> TYPE: DNA
<213> ORGANISM: Artificial Sequence
<220> FEATURE:
<223> OTHER INFORMATION: 3C_23 light chain without leader
<220> FEATURE:
<221> NAME/KEY: CDS
<222> LOCATION: (1)..(639)

<400> SEQUENCE: 69 gac atc cag atg aca cag tcc cca tct acc ctg tct gct tcc gtg gga      48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc      96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac     144
Ala Trp Tyr Gln Gln Lys Pro Gly Lys Ala Pro Lys Leu Leu Thr Tyr
        35                  40                  45 cca acc tcc tcc ctg gaa tcc ggg gtg ccc agc aga ttc tca ggc agt     192
Pro Thr Ser Ser Leu Glu Ser Gly Val Pro Ser Arg Phe Ser Gly Ser
    50                  55                  60 ggc tcc ggc acc gaa ttc acc ctg acc atc agc tca ctg cag cct gac     240
Gly Ser Gly Thr Glu Phe Thr Leu Thr Ile Ser Ser Leu Gln Pro Asp
65                  70                  75                  80 gac ttc gca acc tac tac tgt ctg cag tgg agt agc tac cct tgg aca     288
Asp Phe Ala Thr Tyr Tyr Cys Leu Gln Trp Ser Ser Tyr Pro Trp Thr
                85                  90                  95 ttc ggc ggc ggc acc aag gtg gag atc aag cgg acc gtc gcc gca cca     336
Phe Gly Gly Gly Thr Lys Val Glu Ile Lys Arg Thr Val Ala Ala Pro
            100                 105                 110 agt gtc ttc atc ttc ccg cca tct gat gag cag ttg aaa tct gga act     384
Ser Val Phe Ile Phe Pro Pro Ser Asp Glu Gln Leu Lys Ser Gly Thr
        115                 120                 125 gcc tct gtt gtg tgc ctg ctg aat aac ttc tat ccc aga gag gcc aaa     432
Ala Ser Val Val Cys Leu Leu Asn Asn Phe Tyr Pro Arg Glu Ala Lys
    130                 135                 140 gta cag tgg aag gtg gat aac gcc ctc caa tcg ggt aac tcc cag gag     480
Val Gln Trp Lys Val Asp Asn Ala Leu Gln Ser Gly Asn Ser Gln Glu
145                 150                 155                 160 agt gtc aca gag cag gac agc aag gac agc acc tac agc ctc agc agc     528
Ser Val Thr Glu Gln Asp Ser Lys Asp Ser Thr Tyr Ser Leu Ser Ser
                165                 170                 175 acc ctg acg ctg agc aaa gca gac tac gag aaa cac aaa gtc tac gcc     576
Thr Leu Thr Leu Ser Lys Ala Asp Tyr Glu Lys His Lys Val Tyr Ala
            180                 185                 190
```

```
tgc gaa gtc acc cat cag ggc ctg agc tcg ccc gtc aca aag agc ttc        624
Cys Glu Val Thr His Gln Gly Leu Ser Ser Pro Val Thr Lys Ser Phe
        195                 200                 205 aac agg gga gag tgt                                                    639
Asn Arg Gly Glu Cys
    210

<210> SEQ ID NO 70
<211> LENGTH: 213
<212> TYPE: PRT
<213> ORGANISM: Artificial Sequence
<220> FEATURE:
<223> OTHER INFORMATION: Synthetic Construct

<400> SEQUENCE: 70

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 71
<211> LENGTH: 705
<212> TYPE: DNA
<213> ORGANISM: Artificial Sequence
<220> FEATURE:
<223> OTHER INFORMATION: 3C_23 light chain with leader
<220> FEATURE:
<221> NAME/KEY: CDS
<222> LOCATION: (1)..(705)

<400> SEQUENCE: 71 atg gat atg aga gtg ccc gca cag ctg ctg ggt ctg ctg ctg ctg tgg        48
Met Asp Met Arg Val Pro Ala Gln Leu Leu Gly Leu Leu Leu Leu Trp
1               5                   10                  15 ctg ccc gga gcc aaa tgt gac atc cag atg aca cag tcc cca tct acc        96
Leu Pro Gly Ala Lys Cys Asp Ile Gln Met Thr Gln Ser Pro Ser Thr
```

```
                      20                  25                  30
ctg tct gct tcc gtg gga gat cgg gtg act atc acc tgc aga gca agc      144
Leu Ser Ala Ser Val Gly Asp Arg Val Thr Ile Thr Cys Arg Ala Ser
         35                  40                  45 tcc tcc gtg agg tac atc gct tgg tac cag cag aag cca gga aag gcc      192
Ser Ser Val Arg Tyr Ile Ala Trp Tyr Gln Gln Lys Pro Gly Lys Ala
 50                  55                  60 cca aag ctg ctg acc tac cca acc tcc tcc ctg gaa tcc ggg gtg ccc      240
Pro Lys Leu Leu Thr Tyr Pro Thr Ser Ser Leu Glu Ser Gly Val Pro
65                  70                  75                  80 agc aga ttc tca ggc agt ggc tcc ggc acc gaa ttc acc ctg acc atc      288
Ser Arg Phe Ser Gly Ser Gly Ser Gly Thr Glu Phe Thr Leu Thr Ile
                 85                  90                  95 agc tca ctg cag cct gac gac ttc gca acc tac tac tgt ctg cag tgg      336
Ser Ser Leu Gln Pro Asp Asp Phe Ala Thr Tyr Tyr Cys Leu Gln Trp
            100                 105                 110 agt agc tac cct tgg aca ttc ggc ggc ggc acc aag gtg gag atc aag      384
Ser Ser Tyr Pro Trp Thr Phe Gly Gly Gly Thr Lys Val Glu Ile Lys
        115                 120                 125 cgg acc gtc gcc gca cca agt gtc ttc atc ttc ccg cca tct gat gag      432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc      480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa      528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc      576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag      624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg      672
Lys His Lys Val Tyr Ala Cys Glu Val Thr His Gln Gly Leu Ser Ser
    210                 215                 220 ccc gtc aca aag agc ttc aac agg gga gag tgt                          705
Pro Val Thr Lys Ser Phe Asn Arg Gly Glu Cys
225                 230                 235

<210> SEQ ID NO 72
<211> LENGTH: 235
<212> TYPE: PRT
<213> ORGANISM: Artificial Sequence
<220> FEATURE:
<223> OTHER INFORMATION: Synthetic Construct

<400> SEQUENCE: 72

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
                20                  25                  30

Leu Ser Ala Ser Val Gly Asp Arg Val Thr Ile Thr Cys Arg Ala Ser
            35                  40                  45

Ser Ser Val Arg Tyr Ile Ala Trp Tyr Gln Gln Lys Pro Gly Lys Ala
        50                  55                  60

Pro Lys Leu Leu Thr Tyr Pro Thr Ser Ser Leu Glu Ser Gly Val Pro
65                  70                  75                  80
```

```
Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 73
<211> LENGTH: 1335
<212> TYPE: DNA
<213> ORGANISM: Artificial Sequence
<220> FEATURE:
<223> OTHER INFORMATION: 3C_23 heavy chain without leader
<220> FEATURE:
<221> NAME/KEY: CDS
<222> LOCATION: (1)..(1335)

<400> SEQUENCE: 73 cag gtg cgg ctg gtg cag agc ggg gcc gag gtg aag aag cct gga gcc      48
Gln Val Arg Leu Val Gln Ser Gly Ala Glu Val Lys Lys Pro Gly Ala
1               5                   10                  15 tca gtg aag gtg agt tgc aag gcc tcc ggt tac acc ttc acc agc tac      96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg     144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc     192
Gly Trp Ile Tyr Pro Gly Asp Asp Ser Thr Lys Tyr Ser Gln Lys Phe
    50                  55                  60 cag ggt cgc gtg acc att acc agg gac acc agc gcc tcc act gcc tac     240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt     288
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc     336
Thr Arg Gly Asp Arg Phe Ala Tyr Trp Gly Gln Gly Thr Leu Val Thr
            100                 105                 110 gtc tcg agc gcc agc acc aag ggc cca tcg gtc ttc ccc ctg gca ccc     384
Val Ser Ser Ala Ser Thr Lys Gly Pro Ser Val Phe Pro Leu Ala Pro
        115                 120                 125 tcc tcc aag agc acc tct ggg ggc aca gcg gcc ctg ggc tgc ctg gtc     432
Ser Ser Lys Ser Thr Ser Gly Gly Thr Ala Ala Leu Gly Cys Leu Val
130                 135                 140
```

-continued

| | | |
|---|---|---|
| aag gac tac ttc ccc gaa ccg gtg acg gtg tcg tgg aac tca ggc gcc<br>Lys Asp Tyr Phe Pro Glu Pro Val Thr Val Ser Trp Asn Ser Gly Ala<br>145                      150                      155                    160 | 480 |
| ctg acc agc ggc gtg cac acc ttc ccg gct gtc cta cag tcc tca gga<br>Leu Thr Ser Gly Val His Thr Phe Pro Ala Val Leu Gln Ser Ser Gly<br>                      165                      170                    175 | 528 |
| ctc tac tcc ctc agc agc gtg gtg acc gtg ccc tcc agc agc ttg ggc<br>Leu Tyr Ser Leu Ser Ser Val Val Thr Val Pro Ser Ser Ser Leu Gly<br>                  180                      185                    190 | 576 |
| acc cag acc tac atc tgc aac gtg aat cac aag ccc agc aac acc aag<br>Thr Gln Thr Tyr Ile Cys Asn Val Asn His Lys Pro Ser Asn Thr Lys<br>                195                      200                    205 | 624 |
| gtg gac aag aaa gtt gag ccc aaa tct tgt gac aaa act cac aca tgc<br>Val Asp Lys Lys Val Glu Pro Lys Ser Cys Asp Lys Thr His Thr Cys<br>210                      215                      220 | 672 |
| cca ccg tgc cca gca cct gaa ctc ctg ggg gga ccg tca gtc ttc ctc<br>Pro Pro Cys Pro Ala Pro Glu Leu Leu Gly Gly Pro Ser Val Phe Leu<br>225                      230                      235                    240 | 720 |
| ttc ccc cca aaa ccc aag gac acc ctc atg atc tcc cgg acc cct gag<br>Phe Pro Pro Lys Pro Lys Asp Thr Leu Met Ile Ser Arg Thr Pro Glu<br>                      245                      250                    255 | 768 |
| gtc aca tgc gtg gtg gtg gac gtg agc cac gaa gac cct gag gtc aag<br>Val Thr Cys Val Val Val Asp Val Ser His Glu Asp Pro Glu Val Lys<br>                260                      265                    270 | 816 |
| ttc aac tgg tac gtg gac ggc gtg gag gtg cat aat gcc aag aca aag<br>Phe Asn Trp Tyr Val Asp Gly Val Glu Val His Asn Ala Lys Thr Lys<br>              275                      280                    285 | 864 |
| ccg cgg gag gag cag tac aac agc acg tac cgt gtg gtc agc gtc ctc<br>Pro Arg Glu Glu Gln Tyr Asn Ser Thr Tyr Arg Val Val Ser Val Leu<br>290                      295                      300 | 912 |
| acc gtc ctg cac cag gac tgg ctg aat ggc aag gag tac aag tgc aag<br>Thr Val Leu His Gln Asp Trp Leu Asn Gly Lys Glu Tyr Lys Cys Lys<br>305                      310                      315                    320 | 960 |
| gtc tcc aac aaa gcc ctc cca gcc ccc atc gag aaa acc atc tcc aaa<br>Val Ser Asn Lys Ala Leu Pro Ala Pro Ile Glu Lys Thr Ile Ser Lys<br>                      325                      330                    335 | 1008 |
| gcc aaa ggg cag ccc cga gaa cca cag gtg tac acc ctg ccc cca tcc<br>Ala Lys Gly Gln Pro Arg Glu Pro Gln Val Tyr Thr Leu Pro Pro Ser<br>              340                      345                    350 | 1056 |
| cgg gat gag ctg acc aag aac cag gtc agc ctg acc tgc ctg gtc aaa<br>Arg Asp Glu Leu Thr Lys Asn Gln Val Ser Leu Thr Cys Leu Val Lys<br>              355                      360                    365 | 1104 |
| ggc ttc tat ccc agc gac atc gcc gtg gag tgg gag agc aat ggg cag<br>Gly Phe Tyr Pro Ser Asp Ile Ala Val Glu Trp Glu Ser Asn Gly Gln<br>370                      375                      380 | 1152 |
| ccg gag aac aac tac aag acc acg cct ccc gtg ctg gac tcc gac ggc<br>Pro Glu Asn Asn Tyr Lys Thr Thr Pro Pro Val Leu Asp Ser Asp Gly<br>385                      390                      395                    400 | 1200 |
| tcc ttc ttc ctc tac agc aag ctc acc gtg gac aag agc agg tgg cag<br>Ser Phe Phe Leu Tyr Ser Lys Leu Thr Val Asp Lys Ser Arg Trp Gln<br>                      405                      410                    415 | 1248 |
| cag ggg aac gtc ttc tca tgc tcc gtg atg cat gag gct ctg cac aac<br>Gln Gly Asn Val Phe Ser Cys Ser Val Met His Glu Ala Leu His Asn<br>              420                      425                    430 | 1296 |
| cac tac acg cag aag agc ctc tcc ctg tct ccg ggt aaa<br>His Tyr Thr Gln Lys Ser Leu Ser Leu Ser Pro Gly Lys<br>              435                      440                    445 | 1335 |

<210> SEQ ID NO 74
<211> LENGTH: 445

<212> TYPE: PRT
<213> ORGANISM: Artificial Sequence
<220> FEATURE:
<223> OTHER INFORMATION: Synthetic Construct

<400> SEQUENCE: 74

```
Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 75
<211> LENGTH: 1392
<212> TYPE: DNA
<213> ORGANISM: Artificial Sequence
<220> FEATURE:
<223> OTHER INFORMATION: 3C_23 heavy chain with leader
<220> FEATURE:
<221> NAME/KEY: CDS
<222> LOCATION: (1)..(1392)

<400> SEQUENCE: 75 atg gat tgg aca tgg cga atc ctg ttc ctg gtg gct gcc gca acc ggc      48
Met Asp Trp Thr Trp Arg Ile Leu Phe Leu Val Ala Ala Ala Thr Gly
1               5                   10                  15 gcc cac agc cag gtg cgg ctg gtg cag agc ggg gcc gag gtg aag aag      96
Ala His Ser Gln Val Arg Leu Val Gln Ser Gly Ala Glu Val Lys Lys
            20                  25                  30 cct gga gcc tca gtg aag gtg agt tgc aag gcc tcc ggt tac acc ttc     144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga ctg     192
Thr Ser Tyr His Ile His Trp Val Arg Gln Ala Pro Gly Gln Arg Leu
    50                  55                  60 gag tgg atg ggc tgg atc tac cct gga gat gac tcc acc aag tac tcc     240
Glu Trp Met Gly Trp Ile Tyr Pro Gly Asp Asp Ser Thr Lys Tyr Ser
65                  70                  75                  80 cag aag ttc cag ggt cgc gtg acc att acc agg gac acc agc gcc tcc     288
Gln Lys Phe Gln Gly Arg Val Thr Ile Thr Arg Asp Thr Ser Ala Ser
                85                  90                  95 act gcc tac atg gag ctg tct tcc ctg aga tct gag gat acc gca gtc     336
Thr Ala Tyr Met Glu Leu Ser Ser Leu Arg Ser Glu Asp Thr Ala Val
            100                 105                 110 tac tac tgt aca cgg ggg gac cgc ttt gct tac tgg ggg cag ggc act     384
Tyr Tyr Cys Thr Arg Gly Asp Arg Phe Ala Tyr Trp Gly Gln Gly Thr
        115                 120                 125 ctg gtg acc gtc tcg agc gcc agc acc aag ggc cca tcg gtc ttc ccc     432
Leu Val Thr Val Ser Ser Ala Ser Thr Lys Gly Pro Ser Val Phe Pro
    130                 135                 140 ctg gca ccc tcc tcc aag agc acc tct ggg ggc aca gcg gcc ctg ggc     480
Leu Ala Pro Ser Ser Lys Ser Thr Ser Gly Gly Thr Ala Ala Leu Gly
145                 150                 155                 160 tgc ctg gtc aag gac tac ttc ccc gaa ccg gtg acg gtg tcg tgg aac     528
Cys Leu Val Lys Asp Tyr Phe Pro Glu Pro Val Thr Val Ser Trp Asn
                165                 170                 175 tca ggc gcc ctg acc agc ggc gtg cac acc ttc ccg gct gtc cta cag     576
Ser Gly Ala Leu Thr Ser Gly Val His Thr Phe Pro Ala Val Leu Gln
            180                 185                 190 tcc tca gga ctc tac tcc ctc agc agc gtg gtg acc gtg ccc tcc agc     624
Ser Ser Gly Leu Tyr Ser Leu Ser Ser Val Val Thr Val Pro Ser Ser
        195                 200                 205 agc ttg ggc acc cag acc tac atc tgc aac gtg aat cac aag ccc agc     672
Ser Leu Gly Thr Gln Thr Tyr Ile Cys Asn Val Asn His Lys Pro Ser
```

```
aac acc aag gtg gac aag aaa gtt gag ccc aaa tct tgt gac aaa act      720
Asn Thr Lys Val Asp Lys Lys Val Glu Pro Lys Ser Cys Asp Lys Thr
225                 230                 235                 240 cac aca tgc cca ccg tgc cca gca cct gaa ctc ctg ggg gga ccg tca      768
His Thr Cys Pro Pro Cys Pro Ala Pro Glu Leu Leu Gly Gly Pro Ser
                245                 250                 255 gtc ttc ctc ttc ccc cca aaa ccc aag gac acc ctc atg atc tcc cgg      816
Val Phe Leu Phe Pro Pro Lys Pro Lys Asp Thr Leu Met Ile Ser Arg
            260                 265                 270 acc cct gag gtc aca tgc gtg gtg gtg gac gtg agc cac gaa gac cct      864
Thr Pro Glu Val Thr Cys Val Val Val Asp Val Ser His Glu Asp Pro
        275                 280                 285 gag gtc aag ttc aac tgg tac gtg gac ggc gtg gag gtg cat aat gcc      912
Glu Val Lys Phe Asn Trp Tyr Val Asp Gly Val Glu Val His Asn Ala
    290                 295                 300 aag aca aag ccg cgg gag gag cag tac aac agc acg tac cgt gtg gtc      960
Lys Thr Lys Pro Arg Glu Glu Gln Tyr Asn Ser Thr Tyr Arg Val Val
305                 310                 315                 320 agc gtc ctc acc gtc ctg cac cag gac tgg ctg aat ggc aag gag tac     1008
Ser Val Leu Thr Val Leu His Gln Asp Trp Leu Asn Gly Lys Glu Tyr
                325                 330                 335 aag tgc aag gtc tcc aac aaa gcc ctc cca gcc ccc atc gag aaa acc     1056
Lys Cys Lys Val Ser Asn Lys Ala Leu Pro Ala Pro Ile Glu Lys Thr
            340                 345                 350 atc tcc aaa gcc aaa ggg cag ccc cga gaa cca cag gtg tac acc ctg     1104
Ile Ser Lys Ala Lys Gly Gln Pro Arg Glu Pro Gln Val Tyr Thr Leu
        355                 360                 365 ccc cca tcc cgg gat gag ctg acc aag aac cag gtc agc ctg acc tgc     1152
Pro Pro Ser Arg Asp Glu Leu Thr Lys Asn Gln Val Ser Leu Thr Cys
    370                 375                 380 ctg gtc aaa ggc ttc tat ccc agc gac atc gcc gtg gag tgg gag agc     1200
Leu Val Lys Gly Phe Tyr Pro Ser Asp Ile Ala Val Glu Trp Glu Ser
385                 390                 395                 400 aat ggg cag ccg gag aac aac tac aag acc acg cct ccc gtg ctg gac     1248
Asn Gly Gln Pro Glu Asn Asn Tyr Lys Thr Thr Pro Pro Val Leu Asp
                405                 410                 415 tcc gac ggc tcc ttc ttc ctc tac agc aag ctc acc gtg gac aag agc     1296
Ser Asp Gly Ser Phe Phe Leu Tyr Ser Lys Leu Thr Val Asp Lys Ser
            420                 425                 430 agg tgg cag cag ggg aac gtc ttc tca tgc tcc gtg atg cat gag gct     1344
Arg Trp Gln Gln Gly Asn Val Phe Ser Cys Ser Val Met His Glu Ala
        435                 440                 445 ctg cac aac cac tac acg cag aag agc ctc tcc ctg tct ccg ggt aaa     1392
Leu His Asn His Tyr Thr Gln Lys Ser Leu Ser Leu Ser Pro Gly Lys
    450                 455                 460
```

<210> SEQ ID NO 76
<211> LENGTH: 464
<212> TYPE: PRT
<213> ORGANISM: Artificial Sequence
<220> FEATURE:
<223> OTHER INFORMATION: Synthetic Construct

<400> SEQUENCE: 76

```
Met Asp Trp Thr Trp Arg Ile Leu Phe Leu Val Ala Ala Thr Gly
1               5                   10                  15

Ala His Ser Gln Val Arg Leu Val Gln Ser Gly Ala Glu Val Lys Lys
                20                  25                  30

Pro Gly Ala Ser Val Lys Val Ser Cys Lys Ala Ser Gly Tyr Thr Phe
```

```
                35                  40                  45
Thr Ser Tyr His Ile His Trp Val Arg Gln Ala Pro Gly Gln Arg Leu
 50                  55                  60
Glu Trp Met Gly Trp Ile Tyr Pro Gly Asp Asp Ser Thr Lys Tyr Ser
 65                  70                  75                  80
Gln Lys Phe Gln Gly Arg Val Thr Ile Thr Arg Asp Thr Ser Ala Ser
                 85                  90                  95
Thr Ala Tyr Met Glu Leu Ser Ser Leu Arg Ser Glu Asp Thr Ala Val
                100                 105                 110
Tyr Tyr Cys Thr Arg Gly Asp Arg Phe Ala Tyr Trp Gly Gln Gly Thr
                115                 120                 125
Leu Val Thr Val Ser Ser Ala Ser Thr Lys Gly Pro Ser Val Phe Pro
130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
                180                 185                 190
Ser Ser Gly Leu Tyr Ser Leu Ser Ser Val Val Thr Val Pro Ser Ser
                195                 200                 205
Ser Leu Gly Thr Gln Thr Tyr Ile Cys Asn Val Asn His Lys Pro Ser
                210                 215                 220
Asn Thr Lys Val Asp Lys Lys Val Glu Pro Lys Ser Cys Asp Lys Thr
225                 230                 235                 240
His Thr Cys Pro Pro Cys Pro Ala Pro Glu Leu Leu Gly Gly Pro Ser
                245                 250                 255
Val Phe Leu Phe Pro Pro Lys Pro Lys Asp Thr Leu Met Ile Ser Arg
                260                 265                 270
Thr Pro Glu Val Thr Cys Val Val Val Asp Val Ser His Glu Asp Pro
                275                 280                 285
Glu Val Lys Phe Asn Trp Tyr Val Asp Gly Val Glu Val His Asn Ala
                290                 295                 300
Lys Thr Lys Pro Arg Glu Glu Gln Tyr Asn Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Ala Leu Pro Ala Pro Ile Glu Lys Thr
                340                 345                 350
Ile Ser Lys Ala Lys Gly Gln Pro Arg Glu Pro Gln Val Tyr Thr Leu
                355                 360                 365
Pro Pro Ser Arg Asp Glu Leu Thr Lys Asn Gln Val Ser Leu Thr Cys
                370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Lys Leu Thr Val Asp Lys Ser
                420                 425                 430
Arg Trp Gln Gln Gly Asn Val Phe Ser Cys Ser Val Met His Glu Ala
                435                 440                 445
Leu His Asn His Tyr Thr Gln Lys Ser Leu Ser Leu Ser Pro Gly Lys
                450                 455                 460
```

<210> SEQ ID NO 77
<211> LENGTH: 639
<212> TYPE: DNA
<213> ORGANISM: Artificial Sequence
<220> FEATURE:
<223> OTHER INFORMATION: 6B_78 light chain without leader
<220> FEATURE:
<221> NAME/KEY: CDS
<222> LOCATION: (1)..(639)

<400> SEQUENCE: 77

| | | | | | | | | | | | | | | | | |
|---|---|---|---|---|---|---|---|---|---|---|---|---|---|---|---|---|
| gac | atc | cag | atg | aca | cag | tcc | cca | tct | acc | ctg | tct | gct | tcc | gtg | gga | 48 |
| Asp | Ile | Gln | Met | Thr | Gln | Ser | Pro | Ser | Thr | Leu | Ser | Ala | Ser | Val | Gly | |
| 1 | | | | 5 | | | | | 10 | | | | | 15 | | |
| gat | cgg | gtg | act | atc | acc | tgc | aga | gca | agc | tcc | tcc | gtg | agg | tac | atc | 96 |
| Asp | Arg | Val | Thr | Ile | Thr | Cys | Arg | Ala | Ser | Ser | Ser | Val | Arg | Tyr | Ile | |
| | | | 20 | | | | | 25 | | | | | 30 | | | |
| gct | tgg | tac | cag | cag | aag | cca | gga | aag | gcc | cca | aag | ctg | ctg | atc | tac | 144 |
| Ala | Trp | Tyr | Gln | Gln | Lys | Pro | Gly | Lys | Ala | Pro | Lys | Leu | Leu | Ile | Tyr | |
| | | 35 | | | | | 40 | | | | | 45 | | | | |
| tca | acc | tcc | tcc | ctg | aaa | tcc | ggg | gtg | ccc | agc | aga | ttc | tca | ggc | agt | 192 |
| Ser | Thr | Ser | Ser | Leu | Lys | Ser | Gly | Val | Pro | Ser | Arg | Phe | Ser | Gly | Ser | |
| 50 | | | | | 55 | | | | | 60 | | | | | | |
| ggc | tcc | ggc | acc | gaa | ttc | acc | ctg | acc | atc | agc | tca | ctg | cag | cct | gac | 240 |
| Gly | Ser | Gly | Thr | Glu | Phe | Thr | Leu | Thr | Ile | Ser | Ser | Leu | Gln | Pro | Asp | |
| 65 | | | | 70 | | | | | 75 | | | | | 80 | | |
| gac | ttc | gca | acc | tac | tac | tgt | ctg | cag | tgg | agt | agc | tac | cct | tgg | aca | 288 |
| Asp | Phe | Ala | Thr | Tyr | Tyr | Cys | Leu | Gln | Trp | Ser | Ser | Tyr | Pro | Trp | Thr | |
| | | | 85 | | | | | 90 | | | | | 95 | | | |
| ttc | ggc | ggc | ggc | acc | aag | gtg | gag | atc | aag | cgg | acc | gtc | gcc | gca | cca | 336 |
| Phe | Gly | Gly | Gly | Thr | Lys | Val | Glu | Ile | Lys | Arg | Thr | Val | Ala | Ala | Pro | |
| | | 100 | | | | | 105 | | | | | 110 | | | | |
| agt | gtc | ttc | atc | ttc | ccg | cca | tct | gat | gag | cag | ttg | aaa | tct | gga | act | 384 |
| Ser | Val | Phe | Ile | Phe | Pro | Pro | Ser | Asp | Glu | Gln | Leu | Lys | Ser | Gly | Thr | |
| | | 115 | | | | | 120 | | | | | 125 | | | | |
| gcc | tct | gtt | gtg | tgc | ctg | ctg | aat | aac | ttc | tat | ccc | aga | gag | gcc | aaa | 432 |
| Ala | Ser | Val | Val | Cys | Leu | Leu | Asn | Asn | Phe | Tyr | Pro | Arg | Glu | Ala | Lys | |
| | 130 | | | | | 135 | | | | | 140 | | | | | |
| gta | cag | tgg | aag | gtg | gat | aac | gcc | ctc | caa | tcg | ggt | aac | tcc | cag | gag | 480 |
| Val | Gln | Trp | Lys | Val | Asp | Asn | Ala | Leu | Gln | Ser | Gly | Asn | Ser | Gln | Glu | |
| 145 | | | | | 150 | | | | | 155 | | | | | 160 | |
| agt | gtc | aca | gag | cag | gac | agc | aag | gac | agc | acc | tac | agc | ctc | agc | agc | 528 |
| Ser | Val | Thr | Glu | Gln | Asp | Ser | Lys | Asp | Ser | Thr | Tyr | Ser | Leu | Ser | Ser | |
| | | | | 165 | | | | | 170 | | | | | 175 | | |
| acc | ctg | acg | ctg | agc | aaa | gca | gac | tac | gag | aaa | cac | aaa | gtc | tac | gcc | 576 |
| Thr | Leu | Thr | Leu | Ser | Lys | Ala | Asp | Tyr | Glu | Lys | His | Lys | Val | Tyr | Ala | |
| | | | 180 | | | | | 185 | | | | | 190 | | | |
| tgc | gaa | gtc | acc | cat | cag | ggc | ctg | agc | tcg | ccc | gtc | aca | aag | agc | ttc | 624 |
| Cys | Glu | Val | Thr | His | Gln | Gly | Leu | Ser | Ser | Pro | Val | Thr | Lys | Ser | Phe | |
| | | 195 | | | | | 200 | | | | | 205 | | | | |
| aac | agg | gga | gag | tgt | | | | | | | | | | | | 639 |
| Asn | Arg | Gly | Glu | Cys | | | | | | | | | | | | |
| | 210 | | | | | | | | | | | | | | | |

<210> SEQ ID NO 78
<211> LENGTH: 213
<212> TYPE: PRT
<213> ORGANISM: Artificial Sequence
<220> FEATURE:
<223> OTHER INFORMATION: Synthetic Construct

<400> SEQUENCE: 78

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Ile Tyr
        35                  40                  45

Ser Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 79
<211> LENGTH: 705
<212> TYPE: DNA
<213> ORGANISM: Artificial Sequence
<220> FEATURE:
<223> OTHER INFORMATION: 6B_78 light chain with leader
<220> FEATURE:
<221> NAME/KEY: CDS
<222> LOCATION: (1)..(705)

<400> SEQUENCE: 79 atg gat atg aga gtg ccc gca cag ctg ctg ggt ctg ctg ctg ctg tgg      48
Met Asp Met Arg Val Pro Ala Gln Leu Leu Gly Leu Leu Leu Leu Trp
1               5                   10                  15 ctg ccc gga gcc aaa tgt gac atc cag atg aca cag tcc cca tct acc      96
Leu Pro Gly Ala Lys Cys Asp Ile Gln Met Thr Gln Ser Pro Ser Thr
            20                  25                  30 ctg tct gct tcc gtg gga gat cgg gtg act atc acc tgc aga gca agc     144
Leu Ser Ala Ser Val Gly Asp Arg Val Thr Ile Thr Cys Arg Ala Ser
        35                  40                  45 tcc tcc gtg agg tac atc gct tgg tac cag cag aag cca gga aag gcc     192
Ser Ser Val Arg Tyr Ile Ala Trp Tyr Gln Gln Lys Pro Gly Lys Ala
    50                  55                  60 cca aag ctg ctg atc tac tca acc tcc tcc ctg aaa tcc ggg gtg ccc     240
Pro Lys Leu Leu Ile Tyr Ser Thr Ser Ser Leu Lys Ser Gly Val Pro
65                  70                  75                  80 agc aga ttc tca ggc agt ggc tcc ggc acc gaa ttc acc ctg acc atc     288
Ser Arg Phe Ser Gly Ser Gly Ser Gly Thr Glu Phe Thr Leu Thr Ile
                85                  90                  95
```

```
agc tca ctg cag cct gac gac ttc gca acc tac tac tgt ctg cag tgg      336
Ser Ser Leu Gln Pro Asp Asp Phe Ala Thr Tyr Tyr Cys Leu Gln Trp
        100                 105                 110 agt agc tac cct tgg aca ttc ggc ggc ggc acc aag gtg gag atc aag      384
Ser Ser Tyr Pro Trp Thr Phe Gly Gly Gly Thr Lys Val Glu Ile Lys
            115                 120                 125 cgg acc gtc gcc gca cca agt gtc ttc atc ttc ccg cca tct gat gag      432
Arg Thr Val Ala Ala Pro Ser Val Phe Ile Phe Pro Pro Ser Asp Glu
    130                 135                 140 cag ttg aaa tct gga act gcc tct gtt gtg tgc ctg ctg aat aac ttc      480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa      528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc      576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag      624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg      672
Lys His Lys Val Tyr Ala Cys Glu Val Thr His Gln Gly Leu Ser Ser
    210                 215                 220 ccc gtc aca aag agc ttc aac agg gga gag tgt                          705
Pro Val Thr Lys Ser Phe Asn Arg Gly Glu Cys
225                 230                 235

<210> SEQ ID NO 80
<211> LENGTH: 235
<212> TYPE: PRT
<213> ORGANISM: Artificial Sequence
<220> FEATURE:
<223> OTHER INFORMATION: Synthetic Construct

<400> SEQUENCE: 80

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Ile Tyr Ser Thr Ser Ser Leu Lys Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175
```

```
Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 81
<211> LENGTH: 639
<212> TYPE: DNA
<213> ORGANISM: Artificial Sequence
<220> FEATURE:
<223> OTHER INFORMATION: 3C_23K light chain without leader
<220> FEATURE:
<221> NAME/KEY: CDS
<222> LOCATION: (1)..(639)

<400> SEQUENCE: 81 gac atc cag atg aca cag tcc cca tct acc ctg tct gct tcc gtg gga         48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc         96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg acc tac        144
Ala Trp Tyr Gln Gln Lys Pro Gly Lys Ala Pro Lys Leu Leu Thr Tyr
        35                  40                  45 cca acc tcc tcc ctg aaa tcc ggg gtg ccc agc aga ttc tca ggc agt        192
Pro Thr Ser Ser Leu Lys Ser Gly Val Pro Ser Arg Phe Ser Gly Ser
    50                  55                  60 ggc tcc ggc acc gaa ttc acc ctg acc atc agc tca ctg cag cct gac        240
Gly Ser Gly Thr Glu Phe Thr Leu Thr Ile Ser Ser Leu Gln Pro Asp
65                  70                  75                  80 gac ttc gca acc tac tac tgt ctg cag tgg agt agc tac cct tgg aca        288
Asp Phe Ala Thr Tyr Tyr Cys Leu Gln Trp Ser Ser Tyr Pro Trp Thr
                85                  90                  95 ttc ggc ggc ggc acc aag gtg gag atc aag cgg acc gtc gcc gca cca        336
Phe Gly Gly Gly Thr Lys Val Glu Ile Lys Arg Thr Val Ala Ala Pro
            100                 105                 110 agt gtc ttc atc ttc ccg cca tct gat gag cag ttg aaa tct gga act        384
Ser Val Phe Ile Phe Pro Pro Ser Asp Glu Gln Leu Lys Ser Gly Thr
        115                 120                 125 gcc tct gtt gtg tgc ctg ctg aat aac ttc tat ccc aga gag gcc aaa        432
Ala Ser Val Val Cys Leu Leu Asn Asn Phe Tyr Pro Arg Glu Ala Lys
    130                 135                 140 gta cag tgg aag gtg gat aac gcc ctc caa tcg ggt aac tcc cag gag        480
Val Gln Trp Lys Val Asp Asn Ala Leu Gln Ser Gly Asn Ser Gln Glu
145                 150                 155                 160 agt gtc aca gag cag gac agc aag gac agc acc tac agc ctc agc agc        528
Ser Val Thr Glu Gln Asp Ser Lys Asp Ser Thr Tyr Ser Leu Ser Ser
                165                 170                 175 acc ctg acg ctg agc aaa gca gac tac gag aaa cac aaa gtc tac gcc        576
Thr Leu Thr Leu Ser Lys Ala Asp Tyr Glu Lys His Lys Val Tyr Ala
            180                 185                 190 tgc gaa gtc acc cat cag ggc ctg agc tcg ccc gtc aca aag agc ttc        624
Cys Glu Val Thr His Gln Gly Leu Ser Ser Pro Val Thr Lys Ser Phe
        195                 200                 205 aac agg gga gag tgt                                                    639
Asn Arg Gly Glu Cys
```

Asn Arg Gly Glu Cys
    210

<210> SEQ ID NO 82
<211> LENGTH: 213
<212> TYPE: PRT
<213> ORGANISM: Artificial Sequence
<220> FEATURE:
<223> OTHER INFORMATION: Synthetic Construct

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Thr Tyr
        35                  40                  45

Pro Thr Ser Ser Leu Lys Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 83
<211> LENGTH: 705
<212> TYPE: DNA
<213> ORGANISM: Artificial Sequence
<220> FEATURE:
<223> OTHER INFORMATION: 3C_23K light chain with leader
<220> FEATURE:
<221> NAME/KEY: CDS
<222> LOCATION: (1)..(705)

<400> SEQUENCE: 83 atg gat atg aga gtg ccc gca cag ctg ctg ggt ctg ctg ctg tgg         48
Met Asp Met Arg Val Pro Ala Gln Leu Leu Gly Leu Leu Leu Trp
1               5                   10                  15 ctg ccc gga gcc aaa tgt gac atc cag atg aca cag tcc cca tct acc     96
Leu Pro Gly Ala Lys Cys Asp Ile Gln Met Thr Gln Ser Pro Ser Thr
            20                  25                  30 ctg tct gct tcc gtg gga gat cgg gtg act atc acc tgc aga gca agc    144
Leu Ser Ala Ser Val Gly Asp Arg Val Thr Ile Thr Cys Arg Ala Ser
        35                  40                  45

| | | | | | | | | | | | | | | | | |
|---|---|---|---|---|---|---|---|---|---|---|---|---|---|---|---|---|
| tcc | tcc | gtg | agg | tac | atc | gct | tgg | tac | cag | cag | aag | cca | gga | aag | gcc | 192 |
| Ser | Ser | Val | Arg | Tyr | Ile | Ala | Trp | Tyr | Gln | Gln | Lys | Pro | Gly | Lys | Ala | |
| | 50 | | | | 55 | | | | | 60 | | | | | | |
| cca | aag | ctg | ctg | acc | tac | cca | acc | tcc | tcc | ctg | aaa | tcc | ggg | gtg | ccc | 240 |
| Pro | Lys | Leu | Leu | Thr | Tyr | Pro | Thr | Ser | Ser | Leu | Lys | Ser | Gly | Val | Pro | |
| 65 | | | | | 70 | | | | | 75 | | | | | 80 | |
| agc | aga | ttc | tca | ggc | agt | ggc | tcc | ggc | acc | gaa | ttc | acc | ctg | acc | atc | 288 |
| Ser | Arg | Phe | Ser | Gly | Ser | Gly | Ser | Gly | Thr | Glu | Phe | Thr | Leu | Thr | Ile | |
| | | | | 85 | | | | | 90 | | | | | 95 | | |
| agc | tca | ctg | cag | cct | gac | gac | ttc | gca | acc | tac | tac | tgt | ctg | cag | tgg | 336 |
| Ser | Ser | Leu | Gln | Pro | Asp | Asp | Phe | Ala | Thr | Tyr | Tyr | Cys | Leu | Gln | Trp | |
| | | | 100 | | | | | 105 | | | | | 110 | | | |
| agt | agc | tac | cct | tgg | aca | ttc | ggc | ggc | ggc | acc | aag | gtg | gag | atc | aag | 384 |
| Ser | Ser | Tyr | Pro | Trp | Thr | Phe | Gly | Gly | Gly | Thr | Lys | Val | Glu | Ile | Lys | |
| | | 115 | | | | | 120 | | | | | 125 | | | | |
| cgg | acc | gtc | gcc | gca | cca | agt | gtc | ttc | atc | ttc | ccg | cca | tct | gat | gag | 432 |
| Arg | Thr | Val | Ala | Ala | Pro | Ser | Val | Phe | Ile | Phe | Pro | Pro | Ser | Asp | Glu | |
| 130 | | | | | 135 | | | | | 140 | | | | | | |
| cag | ttg | aaa | tct | gga | act | gcc | tct | gtt | gtg | tgc | ctg | ctg | aat | aac | ttc | 480 |
| Gln | Leu | Lys | Ser | Gly | Thr | Ala | Ser | Val | Val | Cys | Leu | Leu | Asn | Asn | Phe | |
| 145 | | | | | 150 | | | | | 155 | | | | | 160 | |
| tat | ccc | aga | gag | gcc | aaa | gta | cag | tgg | aag | gtg | gat | aac | gcc | ctc | caa | 528 |
| Tyr | Pro | Arg | Glu | Ala | Lys | Val | Gln | Trp | Lys | Val | Asp | Asn | Ala | Leu | Gln | |
| | | | | 165 | | | | | 170 | | | | | 175 | | |
| tcg | ggt | aac | tcc | cag | gag | agt | gtc | aca | gag | cag | gac | agc | aag | gac | agc | 576 |
| Ser | Gly | Asn | Ser | Gln | Glu | Ser | Val | Thr | Glu | Gln | Asp | Ser | Lys | Asp | Ser | |
| | | | 180 | | | | | 185 | | | | | 190 | | | |
| acc | tac | agc | ctc | agc | agc | acc | ctg | acg | ctg | agc | aaa | gca | gac | tac | gag | 624 |
| Thr | Tyr | Ser | Leu | Ser | Ser | Thr | Leu | Thr | Leu | Ser | Lys | Ala | Asp | Tyr | Glu | |
| | | 195 | | | | | 200 | | | | | 205 | | | | |
| aaa | cac | aaa | gtc | tac | gcc | tgc | gaa | gtc | acc | cat | cag | ggc | ctg | agc | tcg | 672 |
| Lys | His | Lys | Val | Tyr | Ala | Cys | Glu | Val | Thr | His | Gln | Gly | Leu | Ser | Ser | |
| 210 | | | | | 215 | | | | | 220 | | | | | | |
| ccc | gtc | aca | aag | agc | ttc | aac | agg | gga | gag | tgt | | | | | | 705 |
| Pro | Val | Thr | Lys | Ser | Phe | Asn | Arg | Gly | Glu | Cys | | | | | | |
| 225 | | | | | 230 | | | | | 235 | | | | | | |

<210> SEQ ID NO 84
<211> LENGTH: 235
<212> TYPE: PRT
<213> ORGANISM: Artificial Sequence
<220> FEATURE:
<223> OTHER INFORMATION: Synthetic Construct

<400> SEQUENCE: 84

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Thr Tyr Pro Thr Ser Ser Leu Lys Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

```
Ser Ser Tyr Pro Trp Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 85
<211> LENGTH: 1335
<212> TYPE: DNA
<213> ORGANISM: Artificial Sequence
<220> FEATURE:
<223> OTHER INFORMATION: 3C_23K heavy chain without leader
<220> FEATURE:
<221> NAME/KEY: CDS
<222> LOCATION: (1)..(1335)

<400> SEQUENCE: 85 cag gtg cgg ctg gtg cag agc ggg gcc gag gtg aag aag cct gga gcc      48
Gln Val Arg Leu Val Gln Ser Gly Ala Glu Val Lys Lys Pro Gly Ala
1               5                   10                  15 tca gtg aag gtg agt tgc aag gcc tcc ggt tac acc ttc acc agc tac      96
Ser Val Lys Val Ser Cys Lys Ala Ser Gly Tyr Thr Phe Thr Ser Tyr
            20                  25                  30 cac atc cac tgg gtc aga cag gct ccc ggc cag aga ctg gag tgg atg     144
His Ile His Trp Val Arg Gln Ala Pro Gly Gln Arg Leu Glu Trp Met
        35                  40                  45 ggc tgg atc tac cct gga gat gac tcc acc aag tac tcc cag aag ttc     192
Gly Trp Ile Tyr Pro Gly Asp Asp Ser Thr Lys Tyr Ser Gln Lys Phe
    50                  55                  60 cag ggt cgc gtg acc att acc agg gac acc agc gcc tcc act gcc tac     240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt     288
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc     336
Thr Arg Gly Asp Arg Phe Ala Tyr Trp Gly Gln Gly Thr Leu Val Thr
            100                 105                 110 gtc tcg agc gcc agc acc aag ggc cca tcg gtc ttc ccc ctg gca ccc     384
Val Ser Ser Ala Ser Thr Lys Gly Pro Ser Val Phe Pro Leu Ala Pro
        115                 120                 125 tcc tcc aag agc acc tct ggg ggc aca gcg gcc ctg ggc tgc ctg gtc     432
Ser Ser Lys Ser Thr Ser Gly Gly Thr Ala Ala Leu Gly Cys Leu Val
    130                 135                 140 aag gac tac ttc ccc gaa ccg gtg acg gtg tcg tgg aac tca ggc gcc     480
Lys Asp Tyr Phe Pro Glu Pro Val Thr Val Ser Trp Asn Ser Gly Ala
145                 150                 155                 160 ctg acc agc ggc gtg cac acc ttc ccg gct gtc cta cag tcc tca gga     528
```

```
Leu Thr Ser Gly Val His Thr Phe Pro Ala Val Leu Gln Ser Ser Gly
                165                 170                 175 ctc tac tcc ctc agc agc gtg gtg acc gtg ccc tcc agc agc ttg ggc      576
Leu Tyr Ser Leu Ser Ser Val Val Thr Val Pro Ser Ser Ser Leu Gly
            180                 185                 190 acc cag acc tac atc tgc aac gtg aat cac aag ccc agc aac acc aag      624
Thr Gln Thr Tyr Ile Cys Asn Val Asn His Lys Pro Ser Asn Thr Lys
            195                 200                 205 gtg gac aag aaa gtt gag ccc aaa tct tgt gac aaa act cac aca tgc      672
Val Asp Lys Lys Val Glu Pro Lys Ser Cys Asp Lys Thr His Thr Cys
210                 215                 220 cca ccg tgc cca gca cct gaa ctc ctg ggg gga ccg tca gtc ttc ctc      720
Pro Pro Cys Pro Ala Pro Glu Leu Leu Gly Gly Pro Ser Val Phe Leu
225                 230                 235                 240 ttc ccc cca aaa ccc aag gac acc ctc atg atc tcc cgg acc cct gag      768
Phe Pro Pro Lys Pro Lys Asp Thr Leu Met Ile Ser Arg Thr Pro Glu
                245                 250                 255 gtc aca tgc gtg gtg gtg gac gtg agc cac gaa gac cct gag gtc aag      816
Val Thr Cys Val Val Val Asp Val Ser His Glu Asp Pro Glu Val Lys
            260                 265                 270 ttc aac tgg tac gtg gac ggc gtg gag gtg cat aat gcc aag aca aag      864
Phe Asn Trp Tyr Val Asp Gly Val Glu Val His Asn Ala Lys Thr Lys
            275                 280                 285 ccg cgg gag gag cag tac aac agc acg tac cgt gtg gtc agc gtc ctc      912
Pro Arg Glu Glu Gln Tyr Asn Ser Thr Tyr Arg Val Val Ser Val Leu
290                 295                 300 acc gtc ctg cac cag gac tgg ctg aat ggc aag gag tac aag tgc aag      960
Thr Val Leu His Gln Asp Trp Leu Asn Gly Lys Glu Tyr Lys Cys Lys
305                 310                 315                 320 gtc tcc aac aaa gcc ctc cca gcc ccc atc gag aaa acc atc tcc aaa     1008
Val Ser Asn Lys Ala Leu Pro Ala Pro Ile Glu Lys Thr Ile Ser Lys
                325                 330                 335 gcc aaa ggg cag ccc cga gaa cca cag gtg tac acc ctg ccc cca tcc     1056
Ala Lys Gly Gln Pro Arg Glu Pro Gln Val Tyr Thr Leu Pro Pro Ser
            340                 345                 350 cgg gat gag ctg acc aag aac cag gtc agc ctg acc tgc ctg gtc aaa     1104
Arg Asp Glu Leu Thr Lys Asn Gln Val Ser Leu Thr Cys Leu Val Lys
            355                 360                 365 ggc ttc tat ccc agc gac atc gcc gtg gag tgg gag agc aat ggg cag     1152
Gly Phe Tyr Pro Ser Asp Ile Ala Val Glu Trp Glu Ser Asn Gly Gln
370                 375                 380 ccg gag aac aac tac aag acc acg cct ccc gtg ctg gac tcc gac ggc     1200
Pro Glu Asn Asn Tyr Lys Thr Thr Pro Pro Val Leu Asp Ser Asp Gly
385                 390                 395                 400 tcc ttc ttc ctc tac agc aag ctc acc gtg gac aag agc agg tgg cag     1248
Ser Phe Phe Leu Tyr Ser Lys Leu Thr Val Asp Lys Ser Arg Trp Gln
                405                 410                 415 cag ggg aac gtc ttc tca tgc tcc gtg atg cat gag gct ctg cac aac     1296
Gln Gly Asn Val Phe Ser Cys Ser Val Met His Glu Ala Leu His Asn
            420                 425                 430 cac tac acg cag aag agc ctc tcc ctg tct ccg ggt aaa                 1335
His Tyr Thr Gln Lys Ser Leu Ser Leu Ser Pro Gly Lys
            435                 440                 445

<210> SEQ ID NO 86
<211> LENGTH: 445
<212> TYPE: PRT
<213> ORGANISM: Artificial Sequence
<220> FEATURE:
<223> OTHER INFORMATION: Synthetic Construct
```

```
<400> SEQUENCE: 86

Gln Val Arg Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415
```

<210> SEQ ID NO 87
<211> LENGTH: 1392
<212> TYPE: DNA
<213> ORGANISM: Artificial Sequence
<220> FEATURE:
<223> OTHER INFORMATION: 3C_23K heavy chain with leader
<220> FEATURE:
<221> NAME/KEY: CDS
<222> LOCATION: (1)..(1392)

<400> SEQUENCE: 87

| | | | | | | | | | | | | | | | | |
|---|---|---|---|---|---|---|---|---|---|---|---|---|---|---|---|---|
| atg | gat | tgg | aca | tgg | cga | atc | ctg | ttc | ctg | gtg | gct | gcc | gca | acc | ggc | 48 |
| Met | Asp | Trp | Thr | Trp | Arg | Ile | Leu | Phe | Leu | Val | Ala | Ala | Ala | Thr | Gly | |
| 1 | | | | 5 | | | | | 10 | | | | | 15 | | |

Gln Gly Asn Val Phe Ser Cys Ser Val Met His Glu Ala Leu His Asn 420 425 430

His Tyr Thr Gln Lys Ser Leu Ser Leu Ser Pro Gly Lys 435 440 445

(Sequence table showing codons and amino acids, positions 1-240, ending at position 720)

Key rows from the sequence:
- Met Asp Trp Thr Trp Arg Ile Leu Phe Leu Val Ala Ala Ala Thr Gly (1-15) — 48
- Ala His Ser Gln Val Arg Leu Val Gln Ser Gly Ala Glu Val Lys Lys (16-30) — 96
- Pro Gly Ala Ser Val Lys Val Ser Cys Lys Ala Ser Gly Tyr Thr Phe (31-45) — 144
- Thr Ser Tyr His Ile His Trp Val Arg Gln Ala Pro Gly Gln Arg Leu (46-60) — 192
- Glu Trp Met Gly Trp Ile Tyr Pro Gly Asp Asp Ser Thr Lys Tyr Ser (61-80) — 240
- Gln Lys Phe Gln Gly Arg Val Thr Ile Thr Arg Asp Thr Ser Ala Ser (81-95) — 288
- Thr Ala Tyr Met Glu Leu Ser Ser Leu Arg Ser Glu Asp Thr Ala Val (96-110) — 336
- Tyr Tyr Cys Thr Arg Gly Asp Arg Phe Ala Tyr Trp Gly Gln Gly Thr (111-125) — 384
- Leu Val Thr Val Ser Ser Ala Ser Thr Lys Gly Pro Ser Val Phe Pro (126-140) — 432
- Leu Ala Pro Ser Ser Lys Ser Thr Ser Gly Gly Thr Ala Ala Leu Gly (141-160) — 480
- Cys Leu Val Lys Asp Tyr Phe Pro Glu Pro Val Thr Val Ser Trp Asn (161-175) — 528
- Ser Gly Ala Leu Thr Ser Gly Val His Thr Phe Pro Ala Val Leu Gln (176-190) — 576
- Ser Ser Gly Leu Tyr Ser Leu Ser Ser Val Val Thr Val Pro Ser Ser (191-205) — 624
- Ser Leu Gly Thr Gln Thr Tyr Ile Cys Asn Val Asn His Lys Pro Ser (206-220) — 672
- Asn Thr Lys Val Asp Lys Lys Val Glu Pro Lys Ser Cys Asp Lys Thr (221-240) — 720

```
cac aca tgc cca ccg tgc cca gca cct gaa ctc ctg ggg gga ccg tca      768
His Thr Cys Pro Pro Cys Pro Ala Pro Glu Leu Leu Gly Gly Pro Ser
                245                 250                 255 gtc ttc ctc ttc ccc cca aaa ccc aag gac acc ctc atg atc tcc cgg      816
Val Phe Leu Phe Pro Pro Lys Pro Lys Asp Thr Leu Met Ile Ser Arg
        260                 265                 270 acc cct gag gtc aca tgc gtg gtg gtg gac gtg agc cac gaa gac cct      864
Thr Pro Glu Val Thr Cys Val Val Val Asp Val Ser His Glu Asp Pro
    275                 280                 285 gag gtc aag ttc aac tgg tac gtg gac ggc gtg gag gtg cat aat gcc      912
Glu Val Lys Phe Asn Trp Tyr Val Asp Gly Val Glu Val His Asn Ala
290                 295                 300 aag aca aag ccg cgg gag gag cag tac aac agc acg tac cgt gtg gtc      960
Lys Thr Lys Pro Arg Glu Glu Gln Tyr Asn Ser Thr Tyr Arg Val Val
305                 310                 315                 320 agc gtc ctc acc gtc ctg cac cag gac tgg ctg aat ggc aag gag tac     1008
Ser Val Leu Thr Val Leu His Gln Asp Trp Leu Asn Gly Lys Glu Tyr
                325                 330                 335 aag tgc aag gtc tcc aac aaa gcc ctc cca gcc ccc atc gag aaa acc     1056
Lys Cys Lys Val Ser Asn Lys Ala Leu Pro Ala Pro Ile Glu Lys Thr
            340                 345                 350 atc tcc aaa gcc aaa ggg cag ccc cga gaa cca cag gtg tac acc ctg     1104
Ile Ser Lys Ala Lys Gly Gln Pro Arg Glu Pro Gln Val Tyr Thr Leu
        355                 360                 365 ccc cca tcc cgg gat gag ctg acc aag aac cag gtc agc ctg acc tgc     1152
Pro Pro Ser Arg Asp Glu Leu Thr Lys Asn Gln Val Ser Leu Thr Cys
    370                 375                 380 ctg gtc aaa ggc ttc tat ccc agc gac atc gcc gtg gag tgg gag agc     1200
Leu Val Lys Gly Phe Tyr Pro Ser Asp Ile Ala Val Glu Trp Glu Ser
385                 390                 395                 400 aat ggg cag ccg gag aac aac tac aag acc acg cct ccc gtg ctg gac     1248
Asn Gly Gln Pro Glu Asn Asn Tyr Lys Thr Thr Pro Pro Val Leu Asp
                405                 410                 415 tcc gac ggc tcc ttc ttc ctc tac agc aag ctc acc gtg gac aag agc     1296
Ser Asp Gly Ser Phe Phe Leu Tyr Ser Lys Leu Thr Val Asp Lys Ser
            420                 425                 430 agg tgg cag cag ggg aac gtc ttc tca tgc tcc gtg atg cat gag gct     1344
Arg Trp Gln Gln Gly Asn Val Phe Ser Cys Ser Val Met His Glu Ala
        435                 440                 445 ctg cac aac cac tac acg cag aag agc ctc tcc ctg tct ccg ggt aaa     1392
Leu His Asn His Tyr Thr Gln Lys Ser Leu Ser Leu Ser Pro Gly Lys
    450                 455                 460

<210> SEQ ID NO 88
<211> LENGTH: 464
<212> TYPE: PRT
<213> ORGANISM: Artificial Sequence
<220> FEATURE:
<223> OTHER INFORMATION: Synthetic Construct

<400> SEQUENCE: 88

Met Asp Trp Thr Trp Arg Ile Leu Phe Leu Val Ala Ala Thr Gly
1               5                   10                  15

Ala His Ser Gln Val Arg Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr His Ile His Trp Val Arg Gln Ala Pro Gly Gln Arg Leu
        50                  55                  60
```

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
            85                  90                  95

Thr Ala Tyr Met Glu Leu Ser Ser Leu Arg Ser Glu Asp Thr Ala Val
                100                 105                 110

Tyr Tyr Cys Thr Arg Gly Asp Arg Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 89
<211> LENGTH: 1335
<212> TYPE: DNA

<213> ORGANISM: Artificial Sequence
<220> FEATURE:
<223> OTHER INFORMATION: 4C_35 heavy chain without leader
<220> FEATURE:
<221> NAME/KEY: CDS
<222> LOCATION: (1)..(1335)

<400> SEQUENCE: 89

```
cag gtg cag ctg gtg cag agc ggg gcc gag gtg aag aag cct gga gcc        48
Gln Val Gln Leu Val Gln Ser Gly Ala Glu Val Lys Lys Pro Gly Ala
1               5                   10                  15 tca gtg aag gtg agt tgc aag gcc tcc ggt tac acc ttc acc agc tac        96
Ser Val Lys Val Ser Cys Lys Ala Ser Gly Tyr Thr Phe Thr Ser Tyr
            20                  25                  30 cac atc cac tgg gtc aga cag gct ccc ggc cag aga cca gag tgg atg       144
His Ile His Trp Val Arg Gln Ala Pro Gly Gln Arg Pro Glu Trp Met
        35                  40                  45 ggc tgg atc tac cct gga gat gac tcc acc aag tac tcc cag aag ttc       192
Gly Trp Ile Tyr Pro Gly Asp Asp Ser Thr Lys Tyr Ser Gln Lys Phe
    50                  55                  60 cag ggt cgc gtg acc att acc agg gac acc agc gcc tcc act gcc tac       240
Gln Gly Arg Val Thr Ile Thr Arg Asp Thr Ser Ala Ser Thr Ala Tyr
65                  70                  75                  80 atg gag ctg tct tcc ctg aga tct gag gat acc gca gtc tac tac tgt       288
Met Glu Leu Ser Ser Leu Arg Ser Glu Asp Thr Ala Val Tyr Tyr Cys
                85                  90                  95 aca cgg ggg gac cgc ttt gct tac tgg ggg cag ggc act ctg gtg acc       336
Thr Arg Gly Asp Arg Phe Ala Tyr Trp Gly Gln Gly Thr Leu Val Thr
            100                 105                 110 gtc agc agc gcc agc acc aag ggc cca tcg gtc ttc ccc ctg gca ccc       384
Val Ser Ser Ala Ser Thr Lys Gly Pro Ser Val Phe Pro Leu Ala Pro
        115                 120                 125 tcc tcc aag agc acc tct ggg ggc aca gcg gcc ctg ggc tgc ctg gtc       432
Ser Ser Lys Ser Thr Ser Gly Gly Thr Ala Ala Leu Gly Cys Leu Val
    130                 135                 140 aag gac tac ttc ccc gaa ccg gtg acg gtg tcg tgg aac tca ggc gcc       480
Lys Asp Tyr Phe Pro Glu Pro Val Thr Val Ser Trp Asn Ser Gly Ala
145                 150                 155                 160 ctg acc agc ggc gtg cac acc ttc ccg gct gtc cta cag tcc tca gga       528
Leu Thr Ser Gly Val His Thr Phe Pro Ala Val Leu Gln Ser Ser Gly
                165                 170                 175 ctc tac tcc ctc agc agc gtg gtg acc gtg ccc tcc agc agc ttg ggc       576
Leu Tyr Ser Leu Ser Ser Val Val Thr Val Pro Ser Ser Ser Leu Gly
            180                 185                 190 acc cag acc tac atc tgc aac gtg aat cac aag ccc agc aac acc aag       624
Thr Gln Thr Tyr Ile Cys Asn Val Asn His Lys Pro Ser Asn Thr Lys
        195                 200                 205 gtg gac aag aaa gtt gag ccc aaa tct tgt gac aaa act cac aca tgc       672
Val Asp Lys Lys Val Glu Pro Lys Ser Cys Asp Lys Thr His Thr Cys
    210                 215                 220 cca ccg tgc cca gca cct gaa ctc ctg ggg gga ccg tca gtc ttc ctc       720
Pro Pro Cys Pro Ala Pro Glu Leu Leu Gly Gly Pro Ser Val Phe Leu
225                 230                 235                 240 ttc ccc cca aaa ccc aag gac acc ctc atg atc tcc cgg acc cct gag       768
Phe Pro Pro Lys Pro Lys Asp Thr Leu Met Ile Ser Arg Thr Pro Glu
                245                 250                 255 gtc aca tgc gtg gtg gtg gac gtg agc cac gaa gac cct gag gtc aag       816
Val Thr Cys Val Val Val Asp Val Ser His Glu Asp Pro Glu Val Lys
            260                 265                 270 ttc aac tgg tac gtg gac ggc gtg gag gtg cat aat gcc aag aca aag       864
Phe Asn Trp Tyr Val Asp Gly Val Glu Val His Asn Ala Lys Thr Lys
```

```
ccg cgg gag gag cag tac aac agc acg tac cgt gtg gtc agc gtc ctc      912
Pro Arg Glu Glu Gln Tyr Asn Ser Thr Tyr Arg Val Val Ser Val Leu
    290                 295                 300 acc gtc ctg cac cag gac tgg ctg aat ggc aag gag tac aag tgc aag      960
Thr Val Leu His Gln Asp Trp Leu Asn Gly Lys Glu Tyr Lys Cys Lys
305                 310                 315                 320 gtc tcc aac aaa gcc ctc cca gcc ccc atc gag aaa acc atc tcc aaa     1008
Val Ser Asn Lys Ala Leu Pro Ala Pro Ile Glu Lys Thr Ile Ser Lys
                325                 330                 335 gcc aaa ggg cag ccc cga gaa cca cag gtg tac acc ctg ccc cca tcc     1056
Ala Lys Gly Gln Pro Arg Glu Pro Gln Val Tyr Thr Leu Pro Pro Ser
            340                 345                 350 cgg gat gag ctg acc aag aac cag gtc agc ctg acc tgc ctg gtc aaa     1104
Arg Asp Glu Leu Thr Lys Asn Gln Val Ser Leu Thr Cys Leu Val Lys
        355                 360                 365 ggc ttc tat ccc agc gac atc gcc gtg gag tgg gag agc aat ggg cag     1152
Gly Phe Tyr Pro Ser Asp Ile Ala Val Glu Trp Glu Ser Asn Gly Gln
370                 375                 380 ccg gag aac aac tac aag acc acg cct ccc gtg ctg gac tcc gac ggc     1200
Pro Glu Asn Asn Tyr Lys Thr Thr Pro Pro Val Leu Asp Ser Asp Gly
385                 390                 395                 400 tcc ttc ttc ctc tac agc aag ctc acc gtg gac aag agc agg tgg cag     1248
Ser Phe Phe Leu Tyr Ser Lys Leu Thr Val Asp Lys Ser Arg Trp Gln
                405                 410                 415 cag ggg aac gtc ttc tca tgc tcc gtg atg cat gag gct ctg cac aac     1296
Gln Gly Asn Val Phe Ser Cys Ser Val Met His Glu Ala Leu His Asn
            420                 425                 430 cac tac acg cag aag agc ctc tcc ctg tct ccg ggt aaa                 1335
His Tyr Thr Gln Lys Ser Leu Ser Leu Ser Pro Gly Lys
        435                 440                 445

<210> SEQ ID NO 90
<211> LENGTH: 445
<212> TYPE: PRT
<213> ORGANISM: Artificial Sequence
<220> FEATURE:
<223> OTHER INFORMATION: Synthetic Construct

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Pro Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 91
<211> LENGTH: 1392
<212> TYPE: DNA
<213> ORGANISM: Artificial Sequence
<220> FEATURE:
<223> OTHER INFORMATION: 4C_35 heavy chain with leader
<220> FEATURE:
<221> NAME/KEY: CDS
<222> LOCATION: (1)..(1392)

<400> SEQUENCE: 91 atg gat tgg aca tgg cga atc ctg ttc ctg gtg gct gcc gca acc ggc      48
Met Asp Trp Thr Trp Arg Ile Leu Phe Leu Val Ala Ala Thr Gly
1               5                   10                  15 gcc cac agc cag gtg cag ctg gtg cag agc ggg gcc gag gtg aag aag      96
Ala His Ser Gln Val Gln Leu Val Gln Ser Gly Ala Glu Val Lys Lys
            20                  25                  30 cct gga gcc tca gtg aag gtg agt tgc aag gcc tcc ggt tac acc ttc     144
```

```
                Pro Gly Ala Ser Val Lys Val Ser Cys Lys Ala Ser Gly Tyr Thr Phe
                         35                  40                  45 acc agc tac cac atc cac tgg gtc aga cag gct ccc ggc cag aga cca          192
Thr Ser Tyr His Ile His Trp Val Arg Gln Ala Pro Gly Gln Arg Pro
     50                  55                  60 gag tgg atg ggc tgg atc tac cct gga gat gac tcc acc aag tac tcc          240
Glu Trp Met Gly Trp Ile Tyr Pro Gly Asp Asp Ser Thr Lys Tyr Ser
 65                  70                  75                  80 cag aag ttc cag ggt cgc gtg acc att acc agg gac acc agc gcc tcc          288
Gln Lys Phe Gln Gly Arg Val Thr Ile Thr Arg Asp Thr Ser Ala Ser
                 85                  90                  95 act gcc tac atg gag ctg tct tcc ctg aga tct gag gat acc gca gtc          336
Thr Ala Tyr Met Glu Leu Ser Ser Leu Arg Ser Glu Asp Thr Ala Val
            100                 105                 110 tac tac tgt aca cgg ggg gac cgc ttt gct tac tgg ggg cag ggc act          384
Tyr Tyr Cys Thr Arg Gly Asp Arg Phe Ala Tyr Trp Gly Gln Gly Thr
            115                 120                 125 ctg gtg acc gtc agc agc gcc agc acc aag ggc cca tcg gtc ttc ccc          432
Leu Val Thr Val Ser Ser Ala Ser Thr Lys Gly Pro Ser Val Phe Pro
            130                 135                 140 ctg gca ccc tcc tcc aag agc acc tct ggg ggc aca gcg gcc ctg ggc          480
Leu Ala Pro Ser Ser Lys Ser Thr Ser Gly Gly Thr Ala Ala Leu Gly
145                 150                 155                 160 tgc ctg gtc aag gac tac ttc ccc gaa ccg gtg acg gtg tcg tgg aac          528
Cys Leu Val Lys Asp Tyr Phe Pro Glu Pro Val Thr Val Ser Trp Asn
                165                 170                 175 tca ggc gcc ctg acc agc ggc gtg cac acc ttc ccg gct gtc cta cag          576
Ser Gly Ala Leu Thr Ser Gly Val His Thr Phe Pro Ala Val Leu Gln
            180                 185                 190 tcc tca gga ctc tac tcc ctc agc agc gtg gtg acc gtg ccc tcc agc          624
Ser Ser Gly Leu Tyr Ser Leu Ser Ser Val Val Thr Val Pro Ser Ser
            195                 200                 205 agc ttg ggc acc cag acc tac atc tgc aac gtg aat cac aag ccc agc          672
Ser Leu Gly Thr Gln Thr Tyr Ile Cys Asn Val Asn His Lys Pro Ser
            210                 215                 220 aac acc aag gtg gac aag aaa gtt gag ccc aaa tct tgt gac aaa act          720
Asn Thr Lys Val Asp Lys Lys Val Glu Pro Lys Ser Cys Asp Lys Thr
225                 230                 235                 240 cac aca tgc cca ccg tgc cca gca cct gaa ctc ctg ggg gga ccg tca          768
His Thr Cys Pro Pro Cys Pro Ala Pro Glu Leu Leu Gly Gly Pro Ser
                245                 250                 255 gtc ttc ctc ttc ccc cca aaa ccc aag gac acc ctc atg atc tcc cgg          816
Val Phe Leu Phe Pro Pro Lys Pro Lys Asp Thr Leu Met Ile Ser Arg
            260                 265                 270 acc cct gag gtc aca tgc gtg gtg gtg gac gtg agc cac gaa gac cct          864
Thr Pro Glu Val Thr Cys Val Val Val Asp Val Ser His Glu Asp Pro
            275                 280                 285 gag gtc aag ttc aac tgg tac gtg gac ggc gtg gag gtg cat aat gcc          912
Glu Val Lys Phe Asn Trp Tyr Val Asp Gly Val Glu Val His Asn Ala
            290                 295                 300 aag aca aag ccg cgg gag gag cag tac aac agc acg tac cgt gtg gtc          960
Lys Thr Lys Pro Arg Glu Glu Gln Tyr Asn Ser Thr Tyr Arg Val Val
305                 310                 315                 320 agc gtc ctc acc gtc ctg cac cag gac tgg ctg aat ggc aag gag tac         1008
Ser Val Leu Thr Val Leu His Gln Asp Trp Leu Asn Gly Lys Glu Tyr
            325                 330                 335 aag tgc aag gtc tcc aac aaa gcc ctc cca gcc ccc atc gag aaa acc         1056
Lys Cys Lys Val Ser Asn Lys Ala Leu Pro Ala Pro Ile Glu Lys Thr
            340                 345                 350
```

-continued

```
atc tcc aaa gcc aaa ggg cag ccc cga gaa cca cag gtg tac acc ctg         1104
Ile Ser Lys Ala Lys Gly Gln Pro Arg Glu Pro Gln Val Tyr Thr Leu
    355                 360                 365 ccc cca tcc cgg gat gag ctg acc aag aac cag gtc agc ctg acc tgc         1152
Pro Pro Ser Arg Asp Glu Leu Thr Lys Asn Gln Val Ser Leu Thr Cys
370                 375                 380 ctg gtc aaa ggc ttc tat ccc agc gac atc gcc gtg gag tgg gag agc         1200
Leu Val Lys Gly Phe Tyr Pro Ser Asp Ile Ala Val Glu Trp Glu Ser
385                 390                 395                 400 aat ggg cag ccg gag aac aac tac aag acc acg cct ccc gtg ctg gac         1248
Asn Gly Gln Pro Glu Asn Asn Tyr Lys Thr Thr Pro Pro Val Leu Asp
                405                 410                 415 tcc gac ggc tcc ttc ttc ctc tac agc aag ctc acc gtg gac aag agc         1296
Ser Asp Gly Ser Phe Phe Leu Tyr Ser Lys Leu Thr Val Asp Lys Ser
            420                 425                 430 agg tgg cag cag ggg aac gtc ttc tca tgc tcc gtg atg cat gag gct         1344
Arg Trp Gln Gln Gly Asn Val Phe Ser Cys Ser Val Met His Glu Ala
            435                 440                 445 ctg cac aac cac tac acg cag aag agc ctc tcc ctg tct ccg ggt aaa         1392
Leu His Asn His Tyr Thr Gln Lys Ser Leu Ser Leu Ser Pro Gly Lys
    450                 455                 460
```

<210> SEQ ID NO 92
<211> LENGTH: 464
<212> TYPE: PRT
<213> ORGANISM: Artificial Sequence
<220> FEATURE:
<223> OTHER INFORMATION: Synthetic Construct

<400> SEQUENCE: 92

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr His Ile His Trp Val Arg Gln Ala Pro Gly Gln Arg Pro
        50                  55                  60

Glu Trp Met Gly Trp Ile Tyr Pro Gly Asp Asp Ser Thr Lys Tyr Ser
65                  70                  75                  80

Gln Lys Phe Gln Gly Arg Val Thr Ile Thr Arg Asp Thr Ser Ala Ser
                85                  90                  95

Thr Ala Tyr Met Glu Leu Ser Ser Leu Arg Ser Glu Asp Thr Ala Val
                100                 105                 110

Tyr Tyr Cys Thr Arg Gly Asp Arg Phe Ala Tyr Trp Gly Gln Gly Thr
            115                 120                 125

Leu Val Thr Val Ser Ser Ala Ser Thr Lys Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220
```

```
Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
            245                 250                 255

Val Phe Leu Phe Pro Pro Lys Pro Lys Asp Thr Leu Met Ile Ser Arg
        260                 265                 270

Thr Pro Glu Val Thr Cys Val Val Val Asp Val Ser His Glu Asp Pro
    275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 93
<211> LENGTH: 639
<212> TYPE: DNA
<213> ORGANISM: Artificial Sequence
<220> FEATURE:
<223> OTHER INFORMATION: 5B_42 light chain without leader
<220> FEATURE:
<221> NAME/KEY: CDS
<222> LOCATION: (1)..(639)

<400> SEQUENCE: 93 gac atc cag atg aca cag tcc cca tct acc ctg tct gct tcc gtg gga      48
Asp Ile Gln Met Thr Gln Ser Pro Ser Thr Leu Ser Ala Ser Val Gly
1               5                   10                  15 gat cgg gtg act atc acc tgc aga gca agc tcc tcc gtg agg tac atc      96
Asp Arg Val Thr Ile Thr Cys Arg Ala Ser Ser Ser Val Arg Tyr Ile
            20                  25                  30 gct tgg tac cag cag aag cca gga aag gcc cca aag ctg ctg atc tac     144
Ala Trp Tyr Gln Gln Lys Pro Gly Lys Ala Pro Lys Leu Leu Ile Tyr
        35                  40                  45 cca acc tcc tcc ctg gaa tcc ggg gtg ccc agc aga ttc tca ggc agt     192
Pro Thr Ser Ser Leu Glu Ser Gly Val Pro Ser Arg Phe Ser Gly Ser
    50                  55                  60 ggc tcc ggc acc gaa ttc acc ctg acc atc agc tca ctg cag cct gac     240
Gly Ser Gly Thr Glu Phe Thr Leu Thr Ile Ser Ser Leu Gln Pro Asp
65                  70                  75                  80
```

```
gac ttc gca acc tac tac tgt ctg cag tgg agt agc tac cct tgg aca    288
Asp Phe Ala Thr Tyr Tyr Cys Leu Gln Trp Ser Ser Tyr Pro Trp Thr
            85                  90                  95 ttc ggc ggc ggc acc aag gtg gag atc aag cgg acc gtc gcc gca cca    336
Phe Gly Gly Gly Thr Lys Val Glu Ile Lys Arg Thr Val Ala Ala Pro
            100                 105                 110 agt gtc ttc atc ttc ccg cca tct gat gag cag ttg aaa tct gga act    384
Ser Val Phe Ile Phe Pro Pro Ser Asp Glu Gln Leu Lys Ser Gly Thr
            115                 120                 125 gcc tct gtt gtg tgc ctg ctg aat aac ttc tat ccc aga gag gcc aaa    432
Ala Ser Val Val Cys Leu Leu Asn Asn Phe Tyr Pro Arg Glu Ala Lys
130             135                 140 gta cag tgg aag gtg gat aac gcc ctc caa tcg ggt aac tcc cag gag    480
Val Gln Trp Lys Val Asp Asn Ala Leu Gln Ser Gly Asn Ser Gln Glu
145             150                 155                 160 agt gtc aca gag cag gac agc aag gac agc acc tac agc ctc agc agc    528
Ser Val Thr Glu Gln Asp Ser Lys Asp Ser Thr Tyr Ser Leu Ser Ser
            165                 170                 175 acc ctg acg ctg agc aaa gca gac tac gag aaa cac aaa gtc tac gcc    576
Thr Leu Thr Leu Ser Lys Ala Asp Tyr Glu Lys His Lys Val Tyr Ala
            180                 185                 190 tgc gaa gtc acc cat cag ggc ctg agc tcg ccc gtc aca aag agc ttc    624
Cys Glu Val Thr His Gln Gly Leu Ser Ser Pro Val Thr Lys Ser Phe
            195                 200                 205 aac agg gga gag tgt                                                 639
Asn Arg Gly Glu Cys
    210
```

```
<210> SEQ ID NO 94
<211> LENGTH: 213
<212> TYPE: PRT
<213> ORGANISM: Artificial Sequence
<220> FEATURE:
<223> OTHER INFORMATION: Synthetic Construct

<400> SEQUENCE: 94

Asp Ile Gln Met Thr Gln Ser Pro Ser Thr Leu Ser Ala Ser Val Gly
1               5                   10                  15

Asp Arg Val Thr Ile Thr Cys Arg Ala Ser Ser Ser Val Arg Tyr Ile
            20                  25                  30

Ala Trp Tyr Gln Gln Lys Pro Gly Lys Ala Pro Lys Leu Leu Ile Tyr
        35                  40                  45

Pro Thr Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Leu Gln Trp Ser Ser Tyr Pro Trp Thr
            85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130             135                 140

Val Gln Trp Lys Val Asp Asn Ala Leu Gln Ser Gly Asn Ser Gln Glu
145             150                 155                 160

Ser Val Thr Glu Gln Asp Ser Lys Asp Ser Thr Tyr Ser Leu Ser Ser
            165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 95
<211> LENGTH: 705
<212> TYPE: DNA
<213> ORGANISM: Artificial Sequence
<220> FEATURE:
<223> OTHER INFORMATION: 5B_42 light chain with leader
<220> FEATURE:
<221> NAME/KEY: CDS
<222> LOCATION: (1)..(705)

<400> SEQUENCE: 95 atg atg atg aga gtg ccc gca cag ctg ctg ggt ctg ctg ctg tgg        48
Met Asp Met Arg Val Pro Ala Gln Leu Leu Gly Leu Leu Leu Trp
1               5                   10                  15 ctg ccc gga gcc aaa tgt gac atc cag atg aca cag tcc cca tct acc    96
Leu Pro Gly Ala Lys Cys Asp Ile Gln Met Thr Gln Ser Pro Ser Thr
                20                  25                  30 ctg tct gct tcc gtg gga gat cgg gtg act atc acc tgc aga gca agc   144
Leu Ser Ala Ser Val Gly Asp Arg Val Thr Ile Thr Cys Arg Ala Ser
            35                  40                  45 tcc tcc gtg agg tac atc gct tgg tac cag cag aag cca gga aag gcc   192
Ser Ser Val Arg Tyr Ile Ala Trp Tyr Gln Gln Lys Pro Gly Lys Ala
        50                  55                  60 cca aag ctg ctg atc tac cca acc tcc tcc ctg gaa tcc ggg gtg ccc   240
Pro Lys Leu Leu Ile Tyr Pro Thr Ser Ser Leu Glu Ser Gly Val Pro
65                  70                  75                  80 agc aga ttc tca ggc agt ggc tcc ggc acc gaa ttc acc ctg acc atc   288
Ser Arg Phe Ser Gly Ser Gly Ser Gly Thr Glu Phe Thr Leu Thr Ile
                85                  90                  95 agc tca ctg cag cct gac gac ttc gca acc tac tac tgt ctg cag tgg   336
Ser Ser Leu Gln Pro Asp Asp Phe Ala Thr Tyr Tyr Cys Leu Gln Trp
            100                 105                 110 agt agc tac cct tgg aca ttc ggc ggc ggc acc aag gtg gag atc aag   384
Ser Ser Tyr Pro Trp Thr Phe Gly Gly Gly Thr Lys Val Glu Ile Lys
        115                 120                 125 cgg acc gtc gcc gca cca agt gtc ttc atc ttc ccg cca tct gat gag   432
Arg Thr Val Ala Ala Pro Ser Val Phe Ile Phe Pro Pro Ser Asp Glu
130                 135                 140 cag ttg aaa tct gga act gcc tct gtt gtg tgc ctg ctg aat aac ttc   480
Gln Leu Lys Ser Gly Thr Ala Ser Val Val Cys Leu Leu Asn Asn Phe
145                 150                 155                 160 tat ccc aga gag gcc aaa gta cag tgg aag gtg gat aac gcc ctc caa   528
Tyr Pro Arg Glu Ala Lys Val Gln Trp Lys Val Asp Asn Ala Leu Gln
                165                 170                 175 tcg ggt aac tcc cag gag agt gtc aca gag cag gac agc aag gac agc   576
Ser Gly Asn Ser Gln Glu Ser Val Thr Glu Gln Asp Ser Lys Asp Ser
            180                 185                 190 acc tac agc ctc agc agc acc ctg acg ctg agc aaa gca gac tac gag   624
Thr Tyr Ser Leu Ser Ser Thr Leu Thr Leu Ser Lys Ala Asp Tyr Glu
        195                 200                 205 aaa cac aaa gtc tac gcc tgc gaa gtc acc cat cag ggc ctg agc tcg   672
Lys His Lys Val Tyr Ala Cys Glu Val Thr His Gln Gly Leu Ser Ser
    210                 215                 220 ccc gtc aca aag agc ttc aac agg gga gag tgt                       705
Pro Val Thr Lys Ser Phe Asn Arg Gly Glu Cys
```

```
Pro Val Thr Lys Ser Phe Asn Arg Gly Glu Cys
225                 230                 235

<210> SEQ ID NO 96
<211> LENGTH: 235
<212> TYPE: PRT
<213> ORGANISM: Artificial Sequence
<220> FEATURE:
<223> OTHER INFORMATION: Synthetic Construct

<400> SEQUENCE: 96

Met Asp Met Arg Val Pro Ala Gln Leu Leu Gly Leu Leu Leu Leu Trp
1               5                   10                  15

Leu Pro Gly Ala Lys Cys Asp Ile Gln Met Thr Gln Ser Pro Ser Thr
            20                  25                  30

Leu Ser Ala Ser Val Gly Asp Arg Val Thr Ile Thr Cys Arg Ala Ser
        35                  40                  45

Ser Ser Val Arg Tyr Ile Ala Trp Tyr Gln Gln Lys Pro Gly Lys Ala
    50                  55                  60

Pro Lys Leu Leu Ile Tyr Pro Thr Ser Ser Leu Glu Ser Gly Val Pro
65                  70                  75                  80

Ser Arg Phe Ser Gly Ser Gly Ser Gly Thr Glu Phe Thr Leu Thr Ile
                85                  90                  95

Ser Ser Leu Gln Pro Asp Asp Phe Ala Thr Tyr Tyr Cys Leu Gln Trp
            100                 105                 110

Ser Ser Tyr Pro Trp Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 97
<211> LENGTH: 1335
<212> TYPE: DNA
<213> ORGANISM: Artificial Sequence
<220> FEATURE:
<223> OTHER INFORMATION: 5B_42 heavy chain without leader
<220> FEATURE:
<221> NAME/KEY: CDS
<222> LOCATION: (1)..(1335)

<400> SEQUENCE: 97 cag gtg cag ctg gtg cag agc ggg gcc gag gtg aag aag cct gga gcc      48
Gln Val Gln Leu Val Gln Ser Gly Ala Glu Val Lys Lys Pro Gly Ala
1               5                   10                  15 tca gtg aag gtg agt tgc aag gcc tcc ggt tac acc ttc acc agc tac      96
Ser Val Lys Val Ser Cys Lys Ala Ser Gly Tyr Thr Phe Thr Ser Tyr
            20                  25                  30
```

-continued

| | |
|---|---|
| cac atc cac tgg gtc aga cag gct ccc ggc cag aga ctg gag tgg atg<br>His Ile His Trp Val Arg Gln Ala Pro Gly Gln Arg Leu Glu Trp Met<br>      35                  40                  45 | 144 |
| ggc tgg atc tac cct gga gat gac tcc acc aag tac tcc cag aag ttc<br>Gly Trp Ile Tyr Pro Gly Asp Asp Ser Thr Lys Tyr Ser Gln Lys Phe<br> 50                        55                  60 | 192 |
| cag ggt cgc gtg acc att acc agg gac gcc agc gcc tcc act gcc tac<br>Gln Gly Arg Val Thr Ile Thr Arg Asp Ala Ser Ala Ser Thr Ala Tyr<br>65                    70                  75                  80 | 240 |
| atg gag ctg tct tcc ctg aga tct gag gat acc gca gtc tac tac tgt<br>Met Glu Leu Ser Ser Leu Arg Ser Glu Asp Thr Ala Val Tyr Tyr Cys<br>                  85                  90                  95 | 288 |
| aca cgg ggg gac cgc ttt gct tac tgg ggg cag ggc act ctg gtg acc<br>Thr Arg Gly Asp Arg Phe Ala Tyr Trp Gly Gln Gly Thr Leu Val Thr<br>              100                 105                110 | 336 |
| gtc agc agc gcc agc acc aag ggc cca tcg gtc ttc ccc ctg gca ccc<br>Val Ser Ser Ala Ser Thr Lys Gly Pro Ser Val Phe Pro Leu Ala Pro<br>          115                 120                125 | 384 |
| tcc tcc aag agc acc tct ggg ggc aca gcg gcc ctg ggc tgc ctg gtc<br>Ser Ser Lys Ser Thr Ser Gly Gly Thr Ala Ala Leu Gly Cys Leu Val<br>130                     135                140 | 432 |
| aag gac tac ttc ccc gaa ccg gtg acg gtg tcg tgg aac tca ggc gcc<br>Lys Asp Tyr Phe Pro Glu Pro Val Thr Val Ser Trp Asn Ser Gly Ala<br>145                  150                155                160 | 480 |
| ctg acc agc ggc gtg cac acc ttc ccg gct gtc cta cag tcc tca gga<br>Leu Thr Ser Gly Val His Thr Phe Pro Ala Val Leu Gln Ser Ser Gly<br>              165                 170                175 | 528 |
| ctc tac tcc ctc agc agc gtg gtg acc gtg ccc tcc agc agc ttg ggc<br>Leu Tyr Ser Leu Ser Ser Val Val Thr Val Pro Ser Ser Ser Leu Gly<br>          180                 185                190 | 576 |
| acc cag acc tac atc tgc aac gtg aat cac aag ccc agc aac acc aag<br>Thr Gln Thr Tyr Ile Cys Asn Val Asn His Lys Pro Ser Asn Thr Lys<br>              195                 200                205 | 624 |
| gtg gac aag aaa gtt gag ccc aaa tct tgt gac aaa act cac aca tgc<br>Val Asp Lys Lys Val Glu Pro Lys Ser Cys Asp Lys Thr His Thr Cys<br>210                     215                220 | 672 |
| cca ccg tgc cca gca cct gaa ctc ctg ggg gga ccg tca gtc ttc ctc<br>Pro Pro Cys Pro Ala Pro Glu Leu Leu Gly Gly Pro Ser Val Phe Leu<br>225                  230                235                240 | 720 |
| ttc ccc cca aaa ccc aag gac acc ctc atg atc tcc cgg acc cct gag<br>Phe Pro Pro Lys Pro Lys Asp Thr Leu Met Ile Ser Arg Thr Pro Glu<br>              245                 250                255 | 768 |
| gtc aca tgc gtg gtg gtg gac gtg agc cac gaa gac cct gag gtc aag<br>Val Thr Cys Val Val Val Asp Val Ser His Glu Asp Pro Glu Val Lys<br>          260                 265                270 | 816 |
| ttc aac tgg tac gtg gac ggc gtg gag gtg cat aat gcc aag aca aag<br>Phe Asn Trp Tyr Val Asp Gly Val Glu Val His Asn Ala Lys Thr Lys<br>          275                 280                285 | 864 |
| ccg cgg gag gag cag tac aac agc acg tac cgt gtg gtc agc gtc ctc<br>Pro Arg Glu Glu Gln Tyr Asn Ser Thr Tyr Arg Val Val Ser Val Leu<br>          290                 295                300 | 912 |
| acc gtc ctg cac cag gac tgg ctg aat ggc aag gag tac aag tgc aag<br>Thr Val Leu His Gln Asp Trp Leu Asn Gly Lys Glu Tyr Lys Cys Lys<br>305                     310                315                320 | 960 |
| gtc tcc aac aaa gcc ctc cca gcc ccc atc gag aaa acc atc tcc aaa<br>Val Ser Asn Lys Ala Leu Pro Ala Pro Ile Glu Lys Thr Ile Ser Lys<br>              325                 330                335 | 1008 |
| gcc aaa ggg cag ccc cga gaa cca cag gtg tac acc ctg ccc cca tcc<br>Ala Lys Gly Gln Pro Arg Glu Pro Gln Val Tyr Thr Leu Pro Pro Ser<br>          340                 345                350 | 1056 |

```
cgg gat gag ctg acc aag aac cag gtc agc ctg acc tgc ctg gtc aaa     1104
Arg Asp Glu Leu Thr Lys Asn Gln Val Ser Leu Thr Cys Leu Val Lys
        355                 360                 365 ggc ttc tat ccc agc gac atc gcc gtg gag tgg gag agc aat ggg cag     1152
Gly Phe Tyr Pro Ser Asp Ile Ala Val Glu Trp Glu Ser Asn Gly Gln
370                 375                 380 ccg gag aac aac tac aag acc acg cct ccc gtg ctg gac tcc gac ggc     1200
Pro Glu Asn Asn Tyr Lys Thr Thr Pro Pro Val Leu Asp Ser Asp Gly
385                 390                 395                 400 tcc ttc ttc ctc tac agc aag ctc acc gtg gac aag agc agg tgg cag     1248
Ser Phe Phe Leu Tyr Ser Lys Leu Thr Val Asp Lys Ser Arg Trp Gln
        405                 410                 415 cag ggg aac gtc ttc tca tgc tcc gtg atg cat gag gct ctg cac aac     1296
Gln Gly Asn Val Phe Ser Cys Ser Val Met His Glu Ala Leu His Asn
    420                 425                 430 cac tac acg cag aag agc ctc tcc ctg tct ccg ggt aaa                 1335
His Tyr Thr Gln Lys Ser Leu Ser Leu Ser Pro Gly Lys
        435                 440                 445
```

<210> SEQ ID NO 98
<211> LENGTH: 445
<212> TYPE: PRT
<213> ORGANISM: Artificial Sequence
<220> FEATURE:
<223> OTHER INFORMATION: Synthetic Construct

<400> SEQUENCE: 98

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Arg Leu Glu Trp Met
        35                  40                  45

Gly Trp Ile Tyr Pro Gly Asp Asp Ser Thr Lys Tyr Ser Gln Lys Phe
    50                  55                  60

Gln Gly Arg Val Thr Ile Thr Arg Asp Ala Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asp Arg Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 99
<211> LENGTH: 1392
<212> TYPE: DNA
<213> ORGANISM: Artificial Sequence
<220> FEATURE:
<223> OTHER INFORMATION: 5B_42 heavy chain with leader
<220> FEATURE:
<221> NAME/KEY: CDS
<222> LOCATION: (1)..(1392)

<400> SEQUENCE: 99 atg gat tgg aca tgg cga atc ctg ttc ctg gtg gct gcc gca acc ggc    48
Met Asp Trp Thr Trp Arg Ile Leu Phe Leu Val Ala Ala Ala Thr Gly
1               5                   10                  15 gcc cac agc cag gtg cag ctg gtg cag agc ggg gcc gag gtg aag aag    96
Ala His Ser Gln Val Gln Leu Val Gln Ser Gly Ala Glu Val Lys Lys
            20                  25                  30 cct gga gcc tca gtg aag gtg agt tgc aag gcc tcc ggt tac acc ttc   144
Pro Gly Ala Ser Val Lys Val Ser Cys Lys Ala Ser Gly Tyr Thr Phe
        35                  40                  45 acc agc tac cac atc cac tgg gtc aga cag gct ccc ggc cag aga ctg   192
Thr Ser Tyr His Ile His Trp Val Arg Gln Ala Pro Gly Gln Arg Leu
    50                  55                  60 gag tgg atg ggc tgg atc tac cct gga gat gac tcc acc aag tac tcc   240
Glu Trp Met Gly Trp Ile Tyr Pro Gly Asp Asp Ser Thr Lys Tyr Ser
65                  70                  75                  80 cag aag ttc cag ggt cgc gtg acc att acc agg gac gcc agc gcc tcc   288
Gln Lys Phe Gln Gly Arg Val Thr Ile Thr Arg Asp Ala Ser Ala Ser
                85                  90                  95 act gcc tac atg gag ctg tct tcc ctg aga tct gag gat acc gca gtc   336
Thr Ala Tyr Met Glu Leu Ser Ser Leu Arg Ser Glu Asp Thr Ala Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 100 |     |     |     |     | 105 |     |     |     |     | 110 |     |     |      |
| tac | tac | tgt | aca | cgg | ggg | gac | cgc | ttt | gct | tac | tgg | ggg | cag | ggc | act | 384  |
| Tyr | Tyr | Cys | Thr | Arg | Gly | Asp | Arg | Phe | Ala | Tyr | Trp | Gly | Gln | Gly | Thr |      |
|     |     |     | 115 |     |     |     |     | 120 |     |     |     |     | 125 |     |     |      |
| ctg | gtg | acc | gtc | agc | agc | gcc | agc | acc | aag | ggc | cca | tcg | gtc | ttc | ccc | 432  |
| Leu | Val | Thr | Val | Ser | Ser | Ala | Ser | Thr | Lys | Gly | Pro | Ser | Val | Phe | Pro |      |
|     |     | 130 |     |     |     |     | 135 |     |     |     |     | 140 |     |     |     |      |
| ctg | gca | ccc | tcc | tcc | aag | agc | acc | tct | ggg | ggc | aca | gcg | gcc | ctg | ggc | 480  |
| Leu | Ala | Pro | Ser | Ser | Lys | Ser | Thr | Ser | Gly | Gly | Thr | Ala | Ala | Leu | Gly |      |
| 145 |     |     |     |     | 150 |     |     |     |     | 155 |     |     |     |     | 160 |      |
| tgc | ctg | gtc | aag | gac | tac | ttc | ccc | gaa | ccg | gtg | acg | gtg | tcg | tgg | aac | 528  |
| Cys | Leu | Val | Lys | Asp | Tyr | Phe | Pro | Glu | Pro | Val | Thr | Val | Ser | Trp | Asn |      |
|     |     |     |     | 165 |     |     |     |     | 170 |     |     |     |     | 175 |     |      |
| tca | ggc | gcc | ctg | acc | agc | ggc | gtg | cac | acc | ttc | ccg | gct | gtc | cta | cag | 576  |
| Ser | Gly | Ala | Leu | Thr | Ser | Gly | Val | His | Thr | Phe | Pro | Ala | Val | Leu | Gln |      |
|     |     |     | 180 |     |     |     |     | 185 |     |     |     |     | 190 |     |     |      |
| tcc | tca | gga | ctc | tac | tcc | ctc | agc | agc | gtg | gtg | acc | gtg | ccc | tcc | agc | 624  |
| Ser | Ser | Gly | Leu | Tyr | Ser | Leu | Ser | Ser | Val | Val | Thr | Val | Pro | Ser | Ser |      |
|     |     | 195 |     |     |     |     | 200 |     |     |     |     | 205 |     |     |     |      |
| agc | ttg | ggc | acc | cag | acc | tac | atc | tgc | aac | gtg | aat | cac | aag | ccc | agc | 672  |
| Ser | Leu | Gly | Thr | Gln | Thr | Tyr | Ile | Cys | Asn | Val | Asn | His | Lys | Pro | Ser |      |
|     | 210 |     |     |     |     | 215 |     |     |     |     | 220 |     |     |     |     |      |
| aac | acc | aag | gtg | gac | aag | aaa | gtt | gag | ccc | aaa | tct | tgt | gac | aaa | act | 720  |
| Asn | Thr | Lys | Val | Asp | Lys | Lys | Val | Glu | Pro | Lys | Ser | Cys | Asp | Lys | Thr |      |
| 225 |     |     |     |     | 230 |     |     |     |     | 235 |     |     |     |     | 240 |      |
| cac | aca | tgc | cca | ccg | tgc | cca | gca | cct | gaa | ctc | ctg | ggg | gga | ccg | tca | 768  |
| His | Thr | Cys | Pro | Pro | Cys | Pro | Ala | Pro | Glu | Leu | Leu | Gly | Gly | Pro | Ser |      |
|     |     |     |     | 245 |     |     |     |     | 250 |     |     |     |     | 255 |     |      |
| gtc | ttc | ctc | ttc | ccc | cca | aaa | ccc | aag | gac | acc | ctc | atg | atc | tcc | cgg | 816  |
| Val | Phe | Leu | Phe | Pro | Pro | Lys | Pro | Lys | Asp | Thr | Leu | Met | Ile | Ser | Arg |      |
|     |     |     | 260 |     |     |     |     | 265 |     |     |     |     | 270 |     |     |      |
| acc | cct | gag | gtc | aca | tgc | gtg | gtg | gtg | gac | gtg | agc | cac | gaa | gac | cct | 864  |
| Thr | Pro | Glu | Val | Thr | Cys | Val | Val | Val | Asp | Val | Ser | His | Glu | Asp | Pro |      |
|     |     | 275 |     |     |     |     | 280 |     |     |     |     | 285 |     |     |     |      |
| gag | gtc | aag | ttc | aac | tgg | tac | gtg | gac | ggc | gtg | gag | gtg | cat | aat | gcc | 912  |
| Glu | Val | Lys | Phe | Asn | Trp | Tyr | Val | Asp | Gly | Val | Glu | Val | His | Asn | Ala |      |
|     | 290 |     |     |     |     | 295 |     |     |     |     | 300 |     |     |     |     |      |
| aag | aca | aag | ccg | cgg | gag | gag | cag | tac | aac | agc | acg | tac | cgt | gtg | gtc | 960  |
| Lys | Thr | Lys | Pro | Arg | Glu | Glu | Gln | Tyr | Asn | Ser | Thr | Tyr | Arg | Val | Val |      |
| 305 |     |     |     |     | 310 |     |     |     |     | 315 |     |     |     |     | 320 |      |
| agc | gtc | ctc | acc | gtc | ctg | cac | cag | gac | tgg | ctg | aat | ggc | aag | gag | tac | 1008 |
| Ser | Val | Leu | Thr | Val | Leu | His | Gln | Asp | Trp | Leu | Asn | Gly | Lys | Glu | Tyr |      |
|     |     |     |     | 325 |     |     |     |     | 330 |     |     |     |     | 335 |     |      |
| aag | tgc | aag | gtc | tcc | aac | aaa | gcc | ctc | cca | gcc | ccc | atc | gag | aaa | acc | 1056 |
| Lys | Cys | Lys | Val | Ser | Asn | Lys | Ala | Leu | Pro | Ala | Pro | Ile | Glu | Lys | Thr |      |
|     |     |     | 340 |     |     |     |     | 345 |     |     |     |     | 350 |     |     |      |
| atc | tcc | aaa | gcc | aaa | ggg | cag | ccc | cga | gaa | cca | cag | gtg | tac | acc | ctg | 1104 |
| Ile | Ser | Lys | Ala | Lys | Gly | Gln | Pro | Arg | Glu | Pro | Gln | Val | Tyr | Thr | Leu |      |
|     |     | 355 |     |     |     |     | 360 |     |     |     |     | 365 |     |     |     |      |
| ccc | cca | tcc | cgg | gat | gag | ctg | acc | aag | aac | cag | gtc | agc | ctg | acc | tgc | 1152 |
| Pro | Pro | Ser | Arg | Asp | Glu | Leu | Thr | Lys | Asn | Gln | Val | Ser | Leu | Thr | Cys |      |
|     | 370 |     |     |     |     | 375 |     |     |     |     | 380 |     |     |     |     |      |
| ctg | gtc | aaa | ggc | ttc | tat | ccc | agc | gac | atc | gcc | gtg | gag | tgg | gag | agc | 1200 |
| Leu | Val | Lys | Gly | Phe | Tyr | Pro | Ser | Asp | Ile | Ala | Val | Glu | Trp | Glu | Ser |      |
| 385 |     |     |     |     | 390 |     |     |     |     | 395 |     |     |     |     | 400 |      |
| aat | ggg | cag | ccg | gag | aac | aac | tac | aag | acc | acg | cct | ccc | gtg | ctg | gac | 1248 |
| Asn | Gly | Gln | Pro | Glu | Asn | Asn | Tyr | Lys | Thr | Thr | Pro | Pro | Val | Leu | Asp |      |
|     |     |     |     | 405 |     |     |     |     | 410 |     |     |     |     | 415 |     |      |
| tcc | gac | ggc | tcc | ttc | ttc | ctc | tac | agc | aag | ctc | acc | gtg | gac | aag | agc | 1296 |

```
Ser Asp Gly Ser Phe Phe Leu Tyr Ser Lys Leu Thr Val Asp Lys Ser
            420                 425                 430 agg tgg cag cag ggg aac gtc ttc tca tgc tcc gtg atg cat gag gct    1344
Arg Trp Gln Gln Gly Asn Val Phe Ser Cys Ser Val Met His Glu Ala
            435                 440                 445 ctg cac aac cac tac acg cag aag agc ctc tcc ctg tct ccg ggt aaa    1392
Leu His Asn His Tyr Thr Gln Lys Ser Leu Ser Leu Ser Pro Gly Lys
        450                 455                 460

<210> SEQ ID NO 100
<211> LENGTH: 464
<212> TYPE: PRT
<213> ORGANISM: Artificial Sequence
<220> FEATURE:
<223> OTHER INFORMATION: Synthetic Construct

<400> SEQUENCE: 100

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr His Ile His Trp Val Arg Gln Ala Pro Gly Gln Arg Leu
    50                  55                  60

Glu Trp Met Gly Trp Ile Tyr Pro Gly Asp Ser Thr Lys Tyr Ser
65              70                  75                  80

Gln Lys Phe Gln Gly Arg Val Thr Ile Thr Arg Asp Ala Ser Ala Ser
            85                  90                  95

Thr Ala Tyr Met Glu Leu Ser Ser Leu Arg Ser Glu Asp Thr Ala Val
            100                 105                 110

Tyr Tyr Cys Thr Arg Gly Asp Arg Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
```

```
            305                 310                 315                 320

Ser Val Leu Thr Val Leu His Gln Asp Trp Leu Asn Gly Lys Glu Tyr
                    325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
        450                 455                 460

<210> SEQ ID NO 101
<211> LENGTH: 19
<212> TYPE: PRT
<213> ORGANISM: Artificial Sequence
<220> FEATURE:
<223> OTHER INFORMATION: Epitopic peptide
<220> FEATURE:
<221> NAME/KEY: PEPTIDE
<222> LOCATION: (1)..(19)

<400> SEQUENCE: 101

Gly Gly Gly Gly Asn Leu Thr Gln Asp Arg Ala Gln Val Glu Met Gln
1               5                   10                  15

Gly Ser Arg

<210> SEQ ID NO 102
<211> LENGTH: 19
<212> TYPE: PRT
<213> ORGANISM: Artificial Sequence
<220> FEATURE:
<223> OTHER INFORMATION: Negative-control epitopic peptide
<220> FEATURE:
<221> NAME/KEY: PEPTIDE
<222> LOCATION: (1)..(19)

<400> SEQUENCE: 102

Gly Gly Gly Gly Asn Leu Thr Gln Ala Arg Gly Gln Val Glu Met Gln
1               5                   10                  15

Gly Ser Arg
```